United States Patent
Ito et al.

(10) Patent No.: US 8,299,074 B2
(45) Date of Patent: *Oct. 30, 2012

(54) P38 MAP KINASE INHIBITORS

(75) Inventors: Kazuhiro Ito, London (GB); Peter Strong, London (GB); William Garth Rapeport, London (GB); Peter John Murray, London (GB); John King-Underwood, Pendock (GB); Jonathan Gareth Williams, Nottingham (GB); Stuart Thomas Onions, Nottingham (GB); Kevin Joly, Nottingham (GB); Catherine Elisabeth Charron, London (GB)

(73) Assignee: RespiVert Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/139,010

(22) PCT Filed: Dec. 11, 2009

(86) PCT No.: PCT/GB2009/051702
§ 371 (c)(1), (2), (4) Date: Aug. 9, 2011

(87) PCT Pub. No.: WO2010/067130
PCT Pub. Date: Jun. 17, 2010

(65) Prior Publication Data
US 2011/0312963 A1    Dec. 22, 2011

Related U.S. Application Data

(60) Provisional application No. 61/166,594, filed on Apr. 3, 2009.

(30) Foreign Application Priority Data

Dec. 11, 2008 (GB) .................................. 0822609.4
Jul. 17, 2009 (GB) .................................. 0912470.2

(51) Int. Cl.
*A61K 31/5377* (2006.01)
*A61K 31/505* (2006.01)
*A61K 31/445* (2006.01)
*A61K 31/4427* (2006.01)
*C07D 413/14* (2006.01)
*C07D 403/02* (2006.01)
*C07D 213/02* (2006.01)
*C07D 211/06* (2006.01)

(52) U.S. Cl. ............. 514/236.5; 514/269; 514/333; 514/340; 544/111; 544/333; 546/193; 546/275.4

(58) Field of Classification Search .......... 514/236.5, 514/269, 333, 340; 544/111, 333; 546/193; 546/275.4
See application file for complete search history.

(56) References Cited

U.S. PATENT DOCUMENTS

| | | |
|---|---|---|
| 6,525,046 B1 | 2/2003 | Cirillo et al. |
| 6,916,814 B2 | 7/2005 | Moss et al. |
| 7,329,670 B1 | 2/2008 | Dumas et al. |
| 7,625,915 B2 | 12/2009 | Dumas et al. |
| 2004/0180906 A1 | 9/2004 | Flynn et al. |
| 2004/0192653 A1 | 9/2004 | Munson et al. |
| 2007/0010529 A1 | 1/2007 | Takahashi et al. |
| 2008/0113967 A1 | 5/2008 | Flynn et al. |
| 2008/0207699 A1 | 8/2008 | Hoelzemann et al. |
| 2008/0300281 A1 | 12/2008 | Dumas et al. |
| 2011/0212962 A1 | 9/2011 | Ito et al. |
| 2011/0269800 A1 | 11/2011 | Ito et al. |
| 2011/0294812 A1 | 12/2011 | Ito et al. |

FOREIGN PATENT DOCUMENTS

| | | |
|---|---|---|
| WO | WO 99-23091 | 5/1999 |
| WO | WO 99/32110 | 7/1999 |
| WO | WO 99/32111 | 7/1999 |
| WO | WO 99/32455 | 7/1999 |
| WO | WO 99/47529 | 9/1999 |
| WO | WO 00/43384 | 7/2000 |
| WO | WO 01/04115 | 1/2001 |
| WO | WO 02/066442 | 8/2002 |
| WO | WO 02/092576 | 11/2002 |

(Continued)

OTHER PUBLICATIONS

Friedenreich, Christine M. State of the epidemiological evidence on physical activity and cancer prevention. European Journal of Cancer, 46, (2010), 2593-2604.*

(Continued)

*Primary Examiner* — Joseph K. McKane
*Assistant Examiner* — Samantha Shterengarts
(74) *Attorney, Agent, or Firm* — Mary A. Appollina

(57) ABSTRACT

The present disclosure relates to compounds of formula (I):

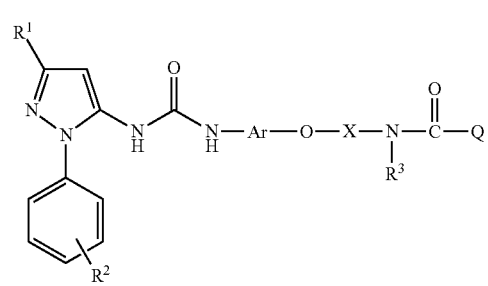

which are inhibitors of p38 mitogen-activated protein kinase enzymes, particularly the alpha and gamma kinase sub-types thereof, and their use in therapy, including in pharmaceutical combinations, especially in the treatment of inflammatory diseases, including inflammatory diseases of the lung, such as COPD.

17 Claims, 4 Drawing Sheets

FOREIGN PATENT DOCUMENTS

| | | |
|---|---|---|
| WO | WO 03/005999 | 1/2003 |
| WO | WO 03/068228 | 8/2003 |
| WO | WO 03/072569 | 9/2003 |
| WO | WO 03/084503 | 10/2003 |
| WO | WO 2004/014387 | 2/2004 |
| WO | WO 2004/021988 | 3/2004 |
| WO | WO 2004/060306 | 7/2004 |
| WO | WO 2004/078746 | 9/2004 |
| WO | WO 2004/089929 | 10/2004 |
| WO | WO 2004/100946 | 11/2004 |
| WO | WO 2005/018624 | 3/2005 |
| WO | WO 2005/048948 | 6/2005 |
| WO | WO 2005/110994 | 11/2005 |
| WO | WO 2005/113511 | 12/2005 |
| WO | WO 2006/009741 | 1/2006 |
| WO | WO 2006/014290 | 2/2006 |
| WO | WO 2006/015775 | 2/2006 |
| WO | WO 2006/028524 | 3/2006 |
| WO | WO 2006/043090 | 4/2006 |
| WO | WO 2006/062984 | 6/2006 |
| WO | WO 2006/068591 | 6/2006 |
| WO | WO 2006/072589 | 7/2006 |
| WO | WO 2006/081034 | 8/2006 |
| WO | WO 2007/002635 | 1/2007 |
| WO | WO 2007/017083 | 2/2007 |
| WO | WO 2007/038425 | 4/2007 |
| WO | WO 2007/059202 | 5/2007 |
| WO | WO 2007/064872 | 6/2007 |
| WO | WO 2008/016192 | 2/2008 |

OTHER PUBLICATIONS

U.S. Appl. No. 13/262,266, filed Dec. 22, 2011, Ito et al.

Dumas et al., "Synthesis and Pharmacological Characterization of a Potent, Orally Active p38 Kinase Inhibitor", Bioorganic & Medicinal Chemistry Letters 12 (2002) 1559-1562.

* cited by examiner

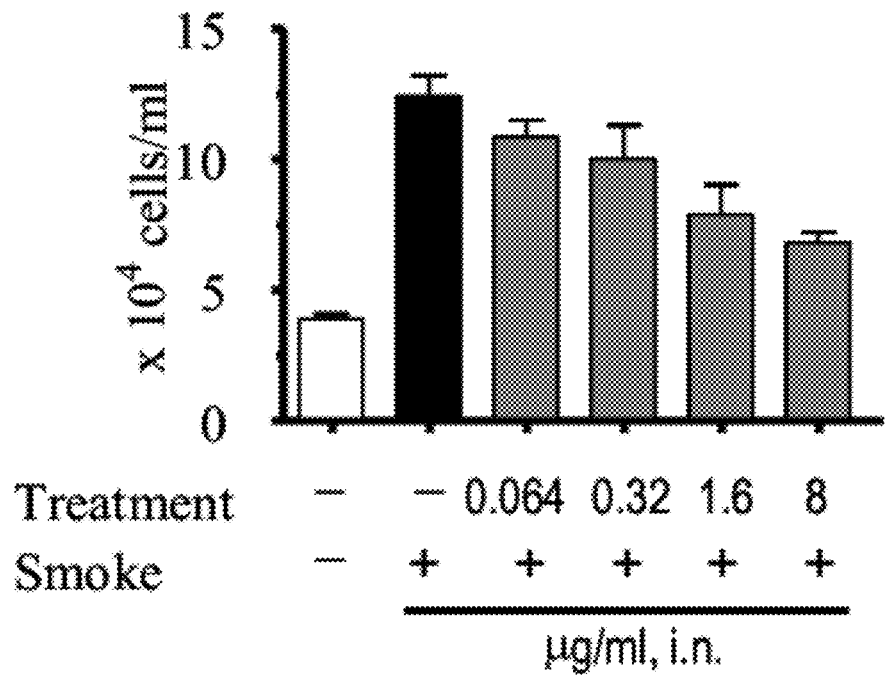
Figure 1: Neutrophil accumulation in BALF (Example 8)
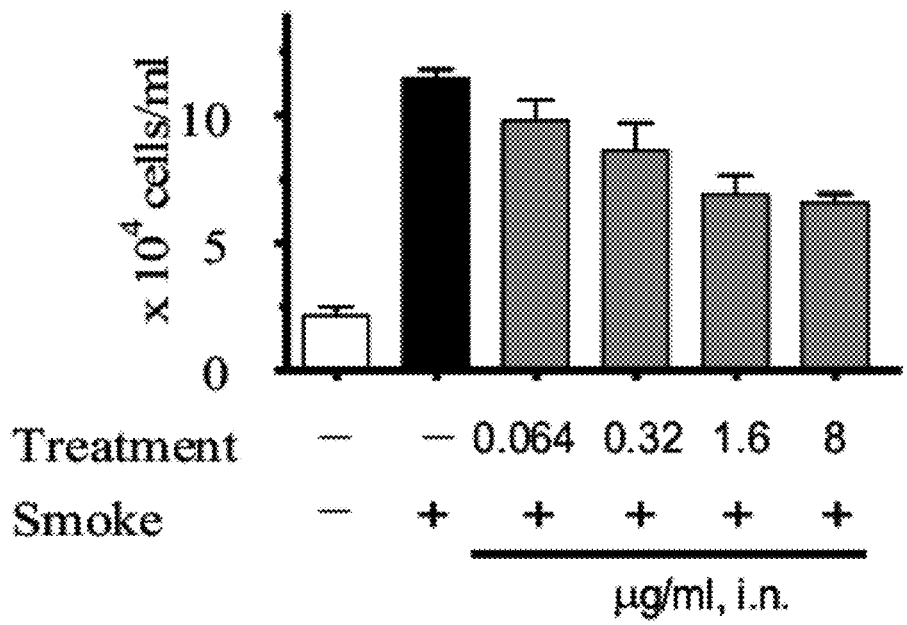
Figure 2: MOMA2+ Macrophage accumulation in BALF (Example 8)

Figure 3: Neutrophil accumulation in BALF (Example 42)
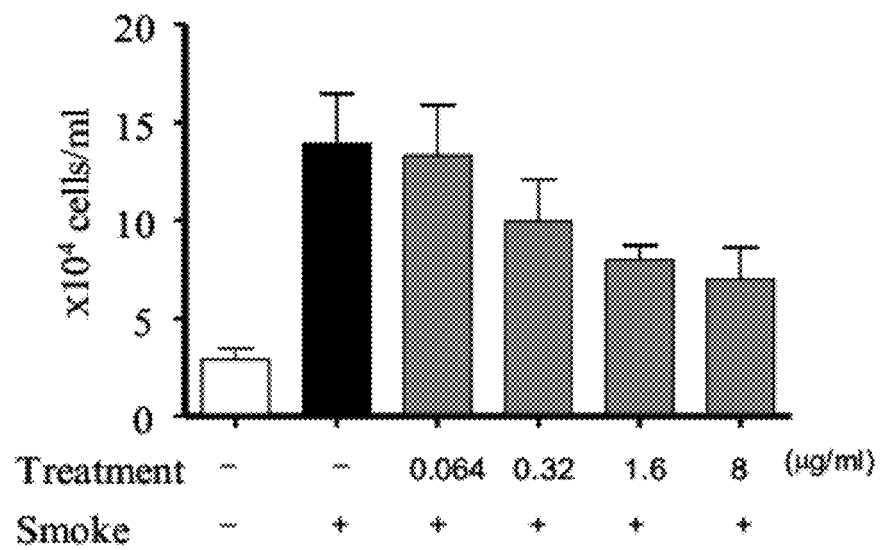
Figure 4: MOMA2+ Macrophage accumulation in BALF (Example 42)
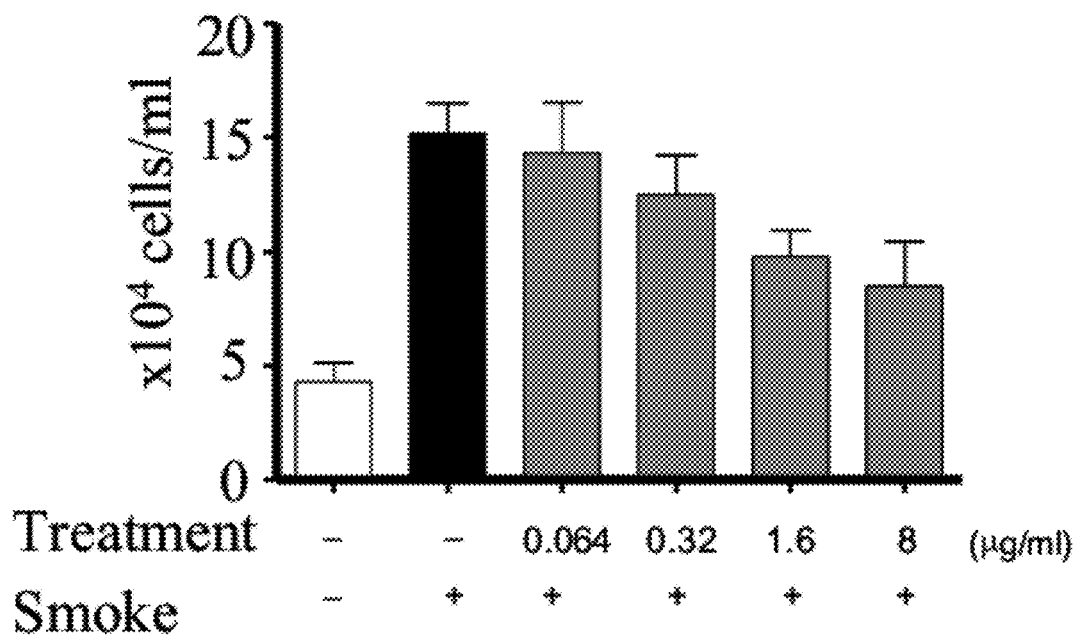

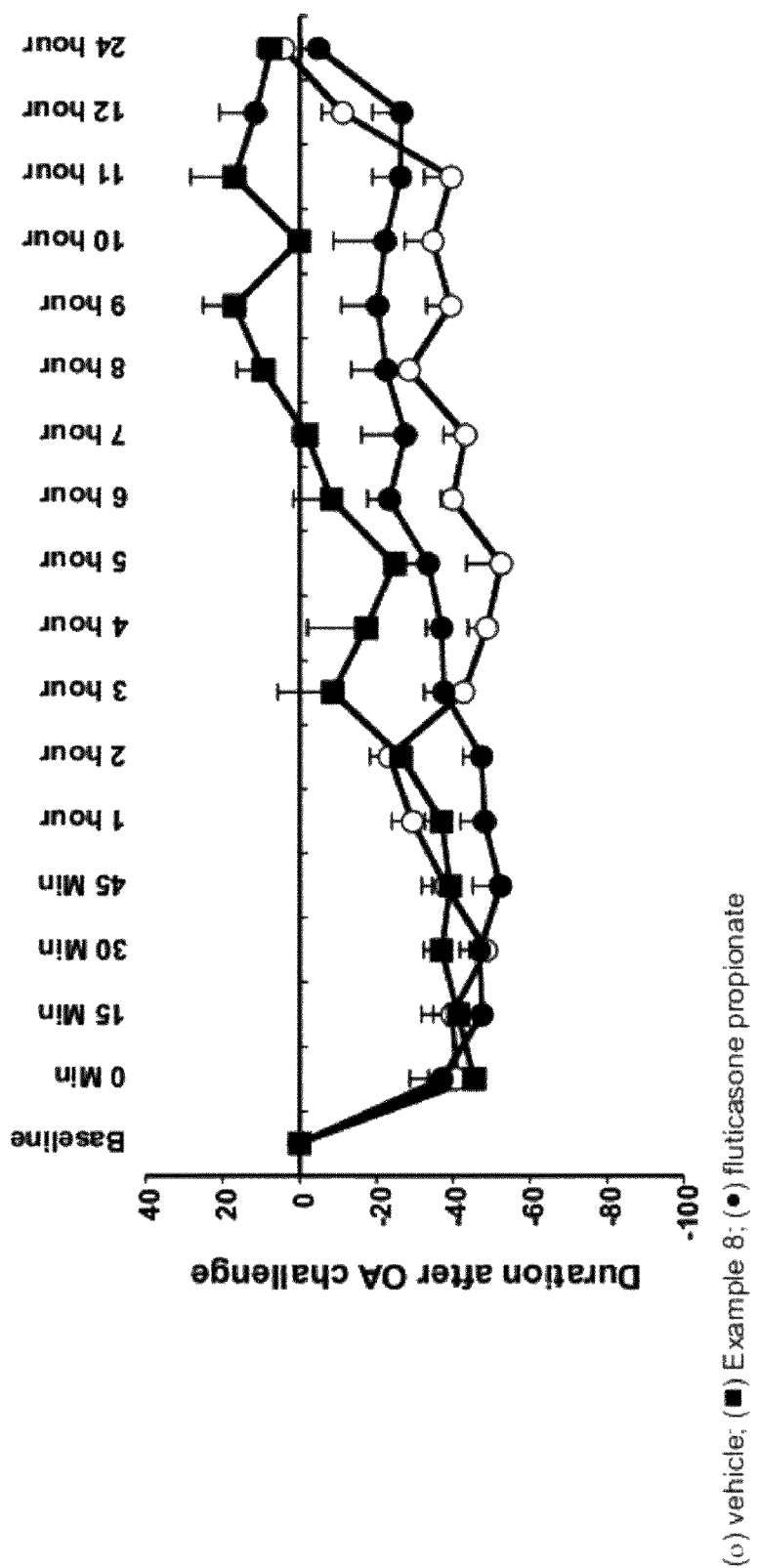

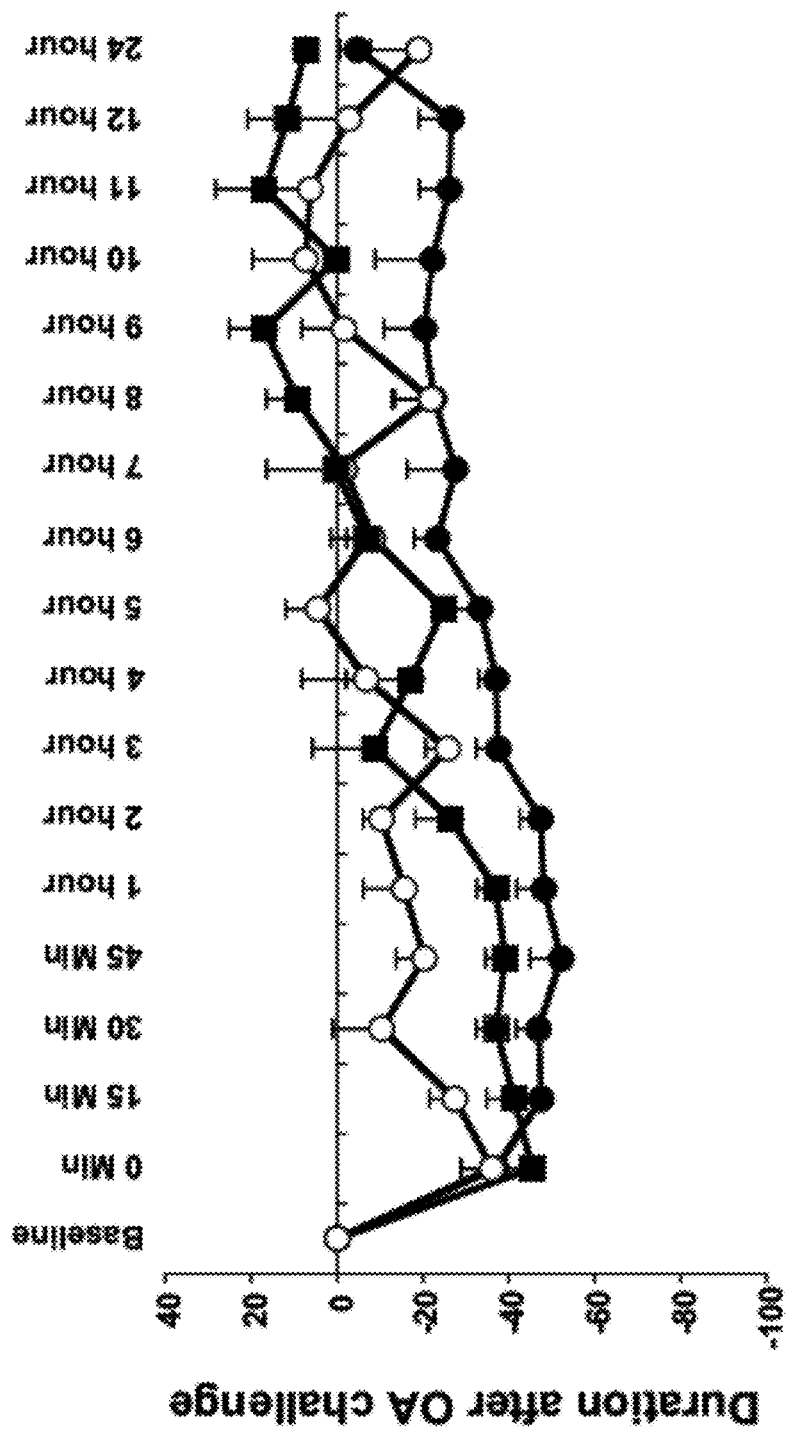

P38 MAP KINASE INHIBITORS

This application is a National Stage application under 35 U.S.C. 371 of PCT International Application No. PCT/GB2009/051702, filed Dec. 11, 2009, which claims priority from Great Britain Patent Applications Nos. GB 0822609.4, filed Dec. 11, 2008, and GB 0912470.2, filed Jul. 17, 2009, and U.S. provisional Patent Application Ser. No. 61/166,594, filed Apr. 3, 2009, the contents of all of which are hereby incorporated by reference in their entirety.

FIELD OF THE INVENTION

The invention relates to compounds which are inhibitors of p38 mitogen-activated protein kinase enzymes (referred to herein as p38 MAP kinase inhibitors), particularly the alpha and gamma kinase sub-types thereof, and their use in therapy, including in pharmaceutical combinations, especially in the treatment of inflammatory diseases, including inflammatory diseases of the lung, such as COPD.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain known small molecule p38 MAPK inhibitors. Earlier generations of compounds were highly toxic due to the ubiquitous expression pattern of these isoforms and off-target effects of the compounds. More recent inhibitors are improved to be highly selective for p38 MAPK alpha and beta isoforms and have a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages (Smith, S. J. (2006) *Br. J. Pharmacol.* 149:393-404) and detectable in neutrophils, CD4+ T cells and endothelial cells (www.genecard.org, Karin, K. (1999) *J. Immunol.*). Very little is known about the expression of p38 MAPK gamma but it is expressed more in brain, skeletal muscle and heart, as well as in lymphocytes and macrophages (www.genecard.org).

Selective small molecule inhibitors of p38 MAPK-gamma and -delta are not currently available, but one existing compound, BIRB 796, is known to have pan-isoform inhibitory activity. The p38 gamma and p38 delta inhibition is observed at higher concentrations of the compound than those required to inhibit p38 MAPK alpha (Kuma, Y. (2005) *J. Biol. Chem.* 280:19472-19479). BIRB 796 also impaired the phosphorylation of p38 MAPKs or JNKs by the upstream kinase MKK6 or MKK4. Kuma discussed the possibility that the conformational change caused by the binding of the inhibitor to the MAPK may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, severe asthma and COPD. There is now abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith, S. J. (2006) *Br. J. Pharmacol.* 149:393-404 describes the inhibitory effect of p38 MAP kinase inhibitors on TNFα (but not IL-8) release from human PBMCs. Use of inhibitors of p38 MAP kinase in the treatment of chronic obstructive pulmonary disease (COPD) is proposed. Small molecule inhibitors targeted to p38 MAPKα/β have proved to be effective in reducing various parameters of inflammation in cells and tissues obtained from patients with COPD, who are generally corticosteroid insensitive, (Smith, S. J. (2006) *Br. J. Pharmacol.* 149:393-404) and in vivo animal models (Underwood, D. C. et al. (2000) 279:895-902; Nath, P. et al. (2006) *Eur. J. Pharmacol.* 544:160-167; Medicherla S. et al. (2008) *J. Pharm. Exp. Ther.* 324:921-929). Irusen and colleagues also suggested the possibility of involvement of p38 MAPK α/β on corticosteroid insensitivity via reduction of binding affinity of glucocorticoid receptor (GR) in nuclei (Irusen, E. et al., (2002) *J. Allergy Clin. Immunol.,* 109:649-657). Clinical experience with a range of p38 MAP kinase inhibitors, including AMG548, BIRB 796, VX702, SCIO469 and SCIO323 is described in Lee et al. (2005) *Current Med. Chem.* 12,:2979-2994.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al (2007; *American Thoracic Society Abstract A*56) demonstrates that silencing p38 gamma has the potential to restore sensitivity to corticosteroids. Thus there may be a "two pronged" benefit to the use of a p38 MAP kinase inhibitor for the treatment of COPD and severe asthma.

There is now a substantial body of evidence which strongly implicates the role of respiratory viral infections in initiating exacerbations in patients suffering from asthma and/or COPD. Exacerbations require an increase in treatment intensity to re-establish control of disease symptomology. If severe, exacerbations may well result in the hospitalisation or, at its most extreme, the death of patients.

The major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specially mentioned above.

There remains a need to identify and develop new compounds therapeutically useful as p38 MAP kinase inhibitors which have improved therapeutic potential, in particular which are more efficacious, longer acting and/or less toxic at the relevant therapeutic dose. An objective of the present invention is to provide compounds which inhibit p38 MAP kinase with certain sub-type specificity, which show good anti-inflammatory potential.

SUMMARY OF THE INVENTION

According to the invention, there is provided a compound of formula (I):

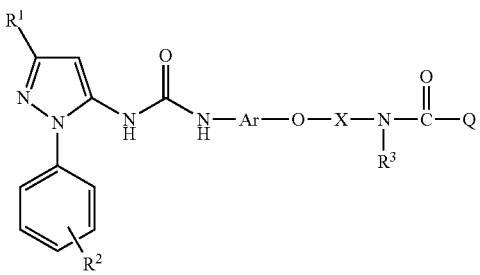

wherein $R^1$ is $C_{1-6}$ alkyl optionally substituted by a hydroxyl group;
$R^2$ is H or $C_{1-6}$ alkyl optionally substituted by a hydroxyl group;
$R^3$ is H, $C_{1-6}$ alkyl or $C_{0-3}$ alkyl$C_{3-6}$ cycloalkyl;
Ar is a naphthyl or a phenyl ring either of which may be optionally substituted by one or more (for example 1 or 2) groups independently selected from $C_{1-6}$ alkyl, $C_{1-6}$ alkoxy, amino, $C_{1-4}$ mono or di-alkyl amino;
X is 5 or 6 membered heteroaryl group containing at least one nitrogen atom and optionally including 1 or 2 further heteroatoms selected from O, S and N;
Q is selected from:
a) a saturated or unsaturated, branched or unbranched $C_{1-10}$ alkyl chain, wherein at least one carbon (for example 1, 2 or 3 carbons, suitably 1 or 2, in particular 1 carbon) is replaced by a heteroatom selected from O, N, S(O)$_p$, wherein said chain is optionally, substituted by one or more groups (for example 1, 2 or 3 groups) independently selected from oxo, halogen, an aryl group, a heteroaryl group, a heterocyclyl group or a $C_{3-8}$ cycloalkyl group,
  each aryl, heteroaryl, heterocyclyl or $C_{3-8}$ cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, S(O)$_q C_{1-6}$ alkyl, $C_{0-6}$ alkylC(O)$C_{1-6}$ alkyl or $C_{0-6}$ alkylC(O)$C_{1-6}$ heteroalkyl,
  with the proviso that the atom linked directly to the carbonyl in —NR$^3$C(O)— is not an oxygen or a sulfur atom; and
b) a $C_{0-8}$ alkyl-heterocycle said heterocyclyl group comprising at least one heteroatom (for example 1, 2 or 3, suitably 1 or 2, in particular 1 heteroatom) selected from O, N, and S, and is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and di-alkyl amino, $C_{1-4}$ mono or di-acyl amino, S(O)$_q C_{1-6}$ alkyl, $C_{0-6}$ alkylC(O)$C_{1-6}$ alkyl or $C_{0-6}$ alkylC(O)$C_{1-6}$ heteroalkyl; and
p is 0, 1 or 2;
q is 0, 1 or 2
a pharmaceutically acceptable salt thereof, including all stereoisomers, tautomers and isotopic derivatives thereof.

BRIEF DESCRIPTION OF THE FIGURES

FIG. 1 shows neutrophil accumulation in BALF from a smoking murine model employing Example 8
FIG. 2 shows macrophage accumulation in BALF from a smoking murine model employing Example 8
FIG. 3 shows neutrophil accumulation in BALF from a smoking murine model employing Example 42
FIG. 4 shows macrophage accumulation in BALF from a smoking murine model employing Example 42
FIG. 5 shows change of sGaw values after OVA exposure in an OVA sensitized PIV3 infected guinea pig model employing Example 8
FIG. 6 shows change of sGaw values after OVA exposure in an OVA sensitized PIV3 infected guinea pig model employing Example 8 and a combination of Example 8 and fluticasone propionate

DETAILED DESCRIPTION OF THE INVENTION

In one aspect there is provided a compound of formula (I):

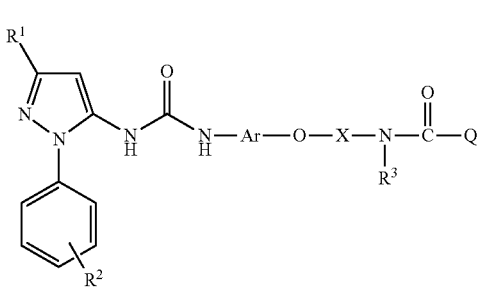

wherein $R^1$ is $C_{1-6}$ alkyl optionally substituted by a hydroxyl group;
$R^2$ is H or $C_{1-6}$ alkyl optionally substituted by a hydroxyl group;
$R^3$ is H, $C_{1-6}$ alkyl or $C_{0-3}$ alkyl$C_{3-6}$ cycloalkyl;
Ar is a naphthyl or a phenyl ring either of which may be optionally substituted by one or more groups independently selected from $C_{1-6}$ alkyl, $C_{1-6}$ alkoxy, amino, $C_{1-4}$ mono or di-alkyl amino;
X is 5 or 6 membered heteroaryl group containing at least one nitrogen atom and optionally including 1 or 2 further heteroatoms selected from O, S and N;
Q is selected from:
a) a saturated or unsaturated, branched or unbranched $C_{1-10}$ alkyl chain, wherein at least one carbon (for example 1, 2 or 3 carbons) is replaced by a heteroatom selected from O, N, S(O)$_p$, wherein said chain is optionally, substituted by one or more groups selected from oxo, halogen, an aryl group, a heteroaryl group or a heterocyclyl group,
  each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, $C_{1-4}$ mono or di-alkyl amino,
  with the proviso that the atom linked directly to the carbonyl in —NR$^3$C(O)— is not an oxygen or a sulfur atom; and
b) a $C_{0-8}$alkylC$_{5-6}$ heterocyclyl said heterocyclyl group comprising at least one heteroatom selected from O, N and S, and optionally substituted by one or two or three groups independently selected from halogen $C_{1-6}$ alkyl, $C_{1-6}$ alkoxy, $C_{1-6}$ haloalkyl, amino, $C_{1-4}$ mono and di-alkyl amino; and
p is 0, 1 or 2;
or a pharmaceutically acceptable salt or solvate thereof, including all stereoisomers and tautomers thereof.

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —$C_{1-3}$ alkylO$C_{1-3}$ alkyl, such as —$CH_2CH_2OCH_3$ or —$CH_2OCH_3$. Thus in one embodiment the alkoxy is linked through carbon to the remainder of the molecule. In one embodiment the alkoxy is linked through oxygen to the remainder of the molecule, for example —$C_0$ alkylO$C_{1-6}$ alkyl. In one embodiment the disclosure relates to straight chain alkoxy.

Heteroalkyl as employed herein is intended to refer to a branched or straight chain alkyl wherein one or more, such as 1, 2 or 3 carbons are replaced by a heteroatom, selected from N, O or $S(O)_q$, wherein q represents 0, 1 or 2. The heteroatom may replace a primary, secondary or tertiary carbon, that is, for example, OH or $NH_2$ for $CH_3$, or NH or O or $SO_2$ for —$CH_2$— or N for a —CH— or a branched carbon group, as technically appropriate.

Haloalkyl as employed herein refers to alkyl groups having 1 to 6 halogen atoms, for example 1 to 5 halogens, such as per haloalkyl, in particular perfluoroalkyl, more specifically —$CF_2CF_3$ or $CF_3$.

$C_{1-4}$ mono or di-acyl amino is intended to refer to —$NHC(O)C_{1-3}$ alkyl and to (—$NC(O)C_{1-3}$ alkyl) $C(O)C_{1-3}$ alkyl) respectively.

$C_{1-4}$ mono or di-alkyl amino is intended to refer to —$NHC_{1-4}$ alkyl and —$N(C_{1-4}$ alkyl) ($C_{1-4}$ alkyl) respectively.

Aryl as used herein refers to, for example $C_{6-14}$ mono or polycyclic groups having from 1 to 3 rings wherein at least one ring is aromatic including phenyl, naphthyl, anthracenyl, 1,2,3,4-tetrahydronaphthyl and the like, such as phenyl and naphthyl.

Heteroaryl is a 6 to 10 membered aromatic monocylic ring or bicyclic ring system wherein at least one ring is an aromatic nucleus comprising one or more, for example 1, 2, 3 or 4 heteroatoms independently selected from O, N and S. Examples of heteroaryls include: pyrrole, oxazole, thiazole, isothiazole, imidazole, pyrazole, isoxazole, pyridine, pyridazine, pyrimidine, pyrazine, benzothiophene, benzofuran, or 1, 2, 3 and 1, 2, 4 triazole.

Heterocyclyl as employed herein refers to a 5 to 6 membered saturated or partially unsaturated non-aromatic ring comprising one or more, for example 1, 2, 3 or 4 heteroatoms independently selected from O, N and S optionally one or two carbons in the ring may bear an oxo substituent. The definition of $C_{5-6}$ heterocycle as employed herein refers to a is a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substituent. Clearly any valancies of a heteroatom not employed in forming or retaining the ring structure may be filled by hydrogen or a substituent, as appropriate. Thus subsituents on heterocycles may be on carbon or on a heteroatom, such as N as appropriate. Examples of heterocycles and $C_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

Halogen includes fluoro, chloro, bromo or iodo, in particular fluoro, chloro or bromo, especially fluoro or chloro.

Oxo as used herein refers to C=O and will usually be represented as C(O).

$C_{3-8}$ cycloalkyl as employed herein is intended to refer to a saturated or partially unsaturated non-aromatic ring containing 3 to 8 carbon atoms.

$C_{1-10}$ alkyl includes $C_2$, $C_3$, $C_4$, $C_5$, $C_6$, $C_7$, $C_8$ or $C_9$ as well as $C_1$ and $C_{10}$ $C_{0-8}$ alkyl includes $C_1$, $C_2$, $C_3$, $C_4$, $C_5$, $C_6$, or $C_7$ as well as $C_0$ and $C_8$.

In relation to a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, $S(O)_p$, wherein said chain is optionally, substituted by one or more groups independently selected from oxo, halogen, an aryl group, a heteroaryl group or a heterocyclyl group, it will be clear to persons skilled in the art that the heteroatom may replace a primary, secondary or tertiary carbon, that is $CH_3$, —$CH_2$— or a —CH— or a branched carbon group, as technically appropriate.

In one embodiment of the disclosure there is provided compounds of formula (I), wherein $R^1$ is methyl, ethyl, propyl, iso-propyl, butyl or tert-butyl, in particular ethyl, iso-propyl or tert-butyl such as tert-butyl.

In one embodiment $R^1$ is —$C(CH_3)_2CH_2OH$.

In one embodiment $R^2$ is methyl, ethyl, n-propyl, iso-propyl, n-butyl or tert-butyl, in particular methyl.

In one embodiment $R^2$ is —$CH_2OH$.

In one embodiment $R^2$ is in the 2, 3, or 4 position (i.e. ortho, meta or para position), in particular the para (4) position.

In one embodiment Ar is substituted with 1 or 2 groups.

In one embodiment Ar is naphthyl.

In one embodiment Ar is not substituted with optional substituents.

In one embodiment Ar is substituted with 1 or 2 groups.

In one embodiment Ar is phenyl optionally substituted by 1 or 2 substituents independently selected from $C_{1-3}$ alkyl or $C_{1-3}$ alkoxy, for example tolyl, xylyl, anisoyl, di-methoxybenzene or methoxy-methylbenzene. The phenyl ring may, for example, be linked to the nitrogen of the urea through carbon 1 and to the group L through carbon 4. In such a case the optional one or two substituents selected from $C_{1-3}$ alkyl or $C_{1-3}$ alkoxy may be located in any of the unoccupied positions in the aromatic ring, for example in position 2 or in position 3 or in positions 2 and 3 or in positions 2 and 6 or in positions 3 and 5. Embodiments encompassing other possible regioisomers also form an aspect of the present disclosure.

In one embodiment $R^3$ is H.

In one embodiment $R^3$ is methyl, ethyl, n-propyl or iso-propyl.

In one embodiment p is 0 or 2.

In one embodiment X is selected from, pyrrole, oxazole, thiazole, isothiazole, imidazole, pyrazole, isoxazole, oxadiazole, pyridazine, pyrimidine, pyrazine, or 1,2,3 and 1,2,4 triazole, such as pyrazole, isoxazole, oxadiazole, pyridine, pyridazine, pyrimidine, pyrazine, or 1,2,3 and 1,2,4 triazole, in particular, pyrimidine, imidazole or pyridine, and especially pyridine or pyrimidine, more specifically pyridine.

In one embodiment 1, 2, 3 or 4 carbon atoms are replaced in the alkyl chain of Q by heteroatoms independently selected from O, N, $S(O)_p$.

In one embodiment the heteroatom(s) replacing carbon(s) in the alkyl chain fragment of Q are selected from N and O.

In one embodiment Q is a saturated or unsaturated, branched or unbranched $C_{1-8}$ alkyl chain or a $C_{1-6}$ alkyl chain, wherein at least one carbon is replaced by a heteroatom selected from —O, —N, $S(O)_p$. Alternatively, in this embodiment the alkyl chain may be a $C_{2-8}$ alkyl or a $C_{3-6}$ alkyl group, such as a $C_4$ alkyl or a $C_5$ alkyl group.

In one embodiment a nitrogen atom in the alkyl chain is directly bonded to the carbonyl of the fragment —$NR^3C(O)$ and additionally may, for example, be a terminal amino group.

In one embodiment Q represents $C_{1-6}$ alkyl$NH_2$ or $NH_2$.
In one embodiment Q represents —$NHC_{1-6}$ alkyl such as —$NHCH_3$ or —$NHCH_2CH_3$ or —$NHCH(CH_3)_2$.

In one embodiment the fragment Q is a saturated or unsaturated, branched or unbranched $C_{1-10}$ alkyl chain wherein at least one carbon (for example 1, 2, 3 or 4 carbons, in particular 1 or 2 carbons) is replaced by a heteroatom selected from O, N, $S(O)_p$, for example in such a manner as to provide a stable N-acyl group, $NR^3C(O)Q$, wherein said chain is optionally substituted by one or more groups selected from oxo, halogen, an aryl group, a heteroaryl group or a heterocyclyl group, each aryl, heteroaryl or heterocyclyl group bearing 0 to 3 substituents independently selected from a relevant substituent listed above for compounds of formula (I), for example halogen, $C_{1-6}$ alkyl, $C_{1-6}$ alkoxy, $C_{1-6}$ haloalkyl, amino, $C_{1-4}$ mono or di-alkyl amino and $C_{1-4}$ mono or di-acyl amino.

In one embodiment the latter chain is optionally substituted by one or more groups selected from oxo, halogen, an aryl group, a heteroaryl group or a heterocyclyl group, each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, and $C_{1-4}$ mono or di-alkyl amino.

In one embodiment Q is $C_{1-4}$alkyl-V—$R^4$, such as $C_{1-3}$alkyl-V—$R^4$ wherein:
V is a heteroatom selected from $NR^V$, O or $S(O)_p$;
$R^4$ represents H or $C_{1-3}$ alkyl;
$R^4$ is H or —$C_{1-3}$alkyl, and p is as defined above,
with the proviso that the total alkyl chain length is not more than 10 carbon atoms, including replacement heteroatoms and that the resulting radical Q is a stable group, for example —$CH_2SCH_3$, —$CH_2SO_2CH_3$, —$CH_2NHCH_3$, —$CH_2N(CH_3)_2$, —$C(CH_3)_2NHCH_3$, —$CH(CH_3)N(CH_3)_2$, —$(CH_2)_3CHNHCH_3$, —$(CH_2)_3N(CH_3)_2$, —$CH_2OH$, —$CH_2OCH_3$, —$CH(CH_3)OCH_3$, or —$(CH_2)_2OCH_3$.

In one embodiment Q is $C_{1-3}$ alkyl-V—($C_{1-3}$ alkyl-Z—$R^5$)$_k$ such as $C_{1-3}$ alkyl-V—($C_{2-3}$ alkyl-Z—$R^5$)$_k$ wherein:
V is a heteroatom selected from N, NH, O or $S(O)_p$, such as N or NH
(V will be selected from N in the case where k=2, or NH, O or $S(O)_p$, in the case where k=1, in particular NH);
Z is independently selected from NH, O or $S(O)_p$;
$R^5$ is H or —$C_{1-3}$alkyl;
k is an integer 1 or 2 (such as 1); and
p is as defined above,
with the proviso that the total alkyl chain length is not more than 10 carbon atoms, including replacement heteroatoms and that the resulting radical Q is a stable group. Suitably Q is $C_{1-3}$alkyl-V—$C_{1-3}$alkyl-$OCH_3$ for example $C_{1-3}$alkyl-V—$C_{2-3}$alkyl-$OCH_3$ such as $C_{1-3}$alkyl-V—$(CH_2)_2OCH_3$, in particular —$CH_2O(CH_2)_2OCH_3$ and $CH_2S(CH_2)_2OCH_3$, or —$CH_2NH(CH_2)_2OCH_3$, $C_{1-3}$alkyl-V—($C_{1-3}$alkyl-$OCH_3)_k$ wherein k represents 2, for example $C_{1-3}$alkyl-V—($C_{2-3}$ alkyl-$OCH_3)_k$ such as —$CH_2N[(CH_2)_2OCH_3]_2$.

In one embodiment Q is $C_{1-3}$ alkyl-V—$C_{1-2}$ alkyl-Z—$C_{1-2}$ alkyl-Y—$R^6$, or $C_{1-3}$ alkyl-V—$C_{2-3}$ alkyl-Z—$C_{2-3}$ alkyl-Y—$R^6$, wherein V, Z and Y are independently a heteroatom selected from NH, O or $S(O)_p$,
$R^6$ is H or methyl, and
p is as defined above,
with the proviso that the total alkyl chain length is not more than 10 carbon atoms, including replacement heteroatoms and that the resulting radical Q is a stable group. Suitably Q is —$CH_2V(CH_2)_2O(CH_2)_2OCH_3$, such as —$CH_2O(CH_2)_2O(CH_2)_2OCH_3$, —$CH_2NH(CH_2)_2O(CH_2)_2OCH_3$, or —$CH_2S(CH_2)_2O(CH_2)_2OCH_3$.

In one embodiment Q represents —$NR^7R^8$ and —$NR^3C(O)Q$ forms a urea, where $R^7$ and $R^8$ independently represent hydrogen or a $C_{1-9}$ saturated or unsaturated, branched or unbranched alkyl chain, wherein one or more carbons, such as 1, 2 or 3 are optionally replaced by a heteroatom selected from O, N or $S(O)_p$. Said chain is optionally substituted by one or more groups independently selected from oxo, halogen, an aryl group, a heteroaryl group, a heterocyclyl or $C_{3-8}$ cycloalkyl group, each aryl, heteroaryl or heterocyclyl group bearing 0 to 3 substituents independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono or di-alkyl amino and $C_{1-4}$ mono or di-acyl amino with the proviso that the total alkyl chain length is not more than 10 carbon atoms, including replacement heteroatoms and that the resulting radical Q is a stable group.

In one embodiment Q represents —$NR^7R^8$ and —$NR^3C(O)Q$ forms a urea, where $R^7$ and $R^8$ independently represent hydrogen or a $C_{1-9}$ saturated or unsaturated, branched or unbranched alkyl chain, wherein one or more carbons, such as 1, 2 or 3 are optionally replaced by a heteroatom selected from O, N or $S(O)_p$. Said chain is optionally substituted by one or more groups independently selected from oxo, halogen, an aryl group, a heteroaryl group or a heterocyclyl group, each aryl, heteroaryl or heterocyclyl group bearing 0 to 3 substituents independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono or di-alkyl amino and $C_{1-4}$ mono or di-acyl amino with the proviso that the total alkyl chain length is not more than 10 carbon atoms, including replacement heteroatoms and that the resulting radical Q is a stable group.

In this urea embodiment in one sub-embodiment $R^7$ represents hydrogen.

Examples of ureas include those in which $R^7$ and $R^8$ are both hydrogen and Q is —$NH_2$, or where Q is —$NHCH_3$ or —$N(CH_3)_2$ to provide, for example, a fragment —$NR^3C(O)NH_2$ or —$NR^3C(O)NHCH_3$ or —$NR^3C(O)N(CH_3)_2$.

Examples of ureas containing a heteroatom in the alkyl chain include those in which Q is: —$NH(CH_2)_2OCH_3$ or —$N[(CH_2)_2OCH_3)]_2$. In one embodiment Q represents —$NHC_{2-6}$alkyl$OC_{1-3}$alkyl, such as —$NHCH_2CH_2OCH_3$.

Examples of ureas containing an oxo substitutent include those in which Q is —$NHCH_2C(O)NH$—$C_{2-3}$alkyl-$X^1$—$C_{1-3}$ alkyl, wherein $X^1$ is a heteroatom selected from N, O or $S(O)_p$ and p is defined as above. Examples of the latter include those wherein Q is —$NHCH_2C(O)NHCH_2CH_2OCH_3$. Thus in one embodiment Q represents —$NHC_{1-4}$ alkyl$C(O)NHC_2$alkyl$OCH_3$ such as —$NHCH_2C(O)NHCH_2CH_2OCH_3$.

In one embodiment Q represents —$NHC_{1-4}$alkyl$C(O)R^Q$ wherein $R^Q$ is selected from OH or —NR'R" where R' is hydrogen or $C_{1-3}$ alkyl and R" is hydrogen or $C_{1-3}$ alkyl, for example —$NHCH_2C(O)OH$, —$NHCH_2C(O)NH_2$ or —$NHCH_2C(O)NHCH_3$ such as —$NHCH_2C(O)OH$ or —$NHCH_2C(O)NHCH_3$.

In one embodiment Q represents —$NHC_{1-4}$ alkyl$C(O)OC_{1-3}$alkyl, such as —$NHCH_2C(O)OCH_2CH_3$.

In a further urea sub-embodiment Q represents —N—$R^9C_{1-3}$ alkyl-V—($C_{1-3}$ alkyl-Z—$R^{10}$)$_k$ for example —N—$R^9C_{2-3}$ alkyl-V—($C_{2-3}$ alkyl-Z—$R^{10}$)$_k$ wherein:
V represents N, NH, O, $S(O)_p$;
Z represents NH, O, $S(O)_p$;

k is an integer 1 or 2;
p is an integer 0, 1 or 2
$R^9$ represents H or $C_{1-3}$ alkyl-V—($C_{1-3}$ alkyl-Z—$R^{10}$)$_k$ such as $C_{2-3}$ alkyl-V—($C_{2-3}$ alkyl-Z—$R^{10}$)$_k$; and
$R^{19}$ is H or $C_{1-3}$ alkyl such as $C_{1-3}$ alkyl;
with the proviso that the total alkyl chain length is not more than 10 carbon atoms, including replacement heteroatoms and that the resulting radical Q is a stable group.

In one embodiment Q is a saturated or unsaturated, branched or unbranched $C_{1-10}$ alkyl chain, wherein at least one carbon is replaced by a heteroatom selected from O, N, and $S(O)_p$, wherein said chain is substituted by an aryl group bearing 0 to 3 substituents, for example 1, 2 or 3, such as 1 or 2 substituents independently selected from the relevant substituents listed above for compounds of formula (I), for example from halogen, $C_{1-6}$ alkyl, $C_{1-6}$ alkoxy, $C_{1-6}$ haloalkyl, amino and $C_{1-4}$ mono or di-alkyl amino and $C_{1-4}$ mono or di-acyl amino, such as a saturated or unsaturated, branched or unbranched $C_{1-10}$ alkyl chain, wherein at least one carbon is replaced by a heteroatom selected from O, N, and $S(O)_p$, wherein said chain is substituted by an aryl group bearing 0 to 3 substituents, for example 1, 2 or 3, such as 1 or 2 substituents independently selected from halogen, $C_{1-6}$ alkyl, $C_{1-6}$ alkoxy, $C_{1-6}$ haloalkyl, amino and $C_{1-4}$ mono or di-alkyl amino. In one embodiment the said aryl group is phenyl, for example substituted phenyl or unsubstituted phenyl.

In one embodiment Q represents —$NHC_{0-6}$ alkylphenyl, such as —NHphenyl or NHbenzyl.

Examples of the fragment —$NR^3C(O)Q$ wherein Q comprises substituted benzyl include: —$NR^3C(O)CH_2NHCH_2C_6H_4(OCH_3)$ such as —$NHC(O)CH_2NHCH_2C_6H_4(OCH_3)$, for example where the methoxy substituent is in the ortho, meta or para position, such as the para position.

In one embodiment Q is a saturated or unsaturated, branched or unbranched $C_{1-10}$ alkyl chain, wherein at least one carbon is replaced by a heteroatom selected from O, N, and $S(O)_p$, wherein said chain is substituted by a heteroaryl group bearing 0 to 3 substituents (for example 1, 2 or 3, such as 1 or 2 substituents) independently selected from the relevant substituents listed above for compounds of formula (I), for example halogen, $C_{1-6}$ alkyl, $C_{1-6}$ alkoxy, $C_{1-6}$ alkyl amino, $C_{1-4}$ mono or di-alkyl amino and $C_{1-4}$ mono or di-acyl amino, such as a saturated or unsaturated, branched or unbranched $C_{1-10}$ alkyl chain, wherein at least one carbon is replaced by a heteroatom selected from O, N, and $S(O)_p$, wherein said chain is substituted by a heteroaryl group bearing 0 to 3 substituents for example 1, 2 or 3, such as 1 or 2 substituents selected from halogen, $C_{1-6}$ alkyl, $C_{1-6}$ alkoxy, $C_{1-6}$ alkyl amino, $C_{1-4}$ mono or di-alkyl amino. In one embodiment the said heteroaryl group is selected from, thiophene, oxazole, thiazole, isothiazole, imidazole, pyrazole, isoxazole, isothiazole, oxadiazole, 1,2,3 or 1,2,4 triazole, pyridine, pyridazine, pyrimidine, pyrazine and, in particular pyridine and pyrimidine, especially pyridine.

In one embodiment Q represents —$NHC_{1-6}$ alkylheteroaryl, for example —$NH(CH_2)_3$imidazolyl or —$NHCH_2$ isoxazole wherein the isoxazole is optionally substituted such as —$NHCH_2$ isoxazole($CH_3$).

In one embodiment Q represents —$NHC_{1-4}$ alkylC(O) $NHC_{1-3}$alkylheteroaryl, for example a nitrogen containing heteroaryl group or a nitrogen and oxygen containing heteroaryl, more specifically —$NHCH_2C(O)NHCH_2CH_2$pyridinyl, in particular where pyridinyl is linked through carbon, for example pyridin-4-yl or —$NHCH_2C(O)NHCH_2CH_2CH_2$imidazolyl, in particular where imidazolyl is linked through nitrogen.

In one embodiment Q is a saturated or unsaturated, branched or unbranched $C_{1-10}$ alkyl chain, wherein at least one carbon is replaced by a heteroatom selected from O, N and $S(O)_p$ wherein said chain is substituted by a heterocyclyl group bearing 0 to 3 substituents (for example 1, 2 or 3, such as 1 or 2 substituents) independently selected from the relevant substituents listed above for compounds of formula (I), for example halogen, $C_{1-6}$ alkyl, $C_{1-6}$ alkoxy, $C_{1-6}$ haloalkyl amino, $C_{1-4}$ mono or di-alkyl amino and $C_{1-4}$ mono or di-acyl amino, such as a saturated or unsaturated, branched or unbranched $C_{1-10}$ alkyl chain, wherein at least one carbon is replaced by a heteroatom selected from O, N and $S(O)_p$ wherein said chain is substituted by a heterocyclyl group bearing 0 to 3 substituents, for example 1, 2 or 3, such as 1 or 2 substituents selected from halogen, $C_{1-6}$ alkyl, $C_{1-6}$ alkoxy, $C_{1-6}$ haloalkyl amino, $C_{1-4}$ mono or di-alkyl amino.

In one embodiment said heterocyclyl is selected, from a 5 or 6 membered saturated or partially unsaturated ring system comprising one or more (for example 1, 2 or 3 in particular 1 or 2) heteroatoms independently selected from O, N and S, for example pyrrolidine, tetrahydrofuran, tetrahydrothiophene, piperidine, piperazine, morpholine, 1,4-dioxane, pyrrolidine and oxoimidazolidine such as pyrrolidine, tetrahydrofuran, tetrahydrothiophene, piperidine, piperazine, morpholine, and 1,4-dioxane, in particular piperidine, piperazine, and morpholine.

A heterocyclic group may be linked to the alkyl chain of Q or to the carbonyl of —$NR^3C(O)$— through carbon or nitrogen, in particular a nitrogen atom.

In one embodiment Q is —$O_{0-3}$alkylheterocycle (for example—$C_{0-1}$alkylheterocycle) said heterocyclyl group comprising at least one heteroatom (for example 1, 2 or 3, in particular 1 or 2, heteroatoms) selected from O, N and S, and is optionally substituted by one or two or three groups independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino and $C_{1-4}$ mono or di-acyl amino.

In one embodiment in which Q is —$C_0$alkylheterocycle, the heterocycle is linked through carbon, and is, for example, a C-linked tetrahydropyran or a C-linked piperidine or a C-linked morpholine or a C-linked piperazine.

In one embodiment in which Q is —$C_0$alkylheterocycle, the heterocyclic group containing one or more N atoms is linked through N. This embodiment provides for ureas in which one of the urea nitrogens is embedded within a heterocyclic ring. Examples of this embodiment include, but are not limited to, an N-linked morpholine or an N-linked piperidine or an N-linked piperazine, said N-linked piperizinyl group optionally bearing an additional C- or N-substituent (such as an N-methyl group or N—$CH_2CH_2OCH_3$ group. In one embodiment Q is a heterocyclyl linked through nitrogen such as piperidinyl, in particular 4-hydroxypiperidinyl or piperazinyl, such as 4-methyl piperazinyl.

In one embodiment Q represents a heterocyclyl group, for example a nitrogen containing heterocyclyl group, in particular linked through N, such as morpholinyl or piperazinyl optionally substituted by methyl, especially 4-methyl, or piperidinyl.

In one embodiment Q is a —$C_1$alkylheterocycle, for example tetrahydropyranylmethyl or a C- or N-linked piperazinylmethyl optionally bearing a substituent (for example a $C_{1-6}$ alkyl substitutent such as methyl or a $C_{1-6}$ alkoxy substituent such as —$CH_2CH_2OCH_3$). Additional examples include a C- or N-linked pyrrolidinylmethyl, or a C- or N-linked oxoimidazolinylmethyl (such as 2-oxoimidazolidinylmethyl, said heterocycle optionally bearing a substitutent (such as N-methyl or N—SO$_2$CH$_3$).

In one embodiment Q represents —NHheterocyclyl (wherein the heterocyclyl bears 0 to 3 substituents selected from the relevant list of substituents listed above for compounds of formula (I), for example halogen, hydroxy, C$_{1-6}$ alkyl, C$_{1-6}$ alkoxy, C$_{1-6}$ haloalkyl, amino, C$_{1-4}$ mono or di-alkyl amino, —S(O)$_q$C$_{1-6}$ alkyl, C$_{1-4}$ mono or di-acyl amino, C$_{0-6}$ alkylC(O)C$_{1-6}$ alkyl or C$_{0-6}$ alkylC(O)C$_{1-6}$ heteroalkyl), such as where the ring is linked through carbon, for example 2-piperidinyl or 3-piperidinyl or 4-piperidinyl, in particular 1-acetylpiperidin-4-yl, 1-methylpiperidin-4-yl, 1-(methylsulfonyl)piperidin-4-yl or 1-(2-(2-methoxyethoxy)acetyl)piperidin-4-yl In one embodiment Q represents —NHC$_{1-6}$ alkylheterocyclyl for example a nitrogen containing heterocyclyl group, in particular one linked through nitrogen, such as —NHCH$_2$CH$_2$-morpholine, —NH(CH$_2$)$_3$-morpholine or —NH(CH$_2$)$_4$-morpholine.

In one embodiment Q represents —NHC$_{1-6}$ alkylC(O)heterocyclyl (wherein the heterocyclyl bears 0 to 3 substituents selected from the relevant list of substituents listed above for compounds of formula (I), for example halogen, hydroxy, C$_{1-6}$ alkyl, C$_{1-6}$ alkoxy, C$_{1-6}$ haloalkyl, amino, C$_{1-4}$ mono or di-alkyl amino, C$_{1-4}$ mono or di-acyl amino, C$_{0-6}$ alkylC(O) C$_{1-6}$ alkyl or C$_{0-6}$ alkylC(O)C$_{1-6}$ heteroalkyl) for example a nitrogen containing heterocyclyl group, in particular one linked through nitrogen, such as —NHCH$_2$C(O)-1-pyrrolidinyl, —NHCH$_2$C(O)-1-piperidinyl, —NHCH$_2$C(O)-4-morpholinyl or —NHCH$_2$C(O)piperazinyl such as —NHCH$_2$C(O)-4-methyl-1-piperazinyl.

In one embodiment Q represents —NHC$_{1-4}$ alkylC(O) NHC$_{1-3}$alkylheterocyclyl for example a nitrogen containing heterocyclyl group or a nitrogen and/or oxygen containing heterocyclyl, such as —NHCH$_2$C(O)NHCH$_2$CH$_2$-morpholinyl, in particular where morpholinyl is linked through nitrogen.

In one embodiment Q represents —N(C$_{1-3}$ alkyl)C$_{1-6}$ alkylheterocyclyl, for example a nitrogen containing heterocyclyl group, in particular linked through nitrogen, such as —N(CH$_3$)CH$_2$CH$_2$-morpholine, —N(CH$_3$)(CH$_2$)$_3$-morpholine or —N(CH$_3$)(CH$_2$)$_4$-morpholine.

In one embodiment Q is —C$_{1-3}$alkyl-G-C$_{1-3}$alkylheterocycle wherein G is a heteroatom selected from NH, O or S(O)$_p$ said heterocyclyl group comprising at least one heteroatom (for example 1, 2 or 3, in particular 1 or 2, heteroatoms) selected from O, N, and S, and is optionally substituted by one or two or three groups independently selected from relevant substituents listed above for compounds of formula (I), for example halogen, C$_{1-6}$ alkyl, C$_{1-6}$ alkoxy, C$_{1-6}$ haloalkyl, amino, C$_{1-4}$ mono and di-alkyl amino and C$_{1-4}$ mono or di-acyl amino such as one or two or three groups halogen, C$_{1-6}$ alkyl, C$_{1-6}$ alkoxy, C$_{1-6}$ haloalkyl, amino, C$_{1-4}$ mono and di-alkyl amino. Suitably Q is —CH$_2$G(CH$_2$)$_2$heterocycle for example —CH$_2$G(CH$_2$)$_2$tetrahydropyranyl; or —CH$_2$G(CH$_2$)$_2$-morpholinyl in which the heterocyclyl is linked through nitrogen or carbon; or CH$_2$G(CH$_2$)$_2$piperazinyl in which the heterocyclyl is linked through nitrogen or carbon and optionally bearing a further C— or N— substitutent (for example a C$_{1-6}$ alkyl substitutent such as methyl or a C$_{1-6}$ alkoxy substituent such as —CH$_2$CH$_2$OCH$_3$); or —CH$_2$G(CH$_2$)$_2$pyrrolidinyl, in which the heterocyclyl is linked through nitrogen or carbon, for example linked through nitrogen; or —CH$_2$G(CH$_2$)$_2$oxoimidazolinyl (such as 2-oxoimidazolidinyl) for example linked through N and optionally bearing an additional C- or N-substitutent (such as N-methyl or N—SO$_2$CH$_3$), and in which G is O or NH.

In one embodiment G is O.

In one embodiment G is NH.

In one embodiment Q is a saturated or unsaturated C$_{1-10}$ alkyl chain wherein at least one carbon (for example 1, 2 or 3 carbons) is replaced by a heteroatom selected from O, N, S(O)$_p$ wherein said chain is substituted by a C$_{3-8}$ carbocyclyl group and said alkyl chain is optionally substituted by one or more (for example 1 or 2) groups selected from oxo and halogen. In one embodiment said C$_{3-8}$ carbocyclyl group bears one or more groups (for example 1, 2 or 3 groups) independently selected from halogen, hydroxyl, C$_{1-6}$ alkyl, C$_{1-6}$ alkoxy, C$_{1-6}$ haloalkyl, amino, C$_{1-4}$ mono or di-alkyl amino, C$_{1-4}$ mono or di-acyl amino, S(O)$_p$C$_{1-6}$ alkyl, C$_{0-6}$ alkylC(O)C$_{1-6}$ alkyl or C$_{0-6}$ alkylC(O)C$_{1-6}$ heteroalkyl.

In one embodiment Q represents —NHC$_{3-6}$ cycloalkyl, such as —NHcyclopropyl, —NHcyclopentyl or —NHcyclohexyl.

In one embodiment the aryl, heteroaryl or heterocyclyl group bears at least one —S(O)$_q$C$_{1-6}$ alkyl substitutent and optionally bears one or two further relevant substituents independently selected from the list of substituents defined above for compounds of formula (I).

In one embodiment the C$_{5-6}$ heterocycle bears at least one —S(O)$_q$C$_{1-6}$ alkyl substitutent and optionally bears one or two further substituents independently selected from the relevant list of substituents defined above for compounds of formula (I).

In one embodiment the aryl, heteroaryl or heterocyclyl group bears at least one hydroxyl substituent and optionally bears one or two further substituents independently selected from the relevant list of substituents defined above for compounds of formula (I).

In one embodiment the C$_{5-6}$heterocycle bears at least one hydroxyl substituent and optionally bears one or two further substituents independently selected from the relevant list of substituents defined above for compounds of formula (I).

In one embodiment the aryl, heteroaryl or heterocyclyl group bears at least one C$_{1-4}$ mono and/or di-acyl amino substituent and optionally bears one or two further substituents independently selected from the relevant list defined above for compounds of formula (I).

In one embodiment the C$_{5-6}$heterocycle bears at least one C$_{1-4}$ mono and/or di-acyl amino substituent and optionally bears one or two further substituents independently selected from the relevant list defined above for compounds of formula (I).

In one embodiment the aryl, heteroaryl or heterocyclyl group bears at least one C$_{0-6}$ alkylC(O)C$_{1-6}$ heteroalkyl substituent and optionally bears one or two further substituents independently selected from the relevant list defined above for compounds of formula (I).

In one embodiment the C$_{5-6}$heterocycle bears at least one C$_{0-6}$ alkylC(O)C$_{1-6}$ heteroalkyl substituent and optionally bears one or two further substituents independently selected from the relevant list defined above for compounds of formula (I).

In one embodiment the aryl, heteroaryl or heterocyclyl group bears at least one C$_{0-6}$ alkylC(O)C$_{1-6}$ alkyl substituent and optionally bears one or two further substituents independently selected from the relevant list defined above for compounds of formula (I).

In one embodiment the C$_{5-6}$heterocycle bears at least one C$_{0-6}$ alkylC(O)C$_{1-6}$ alkyl substituent and optionally bears one or two further substituents independently selected from the relevant substituents defined above for compounds of formula (I).

In one embodiment Q represents tetrahydrofuranyl, morpholinyl, piperidinyl such as piperidinyl bearing one hyroxyl substituent, piperazinyl such as piperazinyl bearing one methyl substituent or pyrrolidinyl such a pyrrolidinyl bearing one di-methyl amino substituent. The ring may be linked through the heteroatom, such as nitrogen. Alternatively, the ring may be linked through carbon. The substituent may, for example be para relative to the atom through which the ring is linked to the remainder of the molecule.

In one embodiment the alkyl chain fragment of Q does not bear any optional substituents.

In one embodiment the alkyl chain is saturated.

In one embodiment the alkyl chain is unbranched.

In one embodiment the alkyl chain fragment of Q bears 1, 2, or 3, for example 1 or 2, in particular 1 optional substituent.

It will be clear to persons skilled in the art that the heteroatom may replace a primary, secondary or tertiary carbon, that is a $CH_3$, $-CH_2-$ or a $-CH-$, group, as technically appropriate.

In one embodiment p is 0 or 2.

In one embodiment p is 1.

In one embodiment compounds of the disclosure include those in which the fragment Q is:
- $-CH_2OH$;
- $-CH_2OC_{1-6}$ alkyl, in particular $-CH_2OCH_3$;
- $-CH_2CH_2OCH_3$;
- $-CH_2O(CH_2)_2OCH_3$;
- $-CH(CH_3)OCH_3$;
- $-CH_2NHCH_3$ or $-CH_2N(CH_3)_2$
- $-CH_2NHCH_2CH_2OCH_3$ or $-CH_2NHC(O)CH_2OCH_3$;
- $-CH_2SCH_3$, $-CH_2S(O)_2CH_3$ or $-CH_2NHC(O)CH_2S(O)_2CH_3$; or
- $-CH_2NHC(O)CH_2$.

In one embodiment compounds of the disclosure include those in which the fragment $-NR^3C(O)Q$ in formula (I) is represented by:
- $-NR^3C(O)CH_2OH$, in particular $-NHC(O)CH_2OH$;
- $-NR^3C(O)CH_2OC_{1-6}$ alkyl, in particular $-NR^3C(O)CH_2OCH_3$, especially $-NHC(O)CH_2OCH_3$;
- $-NR^3C(O)CH_2O(CH_2)_2OCH_3$, in particular $-NHC(O)CH_2O(CH_2)_2OCH_3$;
- $-NR^3C(O)CH(CH_3)OCH_3$ in particular $-NHC(O)CH(CH_3)OCH_3$;
- $-NR^3C(O)CH(CH_3)NHC_{1-3}$alkyl in particular $-NHC(O)CH(CH_3)NHCH_3$;
- $-NR^3C(O)CH(CH_3)N(C_{1-3}$alkyl$)_2$ in particular $-NHC(O)CH(CH_3)N(CH_3)_2$;
- $-NR^3C(O)C(CH_3)_2NHCH_3$ in particular $-NHC(O)C(CH_3)_2NHCH_3$;
- $-NR^3C(O)(CH_2)_2OC_{1-6}$alkyl, such as $-NR^3C(O)(CH_2)_2OCH_3$, in particular $-NHC(O)(CH_2)_2OCH_3$;
- $-NR^3C(O)(CH_2)_3NHC_{1-3}$alkyl in particular $-NHC(O)(CH_2)_3NHCH_3$;
- $-NR^3C(O)(CH_2)_3N(C_{1-3}$alkyl$)_2$ in particular $-NHC(O)(CH_2)_3N(CH_3)_2$;
- $-NR^3C(O)CH_2NHC_{1-3}$alkyl in particular $-NHC(O)CH_2NHCH_3$;
- $-NR^3C(O)CH_2NH(CH_2)_2OCH_3$ in particular $-NHC(O)CH_2NH(CH_2)_2OCH_3$;
- $-NR^3C(O)CH_2SCH_3$, in particular $-NHC(O)CH_2SCH_3$;
- $-NR^3C(O)CH_2S(CH_2)_2OCH_3$, in particular $-NHC(O)CH_2S(CH_2)_2OCH_3$;
- $-NR^3C(O)CH_2S(CH_2)_2O(CH_2)_2OCH_3$, in particular $-NHC(O)CH_2S(CH_2)_2O(CH_2)_2OCH_3$
- $-NR^3C(O)CH_2SOCH_3$, in particular $-NHC(O)CH_2SOCH_3$
- $-NR^3C(O)CH_2S(O)_2CH_3$, in particular $-NHC(O)CH_2S(O)_2CH_3$;
- $-NR^3C(O)CH_2N[CH_2)_2OCH_3]_2$ in particular $-NHC(O)CH_2N[(CH_2)_2OCH_3]_2$;
- $-NR^3C(O)NH_2$ in particular $-NHC(O)NH_2$;
- $NR^3C(O)NHC_{1-9}$ alkyl, such as $NR^3C(O)NHC_{1-7}$ alkyl, in particular $-NHC(O)NHCH_3$
- $-NR^3C(O)N(C_{1-4}$ alkyl$)C_{1-5}$ alkyl in particular $-NHC(O)N(CH_3)_2$; or
- $-NR^3C(O)NHCH_2CONH(CH_2)_2OCH_3$ in particular $-NHC(O)NHCH_2CONH(CH_2)_2OCH_3$.

In one embodiment compounds of the disclosure include compounds of formula (I) in which the fragment $-NR^3C(O)C_{0-8}$alkylheterocyclyl is represented by:
- $-NHC(O)$-(tetrahydropyranyl), such as $-NHC(O)$-(tetrahydro-2H-pyran-4-yl);
- $-NHC(O)$-(morpholinyl) such as $-NHC(O)$-(4-morpholinyl) or $-NHC(O)$-(3-morpholinyl);
- $-NHC(O)$-(pyrrolidinyl), such as $-NHC(O)$-(pyrrolidin-1-yl);
- $-NHC(O)$-(piperazinyl), such as $-NHC(O)$-(piperazin-1-yl);
- $-NHC(O)$-(methylpiperazinyl), such as $-NHC(O)$-(4-methylpiperazin-1-yl);
- $-NHC(O)$-[(methoxyethyl)piperazinyl], such as $-NHC(O)$-[4-(2-methoxyethyl)piperazin-1-yl];
- $-NHC(O)$-(oxoimidazolidinyl) such as $-NHC(O)$-(2-oxoimidazolidinyl), in particular $-NHC(O)$-(2-oxoimidazolidin-1-yl);
- $-NHC(O)CH_2$-(tetrahydropyranyl), such as $-NHC(O)CH_2$-(tetrahydro-2H-pyran-4-yl);
- $-NHC(O)CH_2$-(morpholinyl), such as $-NHC(O)CH_2$-(4-morpholinyl);
- $-NHC(O)CH_2$-(pyrrolidinyl), such as $-NHC(O)CH_2$-(pyrrolidin-1-yl);
- $-NHC(O)CH_2$-(piperazinyl), such as $-NHC(O)CH_2$-(piperazin-1-yl);
- $-NHC(O)CH_2$-(methylpiperazinyl), such as $-NHC(O)CH_2$-(4-methylpiperazin-1-yl);
- $-NHC(O)CH_2$-[(methoxyethyl)piperazinyl], such as $-NHC(O)CH_2$-[4-(2-methoxyethyl)piperazin-1-yl];
- $-NHC(O)CH_2SCH_2CH_2$-(morpholinyl), such as $-NHC(O)CH_2SCH_2CH_2$-(4-morpholinyl), or $-NHC(O)CH_2SCH_2CH_2$-(3-morpholinyl); and
- $-NHC(O)CH_2SO_2CH_2CH_2$-(morpholinyl), such as $-NHC(O)CH_2SO_2CH_2CH_2$-(4-morpholinyl), or $-NHC(O)CH_2SO_2CH_2CH_2$-(3-morpholinyl).

In one embodiment compounds of the disclosure include compounds of formula (I) in which Q is:
- -(tetrahydropyranyl), such as -(tetrahydro-2H-pyran-4-yl);
- -(morpholinyl) such as -(4-morpholinyl);
- -(pyrrolidinyl), such as -(pyrrolidin-1-yl);
- -(piperazinyl), such as -(piperazin-1-yl);
- -(methylpiperazinyl), such as -(4-methylpiperazin-1-yl);
- -(methoxyethyl)piperazinyl, such as -4-(2-methoxyethyl)piperazin-1-yl;
- $-CH_2$-(tetrahydropyranyl), such as $-CH_2-$ (tetrahydro-2H-pyran-4-yl);
- $-CH_2$-(morpholinyl), such as $-CH_2$-(4-morpholinyl);
- $-CH_2$-(pyrrolidinyl), such as $-CH_2$-(pyrrolidin-1-yl);
- $-CH_2$-(piperazinyl), such as $-CH_2$-(piperazin-1-yl);
- $-CH_2$-(methylpiperazinyl), such as $-CH_2$-(4-methylpiperazin-1-yl);
- $-CH_2$-[(methoxyethyl)piperazinyl], such as $-CH_2$-[4-(2-methoxyethyl)piperazin-1-yl];

—CH$_2$NHC(O)-tetrahydrofuran such as —CH$_2$NHC(O)-(tetrahydro-2H-pyran-4-yl);

—CH$_2$NHC(O)-morpholinyl such as —CH$_2$NHC(O)-(4-morpholinyl)

—CH$_2$NHC(O)-(piperazinyl), such as —CH$_2$NHC(O)-(piperazin-1-yl); and

—CH$_2$NHC(O)-(methylpiperazinyl), such as —CH$_2$NHC(O)-(4-methylpiperazin-1-yl).

In one embodiment of the fragment Q, the saturated or unsaturated, branched or unbranched C$_{1-10}$ alkyl chain, wherein at least one carbon is replaced by a heteroatom selected from —O, —N, S(O)$_p$ is selected from: —CH$_2$OCH$_2$—, —CH$_2$NHCH$_2$—, —CH$_2$NH— and —CH$_2$OCH$_2$CH$_2$—. These fragments may optionally terminate in an aryl group, a heteroaryl group a heterocyclyl group or C$_{3-8}$ cycloalkyl group, such as an aryl group, a heteroaryl group a heterocyclyl group as defined for fragment Q above.

In one embodiment the disclosure relates to compounds of formula (IA):

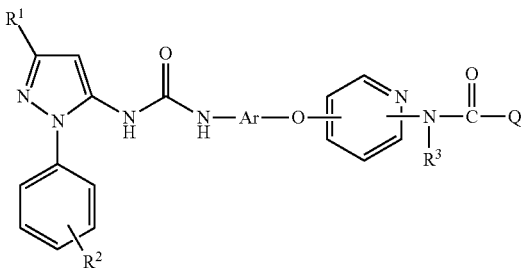

(IA)

wherein R$^1$, R$^2$, Ar, R$^3$ and Q are as defined above.

In a further embodiment the disclosure relates to compounds of formula (IB):

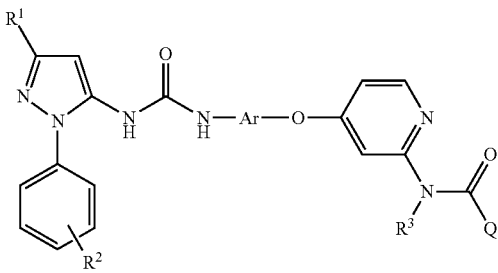

(IB)

wherein R$^1$, R$^2$, Ar, R$^3$ and Q are as defined above.

In yet another embodiment the disclosure relates to compounds of formula (C):

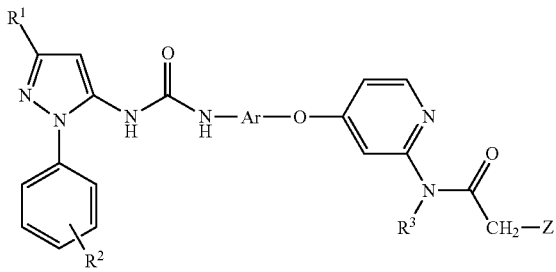

(IC)

wherein R$^1$, R$^2$, Ar and R$^3$ are as defined above and Z represents a saturated or unsaturated, branched or unbranched C$_{1-9}$ alkyl chain, wherein at least one carbon (for example 1, 2 or 3 carbons, suitably 1 or 2, in particular 1) is replaced by a heteroatom selected from O, N, S(O)$_p$, or a C$_{0-7}$ alkyl-heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from the relevant substituents listed above for compounds of formula (I), for example halogen, C$_{1-6}$ alkyl, C$_{1-6}$ alkoxy, C$_{1-6}$ haloalkyl, amino, C$_{1-4}$ mono and di-alkyl amino.

In one embodiment of formula (IC) Z is —OCH$_3$ or —OCH$_2$CH$_2$OCH$_3$.

In one embodiment of formula (IC) Z is —SO$_2$CH$_3$.

In one embodiment of formula (IC) Z is —NR$^A$R$^B$ wherein R$^A$ and R$^B$ are independently selected from hydrogen, C$_{1-6}$ alkyl, and C$_{3-6}$ alkoxy (wherein the alkoxy is not linked through oxygen) such that for example Z represents —NH$_2$, —NHCH$_3$, —N(CH$_3$)$_2$ or —NHCH$_2$CH$_2$OCH$_3$.

In one embodiment of formula (IC) Z is —S(O)$_n$—CH$_3$ wherein n is an integer 0, 1 or 2, such as 0 or 2.

In one embodiment of formula (IC) Z represents a 5 or 6 membered heterocyclyl group said heterocyclyl group comprising at least one heteroatom (for example 1, 2 or 3, suitably 1 or 2, in particular 1 heteroatom) selected from O, N and S, and is optionally substituted by one or two or three groups independently selected from the relevant substituents listed above for compounds of formula (I) for example halogen, C$_{1-6}$ alkyl, C$_{1-6}$ alkoxy, C$_{1-6}$ haloalkyl, amino, C$_{1-4}$ mono and di-alkyl amino, for example:

morpholinyl (in particular linked through nitrogen) or tetrahydropyranyl, or piperazinyl (in particular linked through nitrogen) optionally substituted on the second nitrogen by —CH$_3$ or —CH$_2$CH$_2$OCH$_3$.

In one embodiment the disclosure relates to compounds of formula (ID):

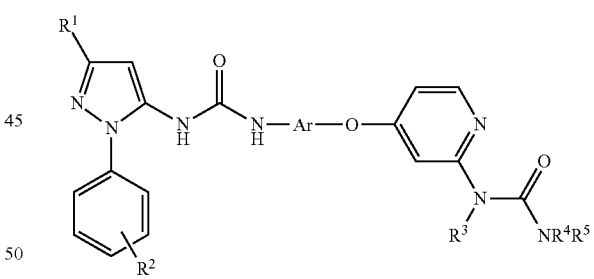

(ID)

wherein R$^1$, R$^2$, Ar and R$^3$ are as defined above and R$^4$ and R$^5$ independently represent hydrogen, C$_{1-6}$ alkyl, or R$^4$ and R$^5$ together with the nitrogen to which they are attached represent a 5 or 6 membered heterocycle optionally comprising a further heteroatom selected from O, N and S, wherein said heterocycle is optionally substituted by one or two or three groups independently selected from the relevant sustituents listed above for compounds of formula (I), for example halogen, C$_{1-6}$ alkyl, C$_{1-6}$ alkoxy, C$_{1-6}$ haloalkyl, amino, C$_{1-4}$ mono and di-alkyl amino.

In one embodiment of compounds of formula (ID) the group —NR$^4$R$^5$ represents —NH$_2$, —NHCH$_3$ or NHCH$_2$CH$_3$.

In one embodiment of compounds of formula (ID) —NR$^4$R$^5$ represents morpholinyl or piperazinyl.

In an alternative embodiment the disclosure relates to compounds of formula (IE):

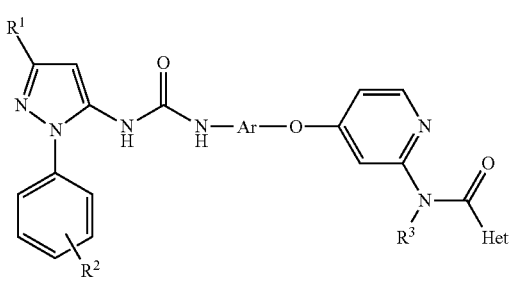

wherein R¹, R², Ar and R³ are as defined above and
Het represents a 5 or 6 membered heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from the relevant substituents listed above for compounds of formula (I) for example halogen, $C_{1-6}$ alkyl, $C_{1-6}$ alkoxy, $C_{1-6}$ haloalkyl, amino, $C_{1-4}$ mono and di-alkyl amino.

In one embodiment of compounds of formula (IE) Het is morpholinyl or tetrahydropyranyl.

In one embodiment the compound is:

N-(4-(4-(3-(3-tert-Butyl-1-p-tolyl-1H-pyrazol-5-yl)ureido)naphthalen-1-yloxy)pyridin-2-yl)-2-(2-methoxyethoxy)acetamide;

N-(4-(4-(3-(3-tert-Butyl-1-p-tolyl-1H-pyrazol-5-yl)ureido)naphthalen-1-yloxy)pyridin-2-yl)tetrahydro-2H-pyran-4-carboxamide;

N-(4-(4-(3-(3-tert-Butyl-1-p-tolyl-1H-pyrazol-5-yl)ureido)naphthalen-1-yloxy)pyridin-2-yl)-2-(methylthio)acetamide;

N-(4-(4-(3-(3-tert-Butyl-1-p-tolyl-1H-pyrazol-5-yl)ureido)naphthalen-1-yloxy)pyridin-2-yl)-3-methoxypropanamide;

N-(4-(4-(3-(3-tert-Butyl-1-p-tolyl-1H-pyrazol-5-yl)ureido)naphthalen-1-yloxy)pyridin-2-yl)-2-hydroxyacetamide;

N-(4-(4-(3-(3-Isopropyl-1-p-tolyl-1H-pyrazol-5-yl)ureido)naphthalen-1-yloxy)pyridin-2-yl)-2-methoxyacetamide;

N-(4-(4-(3-(3-Ethyl-1-p-tolyl-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-methoxyacetamide;

N-(4-(4-(3-(3-(1-Hydroxy-2-methylpropan-2-yl)-1-p-tolyl-1H-pyrazol-5-yl)ureido)naphthalen-1-yloxy)pyridin-2-yl)-2-methoxyacetamide;

N-(4-(4-(3-(3-tert-butyl-1-(2,3,5,6-tetradeutero-4-(trideuteromethyl)phenyl)-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-morpholinoacetamide;

N-(4-(4-(3-(3-tert-Butyl-1-p-tolyl-1H-pyrazol-5-yl)ureido)naphthalen-1-yloxy)pyridin-2-yl)-(dimethylamino)acetamide;

N-(4-(4-(3-(3-tert-Butyl-1-p-tolyl-1H-pyrazol-5-yl)ureido)naphthalen-1-yloxy)pyridin-2-yl)-2-(2-methoxyethylamino)acetamide;

N-(4-(4-(3-(3-tert-Butyl-1-p-tolyl-1H-pyrazol-5-yl)ureido)naphthalen-1-yloxy)pyridin-2-yl)-2-ureidoacetamide;

N-(4-(4-(3-(3-tert-Butyl-1-p-tolyl-1H-pyrazol-5-yl)ureido)naphthalen-1-yloxy)pyridin-2-yl)-2-(2-methoxyacetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)tetrahydro-2H-pyran-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)isonicotinamide;

N-(4-(4-(3-(3-tert-Butyl-1-p-tolyl-1H-pyrazol-5-yl)ureido)naphthalen-1-yloxy)pyridin-2-yl)-2-(2-(methylsulfonyl)acetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-3-morpholinopropanamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)morpholine-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-2,6-difluoro-3-(2-(2-methoxyethoxy)ethoxy)benzamide;

N-(4-(4-(3-(3-tert-Butyl-1-p-tolyl-1H-pyrazol-5-yl)ureido)phenoxy)pyridin-2-yl)-2-methoxyacetamide;

N-(4-(4-(3-(3-tert-Butyl-1-p-tolyl-1H-pyrazol-5-yl)ureido)-2-methylphenoxy)pyridin-2-yl)-2-methoxyacetamide;

N-(4-(4-(3-(3-tert-Butyl-1-p-tolyl-1H-pyrazol-5-yl)ureido)-3-methylphenoxy)pyridin-2-yl)-2-methoxyacetamide;

N-(4-(4-(3-(3-tert-Butyl-1-p-tolyl-1H-pyrazol-5-yl)ureido)-2-methoxyphenoxy)pyridin-2-yl)-2-methoxyacetamide;

N-(4-(4-(3-(3-tert-Butyl-1-p-tolyl-1H-pyrazol-5-yl)ureido)-2,3-dimethylphenoxy)pyridin-2-yl)-2-methoxyacetamide;

N-(4-(4-(3-(3-tert-Butyl-1-p-tolyl-1H-pyrazol-5-yl)ureido)-3-methoxyphenoxy)pyridin-2-yl)-2-methoxyacetamide;

N-Ethyl-N'-4-(4-(3-(3-tert-butyl-1-p-tolyl-1H-pyrazol-5-yl)ureido) naphthalen-1-yloxy)pyridin-2-ylurea;

4-(4-(3-(3-tert-Butyl-1-p-tolyl-1H-pyrazol-5-yl)ureido)naphthalen-1-yloxy)pyridin-2-ylurea;

N-Propan-2-yl-N'-4-(4-(3-(3-tert-butyl-1-p-tolyl-1H-pyrazol-5-yl)ureido)naphthalen-1-yloxy)pyridin-2-ylurea;

1-(3-(tert-Butyl)-1-(p-tolyl)-1H-pyrazol-5-yl)-3-(4-((2-(3-phenylureido)pyridin-4-yl)oxy)naphthalen-1-yl)urea;

1-(4-((2-(3-Benzylureido)pyridin-4-yl)oxy)naphthalen-1-yl)-3-(3-(tert-butyl)-1-(p-tolyl)-1H-pyrazol-5-yl)urea;

1-(4-((2-(3-Cyclopropylureido)pyridin-4-yl)oxy)naphthalen-1-yl)-3-(3-(tert-butyl)-1-(p-tolyl)-1H-pyrazol-5-yl)urea;

1-(3-(tert-Butyl)-1-(p-tolyl)-1H-pyrazol-5-yl)-3-(4-((2-(3-(2-methoxyethyl)ureido)pyridin-4-yl)oxy)naphthalen-1-yl)urea;

1-(3-(tert-Butyl)-1-(p-tolyl)-1H-pyrazol-5-yl)-3-(4-((2-(3-cyclopentyl)ureido)pyridin-4-yl)oxy)naphthalen-1-yl)urea;

1-(3-(tert-Butyl)-1-(p-tolyl)-1H-pyrazol-5-yl)-3-(4-((2-(3-methyl)ureido)pyridin-4-yl)oxy)naphthalen-1-yl)urea;

Ethyl 2-(3-(4-((4-(3-(3-(tert-butyl)-1-(p-tolyl)-1H-pyrazol-5-yl)ureido)naphthalen-1-yl)oxy)pyridin-2-yl)ureido)acetate;

4-(3-(4-(4-(3-(3-tert-Butyl-1-p-tolyl-1H-pyrazol-5-yl)ureido)naphthalen-1-yloxy)pyridin-2-yl)ureido)piperidine;

N-Acetyl 4-(3-(4-(4-(3-(3-tert-butyl-1-p-tolyl-1H-pyrazol-5-yl)ureido)naphthalen-1-yloxy)pyridin-2-yl)ureido)piperidine;

2-(2-Methoxyethoxy)-1-(4-(3-(4-(4-(3-(3-tert-butyl-1-p-tolyl-1H-pyrazol-5-yl)ureido)naphthalen-1-yloxy)pyridin-2-yl)ureido)piperidin-1-yl)ethanone;

N-Methylsulfonyl-4-(3-(4-(4-(3-(3-tert-butyl-1-p-tolyl-1H-pyrazol-5-yl)ureido)naphthalen-1-yloxy)pyridin-2-yl)ureido)piperidine;
N-(4-(4-(3-(3-tert-Butyl-1-p-tolyl-1H-pyrazol-5-yl)ureido)naphthalen-1-yloxy)pyridin-2-yl)morpholine-4-carboxamide;
N-(4-((4-(3-(3-(tert-butyl)-1-(p-tolyl)-1H-pyrazol-5-yl)ureido)naphthalen-1-yl)oxy)pyridin-2-yl)-4-methylpiperazine-1-carboxamide;
3-(4-((4-(3-(3-(tert-butyl)-1-(p-tolyl)-1H-pyrazol-5-yl)ureido)naphthalen-1-yl)oxy)pyridin-2-yl)-1,1-dimethylurea;
N-(4-((4-(3-(3-(tert-Butyl)-1-(p-tolyl)-1H-pyrazol-5-yl)ureido)naphthalen-1-yl)oxy)pyridin-2-yl)piperidine-1-carboxamide;
N-Methyl-N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;
N-(4-(morpholin-4-yl)butyl)-N'-4-(4-(3-(3-tert-butyl-1-p-tolyl-1H-pyrazol-5-yl)ureido)naphthalen-1-yloxy)pyridin-2-ylurea;
N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;
N-(3-methylisoxazol-5-yl)methyl-N'-4-(4-(3-(3-tert-butyl-1-p-tolyl-1H-pyrazol-5-yl)ureido)naphthalen-1-yloxy)pyridin-2-ylurea;
N-(1-methyl)piperidin-4-yl-N'-4-(4-(3-(3-tert-butyl-1-p-tolyl-1H-pyrazol-5-yl)ureido)naphthalen-1-yloxy)pyridin-2-ylurea;
N-(4-(4-(3-(3-tert-Butyl-1-p-tolyl-1H-pyrazol-5-yl)ureido)naphthalen-1-yloxy)pyridin-2-yl)-4-hydroxypiperidine-1-carboxamide;
N-(3-(imidazol-1-yl)propyl)-N'-4-(4-(3-(3-tert-butyl-1-p-tolyl-1H-pyrazol-5-yl)ureido)naphthalen-1-yloxy)pyridin-2-ylurea;
N-(2-(3-(4-(4-(3-(3-tert-Butyl-1-p-tolyl-1H-pyrazol-5-yl)ureido)naphthalen-1-yloxy)pyridin-2-yl)ureido)acetyl)pyrrolidine;
(R)—N-(4-(4-(3-(3-tert-Butyl-1-p-tolyl-1H-pyrazol-5-yl)ureido)naphthalen-1-yloxy)pyridin-2-yl)-3-(dimethylamino)pyrrolidine-1-carboxamide;
N-(4-(4-(3-(3-tert-Butyl-1-p-tolyl-1H-pyrazol-5-yl)ureido)naphthalen-1-yloxy)pyridin-2-yl)pyrrolidine-1-carboxamide;
2-(3-(4-(4-(3-(3-tert-Butyl-1-p-tolyl-1H-pyrazol-5-yl)ureido)naphthalen-1-yloxy)pyridin-2-yl)ureido)-N-methylacetamide;
2-(3-(4-(4-(3-(3-tert-Butyl-1-p-tolyl-1H-pyrazol-5-yl)ureido)naphthalen-1-yloxy)pyridin-2-yl)ureido)-N-(2-morpholinoethyl)acetamide;
2-(3-(4-(4-(3-(3-tert-Butyl-1-p-tolyl-1H-pyrazol-5-yl)ureido)naphthalen-1-yloxy)pyridin-2-yl)ureido)acetyl morpholine;
2-(3-(4-(4-(3-(3-tert-Butyl-1-p-tolyl-1H-pyrazol-5-yl)ureido)naphthalen-1-yloxy)pyridin-2-yl)ureido)-N-(2-(pyridin-4-yl)ethyl)acetamide;
N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide;
1-(2-(3-(4-(4-(3-(3-tert-Butyl-1-p-tolyl-1H-pyrazol-5-yl)ureido)naphthalen-1-yloxy)pyridin-2-yl)ureido)acetyl)-4-methylpiperazine;
N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide;
N-(6-(4-(3-(3-tert-Butyl-1-p-tolyl-1H-pyrazol-5-yl)ureido)naphthalen-1-yloxy)pyrimidin-4-yl)-2-methoxyacetamide;
N-(6-(4-(3-(3-tert-Butyl-1-p-tolyl-1H-pyrazol-5-yl)ureido)phenoxy)pyrimidin-4-yl)-2-methoxyacetamide;
N-(4-(4-(3-(3-tert-Butyl-1-p-tolyl-1H-pyrazol-5-yl)ureido)naphthalen-1-yloxy)pyrimidin-2-yl)-2-methoxyacetamide;
3-(4-(4-(3-(3-tert-Butyl-1-p-tolyl-1H-pyrazol-5-yl)ureido)naphthalen-1-yloxy)pyrimidin-2-yl)urea;
1-Methyl-3-(4-(4-(3-(3-tert-butyl-1-p-tolyl-1H-pyrazol-5-yl)ureido)naphthalen-1-yloxy)pyrimidin-2-yl)urea;
1,1-Dimethyl-3-(4-(4-(3-(3-tert-butyl-1-p-tolyl-1H-pyrazol-5-yl)ureido)naphthalen-1-yloxy)pyrimidin-2-yl)urea;
1-Cyclopropyl-3-(4-(4-(3-(3-tert-butyl-1-p-tolyl-1H-pyrazol-5-yl)ureido)naphthalen-1-yloxy)pyrimidin-2-yl)urea;
(4-(4-(3-(3-tert-butyl-1-p-tolyl-1H-pyrazol-5-yl)ureido)naphthalen-1-yloxy)pyrimidin-2-yl)morpholine-4-carboxamide;
3-(6-(4-(3-(3-tert-Butyl-1-p-tolyl-1H-pyrazol-5-yl)ureido)naphthalen-1-yloxy)pyrimidin-4-yl)urea;
2-(3-(4-(4-(3-(3-tert-Butyl-1-p-tolyl-1H-pyrazol-5-yl)ureido)naphthalen-1-yloxy)pyridin-2-yl)ureido)acetic acid, or a pharmaceutically acceptable salt thereof, including all stereoisomers, tautomers and isotopic derivatives thereof.

Examples of salts of compound (I) include all pharmaceutically acceptable salts, such as, without limitation, acid addition salts of strong mineral acids such as HCl and HBr salts and addition salts of strong organic acids such as a methansulfonic acid salt.

The disclosure herein extends to solvates of compounds of formula (I). Examples of solvates include hydrates.

The compounds of the disclosure include those where the atom specified is replaced by a naturally occurring or non-naturally occurring isotope. In one embodiment the isotope is a stable isotope. Thus the compounds of the disclosure include, for example deuterium containing compounds and the like.

The compounds described herein may include one or more chiral centres, and the disclosure extends to include racemates, enantiomers and stereoisomers resulting therefrom. In one embodiment one enantiomeric form is present in a substantially purified form that is substantially free of the corresponding entaniomeric form.

The disclosure also extends to all polymorphic forms of the compounds herein defined.

Unless the context indicates otherwise references to compounds of formula (I) herein includes references to one or more, such as all structures and compounds disclosed.

Compounds of formula (I) can be prepared by a process comprising reacting compounds of formula (II):

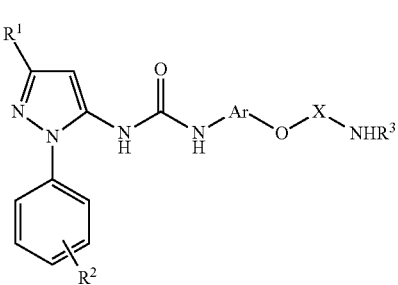

(II)

where Ar, X, $R^1$, $R^2$ and $R^3$ are as defined above for compounds of formula (I)
wherein Q is not —NHR* (wherein R* is the remainder of the Q fragment) with a compound of formula (IIIa):

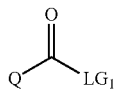

(IIIa)

where $LG_1$ is a leaving group for example halogen, such as chloro.

When $NR^3C(O)Q$ is $NR^3C(O)NHR*$ compounds of formula (I) can be prepared by reacting compounds of formula (II) with a compound of formula (IIIb):

Q=C=O  (IIIb)

The reaction is suitably carried out in the presence of a base (e.g. DIPEA). The reaction is suitably carried out in an aprotic solvent or solvent mixture, e.g. DCM and DMF.

Compounds of formula (II) can be prepared by reacting a compound of formula (IV):

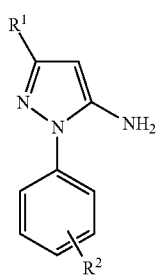

(IV)

where $R^1$ and $R^2$ are as defined above for compounds of formula (I), with a compound of formula (VI):

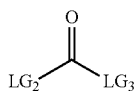

(VI)

wherein $LG_2$ and $LG_3$ each independently represent leaving groups (e.g. $LG_2$ and $LG_3$ both represent imidazolyl followed by reaction with a compound of formula (V):

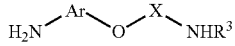

(V)

wherein Ar, X and $R^3$ are defined above for compounds of formula (I)

The reaction is suitably carried out in an aprotic solvent (e.g. dichloromethane), using appropriate protecting groups for chemically sensitive groups and a base, for example DIPEA.

Specifically compounds of formula (II) can be prepared by reacting a compound of formula (IVa):

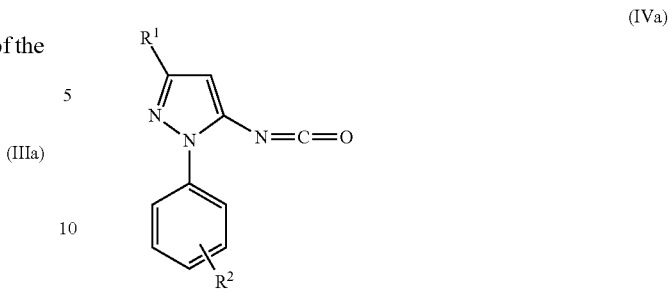

(IVa)

where $R^1$ and $R^2$ are as defined above for compounds of formula (I), with a compound of formula (V).

The reaction may be performed in the presence of a sterically hindered base such as DIPEA, in a suitable inert solvent such as dichloromethane.

Compounds of formula (I) wherein $R^2$ is a hydroxyalkyl may be prepared by reacting a (hydrazinylphenyl)alkanoic acid with an alkanoyl acetonitrile such as $R^1C(O)CH_2CN$, for example. The coupling may be effected in presence of an alcohol solvent such as ethanol and a mineral acid, such as HCl followed by treatment with a lithium hydroxide in a solvent such as THF. The substituent $R^2$ comprising a hydroxyalkyl may be revealed by a reduction employing borane in a suitable solvent, for example THF to afford a compound of formula (IV) where $R^2$ is hydroxylated alkyl. The hydroxyl may then be protected, for example as a silyl ether and (IV) carried through one of the routes described elsewhere in this section to generate a compound of formula (I) in which $R^2$ is a protected hydroxyalkyl group. The hydroxyl can be revealed by cleavage of the silyl group, for example with tetrabutylammonium fluoride.

Compounds of formula (I) wherein $R^1$ is a hydroxylated alkyl species may be prepared by reacting protected benzyloxyalkanoyl acetonitrile an aryl hydrazine employing analogous conditions to those described directly above.

A compound of formula (IVa) can be prepared by reacting a compound of formula (IV) with phosgene or a phosgene equivalent such as diphosgene or triphosgene in the presence of a base such DIPEA. It will be understood by persons skilled in the art that the compound of formula (IVa) is generally a reactive intermediate, and may be isolated and used directly in subsequent transformations or may be a transient intermediate, that is generated in situ and used without isolation.

More specifically compounds of formula (II) may be prepared by reacting a compound of formula (IVb):

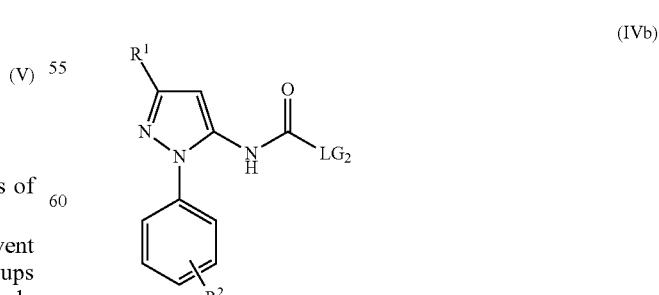

(IVb)

where $LG_2$ is as defined above with a compound of formula (VI).

The reaction may be performed in the presence of a sterically hindered base such as DIPEA, in a suitable inert solvent such as dichloromethane.

A compound of (IVb) can be prepared by reacting a compound of formula (IV) with a compound of formula (VI) in the presence of a base such as DIPEA. It will be understood by persons skilled in the art that the compound of formula (IVb) may be an intermediate, including a transient intermediate, that is not isolated.

A compound of formula (V) may be prepared by reduction of a compound of formula (VII):

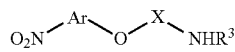

(VII)

wherein Ar, X and $R^3$ are as defined above for compounds of formula (I),
for example by hydrogenation in the presence of a catalyst such as platinum supported on carbon.

The reaction is suitably carried out in polar protic solvent or mixture of solvents (e.g. methanol and acetic acid).

Alternatively, a compound of formula (V) may be prepared by deprotecting compound of formula (VIIIa):

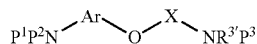

(VIIa)

wherein $P^1$, $P^2$ and $P^3$ are protecting groups and $R^{3'}$ is $R^3$ as defined above for compounds of formula (I) or a protecting group, for example acetyl such as —C(O)CH$_2$OCH$_3$.

A compound of formula (VII) may be prepared by reaction of a compound of formula (VIII)

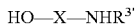  (VIII)

wherein X is as defined above for compounds of formula (I) and $R^{3'}$ is as defined as defined above for compounds of formula (VIIa):
with a compound of formula (IX) or (X):

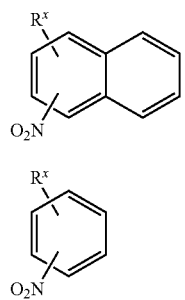

wherein $R^x$ is a halogen, such as fluoro. Compounds (IX) and (X) may bear optional substituents as defined above for compounds of formula (I). In one embodiment $R^x$ and $NO_2$ are arranged para relative to the other.

Where $R^x$ represents halogen such a fluoro then the reaction may be performed in the presence of a strong base such as DBU in a polar aprotic solvent such as acetonitrile.

In an alternative process, certain compounds of formula (V), wherein Ar and X are as defined above for compounds of formula (I) may be prepared by reacting a compound of formula (XI):

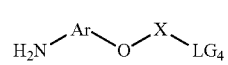

(XI)

or a protected derivative thereof, such as a carbamate, wherein Ar and X are as defined above and $LG_4$ represents a leaving group such as chloro (in particular where X represents O) with an amidation reagent, for example with the carbamate (XII):

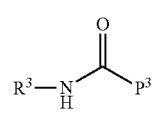

(XII)

wherein $P^3$ and $R^3$ are as defined above in the presence of an dry inert solvent such as THF and a suitable palladium catalyst, for example under a nitrogen atmosphere, followed by deprotection of both the original and newly introduced protected amines, for example employing dichloromethane and TFA.

In one embodiment the compound of formula (XII) is:

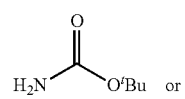

(XIIa)

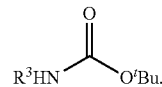

(XIIb)

Compounds of formula (XI) may be prepared by reacting a compound of formula (XIII):

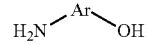

(XIII)

or a protected derivative thereof, for example where the free amine is protected as a carbamate, wherein Ar is as defined above with a compound of formula (XIV):

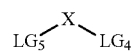

(XIV)

wherein X is as defined above and $LG_4$ represents a leaving group such as chloro and $LG_5$ represents a leaving group such a fluoro.

The reaction may be performed in the presence of a strong base such as sodium hydride in a polar aprotic solvent such as DMF.

The reaction may be performed in an inert solvent in the presence of catalyst, for example Pd⁰.

In one embodiment compound of formula (XIV) is:

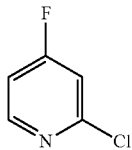

and is reacted with a compound of formula (XV) or (XVI):

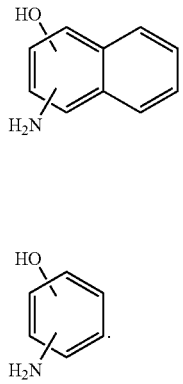

The reaction may be performed in the presence of a strong base such as potassium tert-butoxide in a polar aprotic solvent such as NMP.

Alternatively compounds of formula (I) may be prepared by reacting a compound of formula (XVII):

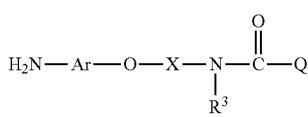
(XVII)

wherein Ar, X, $R^3$ and Q are as defined for compounds of formula (I), with a compound of formula (XVIII):

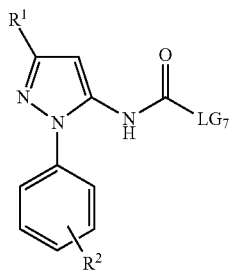

wherein $R^1$ and $R^2$ are as defined for compounds of formula (I) and $LG_7$ is a leaving group.

The reaction may be effected in a polar aprotic solvent, for example DCM at room temperature.

Certain compounds of formula (I), for example compounds where Q represents $C_{1-6}$ alkylNH$_2$ can be converted into other compounds of formula (I) by reaction with an acylating agent.

Compounds of formula (I) wherein Q is linked to —NR³C(O) by —CH₂V', wherein V' is a heteroatom selected from N, O, or S, can be prepared by the process comprising of a nucleophilic displacement reaction on a compound of formula (IIa):

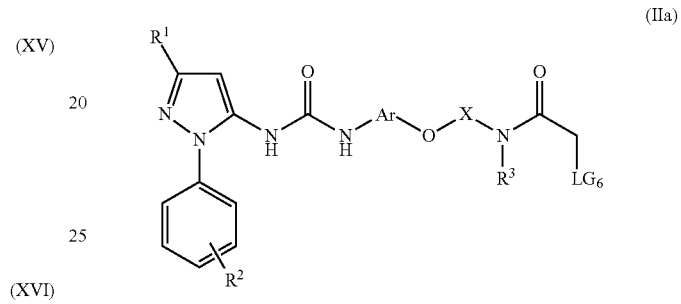
(IIa)

wherein $R^1$, $R^2$, Ar, X and $R^3$ are as defined above for compounds of formula (I) and $LG_6$ represents a leaving group, for example halogen such as chloro, with a compound of formula (XIX):

H—V'-q  (XIX)

wherein H represents hydrogen, V' represents a heteroatom selected from N, NH, O, or S and q represents the residual portion of Q (i.e. —CH₂V'-q=Q).

The reaction may, be performed in the presence of a sterically hindered base, for example DIPEA, in an inert solvent, for example dichloromethane.

Compounds of formula (IIa) may be prepared by reacting a compound of formula (II) with a compound of formula (XX):

(XX)

wherein $LG_6$ is defined above for compounds of formula (IIa), and $LG_7$ is a leaving group, for example a halogen such as chloro.

The reaction may, for example be performed in the presence of a sterically hindered base, for example DIPEA, in an inert solvent, for example dichloromethane.

Compounds of formula (I) wherein Q is NH—(CH$_2$)$_d$—C(O)NHR$^d$, can be prepared by the process comprising of an amide coupling between (IIb):

Compounds of formula (I) wherein Q is NR$^4$R$^5$ can be prepared by the process comprising of reaction between an amine R$^4$R$^5$NH and a compound of formula (IIc):

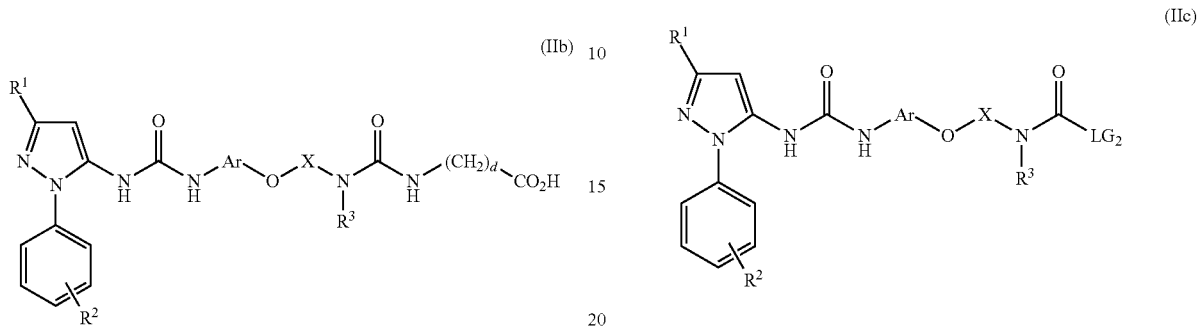

wherein R$^1$, R$^2$, Ar, X and R$^3$ are as defined above for compounds of formula (I) and d is an integer 1 to 5 (such as 1 to 4), and an amine R$^d$NH$_2$ using a coupling reagent such as EDC (wherein Rd represents a fragment of Q).

Compounds of formula (IIb) can be synthesized by reaction of a compound (II) with an isocyanate of formula (IIIb) in which Q is N—(CH$_2$)$_d$—CO$_2$Et, followed by hydrolysis of the resulting ethyl ester product using, for example, aqueous lithium hydroxide in THF.

wherein R$^1$, R$^2$, Ar, X and R$^3$ are as defined above for compounds of formula (I) and LG$_2$ is a leaving group such as 2-isopropenyloxy.

Compounds of formula (IIc) can be synthesized by reaction of a compound of formula (II) with a compound of formula (VI), such as isopropenylchloroformate in the presence of a hindered base such as DIPEA. The reaction may, be performed in the presence of a sterically hindered base, for example DIPEA, in an inert solvent, for example dichloromethane.

An example of a route of preparing certain compounds of formula (I), wherein Ar is napthyl, X is pyridinyl is described below in schemes 1 and 2.

Scheme 1

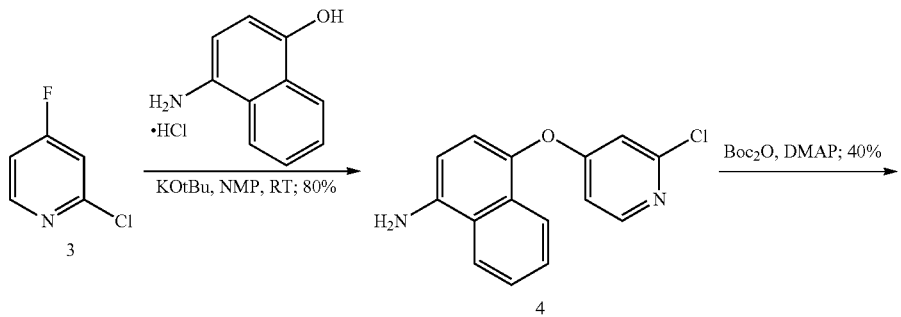

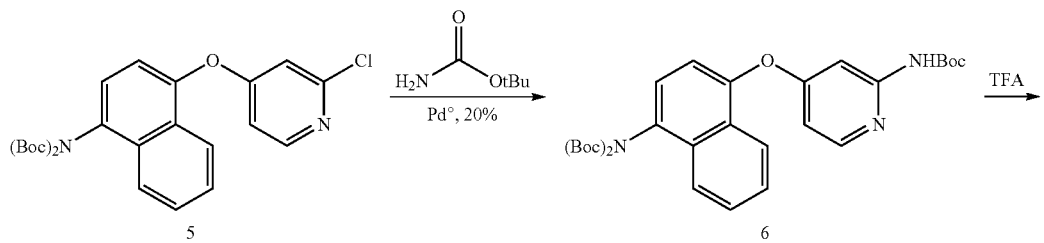

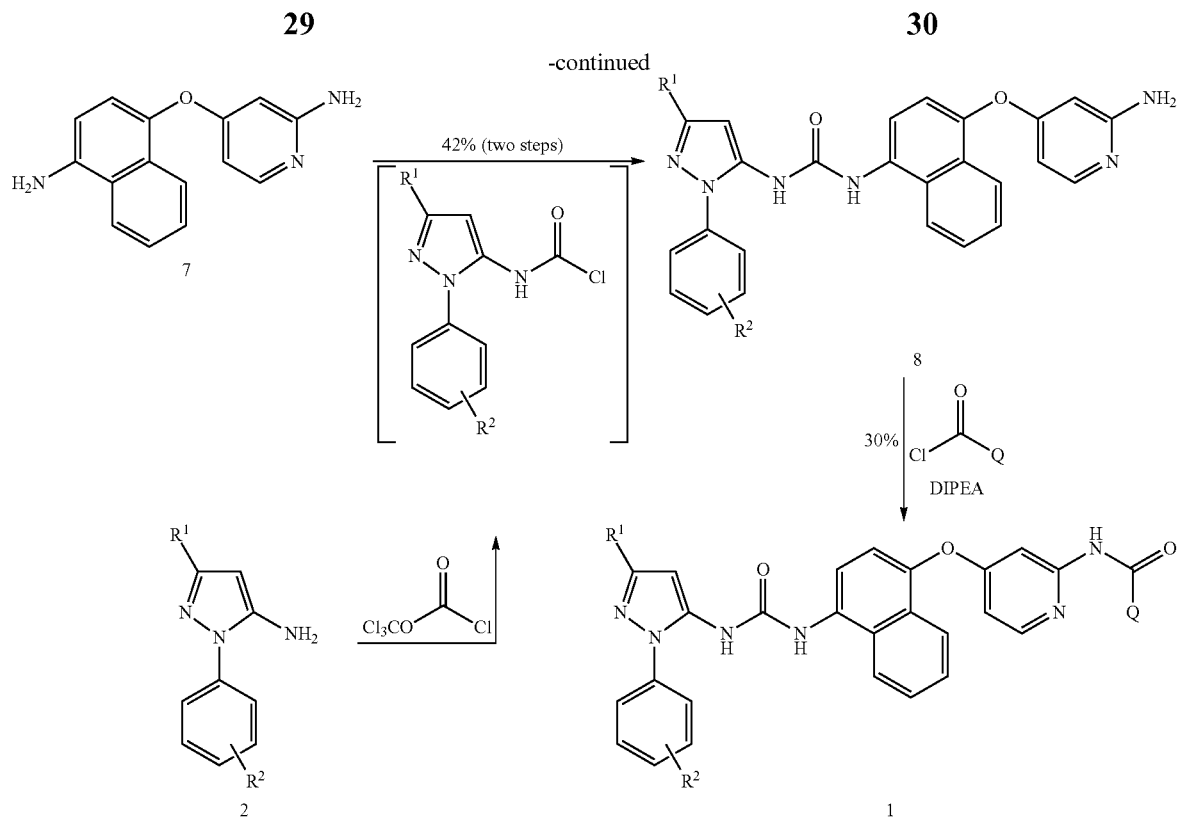
wherein R[1] and R[2] are defined above for compounds of formula (I).
Scheme 2 summarises a route for preparing certain compounds of formula (I)
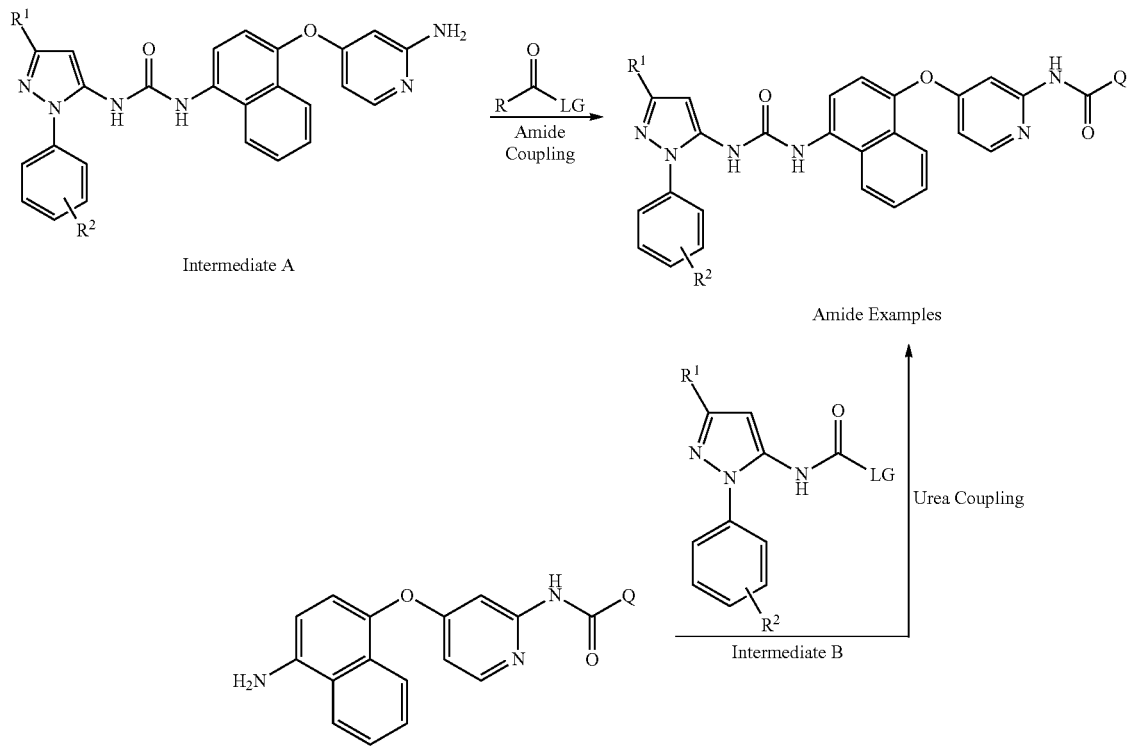

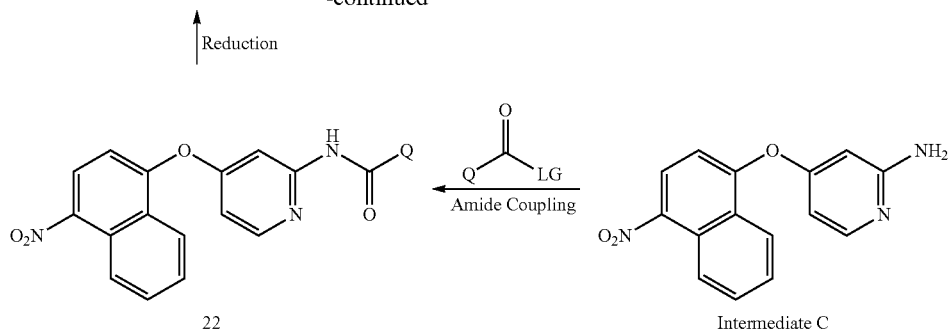

wherein R¹ and R² are defined above for compounds of formula (I).

Compounds of formula (I) wherein XNR³(CO)Q represents N-acyl-2-aminopyrimidinyl or N-acyl-4-aminopyrimidinyl may be prepared as summarised in scheme 3 below:

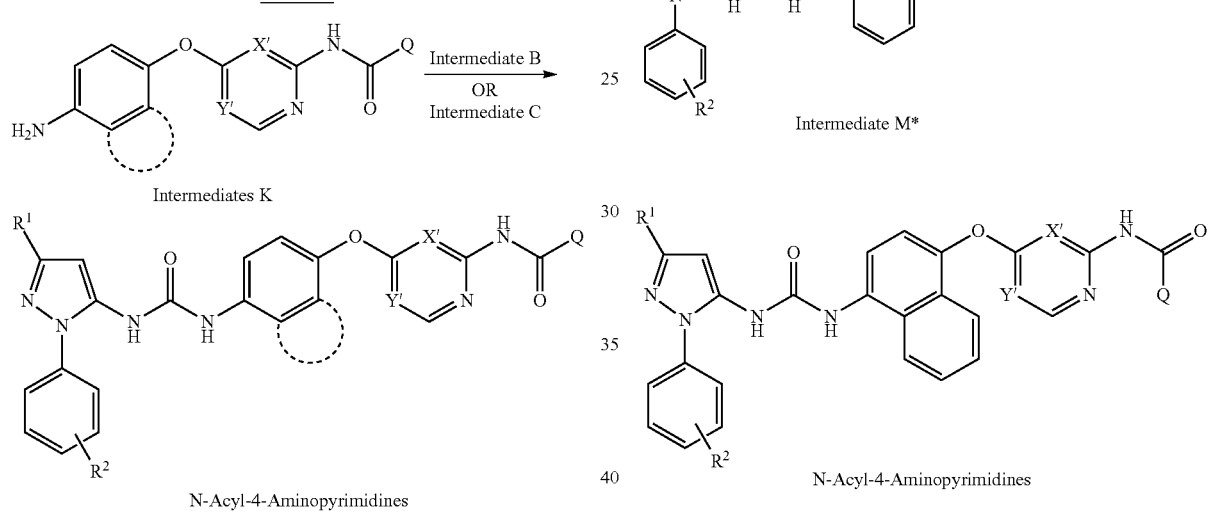

where each X' and Y' independently represents CH or N.

Compounds of formula (I) wherein Ar represents naphthyl and XNR³C(O)Q represents N-acyl-2-aminopyrimidinyl may be prepared as summarised in Scheme 4 below:

where X" and Y" independently represents CH or N.

Compounds of formula (I) wherein XNHR³ represents 2-aminopyrimidinyl or 4-aminopyrimidinyl and NR³(CO)Q is a urea may be prepared as summarised below in Scheme 5:

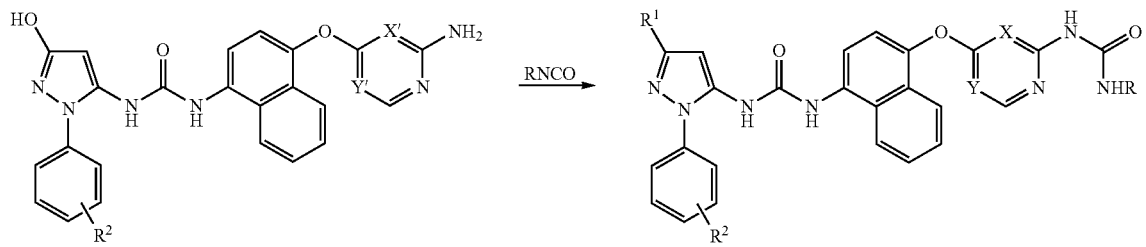

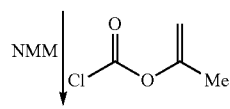

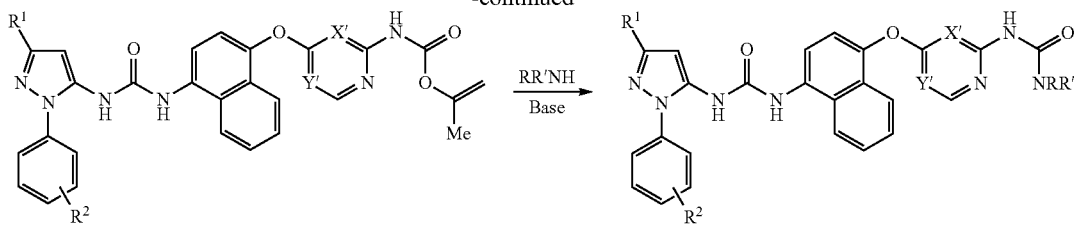

X' = N, Y' = CH; Intermediate P
X' = CH, Y' = N; Intermediate Q

Pyrimidine 3° Urea Examples where X' and Y' independently represents CH or N.

Scheme 6 below summarises the preparation of additional compounds of formula (I) wherein Ar is naphthyl and XNHR³ represents 2-aminopyrimidinyl or 4-aminopyrimidinyl:

Scheme 6

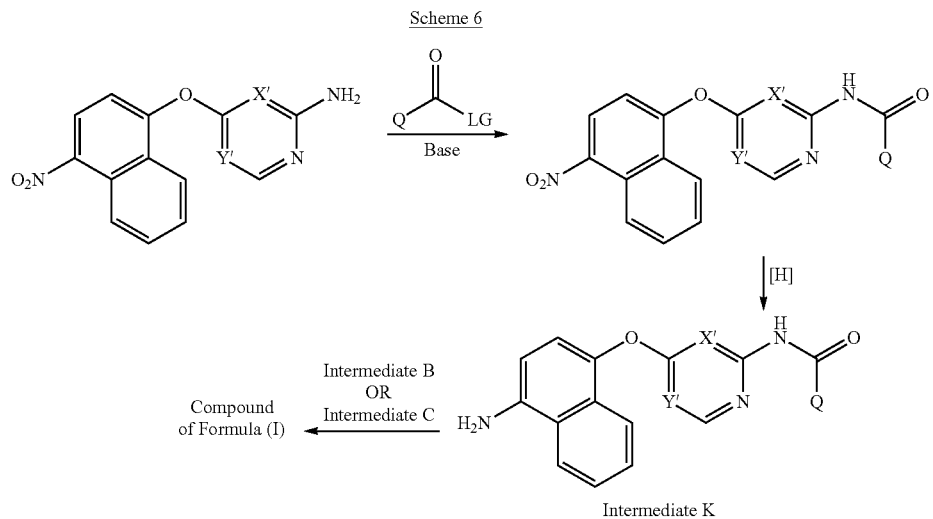

The starting material for use in scheme 6 for the preparation of 4-amino pyrimidines may be prepared as summarised in the scheme 7 below:

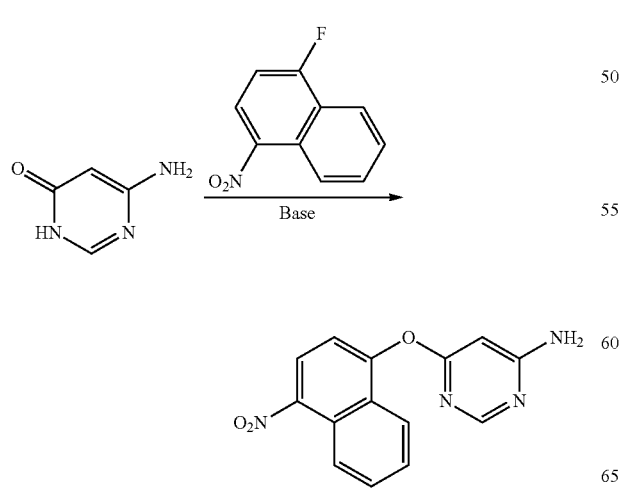

or as shown in scheme 8:

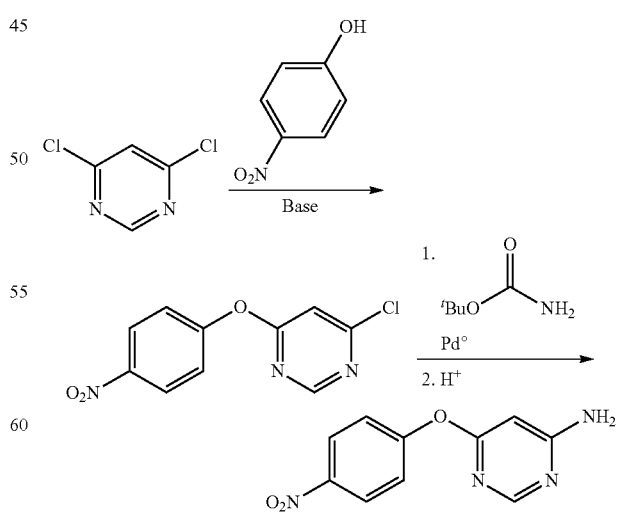

Certain compounds within the definition of intermediate M* in particular intermediate N wherein XNHR³ is 2-aminopyrimidinyl and L is O may be prepared as shown in scheme 9:

Scheme 9

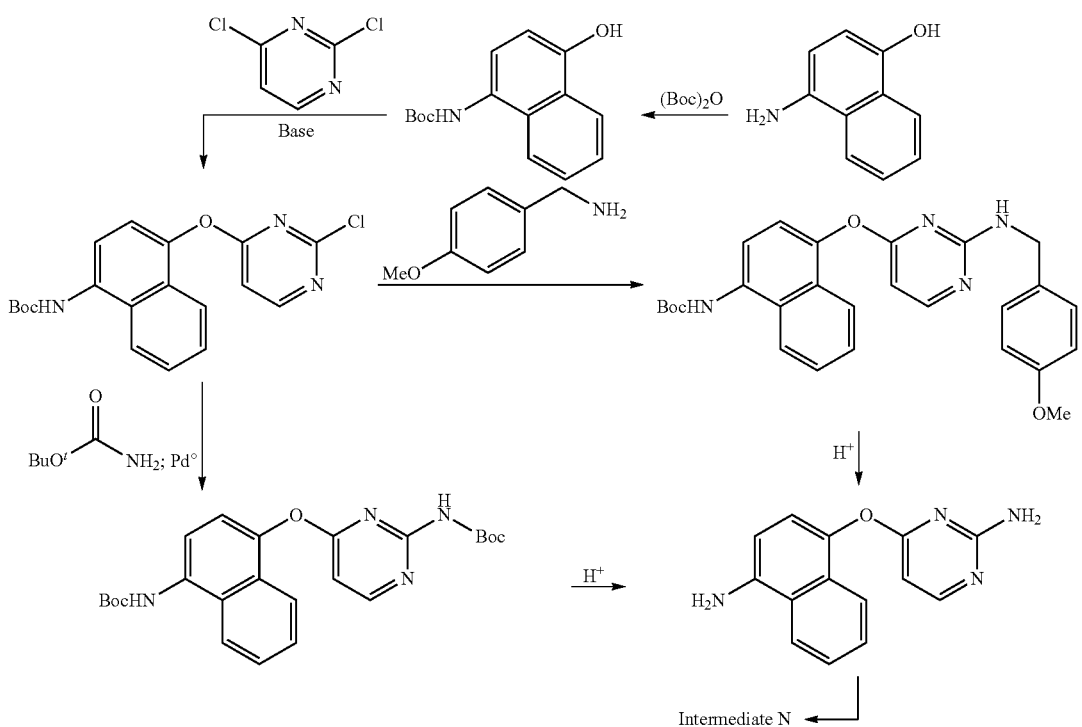

Intermediate K where Q is NRR' may be prepared as summarised in scheme 10 below:

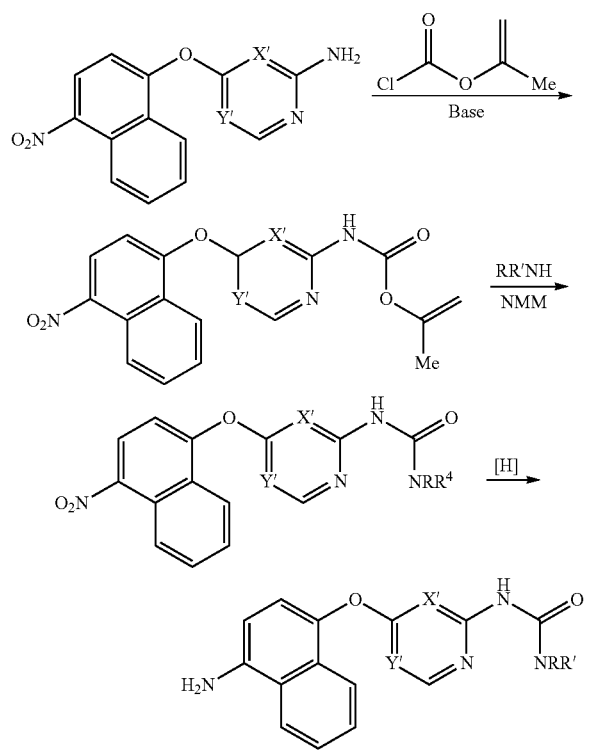

wherein each of X', Y', R and R' are defined above.

Compounds of formulae (III), (IV), (IVa), (IVb), (VI), (VIII), (IX), (X), (XII), (XIIa), (XIIb), (XIV), (XV), (XVI), (XIX) and (XX) are either commercially available, or are known, or are novel and can be readily prepared by conventional methods. See for example Regan, J. et al.; *J. Med. Chem.*, 2003, 46, 4676-4686, WO00/043384, WO2007/087448 and WO2007/089512.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; 4$^{th}$ Rev Ed., 2006, ISBN-10: 0471697540.

Novel intermediates are claimed as an aspect of the invention.

In one aspect the compounds are useful in treatment, for example COPD and/or asthma.

The compounds developed to date have typically been intended for oral administration. This strategy involves optimizing compounds which achieve their duration of action by an appropriate pharmacokinetic profile. This ensures that there is a sufficient drug concentration established and maintained after and between doses to provide clinical benefit. The inevitable consequence of this approach is that all body tissues, especially liver and gut, are likely to be exposed to therapeutically active concentrations of the drug, whether or not they are adversely affected by the disease being treated.

An alternative strategy is to design treatment approaches in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by (i) ensuring that the drug has a sustained duration of action and is retained in the relevant organ to minimize the risks of systemic toxicity or (ii) producing a formulation which generates a "reservoir" of the active drug which is available to sustain the drug's desired effects. Approach (i) is exemplified by the anticholinergic drug tiotropium (Spiriva), which is administered topically to the lung as a treatment for COPD, and which has an exceptionally high affinity for its target receptor resulting in a very slow off rate and a consequent sustained duration of action.

In one aspect of the disclosure the compounds herein are particularly suitable for topical delivery, such as topical delivery to the lungs, in particular for the treatment of COPD.

In one aspect the compounds have a longer duration of actions than BIRB 796.

In one embodiment the compounds are suitable for sensitizing patients to treatment with a corticosteroid.

The compounds herein may also be useful for the treatment of rheumatoid arthritis.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean diameter (MMAD) of 1-10 microns. The formulation will typically contain a topically acceptable diluent such as lactose, usually of large particle size e.g. a mass mean diameter (MMAD) of 100 μm or more. Example dry powder delivery systems include SPINHALER, DISKHALER, TURBOHALER, DISKUS and CLICKHALER.

Compounds according to the disclosure are intended to have therapeutic activity. In a further aspect, the present invention provides a compound of the disclosure for use as a medicament.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

Compounds of the disclosure may also re-sensitise the patient's condition to treatment with a corticosteroid, when the patient's condition has become refractory to the same.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of the disclosure are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

Compounds of the disclosure are believed to be useful as anti-viral agents, for example in the treatment of conditions including influenza infection. In particular the compounds of the present disclosure may be suitable for the use in the treatment or prevention of said viral infection and in particular may be capable of reducing viral load and/or ameliorating symptoms after infection.

Thus, in a further aspect, the present invention provides a compound as described herein for use in the treatment of the above mentioned conditions.

In a further aspect, the present invention provides use of a compound as described herein for the manufacture of a medicament for the treatment of the above mentioned conditions.

In a further aspect, the present invention provides a method of treatment of the above mentioned conditions which comprises administering to a subject an effective amount of a compound of the disclosure or a pharmaceutical composition thereof.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline).

Abbreviations

Abbreviations used herein are as defined in the table below. Any abbreviations not defined have their generally accepted meaning.
AcOH glacial acetic acid
aq aqueous
Ac acetyl
ATP adenosine-5'-triphosphate
BALF bronchoalveolae lavage fluid
9-BBN 9-borabicyclo[3.3.1]nonane
Boc tert-butoxycarbonyl
br broad
BSA bovine serum albumin
CatCart® catalytic cartridge
CBz benzyloxycarbonyl
CDI 1,1-carbonyl-diimidazole
COPD chronic obstructive pulmonary disease
d doublet
DCM dichloromethane
DIAD diisopropylazadicarboxylate
DIBAL-H diisobutylaluminium hydride
DIPEA N,N-diisopropylethylamine
DMF N,N-dimethylformamide
DMSO dimethyl sulfoxide
EDC.HCl 1-ethyl-3-(3-dimethylaminopropyl)carbodiimide-.hydrochloride
(ES$^+$) electrospray ionization, positive mode
Et ethyl
EtOAc ethyl acetate
FCS foetal calf serum
HOBt 1-hydroxybenzotriazole
hr hour(s)
HRP horseradish peroxidase
JNK c-Jun N-terminal kinase
KHMDS potassium hexamethyldisilazane
(M+H)$^+$ protonated molecule
MAPK mitogen protein activated protein kinase
Me methyl
MeOH methanol
MHz megahertz
min minute(s)
MOM-Br bromomethyl methyl ether
MTT 3-(4,5-Dimethylthiazol-2-yl)-2,5-diphenyltetrazolium bromide
m/z: mass-to-charge ratio
NMM N-methylmorpholine; (4-methylmorpholine)
NMP 1-methylpyrrolidin-2-one (N-methyl-2-pyrrolidone)
NMR nuclear magnetic resonance (spectroscopy)
Ph phenyl
PBS phosphate buffered saline
$Pd_2(dba)_3$ tris(dibenzylideneacetone)dipalladium(0)
$PPh_3$ triphenylphosphine
PyBOP® (benzotriazol-1-yloxy)tripyrrolidinophosphonium hexafluorophosphate
q quartet
RT room temperature
RP HPLC reverse phase high performance liquid chromatography
s singlet
SCX solid supported cation exchange (resin)
SDS sodium dodecyl sulfate
t triplet
TFA trifluoroacetic acid
THF tetrahydrofuran
TMB 3,3',5,5'-tetramethylbenzidine
TNFα tumor necrosis factor alpha
TMS-Cl trimethylsilyl chloride [chlorotrimethylsilane]
XantPhos 4,5-bis(diphenylphosphino)-9,9-dimethylxanthene General Procedures All starting materials and solvents were either obtained from commercial sources or prepared according to the literature citation.

Hydrogenations were preformed on a Thales H-cube flow reactor under the conditions stated. Organic solutions were routinely dried over magnesium sulfate.

SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Column chromatography was performed on pre-packed silica (230-400 mesh, 40-63 µM) cartridges using the amount indicated.

Preparative Reverse Phase High Performance Liquid Chromatography:

Agilent Scalar column C18, 5 µm (21.2×50 mm), flow rate 28 mL.min$^{-1}$ eluting with a $H_2O$-MeCN gradient containing 0.1% v/v formic acid over 10 mins using UV detection at 215 and 254 nm. Gradient information: 0.0-0.5 min: 95% $H_2O$-5% MeCN; 0.5-7.0 min; Ramped from 95% $H_2O$-5% MeCN to 5% H₂O-95% MeCN; 7.0-7.9 min: Held at 5% H₂O-95% MeCN; 7.9-8.0 min: Returned to 95% H₂O-5% MeCN; 8.0-10.0 min: Held at 95% H₂O-5% MeCN.

Analytical Methods

Reverse Phase High Performance Liquid Chromatography:
Agilent Scalar column C18, 5 μm (4.6×50 mm) or Waters XBridge C18, 5 μm (4.6×50 mm) flow rate 2.5 mL.min$^{-1}$ eluting with a H₂O-MeCN gradient containing 0.1% v/v formic acid over 7 min employing UV detection at 215 and 254 nm. Gradient information: 0.0-0.1 min: 95% H₂O-5% MeCN; 0.1-5.0 min; Ramped from 95% H₂O-5% MeCN to 5% H₂O-95% MeCN; 5.0-5.5 min: Held at 5% H₂O-95% MeCN; 5.5-5.6 min: Held at 5% H₂O-95% MeCN, flow rate increased to 3.5 mL.min$^{-1}$; 5.6-6.6 min: Held at 5% H₂O-95% MeCN, flow rate 3.5 mL.min$^{-1}$; 6.6-6.75 min: Returned to 95% H₂O-5% MeCN, flow rate 3.5 mL.min$^{-1}$; 6.75-6.9 min: Held at 95% H₂O-5% MeCN, flow rate 3.5 mL.min$^{-1}$; 6.9-7.0 min: Held at 95% H₂O-5% MeCN, flow rate reduced to 2.5 mL.min$^{-1}$.

$^1$H NMR Spectroscopy:
Bruker Avance III 400 MHz Using Residual Undeuterated Solvent as Reference Certain compounds of the disclosure were prepared by a process in which an Intermediate A was N-acylated with a suitable acid derivative. Alternatively certain compounds of the disclosure were obtained by reaction of an Intermediate B with an Intermediate C or an Intermediate D to generate a urea in the final step Compounds represented by Intermediate A were prepared by reaction of Intermediate E with either the species represented by Intermediate C or Intermediate D.

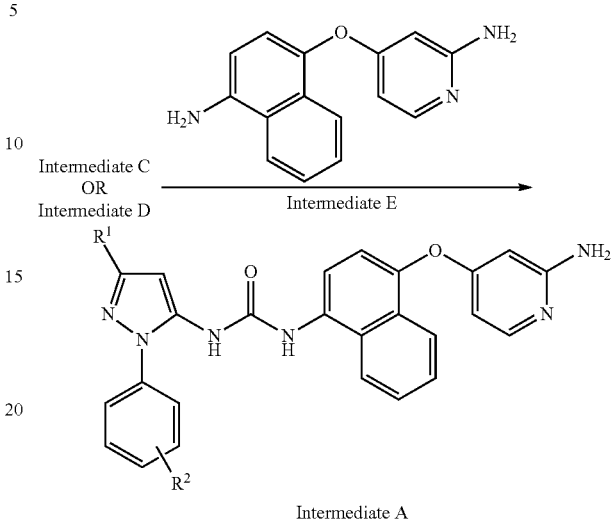

Intermediate A

The compounds represented by Intermediate B were prepared from 2-aminopyridin-4-ol and 1-fluoro-4-nitronaphthalene via an SNAr reaction, followed by acylation of the aminopyridine and reduction of the nitronaphthylene.

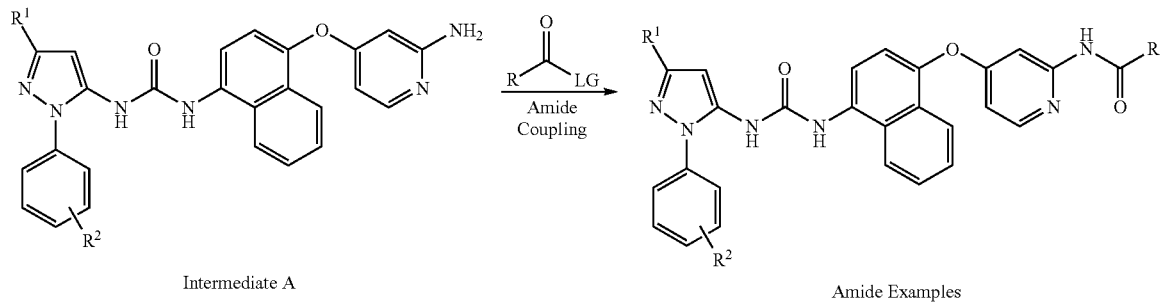

Intermediate A          Amide Examples

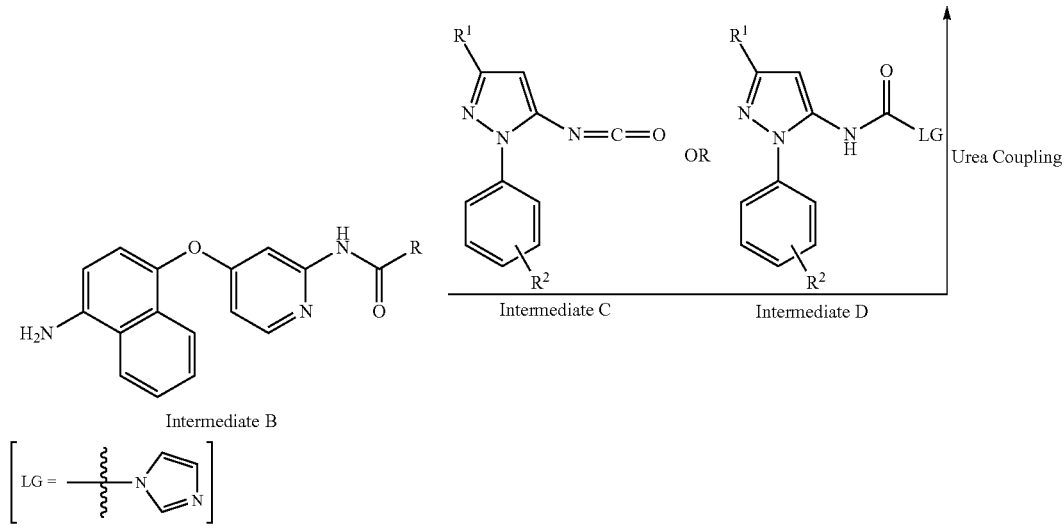

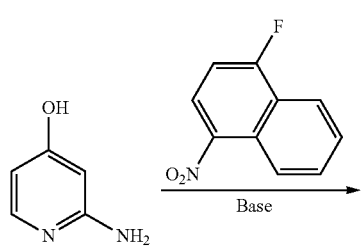

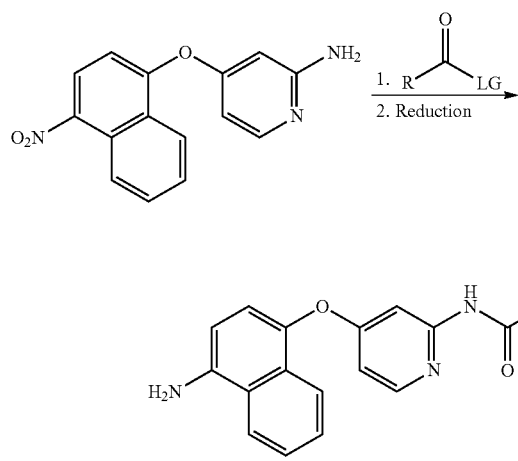

Intermediate B

The electrophilic compounds represented by Intermediate C or Intermediate D were obtained from the corresponding amine by suitable activation and were generally used directly without further purification. The 5-aminopyrazoles from which Intermediate B and Intermediate C were derived were procured from commercial sources where these compounds were available, or were prepared using the cited literature procedure or were obtained by the processes disclosed herein.

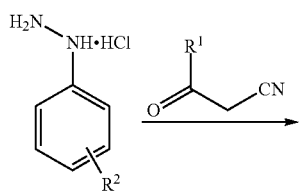

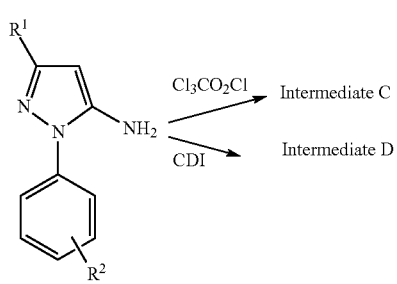

Intermediate A1: 1-(4-(2-Aminopyridin-4-yloxy)naphthalen-1-yl)-3-(3-tert-butyl-1-p-tolyl-1H-pyrazol-5-yl)urea

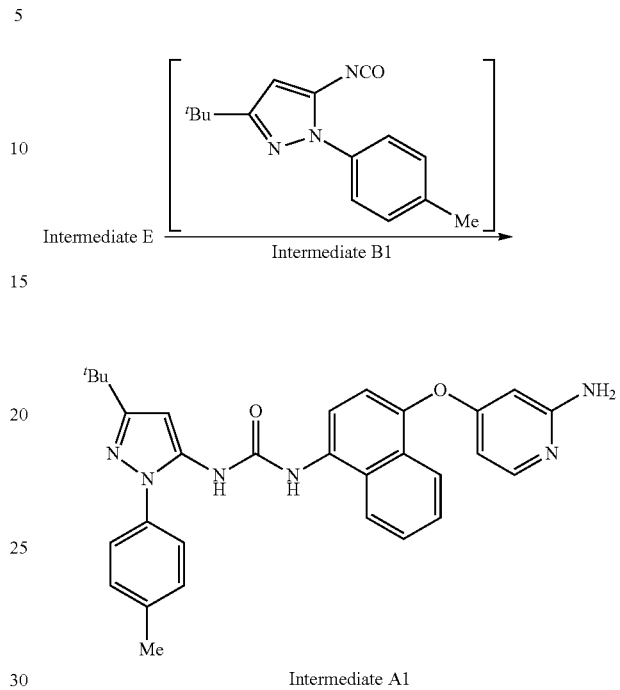

Intermediate A1

A saturated aq. solution of $NaHCO_3$ (14 mL) was added to a solution of 3-tert-butyl-1-p-tolyl-1H-pyrazol-5-amine (WO 2000043384) (206 mg, 0.900 mmol) in DCM (20 mL) and the mixture was cooled to 0° C. and stirred vigorously whilst trichloromethylchloroformate (325 µL, 2.70 mmol) was added in a single portion. The vigorous stirring was continued at 0° C. for a further 80 min. The organic layer was separated and dried and was then evaporated in vacuo to provide 3-tert-butyl-5-isocyanato-1-p-tolyl-1H-pyrazole, Intermediate B1 as orange oil. This material was pumped for 30 min under high vacuum and was then taken up into THF (6.0 mL) and kept under nitrogen at 0° C. and used directly in the next step.

To a stirred solution of 4-(4-aminonaphthalen-1-yloxy)pyridin-2-amine, Intermediate E (116 mg, 0.462 mmol) and DIPEA (240 µl, 1.39 mmol) in THF (3 mL) at 0° C. was added an aliquot of the isocyanate solution prepared above (2.0 mL, 0.300 mmol) and the resulting mixture warmed slowly to RT. Additional aliquots of the isocyanate solution in THF were added to the reaction mixture after 1.5 hr, (1 mL, 0.150 mmol) and after a further 3.5 hr (0.5 mL, 0.075 mmol). After 20 hr water (30 mL) was added and the mixture was extracted with EtOAc (2×30 mL). The combined organic extracts were washed with brine (50 mL), dried and then evaporated in vacuo. The crude material so obtained was purified by flash column chromatography ($SiO_2$; 12 g, 25-100% [5% MeOH in EtOAc] in iso-hexane, gradient elution) to furnish the title compound, Intermediate A1 as a brown oil (127 mg, 49%): m/z 507 $(M+H)^+$ $(ES^+)$.

Intermediate B1: N-(4-(4-Aminonaphthalen-1-yloxy) pyridin-2-yl)-2-methoxyacetamide

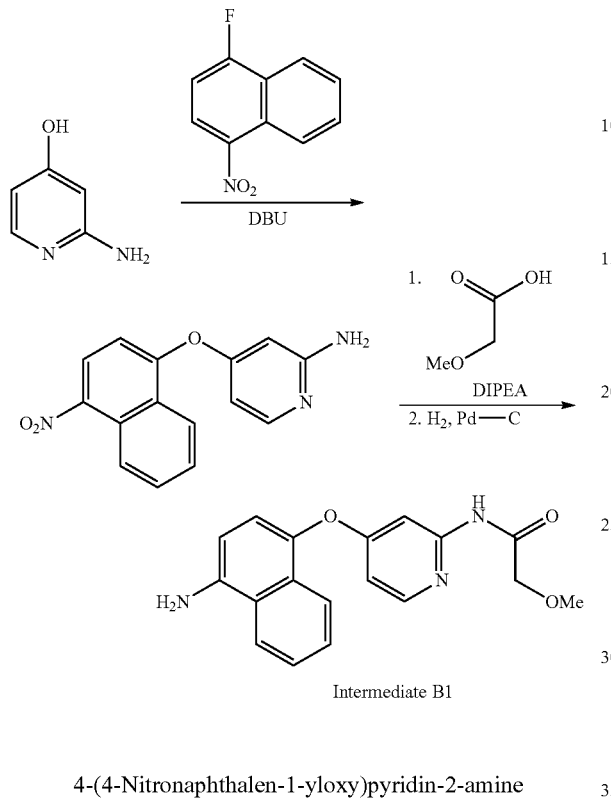

Intermediate B1

4-(4-Nitronaphthalen-1-yloxy)pyridin-2-amine

To a stirred suspension of 2-aminopyridin-4-ol (53.9 g, 489 mmol) in acetonitrile (500 mL) was added DBU (102 mL, 678 mmol) dropwise over 30 min. The resulting solution was stirred at RT for 30 min and was then treated dropwise with a solution of 1-fluoro-4-nitronaphthalene (72.0 g, 377 mmol) in acetonitrile (400 mL) over 50 min. After stirring overnight at RT the reaction was heated at 50° C. for 2 hr. The reaction was removed from the heat, but not cooled and with stirring, treated with water (6×100 mL). The mixture was allowed to cool to RT over 2 hr and was then cooled further to 0° C. The yellow precipitate was collected by filtration and washed sequentially with a mixture of water and acetonitrile (1:1, 2×100 mL) and then with water (500 mL) to give the title compound as a yellow solid (76.0 g, 70%): m/z 283 (M+H)$^+$ (ES$^+$).

2-Methoxy-N-(4-(4-nitronaphthalen-1-yloxy)pyridin-2-yl)acetamide

To a stirred suspension of 4-(4-nitronaphthalen-1-yloxy) pyridin-2-amine (71.8 g, 255 mmol) in dry DCM (1.1 L) and DIPEA (84.0 mL, 511 mmol), cooled in an ice bath, was added dropwise 2-methoxyacetyl chloride (35.0 mL, 383 mmol) over 20 min. The resulting red solution was stirred at RT for 1 hr and was then treated with a solution of NH$_3$ in MeOH (7 M, 100 mL). A precipitate formed immediately and the reaction mixture was stirred for a further 15 min and the volatiles were evaporated in vacuo. The solid residue was triturated with water (900 mL), collected by filtration and washed with water (2×250 mL) to give the title compound as a yellow solid (89.1 g, 96%): m/z 354 (M+H)$^+$ (ES$^+$).

N-(4-(4-Aminonaphthalen-1-yloxy)pyridin-2-yl)-2-methoxyacetamide

To a solution of 2-methoxy-N-(4-(4-nitronaphthalen-1-yloxy)pyridin-2-yl)acetamide (50.0 g, 142 mmol) in DMF (500 mL) under nitrogen was added palladium on carbon (10% w/w Pd/C, 5.0 g, 14.15 mmol) and the mixture was purged with hydrogen and maintained under a slight positive hydrogen atmosphere for 48 hr. The catalyst was removed by filtration through celite and the pad washed with DMF (2×100 mL) and then DCM (100 mL). The solvents were removed in vacuo to afford a dark brown residue which was treated with water (150 mL) and the mixture evaporated. Toluene (100 mL) was added and evaporated to remove residual water. After drying overnight under vacuum, the material was triturated from diethyl ether (250 mL) to give the title compound, Intermediate B1, as a green solid (43.3 g, 85%): m/z 324 (M+H)$^+$ (ES$^+$).

Intermediate E: 4-(4-aminonaphthalen-1-yloxy)pyridin-2-amine [Route 1]

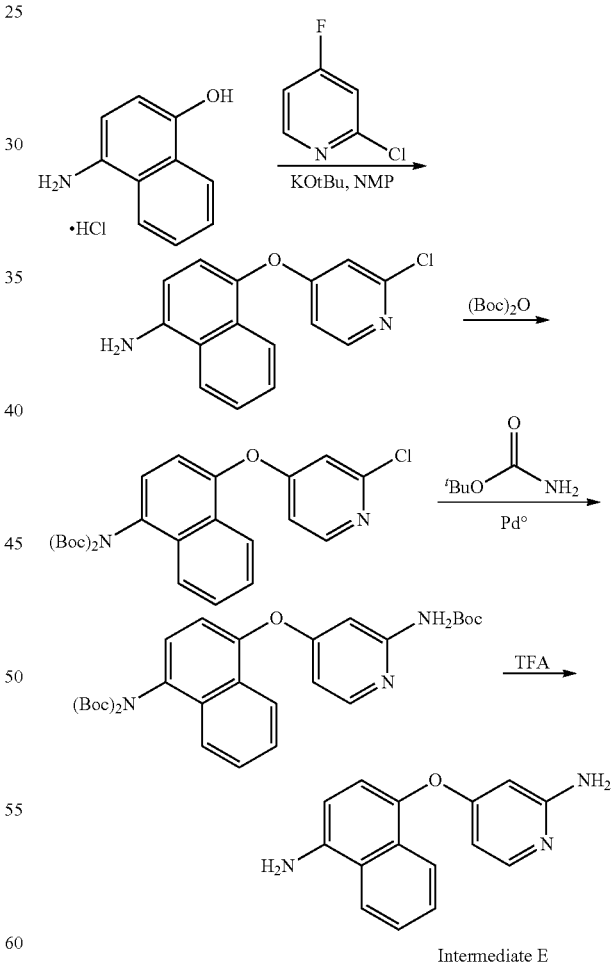

Intermediate E

4-(2-Chloropyridin-4-yloxy)naphthalen-1-amine

To a stirred solution of 2-chloro-4-fluoropyridine (1.26 g, 9.58 mmol) and 4-amino-1-naphthol hydrochloride (750 mg, 3.83 mmol) in NMP (40 mL) at −20° C. was added potassium tert-butoxide (1.290 g, 11.50 mmol). The reaction mixture was allowed to warm to RT and after 2.5 hr was diluted with water (100 mL) and extracted with EtOAc (100 mL then 2×80 mL). The combined organic extracts were washed with brine (150 mL), dried and evaporated in vacuo. The crude product was subjected to SCX capture and release eluting with 1% $NH_3$ in MeOH solution and the solvent was removed in vacuo to give the title compound as a brown solid (1.02 g, 92%): m/z 271 $(M+H)^+$ $(ES^+)$.

4-(2-Chloropyridin-4-yloxy)naphthalen-1-N,N-di-tert-butylcarbamate

To a stirred solution of 4-(2-chloropyridin-4-yloxy)naphthalen-1-amine (1.02 g, 3.76 mmol) in THF (30 mL) at 0° C. was added DMAP (34 mg, 0.282 mmol) and then di-tert-butyl dicarbonate (0.904 g, 4.14 mmol). The reaction mixture was stirred at 0° C. for 30 min, and then allowed to warm to RT. After 1.5 hr, the reaction mixture was cooled to 0° C., and further di-tert-butyl dicarbonate (0.904 g, 4.14 mmol) was added. The resulting mixture was stirred at 0° C. for 15 min and then at RT. After 16 hr the reaction mixture was diluted with water (40 mL) and extracted with EtOAc (2×40 mL). The combined organic extracts were washed with brine (75 mL), dried and evaporated in vacuo. The crude material was purified by flash column chromatography ($SiO_2$; 80 g, 0-40% EtOAc in iso-hexane, gradient elution) to give the title compound as a purple solid (0.892 g, 48%): m/z 471 $(M+H)^+$ $(ES^+)$.

tert-Butyl 4-(4-(N,N-di-tert-butylcarbamyl)naphthalen-1-yloxy)pyridin-2-ylcarbamate A mixture of 4-(2-chloropyridin-4-yloxy)naphthalen-1-N,N-di-tert-butylcarbamate (4) (0.892 g, 1.894 mmol), tert-butyl carbamate (0.666 g, 5.68 mmol), caesium carbonate (0.926 g, 2.84 mmol), $Pd_2(dba)_3$ (0.043 g, 0.047 mmol) and XantPhos (0.055 g, 0.095 mmol) was suspended in THF (10 mL). The reaction mixture was purged thoroughly with nitrogen, and then heated at reflux. After 15 hr the mixture was cooled to RT, diluted with water (35 mL) and extracted with EtOAc (35 mL, 25 mL). The combined organic extracts were washed with brine (50 mL), dried and evaporated in vacuo. The crude material was purified by flash column chromatography ($SiO_2$; 80 g, 0-30% EtOAc in iso-hexane, gradient elution) to give the title compound as a white solid (289 mg, 28%): m/z 552 $(M+H)^+$ $(ES^+)$.

Intermediate E:
4-(4-Aminonaphthalen-1-yloxy)pyridin-2-amine

To a stirred solution of tert-butyl 4-(4-(N,N-di-tert-butylcarbamyl)naphthalen-1-yloxy)pyridin-2-ylcarbamate (289 mg, 0.524 mmol) in DCM (8 mL), at 0° C., was added TFA (4 mL). The resulting mixture was stirred while slowly warming to RT. After 5 hr, the volatiles were removed in vacuo and the residue was taken up in MeOH (5 mL) and subjected to SCX capture and release eluting with 1% $NH_3$ in MeOH solution. The solvent was removed in vacuo to the title compound Intermediate E (116 mg, 85%) as a brown-orange oil: m/z 252 $(M+H)^+$ $(ES^+)$.

Intermediate E:
4-(4-aminonaphthalen-1-yloxy)pyridin-2-amine
[Route 2]

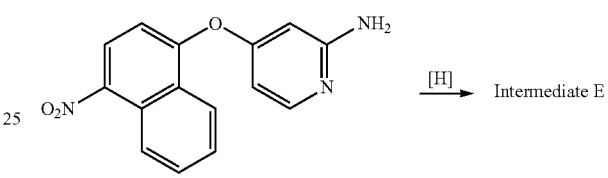

A solution of 4-(4-nitronaphthalen-1-yloxy)pyridin-2-amine (2.00 g, 7.11 mmol) in a mixture of methanol (70 mL), DCM (70 mL) and acetic acid (5 mL) was subjected to hydrogenation by passage through a Thales H-cube (1.0 mL min$^{-1}$, RT, 55 mm 10% Pt/C Cat-Cart, full hydrogen mode) and was then evaporated in vacuo. The residue was taken up into DCM (100 mL), and was washed with sat. $NaHCO_3$ (100 mL) and brine (100 mL) and then dried ($MgSO_4$) and evaporated in vacuo. The crude product was purified by flash column chromatography ($SiO_2$, 80 g, EtOAc in isohexane, 20 to 80%, gradient elution) to afford the title compound, Intermediate E as a brown solid (1.70 g, 85%); R$^t$ 1.04 min (Method 2); m/z 252 $(M+H)^+$ $(ES^+)$.

Example 1

N-(4-(4-(3-(3-tert-Butyl-1-p-tolyl-1H-pyrazol-5-yl)ureido)naphthalen-1-yloxy)pyridin-2-yl)-2-(2-methoxyethoxy)acetamide

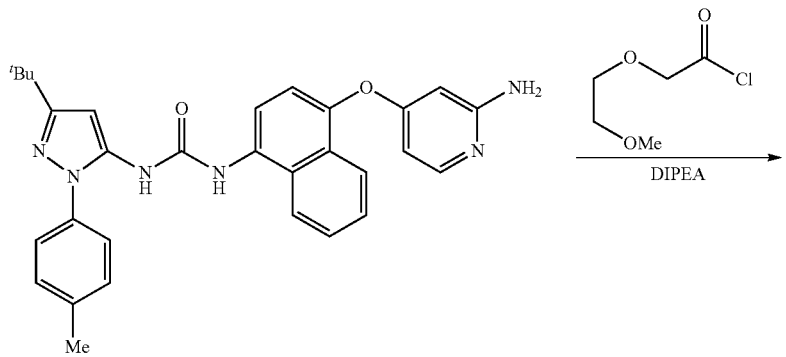

Intermediate A1

-continued

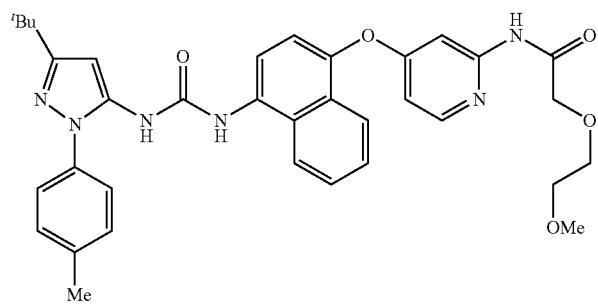

Example 1

To a solution of Intermediate A1 (50 mg, 0.099 mmol) and DIPEA (86 μl, 0.493 mmol) in dry THF (3.0 mL) at 0° C. under nitrogen was added dropwise 2-(2-methoxyethoxy) acetyl chloride (60.2 mg, 0.395 mmol) and the reaction mixture maintained at 0° C. for 30 min and then warmed to RT. After 3 hr the reaction was quenched by the addition of 1% $NH_3$ in MeOH solution (2.0 mL) and after further 45 min the resulting mixture was evaporated in vacuo. The residue was purified by flash column chromatography ($SiO_2$, 12 g, [5% MeOH in EtOAc] in isohexane, 0 to 75%, gradient elution) to afford the title compound, Example 1 as a white solid (40 mg, 62%); $R^t$ 2.56 min (Method 2); m/z 623 (M+H)$^+$ (ES$^+$); $^1$H NMR (400 MHz, DMSO-$d_6$) δ: 1.28 (9H, s), 2.40 (3H, s), 3.27 (3H, s), 3.47 (2H, m), 3.62 (2H, m), 4.05 (2H, s), 6.41 (1H, s), 6.71 (1H, dd), 7.35-7.38 (3H, overlapping m), 7.46 (2H, m), 7.57 (1H, m), 7.64-7.66 (2H, overlapping m), 7.84 (1H, dd), 7.97 (1H, d), 8.09 (1H, d), 8.20 (1H, d), 8.79 (1H, br s), 9.12 (1H, br s), 9.95 (1H, br s).

Example 2

N-(4-(4-(3-(3-tert-Butyl-1-p-tolyl-1H-pyrazol-5-yl) ureido)naphthalen-1-yloxy)pyridin-2-yl)tetrahydro-2H-pyran-4-carboxamide

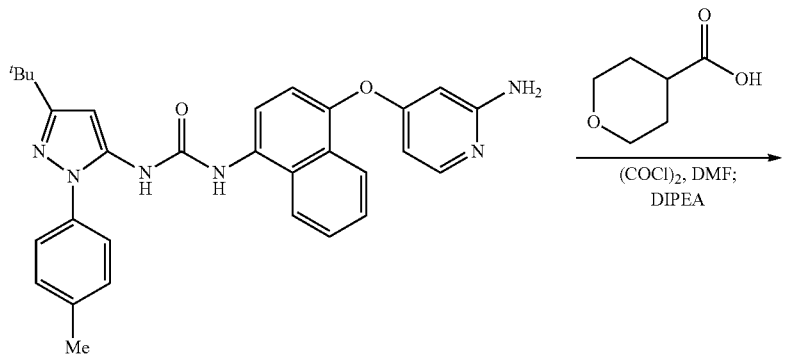

Intermediate A1

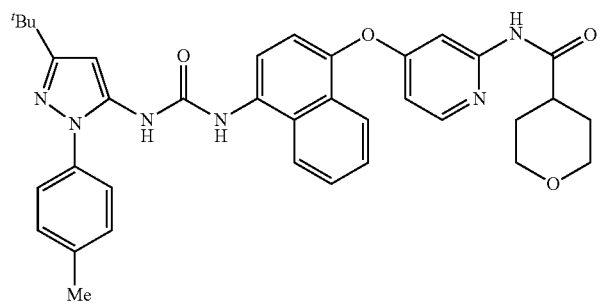

Example 2

To a suspension of tetrahydro-2H-pyran-4-carboxylic acid (38.5 mg, 0.296 mmol) in dry DCM (3.0 mL) under nitrogen at 0° C. was added oxalyl chloride (29.2 µl, 0.345 mmol) followed by DMF (1 drop) and the mixture maintained at 0° C. for 20 min and then warmed to RT. After 1 hr the mixture was cooled to 0° C., and Intermediate A1 (50 mg, 0.099 mmol) and DIPEA (86 µl, 0.493 mmol) were added. The reaction mixture was kept at 0° C. for 30 min and was then warmed to RT and after 2.25 hr was quenched by the addition of a solution of 1% NH$_3$ in MeOH (2.0 mL). After a further 30 min the resulting mixture was evaporated in vacuo and the residue was subjected to SCX capture and release. The crude product so obtained was purified by flash column chromatography (SiO$_2$, 12 g, [5% MeOH in EtOAc] in isohexane, 0-85%, gradient elution) to afford the title compound, Example 2, as a white solid (25 mg, 41%); R$^t$ 2.43 min (Method 2); m/z 619 (M+H)$^+$ (ES$^+$); $^1$H NMR (400 MHz, DMSO-d$_6$) δ: 1.29 (9H, s), 1.48-1.64 (4H, overlapping m), 2.40 (3H, s), 2.68 (1H, m), 3.27 (2H, dt), 3.84 (2H, m), 6.41 (1H, s), 6.71 (1H, dd), 7.33 (1H, d), 7.38 (2H, d) 7.47 (2H, d), 7.57 (1H, m), 7.65 (1H, m), 7.67 (1H, d), 7.84 (1H, dd), 7.97 (1H, d), 8.09 (1H, d), 8.18 (1H, d), 8.62 (1H, br s), 9.14 (1H, br s), 10.49 (1H, br s).

Example 3

N-(4-(4-(3-(3-tert-Butyl-1-p-tolyl-1H-pyrazol-5-yl)ureido)naphthalen-1-yloxy)pyridin-2-yl)-2-(methylthio)acetamide

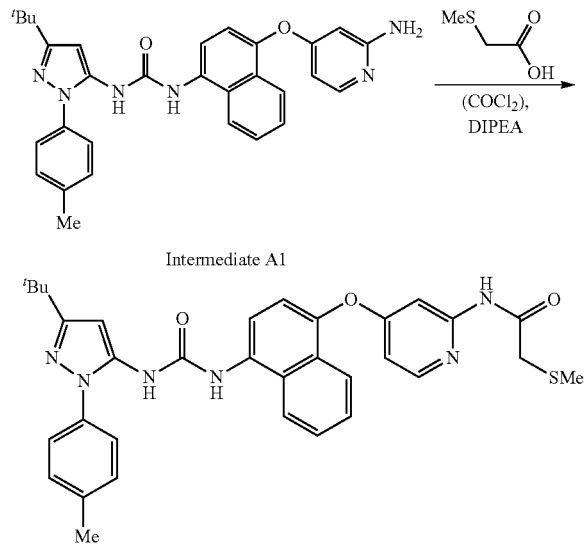

Example 3

To a solution of 2-(methylthio)acetic acid (28.4 µl, 0.326 mmol) in dry DCM (3.0 mL) under nitrogen and at 0° C. was added oxalyl chloride (32.2 µL, 0.380 mmol) followed by DMF (1 drop) and the mixture maintained at 0° C. for 20 min and then warmed to RT. After 1 hr the mixture was cooled to 0° C. and Intermediate A1 (55 mg, 0.109 mmol) and DIPEA (95 µL, 0.543 mmol) were added. The reaction mixture was kept at 0° C. for 30 min and then warmed to RT and after 3 hr was quenched by the addition of a solution 1% NH$_3$ in MeOH (3.0 mL). After a further 16 hr the resulting mixture was evaporated in vacuo and the residue was purified by flash column chromatography (SiO$_2$, 12 g, [5% MeOH in EtOAc] in isohexane, 0-60%, gradient elution). The product so obtained was subjected to SCX capture and release then repurified by flash column chromatography (SiO$_2$, 12 g, [5% MeOH in EtOAc] in isohexane, 0-55%, gradient elution) to afford the title compound, Example 3, as a white solid (12 mg, 18%); R$^t$ 2.57 min (Method 2); m/z 595 (M+H)$^+$ (ES$^+$); $^1$H NMR (400 MHz, DMSO-d$_6$) δ: 1.28 (9H, s), 2.09 (3H, s), 2.40 (3H, s), 3.27 (2H, s), 6.41 (1H, s), 6.66 (1H, dd), 7.34 (1H, d), 7.38 (2H, d), 7.47 (2H, m), 7.57 (1H, m), 7.63-7.67 (2H, overlapping m), 7.84 (1H, dd), 7.97 (1H, d), 8.09 (1H, d), 8.18 (1H, d), 8.82 (1H, br s), 9.15 (1H, br s), 10.62 (1H, br s).

Example 4

N-(4-(4-(3-(3-tert-Butyl-1-p-tolyl-1H-pyrazol-5-yl)ureido)naphthalen-1-yloxy)pyridin-2-yl)-3-methoxypropanamide: RV001148

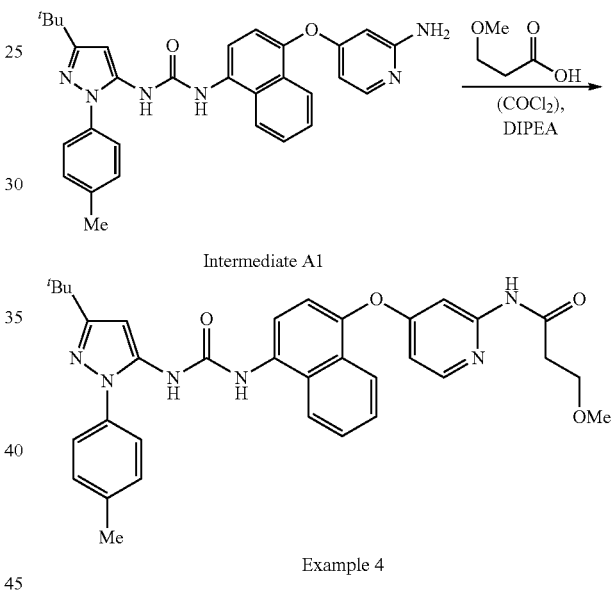

Example 4

To a solution of 3-methoxypropionic acid (30.6 µL, 0.326 mmol) in dry DCM (3.0 mL) under nitrogen at 0° C. was added oxalyl chloride (32.2 µL, 0.380 mmol) followed by DMF (1 drop). The mixture was maintained at 0° C. for 20 min and was then warmed to RT. After 1 hr, the mixture was cooled to 0° C., and Intermediate A1 (55 mg, 0.109 mmol) and DIPEA (95 µl, 0.543 mmol) were added and the reaction mixture kept at 0° C. for 30 min and then warmed to RT. After 2 hr the reaction was quenched by addition of a solution of 1% NH$_3$ in MeOH (3.0 mL) and after a further 16 hr was evaporated in vacuo. The residue was purified by flash column chromatography (SiO$_2$, 12 g, [5% MeOH in EtOAc] in isohexane, 0-70%, gradient elution) to afford the title compound, Example 4, as a white solid (35 mg, 53%); R$^t$ 2.43 min (Method 2); m/z 593 (M+H)$^+$ (ES$^+$); $^1$H NMR (400 MHz, DMSO-d$_6$) δ: 1.28 (9H, s), 2.40 (3H, s), 2.55 (2H, t), 3.18 (3H, s), 3.51 (2H, t), 6.41 (1H, s), 6.70 (1H, dd), 7.33 (1H, d), 7.38 (2H, d), 7.47 (2H, m), 7.57 (1H, m), 7.64-7.66 (2H, overlapping m), 7.84 (1H, dd), 7.97 (1H, d), 8.09 (1H, d), 8.18 (1H, d), 8.81 (1H, br s), 9.13 (1H, br s), 10.53 (1H, br s).

Example 5

N-(4-(4-(3-(3-tert-Butyl-1-p-tolyl-1H-pyrazol-5-yl)ureido)naphthalen-1-yloxy)pyridin-2-yl)-2-hydroxy-acetamide

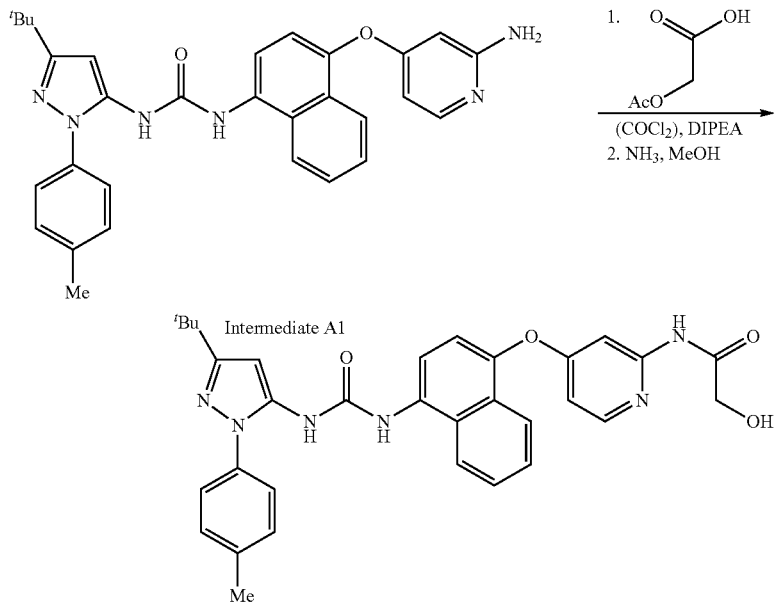

Example 5

To a suspension of acetoxyacetic acid (34.3 mg, 0.290 mmol) in dry DCM (1.5 mL) under nitrogen and at 0° C. was added oxalyl chloride (28.6 µl, 0.339 mmol) followed by DMF (1 drop) and the mixture maintained at 0° C. for 20 min and then warmed to RT. After 1 hr the mixture was cooled to 0° C., and a solution of Intermediate A1 (49 mg, 0.097 mmol) and DIPEA (84 µl, 0.484 mmol) were added. The reaction mixture was kept at 0° C. for 30 min and was then warmed to RT and after 2.75 hr was quenched by addition of a solution of 1% NH$_3$ in MeOH (3.0 mL). After a further 64 hr the volatiles were evaporated in vacuo and the residue was purified by flash column chromatography (SiO$_2$, 12 g, [5% MeOH in EtOAc] in isohexane, 0-70%, gradient elution). The product so obtained was subjected to SCX capture and release and was then re-purified by flash column chromatography (SiO$_2$, 12 g, [5% MeOH in EtOAc] in isohexane, 0-70%, gradient elution) to afford the title compound, Example 5, as a white solid (11 mg, 20%); R$^t$ 2.25 min (Method 2); m/z 565 (M+H)$^+$ (ES$^+$); $^1$H NMR (400 MHz, DMSO-d$_6$) δ: 1.28 (9H, s), 2.40 (3H, s), 3.96 (2H, d), 5.64 (1H, t), 6.41 (1H, s), 6.72 (1H, dd), 7.35 (1H, d), 7.38 (2H, d), 7.47 (2H, m), 7.57 (1H, m), 7.65 (2H, m), 7.83 (1H, dd), 7.97 (1H, d), 8.09 (1H, d), 8.19 (1H, d), 8.81 (1H, br s), 9.14 (1H, br s), 9.75 (1H, br s).

3-Isopropyl-1-p-tolyl-1H-pyrazol-5-amine

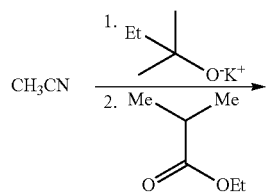

-continued

To a mixture of acetonitrile (0.50 mL, 9.57 mmol) in THF (30 ml) at RT was added potassium 2-methylbutan-2-olate (1.7M solution in 2-methyl-butan-2-ol, 16.9 mL, 28.7 mmol). On completion of the addition ethyl isobutyrate (5.12 mL, 38.3 mmol) was added dropwise and the mixture was maintained at RT for 16 hr. The reaction mixture was concentrated in vacuo to ca 20 mL, was diluted with ethanol (20 mL) and p-tolylhydrazine hydrochloride (1.52 g, 9.57 mmol) was added. The resulting mixture was acidified to pH1 by the addition of conc. hydrochloric acid and the mixture was then heated to 70° C. for 2 hr. The mixture was cooled to RT and was concentrated in vacuo to ca 20 mL and then diluted with water (30 mL). The aq. mixture was adjusted to pH12 by the addition of aq NaOH solution (6M) and was then extracted with EtOAc (2×20 mL). The combined organic extracts were washed with brine (30 mL) and then dried (MgSO$_4$) and evaporated in vacuo to afford the title compound as a brown oil (1.78 g, 90% pure, 72%); R$^t$ 1.32 min (Method 2); m/z 216 (M+H)$^+$ (ES$^+$). This material was used directly in the next step, without further purification.

Example 6

N-(4-(4-(3-(3-Isopropyl-1-p-tolyl-1H-pyrazol-5-yl)ureido)naphthalen-1-yloxy)pyridin-2-yl)-2-methoxy-acetamide 3-Ethyl-1-p-tolyl-1H-pyrazol-5-amine

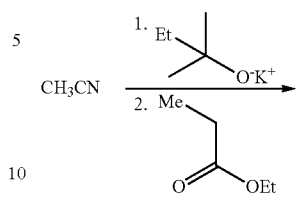

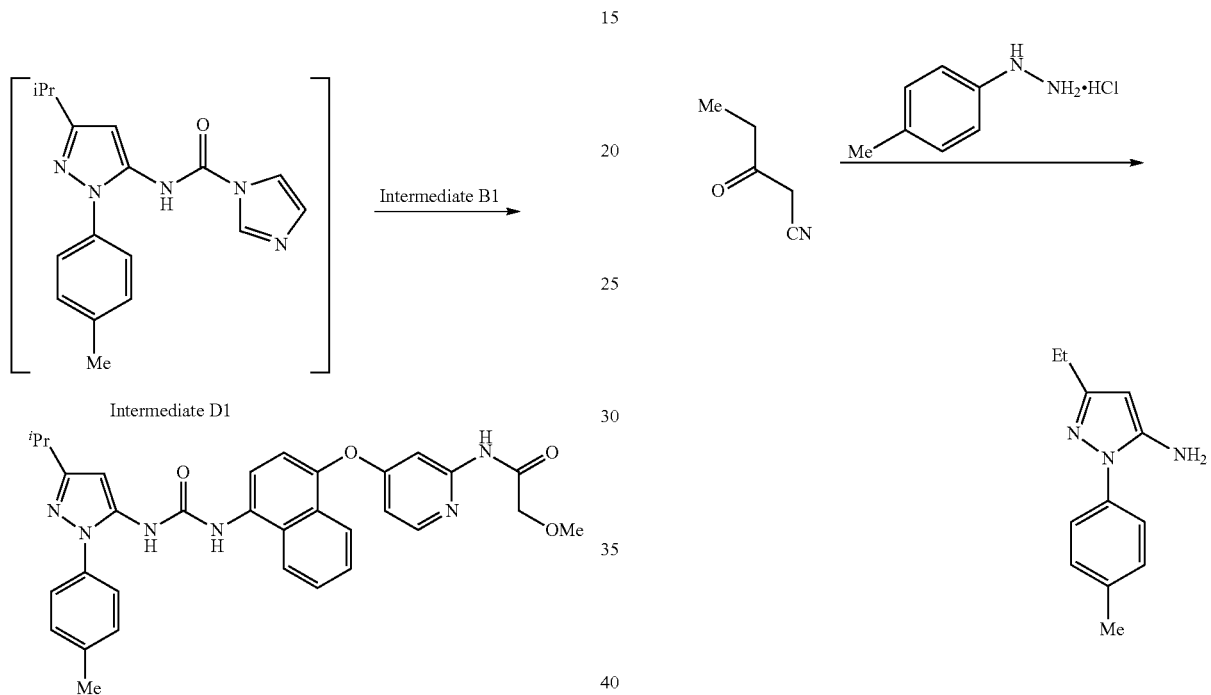

Example 6

To a stirred suspension of CDI (113 mg, 0.696 mmol) in DCM (2 mL) was added 3-isopropyl-1-p-tolyl-1H-pyrazol-5-amine. (176 mg, 90% pure, 0.737 mmol) and the mixture maintained at RT for 3 hr. A solution of Intermediate B1 (90 mg, 0.278 mmol) in DCM (1.2 mL) was added and the reaction mixture kept at RT for a further 16 hr and was then partitioned between DCM (15 mL), and water (15 mL). The organic layer was separated and was washed with brine (15 ml) then dried (MgSO$_4$) and evaporated in vacuo. The residue was purified by flash column chromatography (SiO$_2$, EtOAc in isohexane, 30-100%, gradient elution) and then by trituration (EtOAc followed by MeOH) to afford the title compound, Example 6, as a pale pink solid (32 mg, 20%); R$^t$ 4.80 min (Method 1 basic); m/z 565 (M+H)$^+$ (ES$^+$); $^1$H NMR (400 MHz, DMSO-d$_6$) δ: 1.24 (6H, d), 2.40 (3H, s), 2.89 (1H, m), 3.30 (3H, s), 3.99 (2H, s), 6.37 (1H, s), 6.70 (1H, dd), 7.34 (1H, d), 7.38 (2H, d), 7.46 (2H, d), 7.57 (1H, m), 7.63-7.674 (2H, overlapping m), 7.84 (1H, d), 7.97 (1H, d), 8.09 (1H, d), 8.19 (1H, d), 8.81 (1H, s), 9.13 (1H, s), 10.04 (1H, s)

To a solution of acetonitrile (0.50 mL, 9.57 mmol) in THF (30 ml) at RT was added potassium 2-methylbutan-2-olate (1.7M solution in 2-methyl-butan-2-ol, 16.9 mL, 28.7 mmol). On completion of the addition ethyl propionate (4.40 mL, 38.3 mmol) was added dropwise and the mixture was maintained at RT for 16 hr. The reaction mixture was concentrated in vacuo to ca 20 mL, was diluted with ethanol (20 mL) and p-tolylhydrazine hydrochloride (1.52 g, 9.57 mmol) was added. The resulting mixture was acidified to pH1 by the addition of conc. hydrochloric acid and the mixture was then heated to 70° C. for 2 hr. The mixture was cooled to RT, was concentrated in vacuo to ca 20 mL and diluted with water (30 mL). The aqueous mixture was adjusted to pH12 by the addition of aq NaOH solution (6M) and was then extracted with diethyl ether (2×20 mL). The organic extracts were combined, washed with brine (30 mL), dried (MgSO$_4$) and evaporated in vacuo. The residue was purified by flash column chromatography (SiO$_2$, EtOAc in isohexane, 0-50%, gradient elution) to afford the title compound as a pale brown solid (1.42 g, 72%); R$^t$ 3.30 min (Method 1 basic); m/z 202 (M+H)$^+$ (ES$^+$);

Example 7

N-(4-(4-(3-(3-Ethyl-1-p-tolyl-1H-pyrazol-5-yl)ureido)naphthalen-1-yloxy)pyridin-2-yl)-2-methoxyacetamide

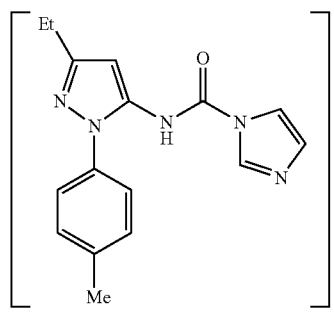

Intermediate D2 → Intermediate B1

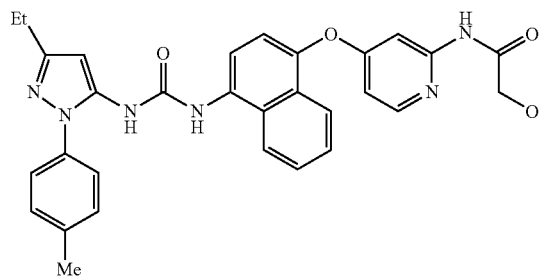

Example 7

To a suspension of CDI (113 mg, 0.696 mmol) in DCM (2.0 mL) at RT was added 3-ethyl-1-p-tolyl-1H-pyrazol-5-amine (140 mg, 0.696 mmol) and after 3 hr a solution of Intermediate B1 (120 mg, 0.371 mmol) in DCM (1.6 mL) was added. The reaction mixture was maintained at RT for a further 16 hr and was then partitioned between DCM (15 mL), and water (15 mL). The organic layer was separated and was washed with brine (15 ml), dried (MgSO$_4$) and evaporated in vacuo. The residue was purified by flash column chromatography (SiO$_2$, EtOAc in isohexane, 30-100%, gradient elution) and then by trituration with MeOH to afford the title compound, Example 7, as a pale pink solid (90 mg, 35%); R$^t$ 4.64 min (Method 1 basic); m/z 551 (M+H)$^+$ (ES$^+$); $^1$H NMR (400 MHz, DMSO-d$_6$) δ: 1.21 (3H, t), 2.40 (3H, s), 2.57 (2H, q), 3.30 (3H, s), 3.99 (2H, s), 6.36 (1H, s), 6.70 (1H, d), 7.33-7.39 (3H, overlapping m), 7.46 (2H, d), 7.57 (1H, t), 7.63-7.67 (2H, overlapping m), 7.84 (1H, d), 7.97 (1H, d), 8.09 (1H, d), 8.18 (1H, d), 8.82 (1H, s), 9.13 (1H, s), 10.05 (1H, s).

Example 8

N-(4-(4-(3-(3-tert-Butyl-1-p-tolyl-1H-pyrazol-5-yl)ureido)naphthalen-1-yloxy)pyridin-2-yl)-2-methoxyacetamide

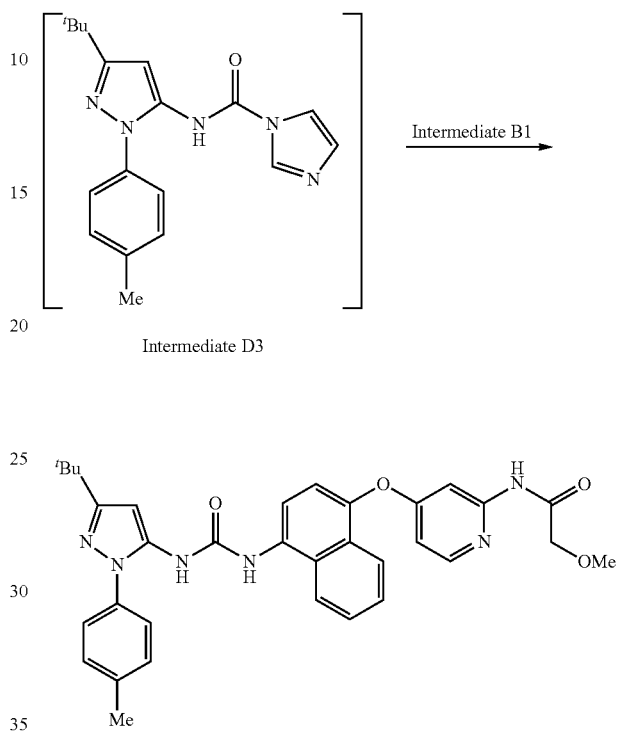

Example 8

To a suspension of CDI (32.5 g, 200 mmol) in dry DCM (300 mL) was added 3-tert-butyl-1-p-tolyl-1H-pyrazol-5-amine (WO 2000/043384) (46.0 g, 200 mmol) portionwise over 1 hr and the mixture was stirred at RT for 2 hr, over which time a yellow solution was formed. An aliquot of this solution (220 mL), containing Intermediate D3, was added dropwise over 20 min to a solution of Intermediate B1 (40.0 g, 111 mmol) in DCM (600 mL) The reaction mixture was stirred at RT for 18 hr and ethanol (50.0 mL) was added. After a further 1.5 hr the solvent was removed in vacuo to yield a purple oil which was dissolved in EtOAc (1.0 L) and washed sequentially with sat. NaHCO$_3$ solution (2×250 mL), water (2×250 mL) and brine (2×200 mL) and was then dried (MgSO$_4$). The solvent was removed in vacuo to yield a dark red viscous oil (75 g). which was purified through a silica plug (silica gel 60, 500 g, [EtOAc in isohexane, 20-100%, gradient elution) to provide a brown solid (64.5 g). This material was combined with a second batch (129 g in total) which was re-crystallised from a mixture of isohexane/EtOAc (2:5, 4.0 L) to give the title compound, Example 8, (101 g, 78% recovery); m/z 579 (M+H)$^+$ (ES$^+$); $^1$H NMR (400 MHz, DMSO-d$_6$) δ: 1.29 (9H, s), 2.40 (3H, s), 3.31 (3H, s), 3.99 (2H, s), 6.41 (1H, s), 6.70 (1H, dd), 7.33-7.39 (3H, m), 7.46-7.48 (2H, m), 7.58 (1H, ddd), 7.63-7.67 (2H, m), 7.84 (1H, dd), 7.97 (1H, d), 8.10 (1H, d), 8.19 (1H, d), 8.79 (1H, s), 9.13 (1H, s), 10.03 (1H, s).

3-(1-(Benzyloxy)-2-methylpropan-2-yl)-1-p-tolyl-1H-pyrazol-5-amine

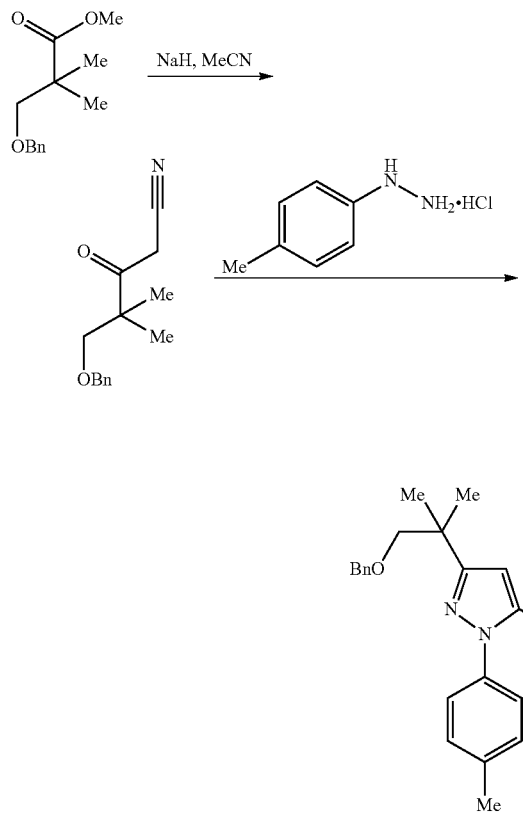

Example 9

N-(4-(4-(3-(3-(1-Hydroxy-2-methylpropan-2-yl)-1-p-tolyl-1H-pyrazol-5-yl)ureido)naphthalen-1-yloxy)pyridin-2-yl)-2-methoxyacetamide

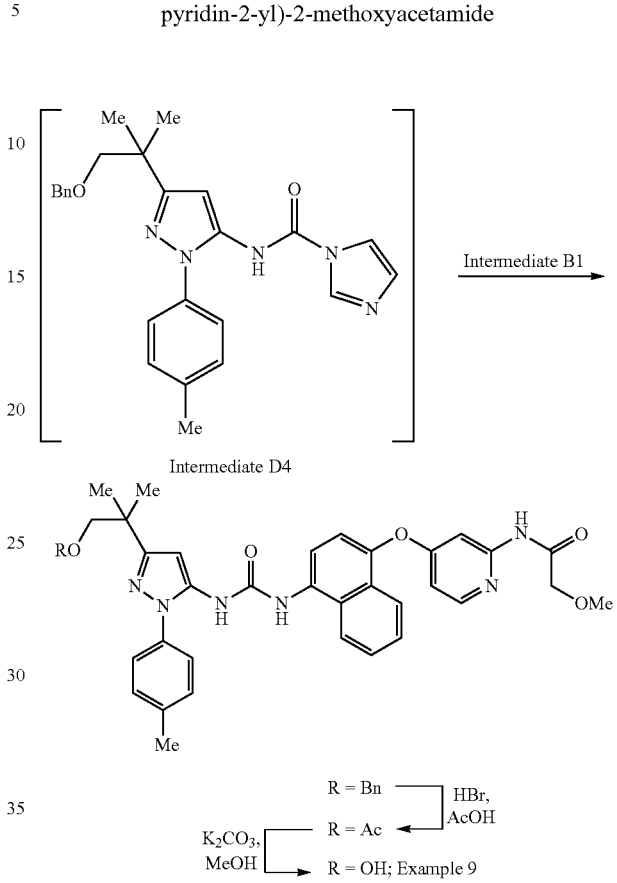

To a suspension of sodium hydride (1.62 g of a 60% w/w dispersion in mineral oil, 40.5 mmol) in toluene (20 mL) at reflux was added a solution of methyl 3-(benzyloxy)-2,2-dimethylpropanoate [*Eur. J. Org. Chem.*, 2007 (6) 934-942] (6.00 g, 27.0 mmol) and acetonitrile (2.12 ml, 40.5 mmol) in toluene, dropwise over 1 hr. The reaction mixture was heated for a further 5 hr at reflux then cooled to RT. The mixture was acidified to pH 4 with aqueous hydrochloric acid (1M) and extracted with EtOAc. The organic extract was washed with water and with brine then dried (MgSO$_4$) and evaporated in vacuo to afford 5-(benzyloxy)-4,4-dimethyl-3-oxopentanenitrile as a yellow oil (7.50 g, 96%): m/z 232 (M+H)$^+$ (ES$^+$), which was used without purification in the next step.

A solution of p-tolylhydrazine hydrochloride (1.99 g, 12.6 mmol) and 5-(benzyloxy)-4,4-dimethyl-3-oxopentanenitrile (4.00 g, 13.8 mmol, 80% purity) in EtOH was heated at reflux for 16 hr and then cooled to RT. The mixture was neutralized with saturated aqueous NaHCO$_3$ solution and extracted with EtOAc. The organic extracts were washed with brine, dried (MgSO$_4$) and evaporated in vacuo. The residue was purified by flash column chromatography (SiO$_2$, 80 g, MeOH in DCM, 0-5%, gradient elution) to afford the title compound, (2.62 g, 60%); R$^t$ 3.05 min (Method 1 basic); m/z 336 (M+H)$^+$ (ES$^+$).

To a suspension of CDI (94 mg, 0.580 mmol) in DCM (1.0 mL) was added a solution of 3-(1-(benzyloxy)-2-methylpropan-2-yl)-1-p-tolyl-1H-pyrazol-5-amine (195 mg, 0.580 mmol) in DCM (1.0 mL) and the mixture maintained at RT for 5 hr. A solution of Intermediate B1 (100 mg, 0.309 mmol) in DCM (1.6 mL) was added and the reaction mixture was kept at RT for a further 16 hr. An additional portion of pyrazole CDI adduct, Intermediate D3, [prepared from CDI (30 mg, 0.18 mmol) and the pyrazole (60 mg, 0.18 mmol)] was added and the mixture maintained at RT for 24 hr and then partitioned between DCM (15 mL), and water (15 mL). The organic layer was washed with brine (15 ml), and was dried (MgSO$_4$) and evaporated in vacuo. The residue was purified by flash column chromatography (SiO$_2$, EtOAc in isohexane, 30-100%, gradient elution) and then by trituration from methanol to afford N-(4-(4-(3-(3-(1-(benzyloxy)-2-methylpropan-2-yl)-1-p-tolyl-1H-pyrazol-5-yl)ureido)naphthalen-1-yloxy)pyridin-2-yl)-2-methoxyacetamide as a pale pink solid (110 mg, 40%); R$^t$ 2.86 min (Method 2); m/z 685 (M+H)$^+$ (ES$^+$). This material was used directly in the next step (below).

To a solution of the benzyl ether, obtained above, (98 mg, 0.143 mmol) in acetic acid (3.0 mL) was added a solution of HBr in acetic acid (45% w/v, 181 μL, 1.431 mmol) and the reaction mixture maintained at RT for 16 hr. The mixture was diluted with water (15 mL) and was basified to pH9 (2M NaOH) and extracted with ethyl acetate (2×15 mL). The organic extracts were combined, washed with brine (15 mL), dried (MgSO$_4$) and evaporated in vacuo. The residue was purified by flash column chromatography (SiO$_2$, EtOAc in isohexane, 30-100%, gradient elution) to afford 2-(5-(3-(4-(2-(2-methoxyacetamido)pyridin-4-yloxy)naphthalen-1-yl)ureido)-1-p-tolyl-1H-pyrazol-3-yl)-2-methylpropyl acetate as a pale pink solid (65 mg, 70%); R$^t$ 4.74 min (Method 1 basic); m/z 637 (M+H)$^+$ (ES$^+$). This material was used directly in the next step (below).

To a solution of the acetate, obtained above, (54 mg, 0.085 mmol) in methanol (2.0 mL) was added a solution of potassium carbonate (23.4 mg, 0.170 mmol) in water (0.5 mL) and the reaction mixture maintained at RT for 3 hr. Additional potassium carbonate (11.7 mg, 0.085 mmol) was added and after a further 1 hr the methanol was evaporated in vacuo and water (10 mL) was added. The mixture was extracted with EtOAc (2×10 mL) and the combined organic extracts were washed with brine (10 mL), then dried (MgSO$_4$) and evaporated in vacuo. The residue was purified by flash column chromatography (SiO$_2$, EtOAc in isohexane, 30-100%, gradient elution) to afford N-(4-(4-(3-(3-(1-hydroxy-2-methylpropan-2-yl)-1-p-tolyl-1H-pyrazol-5-yl)ureido)naphthalen-1-yloxy)pyridin-2-yl)-2-methoxyacetamide, Example 9, as a pale pink solid (33 mg, 65%); R$^t$ 4.50 min (Method 1 basic); m/z 595 (M+H)$^+$ (ES$^+$); $^1$H NMR (400 MHz, DMSO-d$_6$) δ: 1.21 (6H, s), 2.39 (3H, s), 3.29 (3H, s), 3.44 (2H, d), 3.98 (2H, s), 4.61 (1H, t), 6.41 (1H, s), 6.70 (1H, d), 7.33-7.39 (3H, overlapping m), 7.46 (2H, d), 7.57 (1H, t), 7.63-7.66 (2H, overlapping m), 7.83 (1H, d), 7.96 (1H, d), 8.08 (1H, d), 8.18 (1H, d), 8.81 (1H, s), 9.12 (1H, s), 10.06 (1H, s).

3-tert-Butyl-1-(2,3,5,6-tetradeutero-4-(trideuteromethyl)phenyl)-1H-pyrazol-5-amine

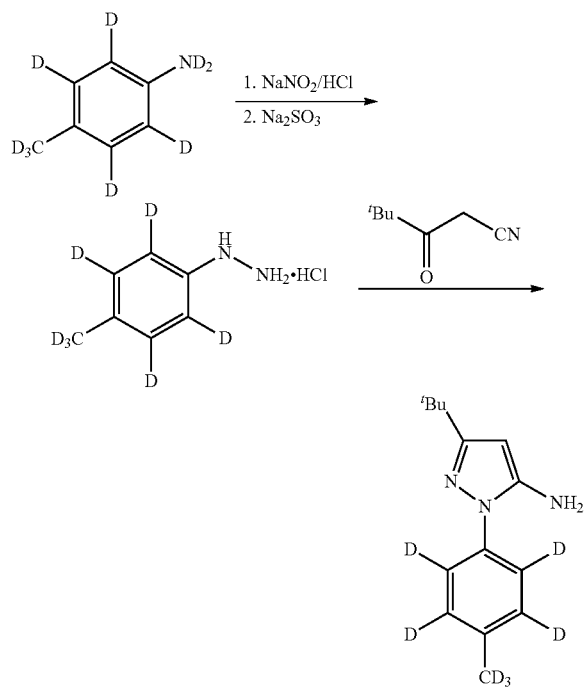

To a stirred solution of nonadeutero-4-toluidine (3.69 g, 31.8 mmol) in AcOH (25 mL) and hydrochloric acid (1M, 12 mL) at 0° C. was added, dropwise, a solution of sodium nitrite (2.52 g, 36.5 mmol) in water (12 mL). The reaction mixture was stirred at 0° C. for 30 min and then added slowly to a solution of sodium sulfite (9.21 g, 73.0 mmol) in water (20 mL) at 0° C. The mixture was stirred at 0° C. for 30 min then warmed to RT and hydrochloric acid (1M 20 mL) was added. After 16 hr at RT the reaction mixture was concentrated in vacuo, resulting in the formation of a precipitate after removal of approximately 20 mL of water. To the mixture was added Et$_2$O (100 mL) and the solid was collected by filtration and was washed with Et$_2$O (200 mL) and then with isohexane to afford 2,3,5,6-tetradeutero-4-(trideuteromethyl)phenylhydrazine hydrochloride as a pale yellow solid (4.87 g, 70%); R$^t$ 2.49 min (Method 1, basic); m/z not observed.

A solution of 4,4-dimethyl-3-oxopentanenitrile (3.64 g, 29.1 mmol) and 2,3,5,6-tetradeutero-4-(trideuteromethyl)phenylhydrazine hydrochloride (4.87 g, 26.5 mmol) in a mixture of hydrochloric acid (2.91 mL, 10M, 29.1 mmol) and EtOH (15 mL) was heated to reflux for 16 hr. The reaction mixture was cooled to RT and was then basified to pH12 with 2M NaOH solution (ca 100 mL) with cooling (ice-water bath) such that the internal temperature was maintained at 20-25° C. The mixture was extracted with Et$_2$O (200 mL) and the ether extract was washed with water (2×200 mL). The aqueous washes were combined and extracted with ether (200 mL) and the combined ether extracts were washed with brine (2×200 mL), and then dried (MgSO$_4$) and evaporated in vacuo. The residue was recrystallized from isohexane (50 mL) to afford an impure sample of the title compound (1.5 g). A portion of this material (800 mg) was purified by flash column chromatography (SiO$_2$, 40 g, EtOAc in isohexane, 0-30%, gradient elution) to afford the title compound as a yellow solid (400 mg, 6%); R$^t$ 4.16 min (Method 1, basic); m/z 237 (M+H)$^+$ (ES$^+$).

Example 10

N-(4-(4-(3-(3-tert-butyl-1-(2,3,5,6-tetradeutero-4-(trideuteromethyl)phenyl)-1H-pyrazol-5-yl)ureido)naphthalen-1-yloxy)pyridin-2-yl)-2-methoxyacetamide

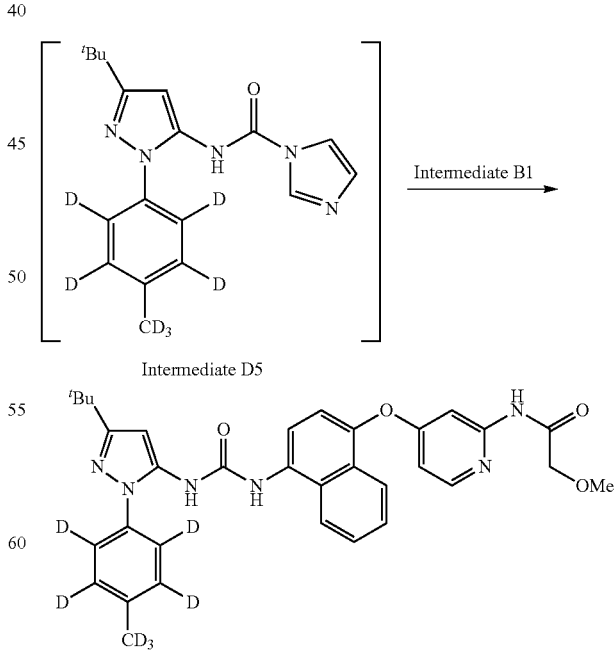

Example 10

To a stirred suspension of CDI (144 mg, 0.888 mmol) in DCM (1.0 mL) was added a solution of 3-tert-butyl-1-(2,3,5,6-tetradeutero-4-(trideuteromethyl)phenyl)-1H-pyrazol-5-amine (210 mg, 0.888 mmol) in DCM (2.0 mL) over 1 hr and the reaction mixture maintained at RT for 1 hr. A solution of Intermediate B1 (180 mg, 0.557 mmol) in DCM (1.0 mL) was added in one portion to the mixture and after a further 1 hr MeOH (0.5 mL) was added and the reaction mixture was concentrated (to ~1 mL) in vacuo. The residue was purified by flash column chromatography (SiO$_2$, 40 g, EtOAc in isohexane, 0-100%, gradient elution) and then recrystallized from heptane/EtOAc to afford the title compound, Example 10, as an off white solid (125 mg, 45%); R$^t$ 5.18 (Method 1, basic); m/z 587 (M+H)$^+$ (ES$^+$); $^1$H NMR (400 MHz, DMSO-d$_6$) δ: 1.29 (9H, s), 3.31 (3H, s), 3.99 (2H, d), 6.42 (1H, s), 6.69 (1H, dd), 7.34 (1H, d), 7.59 (1H, m), 7.65 (2H, m), 7.84 (1H, d), 7.97 (1H, d), 8.09 (1H, d), 8.18 (1H, d), 8.79 (1H, s), 9.13 (1H, s), 10.02 (1H, s).

Additional examples of the disclosure were prepared by a process in which an Intermediate A was converted into an Intermediate F followed by the reaction of Intermediate F with an amine.

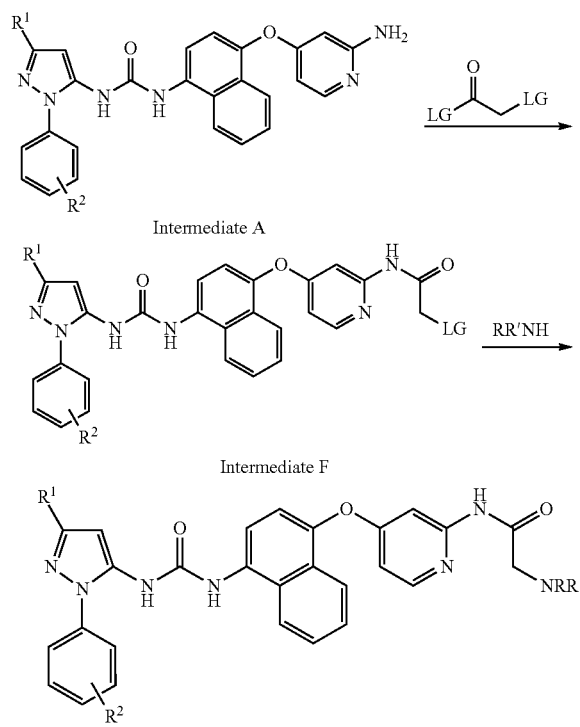

Intermediate A

Intermediate F

Intermediate F1: N-(4-(4-(3-(3-tert-Butyl-1-p-tolyl-1H-pyrazol-5-yl)ureido)naphthalen-1-yloxy)pyridin-2-yl)-2-chloroacetamide

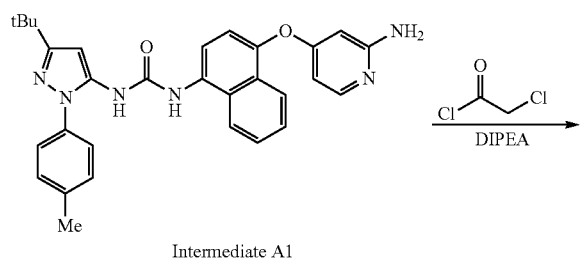

Intermediate A1

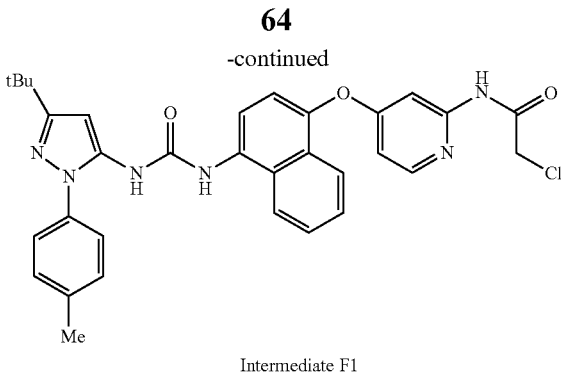

Intermediate F1

To a solution of Intermediate A1 (488 mg, 0.963 mmol) and DIPEA (755 µL, 4.33 mmol) in dry THF (25 mL) under nitrogen at 0° C. was added chloroacetyl chloride (268 µl, 3.37 mmol). The reaction mixture was maintained at 0° C. for a further 30 min and was then warmed to RT. After 1.5 hr the reaction was quenched by addition of a solution 1% NH$_3$ in MeOH (15 mL) and after a further 45 min was evaporated in vacuo. The residue was purified by flash column chromatography (SiO$_2$, 40 g, [5% MeOH in EtOAc] in isohexane, 0-50%, gradient elution) to afford the title compound, Intermediate F1, as a beige solid (527 mg, 69%, 73% pure); R$^t$ 2.63 min (Method 2); m/z 583 (M+H)$^+$ (ES$^+$)

Example 11

N-(4-(4-(3-(3-tert-Butyl-1-p-tolyl-1H-pyrazol-5-yl)ureido)naphthalen-1-yloxy)pyridin-2-yl)-2-morpholinoacetamide

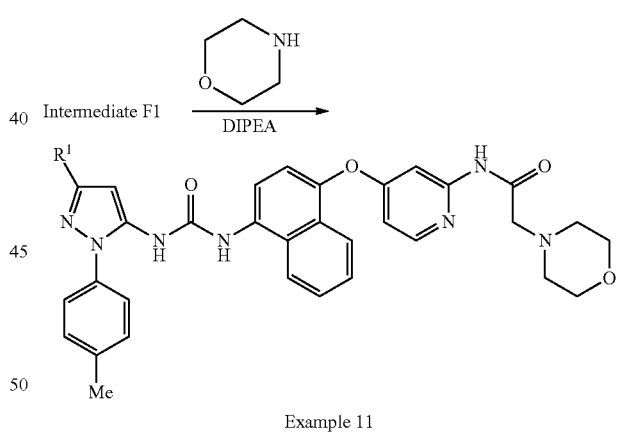

Example 11

To a solution of Intermediate F1 (50 mg, 0.086 mmol) and DIPEA (26.1 µL, 0.150 mmol) in dry THF (3 mL) under nitrogen at 0° C. was added morpholine (13.1 µL, 0.150 mmol) and the mixture maintained at 0° C. for 30 min and then a RT for 22 hr. The resulting mixture was cooled to 0° C. and an additional aliquot of morpholine (75 µL, 0.86 mmol) was added and after 23 hr at RT the mixture was evaporated in vacuo. The residue was subjected to SCX capture and release and the crude product so obtained was purified by flash column chromatography (SiO$_2$, 12 g, [5% MeOH in EtOAc] in isohexane, 0-85%, gradient elution) to afford the title compound, Example 11, as a white solid (16 mg, 29%); R$^t$ 2.22 min (Method 2); m/z 634 (M+H)$^+$ (ES$^+$); $^1$H NMR (400 MHz, DMSO-d$_6$) δ: 1.28 (9H, s), 2.40 (3H, s), 2.48 (4H, m), 3.11

(2H, s), 3.59 (4H, t), 6.41 (1H, s), 6.71 (1H, dd), 7.33 (1H, d), 7.37 (2H, m), 7.47 (2H, m), 7.57 (1H, m), 7.64-7.66 (2H, overlapping m), 7.83 (1H, dd), 7.97 (1H, d), 8.10 (1H, d), 8.19 (1H, d), 8.82 (1H, br s), 9.15 (1H, br s), 9.98 (1H, br s).

Example 12

N-(4-(4-(3-(3-tert-Butyl-1-p-tolyl-1H-pyrazol-5-yl)ureido)naphthalen-1-yloxy)pyridin-2-yl)-(dimethylamino)acetamide

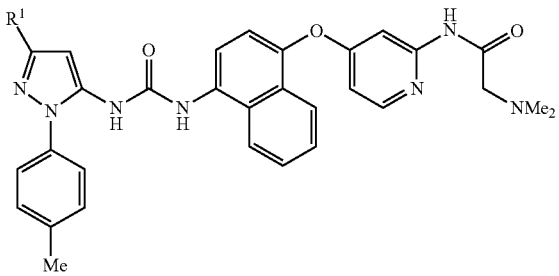

Example 12

To a solution of Intermediate F1 (50 mg, 0.086 mmol) and DIPEA (44.8 μL, 0.257 mmol) in dry THF (3 mL) under nitrogen at 0° C. was added dimethylamine (2 M in THF, 643 μl, 1.29 mmol) and the mixture maintained at 0° C. for 20 min and then warmed to RT. After 19 hr the mixture was evaporated in vacuo and the residue was purified by flash column chromatography (SiO$_2$, 12 g, [5% MeOH in EtOAc] in isohexane, 0-25%, gradient elution) to afford the title compound, Example 12, as an off-white solid (13 mg, 26%); R$^t$ 1.92 min (Method 2); m/z 592 (M+H)$^+$ (ES$^+$); $^1$H NMR (400 MHz, DMSO-d$_6$) δ: 1.28 (9H, s), 2.25 (6H, s), 2.40 (3H, s), 3.04 (2H, s), 6.41 (1H, s), 6.70 (1H, dd), 7.34 (1H, d), 7.38 (2H, d), 7.47 (2H, m), 7.57 (1H, m), 7.64-7.67 (2H, overlapping m), 7.84 (1H, dd), 7.97 (1H, d), 8.09 (1H, d), 8.18 (1H, d), 8.82 (1H, br s), 9.15 (1H, br s), 9.90 (1H, br s).

Example 13

N-(4-(4-(3-(3-tert-Butyl-1-p-tolyl-1H-pyrazol-5-yl)ureido)naphthalen-1-yloxy)pyridin-2-yl)-2-(2-methoxyethylamino)acetamide

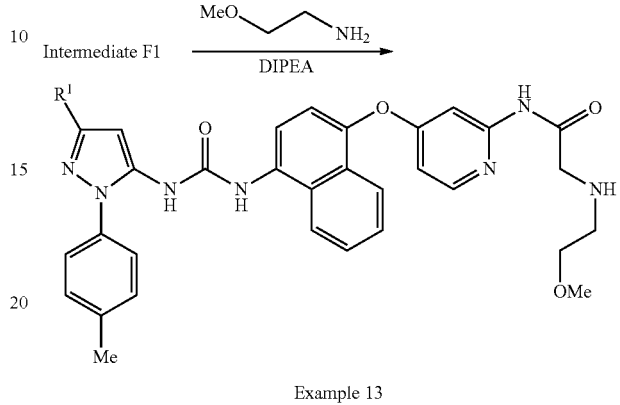

Example 13

To a solution of Intermediate F1 (50 mg, 0.086 mmol) and DIPEA (59.7 μL, 0.343 mmol) in dry THF (3 mL) under nitrogen at 0° C. was added 2-methoxyethylamine (89 μL, 1.03 mmol). The reaction mixture was maintained at 0° C. for 30 min, was then warmed to RT and after 19 hr an additional aliquot of 2-methoxyethylamine (45 μL, 0.520 mmol) was added. The mixture was kept at RT for a further 21 hr and was then evaporated in vacuo. The residue was purified by flash column chromatography (SiO$_2$, 12 g, [5% MeOH in EtOAc] in isohexane, 0-25%, gradient elution) to afford the title compound, Example 13, as an off-white solid (14 mg, 25%); R$^t$ 2.04 (Method 2); m/z 622 (M+H)$^+$ (ES$^+$); $^1$H NMR (400 MHz, DMSO-d$_6$) δ: 1.28 (9H, s), 2.40 (3H, s), 2.64 (2H, t), 3.21 (3H, s), 3.24 (2H, br s), 3.35 (2H, t), 6.41 (1H, s), 6.71 (1H, dd), 7.34 (1H, d), 7.38 (2H, d), 7.47 (2H, m), 7.57 (1H, m), 7.64-7.66 (2H, overlapping m), 7.83 (1H, dd), 7.97 (1H, d), 8.09 (1H, d), 8.18 (1H, d), 8.81 (1H, br s), 9.14 (1H, br s), 10.21 (1H, br s).

Other examples of the disclosure were prepared by a process in which an Intermediate A was converted into an Intermediate G, followed by N-acylation

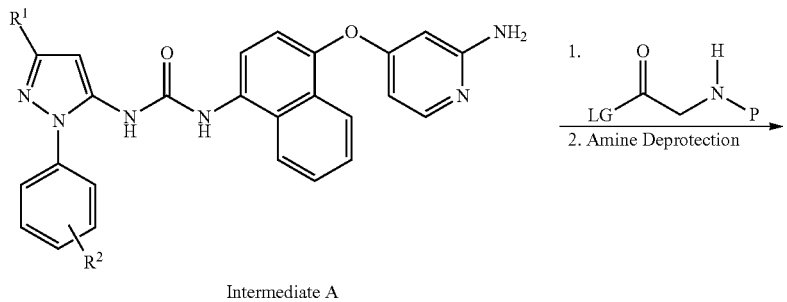

Intermediate A

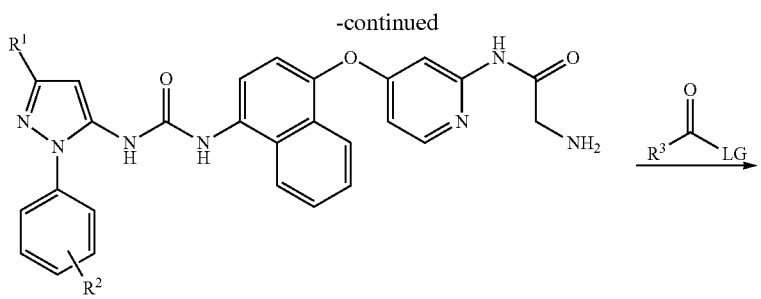

Intermediate G

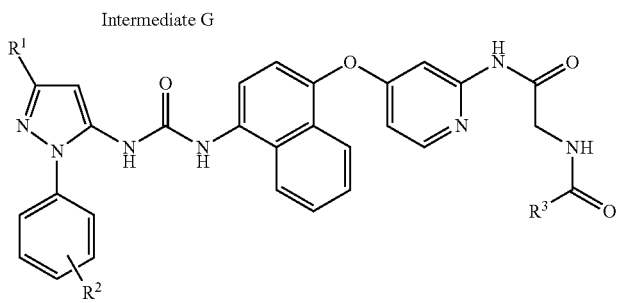

Intermediate G1: 2-Amino-N-(4-(4-(3-(3-tert-butyl-1-p-tolyl-1H-pyrazol-5-yl)ureido)naphthalen-1-yloxy)pyridin-2-yl)acetamide

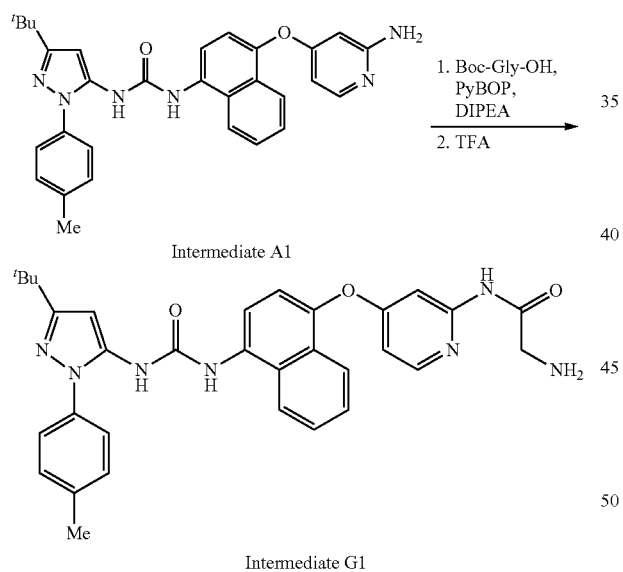

To a mixture of 2-(tert-butoxycarbonylamino)acetic acid [Boc-Gly-OH] (415 mg, 2.37 mmol), PyBOP (1.23 g, 2.37 mmol) and DIPEA (413 µL, 2.37 mmol) in dry DMF (12 mL) at 0° C. under nitrogen was added Intermediate A1 (300 mg, 0.592 mmol) and the mixture warmed to 50° C. for 16 hr. The resulting mixture was cooled to RT and was partitioned between EtOAc (60 mL) and saturated aq NaHCO₃ solution (80 mL). The aq layer was extracted with EtOAc (60 mL) and the combined organic extracts were washed with brine (80 mL) and then dried (MgSO₄) and evaporated in vacuo. The residue was purified by flash column chromatography (SiO₂, 40 g, EtOAc in isohexane, 0-65%, gradient elution) to afford tert-butyl 2-(4-(4-(3-(3-tert-butyl-1-p-tolyl-1H-pyrazol-5-yl)ureido)naphthalen-1-yloxy)pyridin-2-yl amino)-2-oxoethylcarbamate as a purple solid (197 mg, 92% purity, 46%); R$^t$ 2.65 min (Method 2); m/z 664 (M+H)⁺ (ES⁺).

To a stirred solution of tert-butyl 2-(4-(4-(3-(3-tert-butyl-1-p-tolyl-1H-pyrazol-5-yl)ureido)naphthalen-1-yloxy)pyridin-2-ylamino)-2-oxoethylcarbamate (187 mg, 92% pure, 0.259 mmol) in dry DCM (6 mL) 0° C. under nitrogen was added TFA (2.0 mL) and the reaction mixture maintained at 0° C. for 20 min and then warmed to RT for 3 hr. The resulting mixture was evaporated in vacuo and the residue was purified by SCX capture and release to afford the title compound, Intermediate G1, as a brown solid (130 mg, 87%); R$^t$ 1.82 min (Method 2); m/z 564 (M+H)⁺ (ES⁺).

Example 14

N-(4-(4-(3-(3-tert-Butyl-1-p-tolyl-1H-pyrazol-5-yl)ureido)naphthalen-1-yloxy)pyridin-2-yl)-2-ureidoacetamide

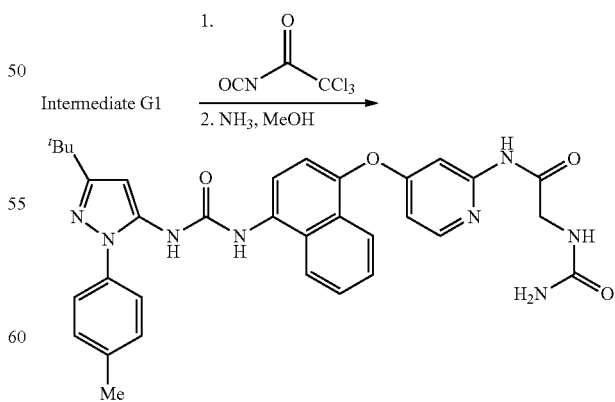

Example 14

To a solution of Intermediate G1 (35 mg, 62 µmol) in dry DCM (2.5 mL) under nitrogen at 0° C. was added trichloroacetyl isocyanate (8.5 μL, 71 μmol) and the reaction mixture maintained at 0° C. for 15 min and then warmed to RT. After 2.25 hr the mixture was cooled to 0° C. and an additional aliquot of trichloroacetyl isocyanate (4.0 μL, 31 μmol) was added. After a further 1 hr the reaction was quenched by the addition of a solution of 1% $NH_3$ in MeOH (2.0 mL) and the resulting mixture kept at RT for 1 hr and was then evaporated in vacuo. The residue was subjected to SCX capture and release and the crude product so obtained was purified by flash column chromatography ($SiO_2$, 12 g, [5% MeOH in EtOAc] in isohexane, 50-100%, gradient elution) to afford the title compound, Example 14, as a beige solid (16 mg, 40%); $R^t$ 2.06 min (Method 2); m/z 607 (M+H)$^+$ (ES$^+$); $^1$H NMR (400 MHz, DMSO-$d_6$) δ: 1.28 (9H, s), 2.40 (3H, s), 3.76 (2H, d), 5.66 (2H, s), 6.16 (1H, t), 6.41 (1H, s), 6.72 (1H, dd), 7.34 (1H, d), 7.38 (2H, d), 7.47 (2H, m), 7.57 (1H, m), 7.63-7.66 (2H, overlapping m), 7.83 (1H, dd), 7.96 (1H, d), 8.09 (1H, d), 8.18 (1H, d), 8.81 (1H, br s), 9.15 (1H, br s), 10.43 (1H, br s).

Example 15

N-(4-(4-(3-(3-tert-Butyl-1-p-tolyl-1H-pyrazol-5-yl)ureido)naphthalen-1-yloxy)pyridin-2-yl)-2-(2-methoxyacetamido)acetamide

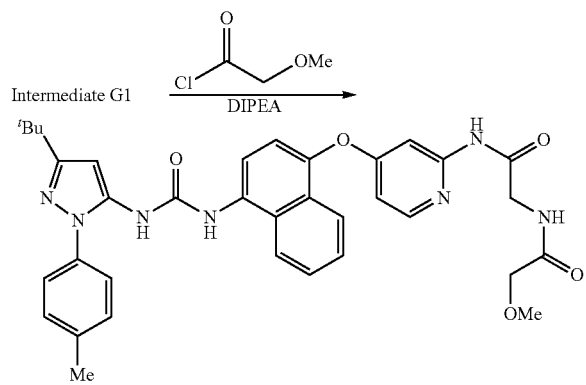

Example 15

To a solution of Intermediate G1 (35 mg, 62 μmol) and DIPEA (43.3 μl, 248 μmol) in dry THF (2.5 mL) under nitrogen at 0° C. was added 2-methoxyacetyl chloride (17.0 μl, 186 μmol) and the reaction mixture maintained at 0° C. for 15 min and then warmed to RT. After 1.75 hr the reaction was quenched by the addition of a 1% solution of $NH_3$ in MeOH (2.0 mL) and the resulting mixture kept at RT for 1 hr and was then evaporated in vacuo. The residue was subjected to SCX capture and release and the crude product so obtained was purified by flash column chromatography ($SiO_2$, 12 g, [5% MeOH in EtOAc] in isohexane, 25-100%, gradient elution) to afford the title compound, Example 15, as a beige solid (14 mg, 34%); $R^t$ 2.28 min (Method 2); m/z 636 (M+H)$^+$ (ES$^+$); $^1$H NMR (400 MHz, DMSO-$d_6$) δ: 1.28 (9H, s), 2.40 (3H, s), 3.30 (3H, s), 3.82 (2H, s), 3.90 (2H, d), 6.41 (1H, s), 6.72 (1H, dd), 7.33 (1H, d), 7.38 (2H, d), 7.47 (2H, m), 7.57 (2H, m), 7.64 (1H, m), 7.83 (1H, dd), 7.92 (1H, t), 7.96 (1H, d), 8.09 (1H, d), 8.20 (1H, d), 8.82 (1H, br s), 9.14 (1H, br s), 10.59 (1H, br s).

Example 16

N-(2-(4-(4-(3-(3-tert-Butyl-1-p-tolyl-1H-pyrazol-5-yl)ureido)naphthalen-1-yloxy)pyridin-2-ylamino)-2-oxoethyl)tetrahydro-2H-pyran-4-carboxamide

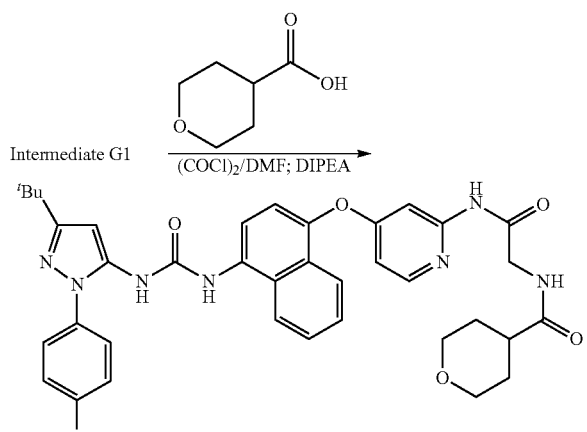

Example 16

To a suspension of tetrahydro-2H-pyran-4-carboxylic acid (34.6 mg, 0.266 mmol) in dry DCM (3.0 mL) under nitrogen at 0° C. was added oxalyl dichloride (26.3 μL, 0.310 mmol), followed by 1 drop of DMF. The reaction mixture was maintained at 0° C. for 20 min and was then warmed to RT. After 1 hr the mixture was cooled to 0° C. and Intermediate G1 (50 mg, 0.089 mmol) and DIPEA (77.0 μL, 0.444 mmol) were added and the resulting mixture was kept at 0° C. for 30 min and was then warmed to RT for 1.5 hr. The reaction was quenched by addition of a 1% solution of $NH_3$ in MeOH (3.0 mL) and the resulting mixture maintained at RT for 30 min and was then evaporated in vacuo. The residue was subjected to SCX capture and release and the crude product so obtained was purified by flash column chromatography ($SiO_2$, 12 g, [5% MeOH in EtOAc] in isohexane, 40-100%, gradient elution) to afford the title compound, Example 16, as a beige solid (18 mg, 29%); $R^t$ 2.25 min (Method 2); m/z 676 (M+H)$^+$ (ES$^+$); $^1$H NMR (400 MHz, DMSO-$d_6$) δ: 1.28 (9H, s), 1.54 (4H, m), 2.40-2.42 (4H, overlapping m), 3.27 (2H, dt), 3.83 (4H, m), 6.41 (1H, s), 6.71 (1H, dd), 7.33 (1H, d), 7.38 (2H, d), 7.47 (2H, m), 7.56-7.64 (3H, overlapping m), 7.83 (1H, dd), 7.96 (1H, d), 8.02 (1H, t), 8.09 (1H, d), 8.99 (1H, d), 8.82 (1H, br s), 9.14 (1H, br s), 10.54 (1H, br s).

Example 17

N-(2-(4-(4-(3-(3-tert-Butyl-1-p-tolyl-1H-pyrazol-5-yl)ureido)naphthalen-1-yloxy)pyridin-2-ylamino)-2-oxoethyl)isonicotinamide

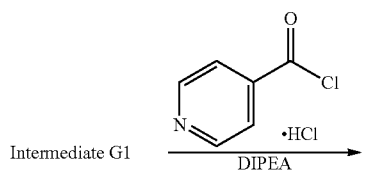

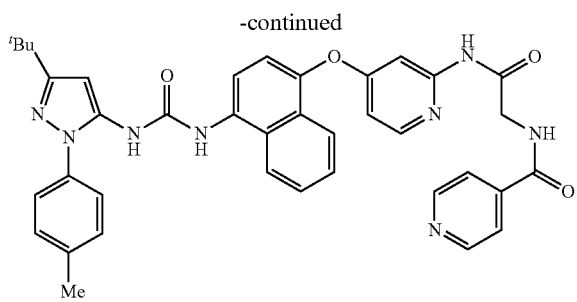

Example 17

To a solution of Intermediate G1 (50 mg, 89 μmol) and DIPEA (77 μL, 444 μmol) in dry THF (2.5 mL) under nitrogen at 0° C. was added isonicotinoyl chloride hydrochloride (47.4 mg, 266 μmol) and the reaction mixture maintained at 0° C. for 15 min and then at RT for 1.5 hr. The reaction was quenched by addition of a 1% solution of $NH_3$ in MeOH (3.0 mL) and the resulting mixture was kept at RT for 45 min and was then evaporated in vacuo. The residue was subjected to SCX capture and release and the crude product so obtained was purified by flash column chromatography ($SiO_2$, 12 g, [5% MeOH in EtOAc] in isohexane, 50-100%, gradient elution) to afford the title compound, Example 17, as a beige solid (31 mg, 52%); $R^t$ 2.17 min (Method 2); m/z 669 $(M+H)^+$ $(ES^+)$; $^1H$ NMR (400 MHz, DMSO-$d_6$) δ: 1.28 (9H, s), 2.39 (3H, s), 4.09 (2H, dd), 6.39 (1H, s), 6.74 (1H, dd), 7.33 (1H, d), 7.36 (2H, d), 7.46 (2H, m), 7.56-7.63 (3H, overlapping m), 7.75 (2H, dd), 7.83 (1H, dd), 7.95 (1H, d), 8.07 (1H, d), 8.21 (1H, d), 8.72 (2H, dd), 8.80 (1H, br s), 9.05 (1H, br s), 9.12 (1H, br s), 10.72 (1H, br s).

Example 18

N-(4-(4-(3-(3-tert-Butyl-1-p-tolyl-1H-pyrazol-5-yl)ureido)naphthalen-1-yloxy)pyridin-2-yl)-2-(2-(methylsulfonyl)acetamido)acetamide

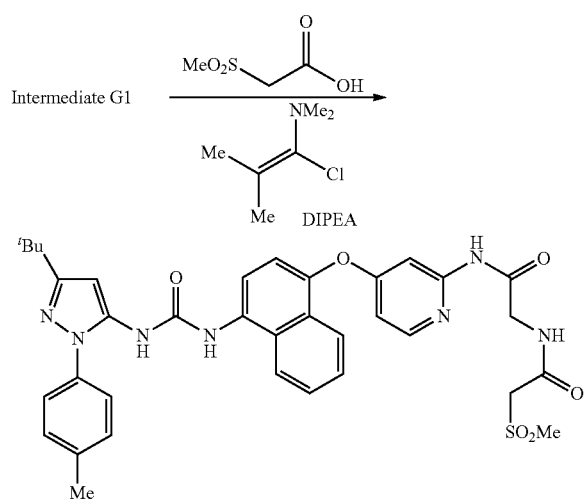

Example 18

To a solution of 2-(methylsulfonyl)acetic acid (33.1 mg, 240 μmol) in dry DCM (3.0 mL) under nitrogen was added 1-chloro-N,N,2-trimethylprop-1-en-1-amine (31.7 μL, 240 μmol) and the reaction mixture maintained at RT for 1.5 hr. The resulting mixture was added to a solution of Intermediate G1 (45 mg, 80 μmol) and DIPEA (55.6 μL, 319 μmol) in dry DCM (2.0 mL) at 0° C. under nitrogen and the combined reaction mixture was kept at 0° C. for 30 min and then at RT for 2 hr. The reaction was quenched by addition of a 1% solution of $NH_3$ in MeOH (3.0 mL) and the resulting mixture was maintained at RT for 1 hr and was then evaporated in vacuo. The residue was subjected to SCX capture and release and the crude product so obtained was purified by flash column chromatography ($SiO_2$, 12 g, [5% MeOH in EtOAc] in isohexane, 35-85%, gradient elution) followed by trituration with ethyl acetate to afford the title compound, Example 18, as a pale brown solid (7 mg, 12%); $R^t$ 2.21 min (Method 2); m/z 684 $(M+H)^+$ $(ES^+)$; $^1H$ NMR (400 MHz, DMSO-$d_6$) δ: 1.29 (9H, s), 2.40 (3H, s), 3.08 (3H, s), 3.98 (2H, d), 4.14 (2H, s), 6.41 (1H, s), 6.75 (1H, dd), 7.34 (1H, d), 7.38 (2H, d), 7.47 (2H, m), 7.57 (2H, m), 7.64 (1H, m), 7.83 (1H, dd), 7.96 (1H, d), 8.09 (1H, d), 8.21 (1H, d), 8.55 (1H, t), 8.79 (1H, br s), 9.12 (1H, br s), 10.65 (1H, br s).

Example 19

N-(2-(4-(4-(3-(3-tert-Butyl-1-p-tolyl-1H-pyrazol-5-yl)ureido)naphthalen-1-yloxy)pyridin-2-ylamino)-2-oxoethyl)-3-morpholinopropanamide

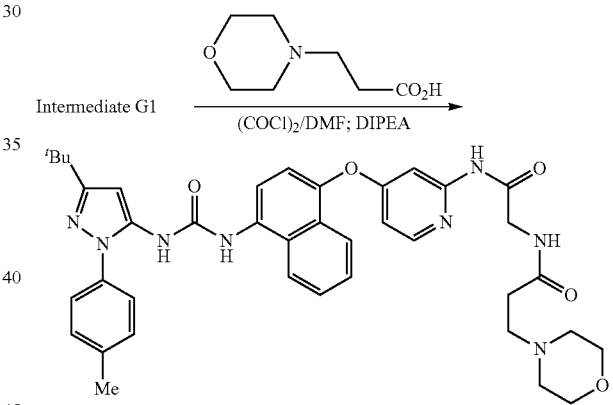

Example 19

To a suspension of 3-morpholinopropanoic acid (33.9 mg, 213 μmol) in dry DCM (3.0 mL) under nitrogen at 0° C. was added oxalyl dichloride (21.0 μL, 248 μmol), followed by 1 drop of DMF and the reaction mixture maintained at 0° C. for 20 min and the at RT for 1.25 hr. The mixture was cooled to 0° C. and Intermediate G1 (40 mg, 71 μmol) and DIPEA (61.8 μL, 355 μmol) were added and the combined reaction mixture was kept at 0° C. for 30 min and then at RT for 2.25 hr. The reaction was quenched by addition of a 1% solution of $NH_3$ in MeOH (3.0 mL) and the resulting mixture maintained at RT for 16 hr and was then evaporated in vacuo The residue was subjected to SCX capture and release and the crude product so obtained was purified by flash column chromatography ($SiO_2$, 12 g, [5% MeOH in EtOAc] in isohexane, 50-100%, gradient elution, then 10% MeOH in EtOAc) to afford the title compound, Example 19, as a beige solid (20 mg, 39%); $R^t$ 2.00 min (Method 2); m/z 705 $(M+H)^+$ $(ES^+)$; $^1H$ NMR (400 MHz, DMSO-$d_6$) δ: 1.29 (9H, s), 2.29 (2H, t), 2.33 (4H, m), 2.40 (3H, s), 2.47 (2H, m), 3.52 (4H, t), 3.87 (2H, d), 6.40 (1H, s), 6.72 (1H, dd), 7.33 (1H, d), 7.37 (2H, d), 7.47 (2H, m), 7.57-7.64 (3H, overlapping m), 7.83 (1H, dd), 7.96 (1H, d), 8.09 (1H, d), 8.19 (1H, d), 8.22 (1H, t), 8.85 (1H, br s), 9.16 (1H, br s), 10.48 (1H, br s).

Example 20

N-(2-(4-(4-(3-(3-tert-Butyl-1-p-tolyl-1H-pyrazol-5-yl)ureido)naphthalen-1-yloxy)pyridin-2-ylamino)-2-oxoethyl)morpholine-4-carboxamide

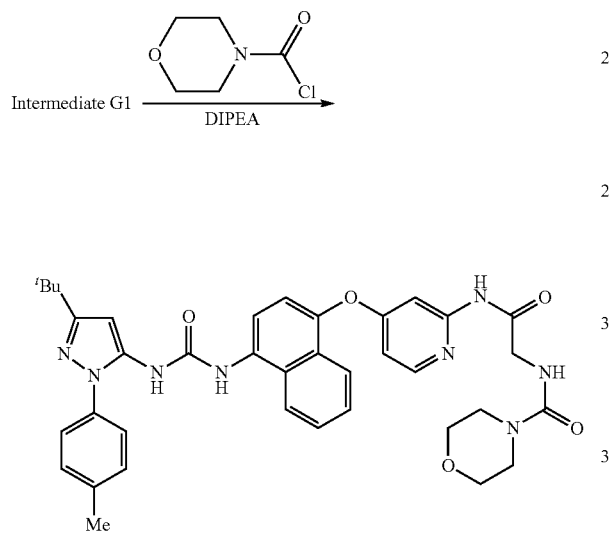

Example 20

To a solution of Intermediate G1 (45 mg, 80 µmol) and DIPEA (48.7 µL, 279 µmol) in dry THF (3.0 mL) under nitrogen at 0° C. was added morpholine-4-carbonyl chloride (22.9 µl, 200 µmol) and the reaction mixture maintained at 0° C. for 20 min and then at RT for 2.5 hr. The reaction was quenched by addition of a 1% solution of $NH_3$ in MeOH (3.0 mL) and the resulting mixture was kept at RT for 1.5 hr and was then evaporated in vacuo. The residue was subjected to SCX capture and release and the crude product so obtained was purified by flash column chromatography ($SiO_2$, 12 g, [5% MeOH in EtOAc] in isohexane, 40-100%, gradient elution) followed by trituration with isohexane/EtOAc (2:1 v/v). This material was taken up into EtOAc (15 mL) and was washed with water (2×20 mL) then dried ($MgSO_4$) and was evaporated in vacuo to afford the title compound, Example 20, as a beige solid (12 mg, 22%); $R^t$ 2.24 min (Method 2); m/z 677 (M+H)$^+$ (ES$^+$); $^1$H NMR (400 MHz, DMSO-d$_6$) δ: 1.29 (9H, s), 2.40 (3H, s), 3.24 (4H, t), 3.52 (4H, t), 3.77 (2H, d), 6.41 (1H, s), 6.72 (1H, dd), 6.83 (1H, t), 7.32 (1H, d), 7.38 (2H, d), 7.47 (2H, m), 7.58 (2H, m), 7.64 (1H, m), 7.83 (1H, dd), 7.96 (1H, d), 8.09 (1H, d), 8.19 (1H, br s), 8.79 (1H, br s), 9.12 (1H, br s), 10.39 (1H, br s).

2,6-difluoro-3-(2-(2-methoxyethoxy)ethoxy)benzoic acid

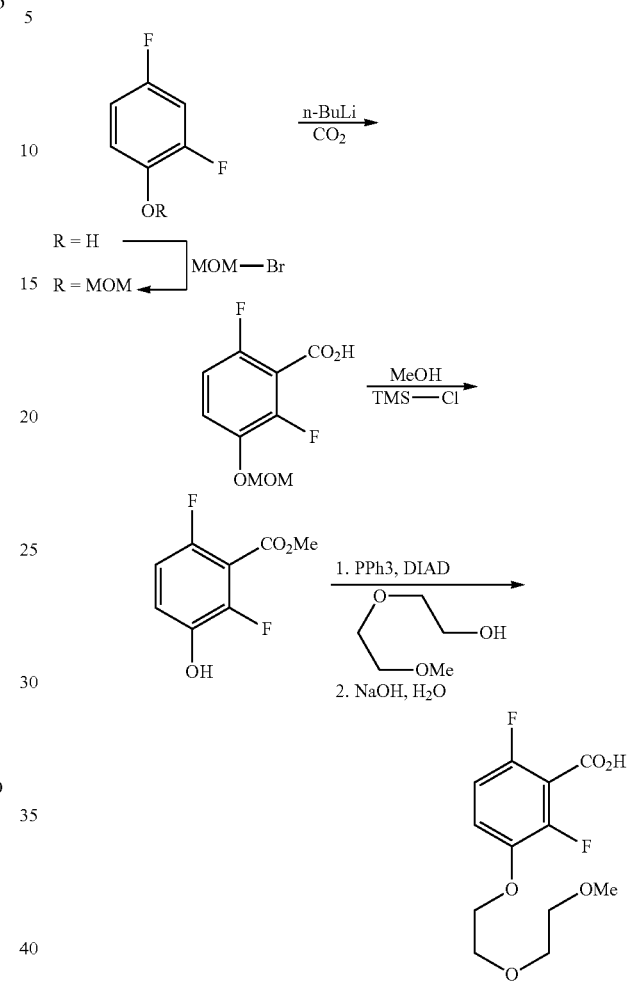

To a solution of 2,4-difluorophenol (11.0 g, 85 mmol) and DIPEA (15.5 mL, 89 mmol) in DCM (150 ml) at 0° C. under nitrogen was added MOM-Br (7.33 mL, 89 mmol) over 1 hr and the reaction mixture then maintained at RT for 16 hr. The resulting mixture was washed successively with water, aq 2M NaOH solution, water and brine, and was then dried ($MgSO_4$) and evaporated in vacuo to afford 2,4-difluoro-1-(methoxymethoxy)benzene as a colourless oil (13.7 g, 88% yield). $R^t$ 3.17 min (Method 1, basic, no ionization observed), which was used directly in the next step (below).

To a solution of 2,4-difluoro-1-(methoxymethoxy)benzene (2.00 g, 11.5 mmol) in THF (30 mL) under nitrogen at −70° C. was added a solution of n-butyllithium in hexanes (1.4 M, 8.20 mL, 11.48 mmol) dropwise over 10 min. The mixture was stirred at −70° C. for 1.5 hr and was then decanted onto freshly pulverized dry ice (~20 g). Once the effervescence had subsided the mixture was allowed to warm to RT and water (20 mL) was added. The aq solution was extracted twice with ether and was then acidified to pH 1 by the addition of concentrated hydrochloric acid. The resulting suspension was sonicated for 5 min and was then extracted twice with DCM and the combined DCM extracts were dried ($MgSO_4$) and evaporated in vacuo. The residue was triturated with a mixture of isohexane and ether (50:3 v/v) to furnish 2,6- difluoro-3-(methoxymethoxy)benzoic acid as a white solid (1.99 g, 77% yield); R' 2.31 min (Method 1, basic); m/z 219 (M+H)⁺ (ES⁺), which was used directly in the next step (below). To a solution of 2,6-difluoro-3-(methoxymethoxy)benzoic acid (2.74 g, 12.6 mmol) in MeOH (50 mL) was added TMS-Cl (7.94 mL, 62.8 mmol) dropwise and the resulting colourless solution heated at reflux for 3 hr. The resulting mixture was cooled to RT and was then evaporated in vacuo and the residue was subjected to SCX capture and release to afford methyl 2,6-difluoro-3-hydroxybenzoate as a white solid (2.38 g, 100%); R' 2.29 min (Method 1, basic); m/z 187 (M–H)⁻ (ES⁻).

A mixture of methyl 2,6-difluoro-3-hydroxybenzoate (500 mg, 2.66 mmol), diethyleneglycol-monomethyl ether (479 mg, 3.99 mmol) and PPh₃ (1046 mg, 3.99 mmol) in THF (12.0 mL) was purged with nitrogen, cooled to –78° C. and then DIAD (753 µl, 3.99 mmol) added over 5 min. The reaction mixture was warmed to RT and after 1 hr an aq solution of NaOH (2M, 10 mL) and water (10 mL) were added and the mixture was stirred rapidly at RT for 1 hr. The resulting mixture was extracted with ether (50 mL) and the organic layer was back-extracted with aq NaOH (1M, 20 mL). The combined (basic) aqueous phases were extracted twice with ether and then acidified to pH 1 by the addition of conc. hydrochloric acid and the mixture extracted three times with ether. The combined ether extracts were dried (MgSO₄) and evaporated in vacuo to afford the title compound as a white solid (0.51 g, 65%); R' 1.81 min, (Method 1, basic); m/z 275 (M–H)⁻ (ES⁻).

Example 21

N-(2-(4-(4-(3-(3-tert-Butyl-1-p-tolyl-1H-pyrazol-5-yl)ureido)naphthalen-1-yloxy)pyridin-2-ylamino)-2-oxoethyl)-2,6-difluoro-3-(2-(2-methoxyethoxy)ethoxy)benzamide

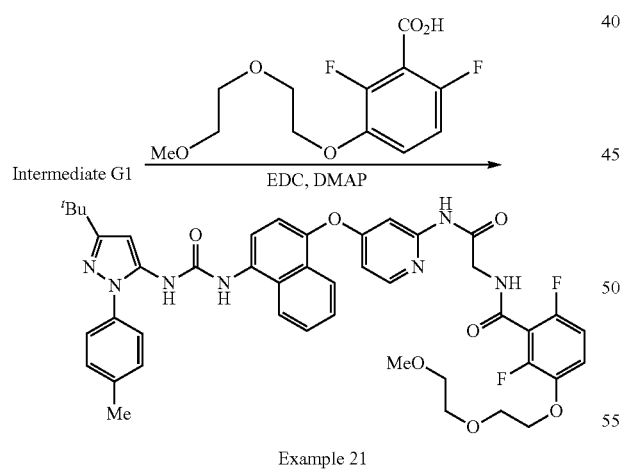

Example 21

To a solution of 2,6-difluoro-3-(2-(2-methoxyethoxy)ethoxy)benzoic acid (29.4 mg, 106 µmol), Intermediate G1 (50 mg, 89 µmol), and EDC.HCl (22.1 mg, 115 µmol) in dry DCM (4 mL) under nitrogen at 0° C. was added DMAP (1.6 mg, 0.013 mmol) and the reaction mixture maintained to RT for 24 hr. The resulting mixture was partitioned between saturated aqueous NaHCO₃ solution (15 mL) and DCM (15 mL). The aqueous layer was separated and extracted with DCM (15 mL) and the combined organic extracts were washed with brine (20 mL) and then dried (MgSO₄) and evaporated in vacuo. The residue was purified by flash column chromatography (SiO₂, 12 g, [5% MeOH in EtOAc] in isohexane, 20-80% gradient elution and then SiO₂, 12 g, MeOH in DCM, 0-10%, gradient elution) to afford the title compound, Example 21, as a white solid (9 mg, 15%); R' 2.55 min (Method 2); m/z 822 (M+H)⁺ (ES⁺); ¹H NMR (400 MHz, DMSO-d₆) δ: 1.28 (9H, s), 2.39 (3H, s), 3.23 (3H, s), 3.44 (2H, m), 3.58 (2H, m), 3.73 (2H, m), 4.10 (2H, d), 4.16 (2H, m), 6.40 (1H, s), 6.69 (1H, dd), 7.06 (1H, dt), 7.26 (1H, dt), 7.34 (1H, d), 7.37 (2H, d), 7.47 (2H, m), 7.57 (1H, m), 7.63-7.65 (2H, overlapping m), 7.84 (1H, dd), 7.95 (1H, d), 8.09 (1H, d), 8.20 (1H, d), 8.85 (1H, br s), 8.95 (1H, t), 9.17 (1H, br s), 10.60 (1H, br s).

Still other examples of the disclosure were prepared by a process in which an Intermediate H was reacted with an Intermediate C or an Intermediate D.

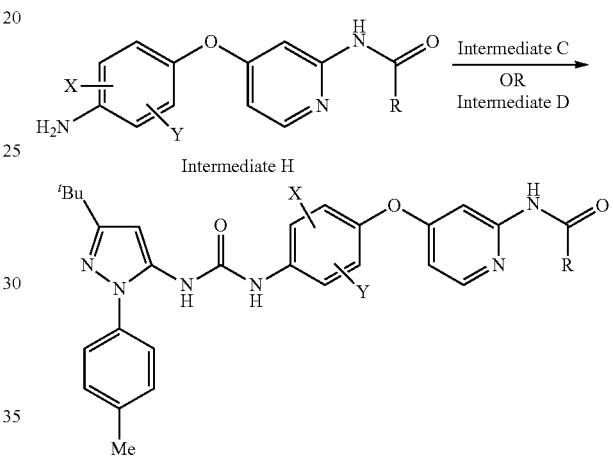

Intermediate H1: N-(4-(4-Aminophenoxy)pyridin-2-yl)-2-methoxyacetamide

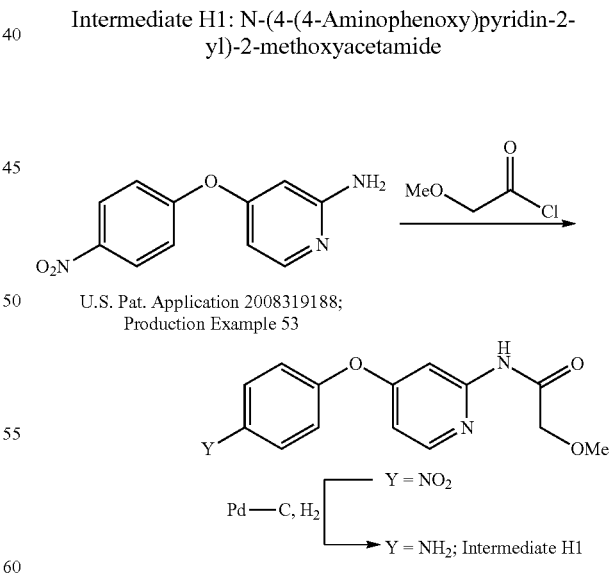

To a solution of 4-(4-nitrophenoxy)pyridin-2-amine [US Pat Appl 2008319188, Production Example 53] (0.60 g, 2.60 mmol) and DIPEA (0.680 µL, 3.89 mmol) in DCM (15.0 mL) under nitrogen at 0° C. was added 2-methoxyacetyl chloride (225 µL, 3.89 mmol) dropwise over 5 min. The reaction was maintained at RT for 16 hr and was quenched by the addition of a 1% solution of NH₃ in MeOH (10 mL). The mixture was evaporated in vacuo and the residue was taken up into DCM (50 mL) and was washed with water (25 mL) and brine (25 mL), and then dried (MgSO₄) and evaporated in vacuo. The residue was purified by flash column chromatography (SiO₂, EtOAc in DCM, 0-30%, gradient elution) to afford 2-methoxy-N-(4-(4-nitrophenoxy)pyridin-2-yl)acetamide as a white solid (0.73 g, 92%); $R^t$ 1.88 min (Method 2); m/z 304 (M+H)⁺ (ES⁺).

A solution of 2-methoxy-N-(4-(4-nitrophenoxy)pyridin-2-yl)acetamide (730 mg, 2.41 mmol) in MeOH/DCM (1:1 v/v, 80 mL) containing AcOH (5 drops) was subjected to hydrogenation by passage through a Thales H-cube (1.0 mL min⁻¹, RT, 70 mm 10% Pt/C Cat-Cart, full hydrogen mode) and was then evaporated in vacuo. The residue was partitioned between DCM (20 mL) and saturated aqueous NaHCO₃ solution (10 mL). The organic layer was washed with brine (20 mL) and was dried (MgSO₄) and evaporated in vacuo to afford the title compound, Intermediate H1, as a white solid (0.63 g, 91%); $R^t$ 0.88 min (Method 2); m/z 274 (M+H)⁺ (ES⁺).

Example 22

N-(4-(4-(3-(3-tert-Butyl-1-p-tolyl-1H-pyrazol-5-yl)ureido)phenoxy)pyridin-2-yl)-2-methoxyacetamide

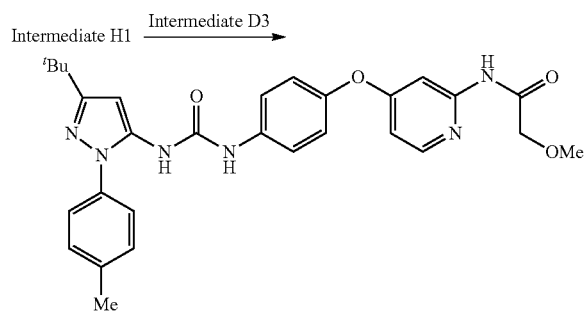

Example 22

To a suspension of CDI (0.148 g, 0.915 mmol) in DCM (5.0 mL) was added 3-tert-butyl-1-p-tolyl-1H-pyrazol-5-amine (210 mg, 0.915 mmol) in three portions and the mixture maintained at RT for 16 hr. A solution of Intermediate H1 (60 mg, 220 µmol) in DCM (0.6 mL) was added and after 1 hr at RT a second aliquot of Intermediate H1 (7.5 mg, 28 µmol) in DCM (0.075 mL) was added. The reaction was quenched with MeOH (10 mL) and after 30 min at RT was evaporated in vacuo. The residue was partitioned between EtOAc (50 mL) and water (20 mL) and the organic phase was separated and was washed with brine (20 mL), then dried (MgSO₄) and evaporated in vacuo. The residue was purified by flash column chromatography (SiO₂, 40 g, EtOAc in isohexane, 0-100%, gradient elution) to afford the title compound, Example 22, as a white solid (112 mg, 86%); $R^t$ 2.40 min (Method 2); m/z 529 (M+H)⁺ (ES⁺); ¹H NMR (400 MHz, DMSO-d₆) δ: 1.27 (9H, s), 2.37 (3H, s), 3.33 (3H, s), 4.01 (2H, s), 6.36 (1H, s), 6.66 (1H, dd), 7.10 (2H, d), 7.35 (2H, d), 7.39 (2H, d), 7.50 (2H, d), 7.61 (1H, m), 8.17 (1H, d), 8.37 (1H, s), 9.14 (1H, s), 10.03 (1H, s).

Intermediate H2: N-(4-(4-Amino-2-methylphenoxy)pyridin-2-yl)-2-methoxyacetamide

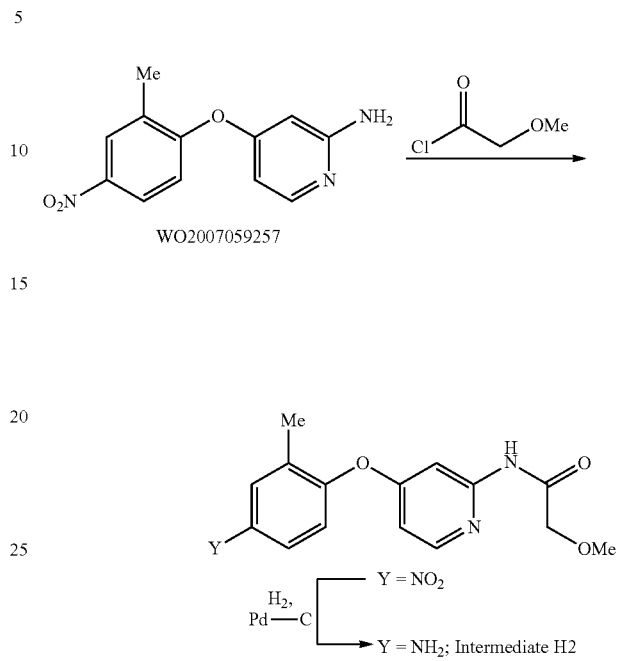

To a suspension of 4-(2-methyl-4-nitrophenoxy)pyridin-2-amine [WO2007059257] (405 mg, 1.65 mmol) in THF (5.0 mL) at 0° C. was added 2-methoxyacetyl chloride (604 µL, 6.61 mmol) and DIPEA (1.44 mL, 8.26 mmol) and the reaction mixture warmed to RT for 30 min. The reaction was quenched by addition of a 1% solution of NH₃ in MeOH (3.0 mL) and was kept at RT for 16 hr. A second aliquot of a solution of NH₃ in MeOH (7M, 1.0 mL) was added and after 30 min at RT the resulting mixture was evaporated in vacuo. The residue was subjected to SCX capture and release to afford 2-methoxy-N-(4-(2-methyl-4-nitrophenoxy)pyridin-2-yl)acetamide as an orange oil (357 mg, 92% pure, 63%); $R^t$ 2.07 min (Method 2); m/z 318 (M+H)⁺ (ES⁺), which was used directly in the next step (below).

A solution of 2-methoxy-N-(4-(2-methyl-4-nitrophenoxy)pyridin-2-yl)acetamide (357 mg, estimated purity 92%, 1.04 mmol) in a mixture of MeOH (20 mL) and AcOH (2.0 mL) was subjected to hydrogenation by passage through a Thales H-cube (1.0 mL min⁻¹, 25° C., 55 mm 10% Pt/C Cat-Cart, full hydrogen mode) and was then evaporated in vacuo. The residue was taken up into a mixture of MeOH (20 mL) and AcOH (2 mL) and re-subjected to hydrogenation under the same flow conditions, at an elevated temperature (1.0 mL min⁻¹, 40° C., 55 mm 10% Pt/C Cat-Cart, full hydrogen mode). The mixture was concentrated by evaporation in vacuo to afford the title compound, Intermediate H2, as a viscous liquid; $R^t$ 1.05 min (Method 1); m/z 288 (M+H)⁺ (ES⁺); which was used directly in the next step (below).

Example 23

N-(4-(4-(3-(3-tert-Butyl-1-p-tolyl-1H-pyrazol-5-yl)ureido)-2-methylphenoxy)pyridin-2-yl)-2-methoxyacetamide Intermediate H2 —Intermediate D3→

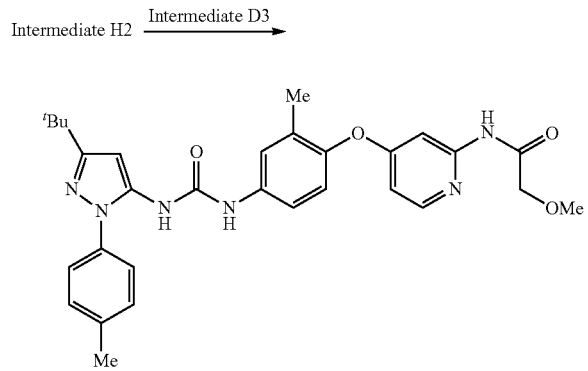

Example 23

To a suspension of CDI (0.811 g, 5.00 mmol) in DCM (10 mL) at RT was added, dropwise, a solution of 3-tert-butyl-1-p-tolyl-1H-pyrazol-5-amine (1.15 g, 5.00 mmol) in DCM (10 mL). An aliquot of this solution (7.0 mL) was added to the sample of Intermediate H2 prepared above) in DCM (5.0 mL) and the reaction mixture maintained at RT for 16 hr. The resulting reaction mixture was evaporated in vacuo and the residue was purified by flash column chromatography (SiO$_2$, 12 g, 1% [1% NH$_3$ in MeOH] in DCM, isocratic elution) to afford the title compound, Example 23, as a yellow solid (54 mg, 10% overall for two steps); R$^t$ 2.52 min (Method 2); m/z 543 (M+H)$^+$ (ES$^+$); $^1$H NMR (400 MHz, DMSO-d$_6$) δ: 1.28 (9H, s), 2.06 (3H, s), 2.38 (3H, s), 3.33 (3H, s), 4.01 (2H, s), 6.36 (1H, s), 6.60 (1H, dd), 7.01 (1H, d), 7.29 (1H, dd), 7.34 (2H, d), 7.40 (2H, d), 7.44 (1H, d), 7.54 (1H, d), 8.16 (1H, d), 8.36 (1H, s), 9.07 (1H, s), 9.98 (1H, s).

Intermediate H3: N-(4-(4-Amino-3-methylphenoxy)pyridin-2-yl)-2-methoxyacetamide

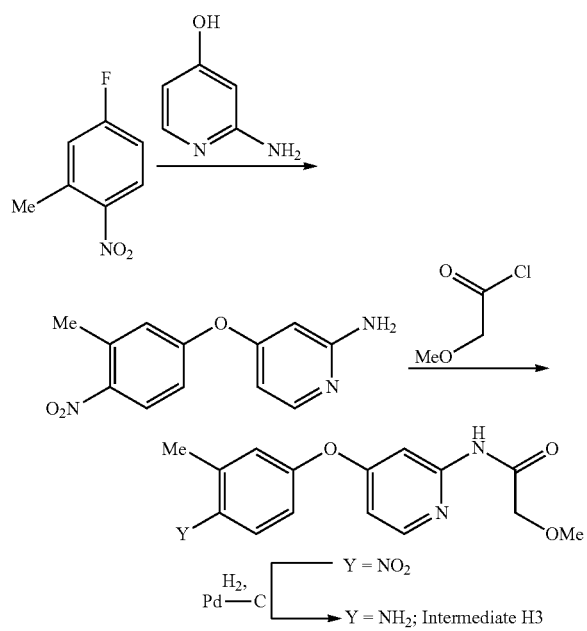

To a solution of 2-aminopyridin-4-ol (355 mg, 3.22 mmol) in DMF (4.0 mL) at 0° C. under nitrogen was added portionwise sodium hydride (60% dispersion in mineral oil, 193 mg, 4.83 mmol) and the reaction mixture warmed to RT for 2 hr, The mixture cooled to 0° C. and a solution of 4-fluoro-2-methyl-1-nitrobenzene (500 mg, 3.22 mmol) in DMF (2.0 mL) was added, dropwise and the reaction mixture warmed to RT for 16 hr. The resulting mixture was diluted with water (20 mL) and was extracted with ethyl acetate (3×30 mL). The combined organic extracts were washed with brine (20 mL), then dried (MgSO$_4$) and evaporated in vacuo and the residue was purified by flash column chromatography (SiO$_2$, 40 g, 25% EtOAc in DCM, isocratic elution) to afford 4-(3-methyl-4-nitrophenoxy)pyridin-2-amine as a yellow solid (351 mg, 44%); R$^t$ 1.20 min (Method 2); m/z 246 (M+H)$^+$ (ES$^+$).

To a suspension of 4-(3-methyl-4-nitrophenoxy)pyridin-2-amine (300 mg, 1.22 mmol) in THF (5.0 mL) and DIPEA (1.7 mL, 6.12 mmol) at 0° C. was added 2-methoxyacetyl chloride (447 μL, 4.89 mmol) in a single portion and the reaction mixture warmed to RT for 30 min. A solution of NH$_3$ in MeOH (7M, 3.0 mL) was added and after 30 min at RT the mixture was evaporated in vacuo. The residue was partitioned between DCM (50 mL) and water (40 mL) and the organic phase was separated and dried (MgSO$_4$) and was evaporated in vacuo. The residue was purified by flash column chromatography (SiO$_2$, 40 g, 5% MeOH in DCM, isocratic elution) to afford 2-methoxy-N-(4-(3-methyl-4-nitrophenoxy)pyridin-2-yl)acetamide (210 mg, 53%) as a yellow oil; R$^t$ 2.06 min (Method 2); m/z 318 (M+H)$^+$ (ES$^+$).

A solution of 2-methoxy-N-(4-(3-methyl-4-nitrophenoxy)pyridin-2-yl)acetamide (208 mg, 0.656 mmol) in a mixture of MeOH (10.0 mL) and AcOH (0.5 mL) was subjected to hydrogenation by passage through a Thales H-cube (1.0 mL min$^{-1}$, 40° C., 55 mm 10% Pt/C Cat-Cart, full hydrogen mode) and was then evaporated in vacuo to afford the title compound, Intermediate H3, (192 mg, 97%); R$^t$ 1.19 min (Method 2); m/z 288 (M+H)$^+$ (ES$^+$); which was used directly in the next step (below).

Example 24

N-(4-(4-(3-(3-tert-Butyl-1-p-tolyl-1H-pyrazol-5-yl)ureido)-3-methylphenoxy)pyridin-2-yl)-2-methoxyacetamide Intermediate H3 —Intermediate D3→

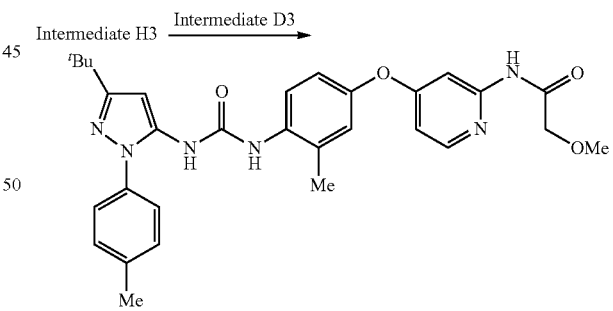

Example 24

To a suspension of CDI (811 mg, 5.00 mmol) in DCM (10.0 mL) was added dropwise a solution of 3-tert-butyl-1-p-tolyl-1H-pyrazol-5-amine (1.147 g, 5.00 mmol) in DCM (10.0 mL) and the reaction mixture maintained at RT for 16 hr. An aliquot of this solution (1.34 mL) was added dropwise to a solution of Intermediate H3 (192 mg, 0.668 mmol) in DCM (3.0 mL) and the combined reaction mixture was kept at RT for 30 min and was then treated with MeOH (1.0 mL). After 5 min the reaction mixture was evaporated in vacuo and the residue was purified by flash column chromatography (SiO$_2$, 40 g, MeOH in DCM, 0-5%, gradient elution) to afford the title compound, Example 24, as a yellow solid (145 mg, 38%); $R^t$ 2.48 min (Method 2); m/z 543 (M+H)$^+$ (ES$^+$); $^1$H NMR (400 MHz, DMSO-d$_6$) δ: 1.27 (9H, s), 2.19 (3H, s), 2.38 (3H, s), 3.33 (3H, s), 4.02 (2H, s), 6.36 (1H, s), 6.66 (1H, dd), 6.96 (1H, dd), 7.03 (1H, d), 7.34 (2H, d), 7.42 (2H, d), 7.63 (1H, d), 7.81 (1H, d), 8.18 (1H, d), 8.29 (1H, s), 8.73 (1H, s), 10.03 (1H, s).

Intermediate H4: N-(4-(4-Amino-2-methoxyphenoxy)pyridin-2-yl)-2-methoxyacetamide

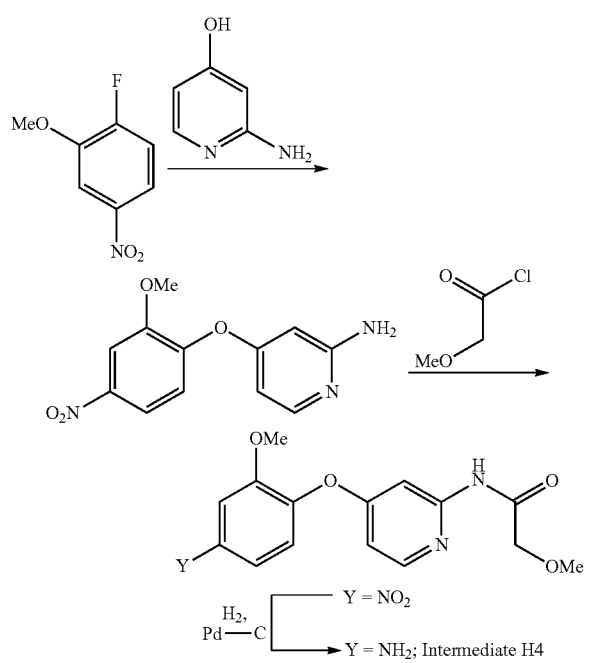

To a suspension of 2-aminopyridin-4-ol (0.251 g, 2.28 mmol) in MeCN (4.0 mL) at RT was added DBU (423 μl, 2.80 mmol) and after 30 min a solution of 1-fluoro-2-methoxy-4-nitrobenzene (300 mg, 1.75 mmol) in DMF (2.0 mL) was added dropwise. The reaction mixture was maintained at RT for 1 hr and was then heated to 80° C. for 16 hr. After cooling to RT water (2.0 mL) was added and the mixture was evaporated in vacuo. The residue was partitioned between DCM (30 mL) and brine (20 mL) and the organic layer was separated and dried (MgSO$_4$) and was evaporated in vacuo. The residue was purified by flash column chromatography (SiO$_2$, 40 g, EtOAc in isohexane, 20-100%, gradient elution) to afford 4-(2-methoxy-4-nitrophenoxy)pyridin-2-amine as a bright yellow solid (234 mg, 50%); $R^t$ 1.25 min (Method 2); m/z 262 (M+H)$^+$ (ES$^+$).

To a suspension of 4-(2-methoxy-4-nitrophenoxy)pyridin-2-amine (233 mg, 0.892 mmol) in THF (5.0 mL) and DIPEA (775 μL, 6.12 mmol) at 0° C. was added 2-methoxyacetyl chloride (325 μL, 3.57 mmol) in a single portion. The reaction mixture was warmed to RT for 1 hr and then a solution of NH$_3$ in MeOH (7M, 2.0 mL) was added. After 30 min at RT the mixture was evaporated in vacuo and the residue was partitioned between DCM (50 mL) and brine (40 mL). The organic phase was separated and dried (MgSO$_4$) and was evaporated in vacuo. The residue was purified by flash column chromatography (SiO$_2$, 40 g, 2% MeOH in DCM, isocratic elution) to afford 2-methoxy-N-(4-(2-methoxy-4-nitrophenoxy)pyridin-2-yl)acetamide as an orange oil (234 mg, 78%); $R^t$ 1.89 min (Method 2); m/z 334 (M+H)$^+$ (ES$^+$).

A solution of 2-methoxy-N-(4-(2-methoxy-4-nitrophenoxy)pyridin-2-yl)acetamide (232 mg, 696 μmol) in a mixture of MeOH (30 mL) and AcOH (2.0 mL) was subjected to hydrogenation by passage through a Thales H-cube (1.0 mL min$^{-1}$, 50° C., 55 mm 10% Pt/C Cat-Cart, full hydrogen mode) and was then evaporated in vacuo to afford the title compound, Intermediate H4 as an impure oily liquid; $R^t$ 1.08 min (Method 2); m/z 304 (M+H)$^+$ (ES$^+$). This material, containing residual acetic acid was used directly, without further purification, in the next step (below).

Example 25

N-(4-(4-(3-(3-tert-Butyl-1-p-tolyl-1H-pyrazol-5-yl)ureido)-2-methoxy phenoxy)pyridin-2-yl)-2-methoxyacetamide

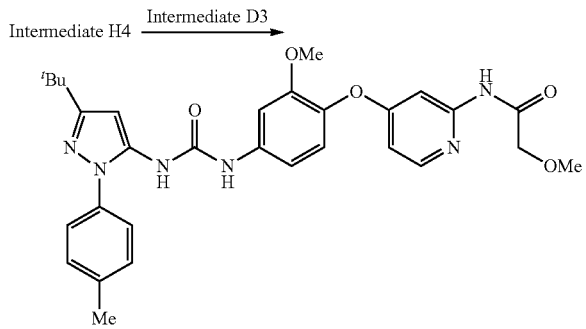

Example 25

To a suspension of CDI (17.2 g, 106 mmol) in DCM (150 mL) at RT was added 3-tert-butyl-1-p-tolyl-1H-pyrazol-5-amine (24.4 g, 106 mmol) in 1 g portions over 40 min and the reaction mixture stirred at RT for 2 hr. An aliqout of this solution (1.39 mL) was added dropwise to the preparation of Intermediate H4, obtained above, in DCM (3.0 mL) and the mixture maintained at RT for 16 hr. The reaction mixture was quenched with MeOH (2.0 mL) and after 30 min was evaporated in vacuo. The residue was purified by flash column chromatography (SiO$_2$, 40 g, EtOAc in isohexane, 20-100%, gradient elution) to afford the title compound, Example 25, as a pale yellow solid (254 mg, 64%); $R^t$ 2.42 min (Method 2); m/z 559 (M+H)$^+$ (ES$^+$); $^1$H NMR (400 MHz, DMSO-d$_6$) δ: 1.28 (9H, s), 2.38 (3H, s), 3.33 (3H, s), 3.69 (3H, s), 4.00 (2H, s), 6.37 (1H, s), 6.58 (1H, dd), 6.94 (1H, dd), 7.07 (1H, d), 7.35 (2H, d), 7.40-7.42 (3H, overlapping m), 7.52 (1H, d), 8.12 (1H, d), 8.36 (1H, s), 9.17 (1H, s), 9.94 (1H, s).

Intermediate H5: N-(4-(4-amino-2,3-dimethylphenoxy)pyridin-2-yl)-2-methoxy acetamide

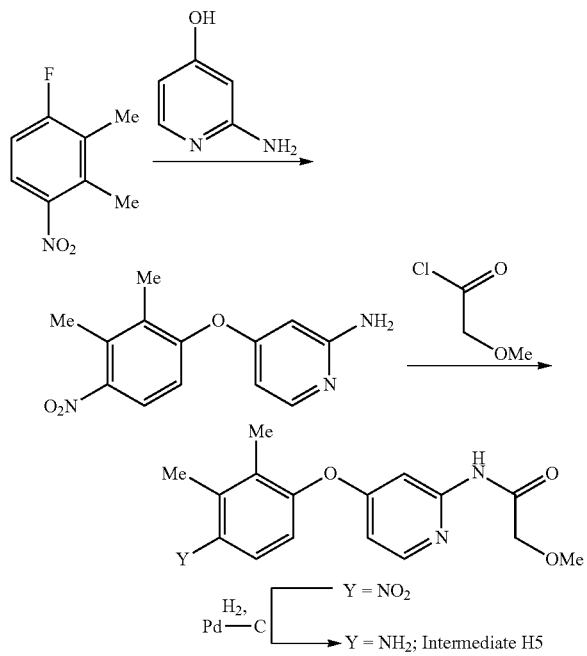

To a suspension of 2-aminopyridin-4-ol (339 mg, 3.07 mmol) in MeCN (4.0 mL) at RT was added DBU (570 μL, 3.78 mmol) and after 30 min a solution of 1-fluoro-2,3-dimethyl-4-nitrobenzene (400 mg, 2.36 mmol) in MeCN (2.0 mL) was added dropwise. The reaction mixture was maintained at RT for 16 hr; DMF (2.0 mL) was added and the mixture heated to 80° C. for 72 hr and then cooled to RT for 64 hr. The resulting mixture was evaporated in vacuo and the residue was partitioned between DCM (50 mL) and brine (30 mL). The organic layer was separated and dried (MgSO4) and was evaporated in vacuo. The residue was purified by flash column chromatography (SiO$_2$, 40 g, EtOAc in isohexane, 20-100%, gradient elution and then SiO$_2$, 12 g, 50% EtOAc in isohexane, isocratic elution) to afford 4-(2,3-dimethyl-4-nitrophenoxy)pyridin-2-amine, as a yellow solid (117 mg, 19%); R$^t$ 1.47 min (Method 2); m/z 260 (M+H)$^+$ (ES$^+$).

To a suspension of 4-(2,3-dimethyl-4-nitrophenoxy)pyridin-2-amine (110 mg, 0.424 mmol) in THF (3.0 mL) containing DIPEA (370 μL, 2.12 mmol) at 0° C. was added 2-methoxyacetyl chloride (155 μL, 1.70 mmol) in a single portion. The reaction mixture was warmed to RT for 1 hr and a solution of NH$_3$ in MeOH (7M, 2.0 mL) was added and the resulting mixture maintained at RT for 16 hr and then evaporated in vacuo. The residue was partitioned between DCM (50 mL) and brine (40 mL) and the organic phase was seprated and dried (MgSO$_4$) and was evaporated in vacuo. The residue was purified by flash column chromatography (SiO$_2$, 40 g, 20-50% EtOAc in isohexane, gradient elution) to afford N-(4-(2,3-dimethyl-4-nitrophenoxy)pyridin-2-yl)-2-methoxyacetamide (94 mg, 67%) as an orange oil; R$^t$ 2.14 min (Method 2); m/z 332 (M+H)$^+$ (ES$^+$).

A solution of N-(4-(2,3-dimethyl-4-nitrophenoxy)pyridin-2-yl)-2-methoxyacetamide (90 mg, 0.272 mmol) in a mixture MeOH (30 mL) and AcOH (2.0 mL) was subjected to hydrogenation by passage through a Thales H-cube (1.0 mL min$^{-1}$, 50° C., 55 mm 10% Pt/C Cat-Cart, full hydrogen mode) and was then evaporated in vacuo to afford the title compound, Intermediate H5, (82 mg, 100%); R$^t$ 1.21 min (Method 2); m/z 302 (M+H)$^+$ (ES$^+$).

Example 26

N-(4-(4-(3-(3-tert-Butyl-1-p-tolyl-1H-pyrazol-5-yl)ureido)-2,3-dimethyl phenoxy)pyridin-2-yl)-2-methoxyacetamide

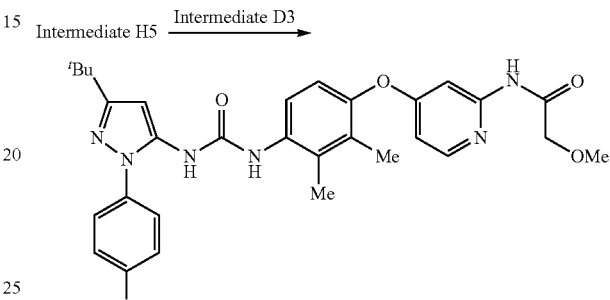

Example 26

To a suspension of CDI (17.2 g, 106 mmol) in DCM (150 mL) was added 3-tert-butyl-1-p-tolyl-1H-pyrazol-5-amine (24.3 g, 106 mmol) in 1 g portions over 40 min and the reaction stirred at RT for 2 hr. An aliquot of this solution (0.54 mL) containing Intermediate D3, was added dropwise to a solution of Intermediate H5 (82 mg, 0.272 mmol) in DCM (2.0 mL) at RT. A second aliquot (0.54 mL) of the solution containing Intermediate D3 was added after 40 min and a third aliquot (0.2 mL) was added after 2 hr and the resulting mixture maintained at RT 16 hr. The reaction ws quenched with MeOH (2.0 mL) and after a further 30 min the mixture was evaporated in vacuo. The residue was purified by flash column chromatography (SiO$_2$, 40 g, EtOAc in isohexane, 20-100%, gradient elution) to afford the title compound, Example 26, as a pale yellow solid (110 mg, 72%); R$^t$ 2.50 min (Method 2); m/z 557 (M+H)$^+$ (ES$^+$); $^1$H NMR (400 MHz, DMSO-d$_6$) δ: 1.27 (9H, s), 2.03 (3H, s), 2.13 (3H, s), 2.38 (3H, s), 3.33 (3H, s), 4.01 (2H, s), 6.34 (1H, s), 6.56 (1H, dd), 6.92 (1H, d), 7.34 (2H, d), 7.42 (2H, d), 7.52 (1H, d), 7.56 (1H, d), 8.16 (1H, d), 8.33 (1H, s), 8.61 (1H, s), 9.99 (1H, s).

Intermediate H6: N-(4-(4-amino-3-methoxyphenoxy)pyridin-2-yl)-2-methoxyacetamide

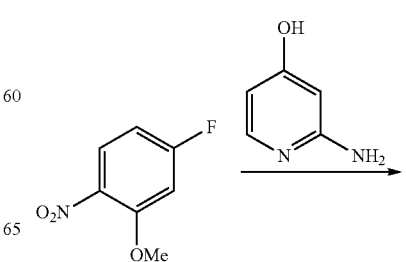

-continued

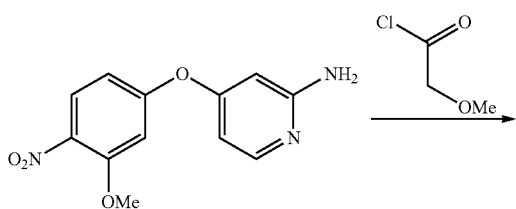

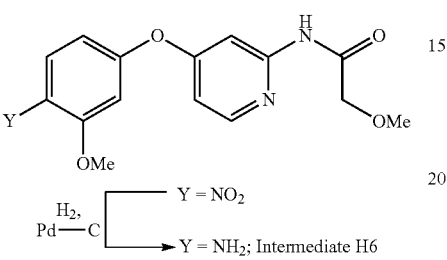

To a suspension of 2-aminopyridin-4-ol (483 mg, 4.38 mmol) in MeCN (2.0 mL) was added DBU (661 µL, 4.38 mmol) and the reaction mixture maintained at RT until a homogeneous solution had formed at which time, 1-fluoro-3-methoxy-4-nitrobenzene (500 mg, 2.92 mmol) was added. The reaction mixture was kept at RT for 5 hr, was heated to 80° C. for a further 16 hr. and was then cooled to RT, The reaction was diluted with water (5.0 mL) and the mixture was evaporated in vacuo. The residue was partitioned between EtOAc (20 mL) and water (20 mL) and the aq layer was separated and extracted with EtOAc (20 mL). The combined organic extracts were washed with brine (50 mL) and dried ($Na_2SO_4$) and were evaporated in vacuo. The residue was purified by flash column chromatography ($SiO_2$, 40 g, EtOAc in DCM, 0-100%, gradient elution) to afford 4-(3-methoxy-4-nitrophenoxy)pyridin-2-amine as a yellow solid (420 mg, 55%); $R^t$ 1.30 min (Method 2); m/z 262 (M+H)$^+$ (ES$^+$).

To a suspension of 4-(3-methoxy-4-nitrophenoxy)pyridin-2-amine (420 mg, 1.61 mmol) in DCM (4.0 mL) containing DIPEA (562 µL, 3.22 mmol) at 0° C. was added 2-methoxy-acetyl chloride (220 µL, 2.41 mmol) in a single portion. The reaction mixture was warmed to RT for 1 hr and then a solution of $NH_3$ in MeOH (7M, 2.0 mL) was added. The resulting mixture was kept at RT for 30 min, was evaporated in vacuo and the residue was partitioned between DCM (5.0 mL) and water (5.0 mL). The organic phase was separated and evaporated in vacuo and the residue was purified by flash column chromatography ($SiO_2$, 40 g, EtOAc in isohexane, 0-100%, gradient elution) to afford 2-methoxy-N-(4-(3-methoxy-4-nitrophenoxy)pyridin-2-yl)acetamide as pale yellow oil (401 mg, 75%); $R^t$ 1.87 min (Method 2); m/z 334 (M+H)$^+$ (ES$^+$).

A solution of 2-methoxy-N-(4-(3-methoxy-4-nitrophenoxy)pyridin-2-yl)acetamide (400 mg, 1.20 mmol) in a mixture of DCM (5.0 mL), MeOH, (5.0 mL) and AcOH (0.5 mL) was subjected to hydrogenation by passage through a Thales H-cube (0.8 mL min$^{-1}$, 60° C., 30 mm 10% Pt/C Cat-Cart, full hydrogen mode) and was then evaporated in vacuo to afford the title compound, Intermediate H6; $R^t$ 1.10 min (Method 2); m/z 304 (M+H)$^+$ (ES$^+$). This sample, containing residual acetic acid, was used without further purification in the next step (below).

Example 27

N-(4-(4-(3-(3-tert-Butyl-1-p-tolyl-1H-pyrazol-5-yl)ureido)-3-methoxy phenoxy)pyridin-2-yl)-2-methoxyacetamide

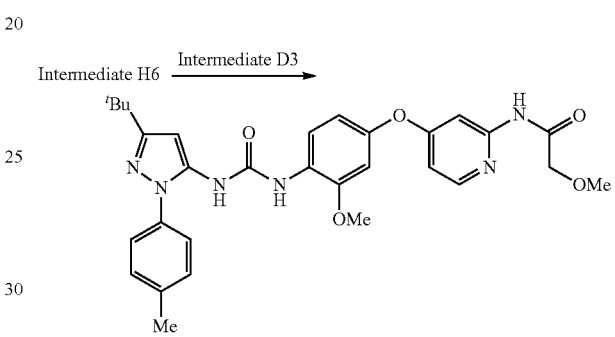

Example 27

To a suspension of CDI (17.2 g, 106 mmol) in DCM (150 mL) was added 3-tert-butyl-1-p-tolyl-1H-pyrazol-5-amine (24.4 g, 106 mmol) in 1 g portions over 40 min and the mixture stirred at RT for 2 hr. An aliquot of this solution (5.0 mL), containing Intermediate D3, was added dropwise to the sample of Intermediate H6 prepared above in DCM (2.0 mL) and the mixture kept at RT for 1 hr. The reaction mixture was quenched with MeOH (6.0 mL) and was then evaporated in vacuo (onto silica) and the residue was purified by flash column chromatography ($SiO_2$, 40 g, EtOAc in isohexane, 0-100%, gradient elution). The crude product so obtained was taken up in a mixture of DCM (2.0 mL) and $Et_2O$ (2.0 mL) and isohexane was added (4.0 mL) which resulted in the formation of a precipitate. The supernatant was decanted and the solid was dried in vacuo to afford the title compound, Intermediate 27, as a pale brown solid (485 mg, 65%); $R^t$ 2.50 min (Method 2); m/z 559 (M+H)$^+$ (ES$^+$); $^1$H NMR (400 MHz, DMSO-d$_6$, 100° C.) δ: 1.24 (9H, s), 2.38 (3H, s), 3.40 (3H, s), 3.84 (3H, s), 4.01 (2H, s), 6.31 (1H, s), 6.67 (1H, m), 6.69 (1H, d), 6.86 (1H, d), 7.31 (2H, d), 7.39 (2H, d), 7.65 (1H, d), 8.06 (1H, d), 8.17 (1H, d), 8.30 (1H, s), 8.70 (1H, s) and 9.47 (1H, s).

Other examples of the disclosure were derived by the reaction of an Intermediate A with an isocyanate or a carbamoyl chloride. Alternatively Intermediate A was converted into a compound represented by Intermediate J which was then reacted with an amine

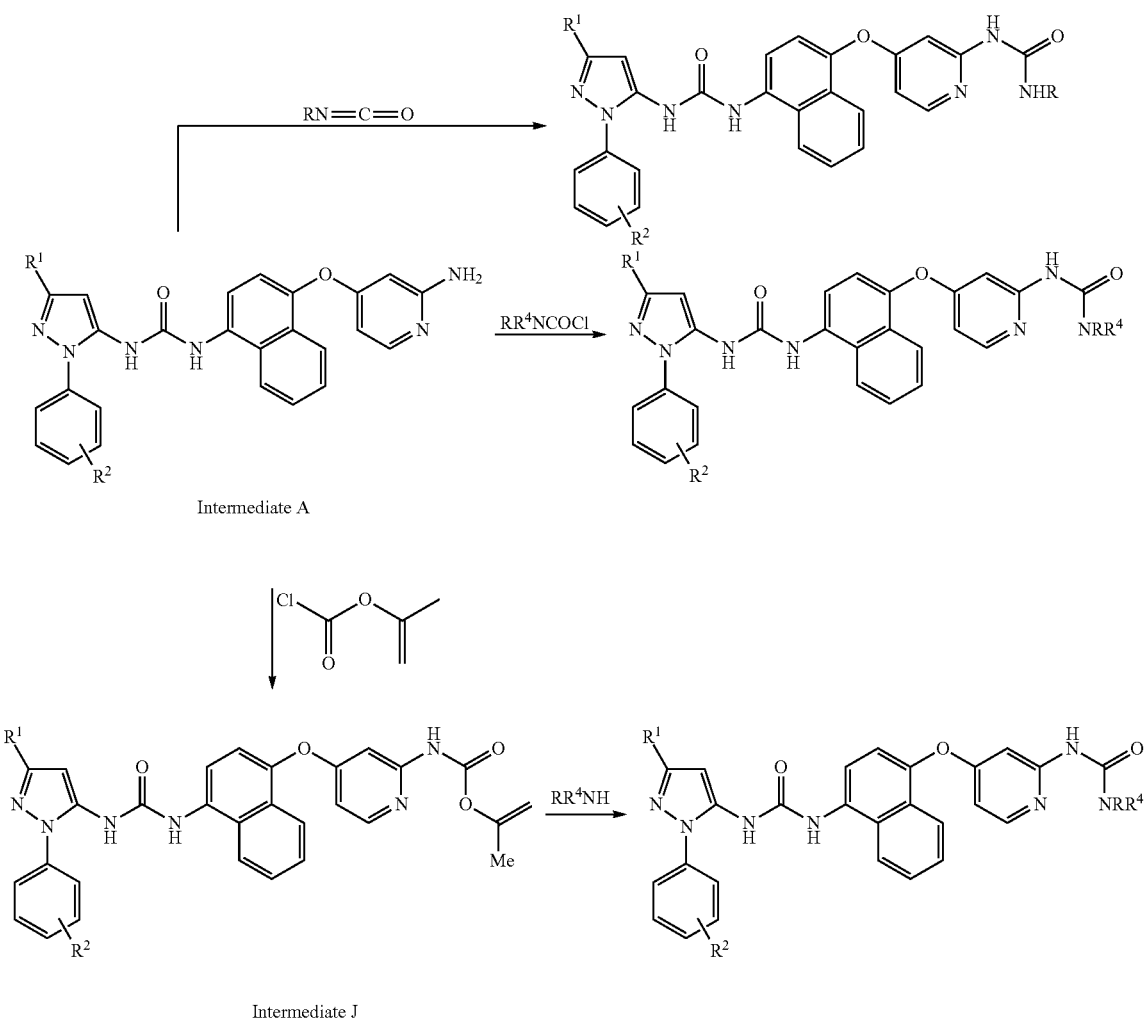

Intermediate A

Intermediate J

Example 28

N-Ethyl-N'-4-(4-(3-(3-tert-butyl-1-p-tolyl-1H-pyrazol-5-yl)ureido)naphthalen-1-yloxy)pyridin-2-ylurea

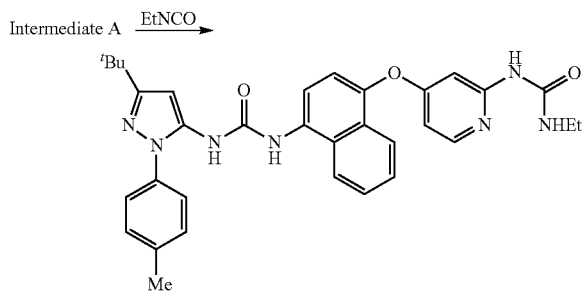

Example 28

To a solution of Intermediate A (53 mg, 0.105 mmol) in dry DCM (3.0 mL) at 0° C. under nitrogen was added ethyl isocyanate (21 μL, 0.26 mmol) and after 20 min at 0° C. the reaction mixture was warmed to RT for 45 hr. The mixture was cooled to 0° C. and a second aliquot of ethyl isocyanate (21 μL, 0.26 mmol) was added and after 20 min the resulting mixture was warmed to RT. In addition a second reaction was conducted as follows: To a solution of Intermediate A (50 mg, 0.099 mmol) in dry pyridine (2 mL) under nitrogen at 0° C. was added ethyl isocyanate (23 μL, 0.30 mmol) dropwise and the reaction mixture was slowly warmed to RT. After 48 hr a second aliquot of ethyl isocyanate (23 μL, 0.29 mmol) was added. After a further 3 hr both reaction mixtures were quenched by the addition of 1% $NH_3$ in MeOH (2.0 mL) and after 30 min were evaporated in vacuo. The crude residues were combined and purified by flash column chromatography ($SiO_2$, 12 g, [5% MeOH in EtOAc] in isohexane, 0-80%, gradient elution) to afford the title compound, Example 28 as a white solid (29 mg, 25%): $R^t$ 2.42 min (Method 2); m/z 578 $(M+H)^+$ $(ES^+)$; $^1H$ NMR (400 MHz, DMSO-$d_6$) δ ppm 1.03 (3H, t), 1.28 (9H, s), 2.40 (3H, s), 3.08-3.14 (2H, m), 6.41 (1H, s), 6.55 (1H, dd), 6.91 (1H, d), 7.31 (1H, d), 7.37 (2H, d), 7.46 (2H, d), 7.55-7.59 (1H, m), 7.63-7.67 (1H, m), 7.82 (1H, dd), 7.89-7.99 (2H, m), 8.06 (1H, d), 8.09 (1H, d), 8.78 (1H, s), 9.02 (1H, s), 9.12 (1H, s).

Example 29

4-(4-(3-(3-tert-Butyl-1-p-tolyl-1H-pyrazol-5-yl)ureido)naphthalen-1-yloxy)pyridin-2-yl urea

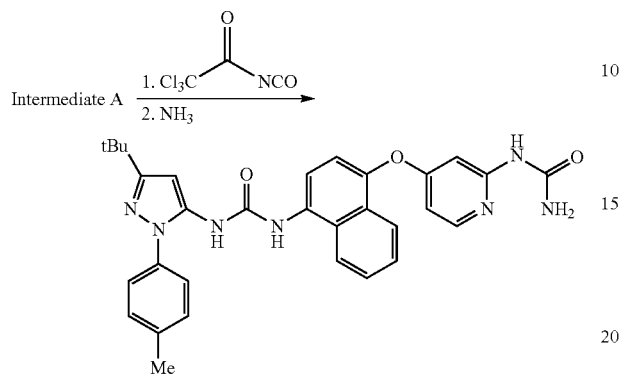

Example 29

To a solution of Intermediate A (50 mg, 0.099 mmol) in dry pyridine (1.5 mL) at 0° C. under nitrogen was added trichloroacetyl isocyanate (15 μL, 0.12 mmol) and after 30 min at 0° C. the reaction mixture was warmed to RT. After 24 hr a further aliquot of trichloroacetyl isocyanate (29 μL, 0.25 mmol) was added and after 42 hr the reaction was quenched by addition of 1% NH$_3$ in MeOH (2.0 mL). After an additional 30 min the resulting mixture was evaporated in vacuo and the residue was purified by flash column chromatography (SiO$_2$, 12 g, [5% MeOH in EtOAc] in isohexane, 0-75%, gradient elution) to afford the title compound, Example 29 as a white solid (7 mg, 13%): R$^t$ 2.21 min (Method 2); m/z 550 (M+H)$^+$ (ES$^+$); $^1$H NMR (400 MHz, DMSO-d$_6$) δ ppm 1.28 (9H, s), 2.40 (3H, s), 6.41 (1H, s), 6.52 (1H, dd), 6.95 (1H, d), 7.31 (1H, d), 7.37 (2H, d), 7.45-7.47 (2H, m), 7.54-7.61 (1H, m), 7.62-7.67 (1H, m), 7.83 (1H, dd), 7.95 (1H, d), 8.06 (1H, d), 8.09 (1H, d), 8.81 (1H, s), 9.03 (1H, s), 9.15 (1H, s).

Example 30

N-Propan-2-yl-N'-4-(4-(3-(3-tert-butyl-1-p-tolyl-1H-pyrazol-5-yl)ureido)naphthalen-1-yloxy)pyridin-2-ylurea

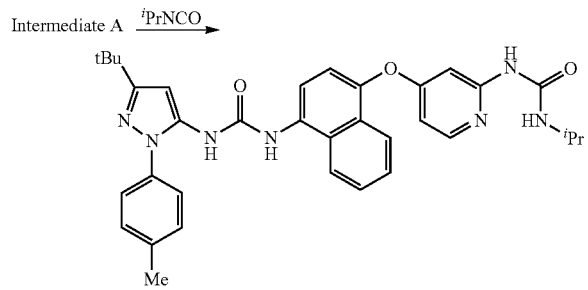

Example 30

To a solution of Intermediate A (70 mg, 0.138 mmol) in pyridine (1.5 mL) was added 2-isocyanatopropane (68 μL, 0.691 mmol) and after 24 hr at RT a further aliquot of 2-isocyanatopropane (68 μL, 0.69 mmol) was added. After 72 hr the reaction was quenched by addition of 1% NH$_3$ in MeOH (2.0 mL) and after a further 30 min the resulting mixture was evaporated in vacuo. The residue was purified by flash column chromatography (SiO$_2$, 12 g, MeOH in DCM, 0-5%, gradient elution) and by recrystallization from MeOH to afford the title compound, Example 30 as a pink solid (32 mg, 39%): R$^t$ 5.47 min (Method 1 basic); m/z 592 (M+H)$^+$ (ES$^+$); $^1$H NMR (400 MHz, DMSO-d$_6$) δ ppm 1.08 (6H, d), 1.28 (9H, s), 2.40 (3H, s), 3.69-3.77 (1H, m), 6.41 (1H, s), 6.55 (1H, dd), 6.94 (1H, d), 7.31 (1H, d), 7.38 (2H, d), 7.46 (2H, d), 7.57 (1H, t), 7.65 (1H, t), 7.78 (1H, br d), 7.82 (1H, d), 7.96 (1H, d), 8.05-8.09 (2H, overlapping m), 8.78 (1H, s), 8.94 (1H, s), 9.12 (1H, s).

Example 31

1-(3-(tert-Butyl)-1-(p-tolyl)-1H-pyrazol-5-yl)-3-(4-((2-(3-phenylureido)pyridin-4-yl)oxy)naphthalen-1-yl)urea

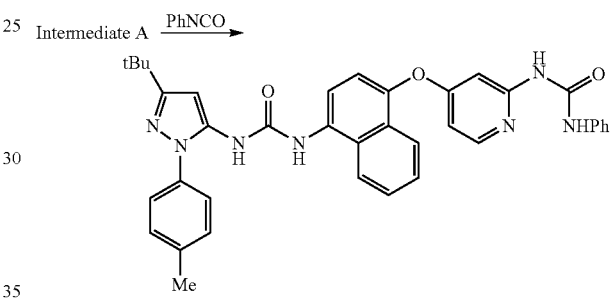

Example 31

To a solution of Intermediate A (70 mg, 0.138 mmol) in pyridine (1.5 mL) was added phenyl isocyanate (75 μL, 0.691 mmol) and after 16 hr the reaction mixture was quenched by the addition of 1% NH$_3$ in MeOH (2.0 mL). After a further 30 min the resulting mixture was evaporated in vacuo and the residue was purified by flash column chromatography (SiO$_2$, 12 g, MeOH in DCM, 0-5%, gradient elution) and then by trituration from MeOH, to afford the title compound, Example 31 as an off-white solid (17 mg, 19%): R$^t$ 5.70 min (Method 1 basic); m/z 626 (M+H)$^+$ (ES$^+$); $^1$H NMR (400 MHz, DMSO-d$_6$) δ ppm 1.29 (9H, s), 2.40 (3H, s), 6.42 (1H, s), 6.65 (1H, dd), 6.98-7.03 (2H, overlapping m), 7.28 (2H, m), 7.34-7.39 (3H, overlapping m), 7.44-7.48 (4H, overlapping m), 7.59 (1H, t), 7.66 (1H, t), 7.84 (1H, d), 7.98 (1H, d), 8.10 (1H, d), 8.17 (1H, d), 8.79 (1H, s), 9.14 (1H, s), 9.33 (1H, s), 10.41 (1H, s).

Example 32

1-(4-((2-(3-Benzylureido)pyridin-4-yl)oxy)naphthalen-1-yl)-3-(3-(tert-butyl)-1-(p-tolyl)-1H-pyrazol-5-yl)urea

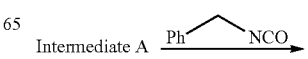

d), 7.57 (1H, t), 7.65 (1H, t), 7.81 (1H, d), 7.92 (1H, br s), 7.96 (1H, d), 8.04-8.10 (2H, overlapping m), 8.78 (1H, s), 8.96 (1H, s), 9.12 (1H, s).

Example 34

1-(3-(tert-Butyl)-1-(p-tolyl)-1H-pyrazol-5-yl)-3-(4-((2-(3-(2-methoxyethyl)ureido)pyridin-4-yl)oxy)naphthalen-1-yl)urea

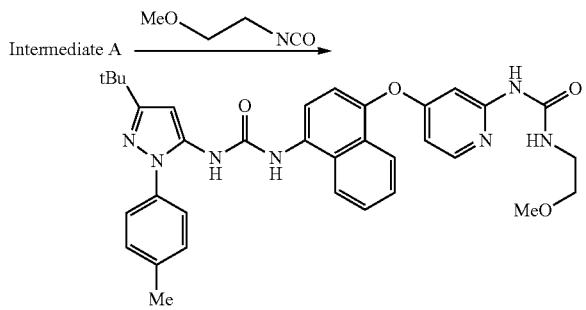

Example 34

To a solution of Intermediate A (70 mg, 0.138 mmol) in pyridine (1.5 mL) was added 1-isocyanato-2-methoxyethane (14.0 mg, 0.138 mmol) and the mixture maintained at RT for 64 hr. The reaction was quenched by the addition of MeOH (1.0 mL) and after 30 min the resulting mixture was evaporated in vacuo. The residue was purified by flash column chromatography (SiO₂, 12 g, MeOH in DCM, 0-5%, gradient elution) and then by trituration from MeOH to afford the title compound, Example 34 as an off-white solid (27 mg, 32%): R$^t$ 5.27 min (Method 1 basic); m/z 608 (M+H)⁺ (ES⁺); ¹H NMR (400 MHz, DMSO-d₆) δ ppm 1.28 (9H, s), 2.40 (3H, s), 3.23-3.27 (5H, m), 3.33-3.36 (2H, m), 6.41 (1H, s), 6.56 (1H, dd), 6.94 (1H, s), 7.31 (1H, d), 7.38 (2H, d), 7.46 (2H, d), 7.57 (1H, t), 7.65 (1H, t), 7.82 (1H, d), 7.96 (1H, d), 8.03 (1H, br s), 8.05-8.09 (2H, overlapping m), 8.78 (1H, s), 9.10 (1H, s), 9.12 (1H, s).

Example 35

1-(3-(tert-Butyl)-1-(p-tolyl)-1H-pyrazol-5-yl)-3-(4-((2-(3-cyclopentyl)ureido)pyridin-4-yl)oxy)naphthalen-1-yl)urea

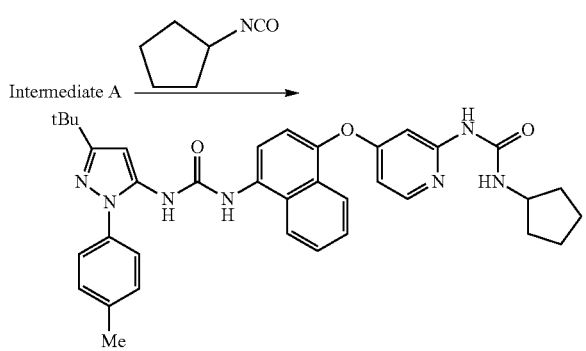

Example 35

---

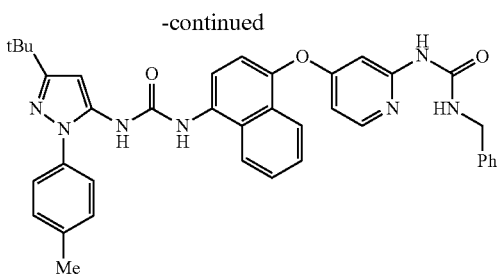

Example 32

To a solution of Intermediate A (70 mg, 0.138 mmol) in pyridine (1.5 mL) was added benzyl isocyanate (85 μL, 0.691 mmol) and after 16 hr at RT. the reaction mixture was quenched by the addition of 1% NH₃ in MeOH (2.0 mL). After a further 30 min the resulting mixture was evaporated in vacuo and the residue was purified by flash column chromatography (SiO₂, 12 g, MeOH in DCM, 0-5%, gradient elution) and then by trituration from MeOH to afford the title compound, Example 32 as an off-white solid (42 mg, 47%): R$^t$ 5.64 min (Method 1 basic); m/z 640 (M+H)⁺ (ES⁺); ¹H NMR (400 MHz, DMSO-d₆) δ ppm 1.28 (9H, s), 2.40 (3H, s), 4.33 (2H, d), 6.41 (1H, s), 6.57 (1H, dd), 6.93 (1H, s), 7.21-7.27 (3H, overlapping m), 7.30-7.32 (3H, m), 7.37 (2H, d), 7.46 (2H, d), 7.57 (1H, t), 7.65 (1H, t), 7.83 (1H, d), 7.96 (1H, d), 8.06-8.09 (2H, overlapping m), 8.45 (1H, br, s), 8.77 (1H, s), 9.12 (1H, s), 9.18 (1H, s).

Example 33

1-(4-((2-(3-Cyclopropylureido)pyridin-4-yl)oxy)naphthalen-1-yl)-3-(3-(tert-butyl)-1-(p-tolyl)-1H-pyrazol-5-yl)urea

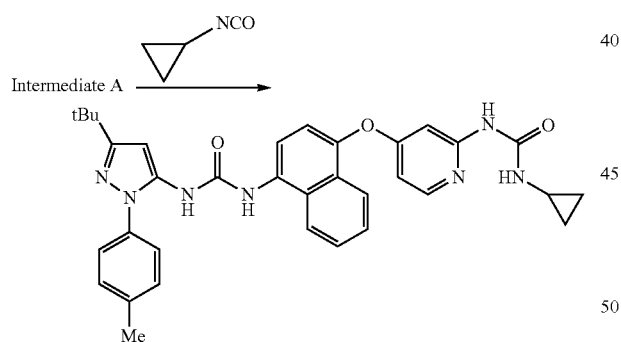

Example 33

To a solution of Intermediate A (70 mg, 0.138 mmol) in pyridine (1.5 mL) was added cyclopropyl isocyanate (57.4 mg, 0.691 mmol) and the mixture maintained at RT for 64 hr. The reaction was quenched by the addition of MeOH (1.0 mL) and after 30 min the mixture was evaporated in vacuo. The residue was purified by flash column chromatography (SiO₂, 12 g, MeOH in DCM, 0-5%, gradient elution) and then by recrystallization from MeOH to afford the title compound, Example 33 as an off-white solid (11 mg, 13%): R$^t$ 5.47 min (Method 1 basic); m/z 590 (M+H)⁺ (ES⁺); ¹H NMR (400 MHz, DMSO-d₆) δ ppm 0.36-0.40 (2H, m), 0.59-0.63 (2H, m), 1.28 (9H, s), 2.40 (3H, s), 2.52 (1H, m), 6.41 (1H, s), 6.57 (1H, dd), 6.97 (1H, br s), 7.31 (1H, d), 7.38 (2H, d), 7.46 (2H, To a solution of Intermediate A (70 mg, 0.138 mmol) in pyridine (1.5 mL) was added cyclopentyl isocyanate (78 μL, 0.691 mmol) and the mixture maintained at RT for 64 hr. A further aliquot of cyclopentyl isocyanate (78 μL, 0.691 mmol) was added and after an additional 24 hr the reaction mixture was quenched by the addition of 1% NH$_3$ in MeOH (2.0 mL) After 30 min the resulting mixture was evaporated in vacuo and the residue was purified by flash column chromatography (SiO$_2$, 12 g, MeOH in DCM, 0-5%, gradient elution) and then by trituration from acetone to afford the tite compound, Example 35 as a pink solid (17 mg, 20%): R$^t$ 5.74 min (Method 1 basic); m/z 618 (M+H)$^+$ (ES$^+$); $^1$H NMR (400 MHz, DMSO-d$_6$) δ ppm 1.28 (9H, s), 1.28-1.38 (2H, m), 1.49-1.64 (4H, m), 1.77-1.85 (2H, m), 2.40 (3H, s), 3.88-3.93 (1H, m), 6.41 (1H, s), 6.55 (1H, dd), 6.95 (1H, d), 7.31 (1H, d), 7.38 (2H, d), 7.46 (2H, d), 7.57 (1H, t), 7.65 (1H, t), 7.82 (1H, d), 7.89 (1H, br s), 7.96 (1H, d), 8.05-8.10 (2H, overlapping m), 8.78 (1H, s), 8.92 (1H, s), 9.12 (1H, s).

Example 36

1-(3-(tert-Butyl)-1-(p-tolyl)-1H-pyrazol-5-yl)-3-(4-((2-(3-methyl)ureido)pyridin-4-yl)oxy)naphthalen-1-yl)urea

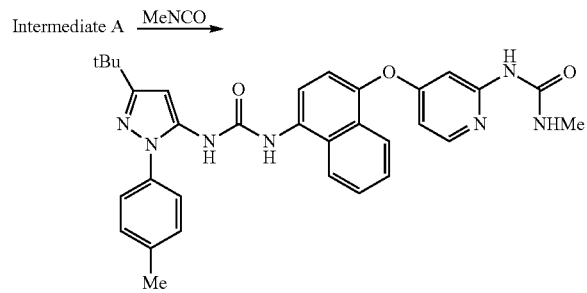

Example 36

To a solution of Intermediate A (50 mg, 0.099 mmol) in pyridine (1.0 mL) was added methyl isocyanate (50 μL, 0.806 mmol) and the mixture maintained at RT for 24 hr. Additional aliquots of methyl isocyanate (150 μL, 0.26 mmol) and pyridine (0.5 mL) were added and the reaction mixture maintained at RT for 96 hr and then partitioned between DCM (30 mL) and saturated aq. NaHCO$_3$ (10 mL). The aqueous layer was separated and extracted with DCM (10 mL) and the combined organic extracts were dried (MgSO$_4$) and evaporated in vacuo. The residue was purified by flash column chromatography (SiO$_2$, 12 g, MeOH in DCM, 0-10%, gradient elution) to afford the title compound, Example 36 as a white solid (12 mg, 21%): R$^t$ 5.24 min (Method 1 basic); m/z 564 (M+H)$^+$ (ES$^+$); $^1$H NMR (400 MHz, DMSO-d$_6$) δ ppm $^1$H NMR (400 MHz, DMSO-d$_6$) δ ppm 1.28 (9H, s), 2.39 (3H, s), 2.65 (3H, d), 6.40 (1H, s), 6.54 (1H, dd), 6.87 (1H, d), 7.31 (1H, d), 7.37 (2H, d), 7.46 (2H, m), 7.58 (1H, m), 7.64 (1H, m), 7.81 (1H, d), 7.88 (1H, br s), 7.95 (1H, d), 8.05 (1H, d), 8.08 (1H, d), 8.76 (1H, s), 9.09 (1H, s), 9.11 (1H, s).

Example 37

Ethyl 2-(3-(4-((4-(3-(3-(tert-butyl)-1-(p-tolyl)-1H-pyrazol-5-yl)ureido)naphthalen-1-yl)oxy)pyridin-2-yl)ureido)acetate

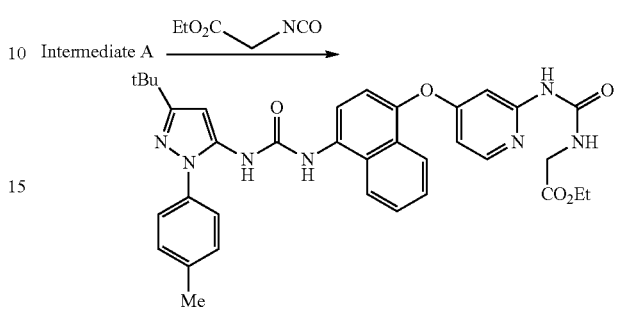

Example 37

To a solution of Intermediate A (200 mg, 0.395 mmol) in pyridine (1.5 mL) was added ethyl 2-isocyanatoacetate (135 μL, 1.18 mmol) and the mixture maintained at RT for 16 hr. The reaction was quenched by addition of MeOH (2.0 mL) and after a further 30 min the resulting mixture was evaporated in vacuo. Toluene (10 mL) was added and mixture was again evaporated in vacuo. The crude product so obtained was triturated with MeOH (10 mL) to afford the title compound Example 37 as an off white solid (160 mg, 61%): R$^t$ 2.47 min (Method 2); m/z 636 (M+H)$^+$ (ES$^+$); $^1$H NMR (400 MHz, DMSO-d$_6$) δ ppm 1.18 (3H, t), 1.28 (9H, s), 2.40 (3H, s), 3.90 (2H, d), 4.08 (2H, q), 6.41 (1H, s), 6.59 (1H, dd), 6.88 (1H, br s), 7.33 (1H, d), 7.38 (2H, d), 7.46 (2H, d), 7.57 (1H, t), 7.65 (1H, t), 7.82 (1H, d), 7.96 (1H, d), 8.09 (2H, d), 8.37 (1H, br s), 8.78 (1H, s), 9.13 (1H, s), 9.33 (1H, s).

Example 38

4-(3-(4-(4-(3-(3-tert-Butyl-1-p-tolyl-1H-pyrazol-5-yl)ureido)naphthalen-1-yloxy)pyridin-2-yl)ureido)piperidine

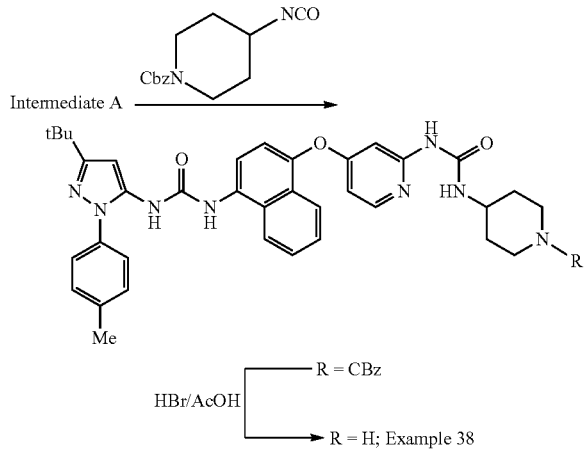

To a solution of Intermediate A (100 mg, 0.197 mmol) in pyridine (2.0 mL) was added a suspension of benzyl 4-isocyanatopiperidine-1-carboxylate (154 mg, 0.592 mmol) in pyridine (1.0 mL) and the mixture maintained at RT for 48 hr. A second aliquot of benzyl 4-isocyanatopiperidine-1-carboxylate (102 mg, 0.394 mmol) was added and after 96 hr at RT the mixture was evaporated in vacuo. The residue was extracted with MeOH and the alcoholic extract was evaporated in vacuo to give a residue that was purified by flash column chromatography (SiO$_2$, 12 g, MeOH in DCM, 0-5%, gradient elution) and then by recrystallization from MeOH to afford the N-benzylcarbamate: benzyl 4-(3-(4-((4-(3-(3-(tert-butyl)-1-(p-tolyl)-1H-pyrazol-5-yl)ureido)naphthalen-1-yl)oxy)pyridin-2-yl)ureido)piperidine-1-carboxylate (R=CBz) as a pale pink solid (25 mg, 16%): R$^t$ 5.72 min (Method 1 basic); m/z 768 (M+H)$^+$ (ES$^+$); $^1$H NMR (400 MHz, DMSO-d$_6$) δ ppm 1.24-1.32 (11H, m), 1.78-1.81 (2H, m), 2.40 (3H, s), 3.03 (2H, brs), 3.67 (1H, brs), 3.81-3.84 (2H, m), 5.06 (2H, s), 6.41 (1H, s), 6.57 (1H, dd), 6.94 (1H, s), 7.30-7.39 (8H, m), 7.46 (2H, d), 7.57 (1H, t), 7.65 (1H, t), 7.81 (1H, d), 7.96 (2H, d), 8.06-8.09 (2H, m), 8.77 (1H, s), 8.99 (1H, s), 9.12 (1H, s).

To a solution of the N-benzylcarbamate, prepared above, (150 mg, 0.196 mmol) in acetic acid (5.0 mL) at 0° C. was added HBr (45% solution in AcOH, 248 μL, 1.956 mmol) and the reaction mixture was warmed to RT. After 16 hr the reaction mixture was diluted with MeCN (3.0 mL) and purified by SCX capture and release. The crude product so obtained was purified by flash column chromatography (SiO$_2$, [5% MeOH in EtOAc] in isohexane, 50-100%, gradient elution) to afford the title compound, Example 38 as an off-white solid (100 mg, 80%): R$^t$ 1.87 min (Method 2); m/z 633 (M+H)$^+$ (ES$^+$); $^1$H NMR (400 MHz, DMSO-d$_6$) δ ppm 1.12-1.27 (2H, m), 1.29 (9H, s), 1.70-1.74 (2H, m), 2.40 (3H, s), 2.42-2.50 (3H, m), 2.84-2.88 (2H, m), 3.50 (1H, br s), 6.41 (1H, s), 6.56 (1H, dd), 6.95 (1H, br s), 7.31 (1H, d), 7.37 (2H, d), 7.46 (2H, d), 7.57 (1H, t), 7.65 (1H, t), 7.82 (1H, d), 7.87 (1H, br s), 7.96 (1H, d), 8.05-8.10 (2H, m), 8.79 (1H, br s), 8.94 (1H, s), 9.13 (1H, s).

Example 39

N-Acetyl 4-(3-(4-(4-(3-(3-tert-butyl-1-p-tolyl-1H-pyrazol-5-yl)ureido)naphthalen-1-yloxy)pyridin-2-yl)ureido)piperidine

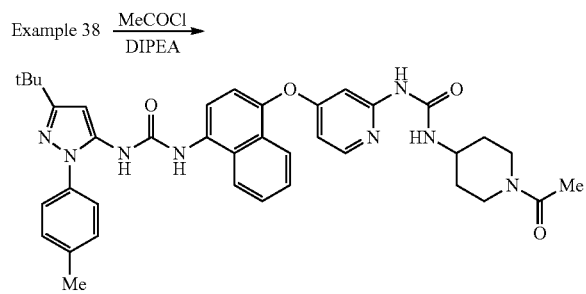

Example 39

To a solution of Example 38 (30 mg, 47 μmol) and DIPEA (16.5 μL, 95 μmol) in DCM (1.0 mL) at 0° C. under nitrogen was added a solution of acetyl chloride (4.1 μL, 57 μmol) in DCM (0.5 mL) and the reaction mixture warmed to RT for 1 hr. An additional aliquot of acetyl chloride (2.0 μL, 28 μmol) in DCM (0.3 mL) was added and after 1 hr saturated aq NaHCO$_3$ (2.0 mL) was added and the reaction mixture filtered through a phase separation cartridge. The organic phase was evaporated in vacuo and the residue was purified by flash column chromatography (SiO$_2$, [5% MeOH in EtOAc] in isohexane, 50-100%, gradient elution) to afford the title compound Example 39 as an off-white solid (25 mg, 76%): R$^t$ 5.15 min (Method 1 basic); m/z 675 (M+H)$^+$ (ES$^+$); $^1$H NMR (400 MHz, DMSO-d$_6$) δ ppm 1.13-1.40 (11H, m), 1.70-1.84 (2H, m), 1.98 (3H, s), 2.40 (3H, s), 2.81 (1H, t), 3.14 (1H, t), 3.66-3.71 (2H, m), 4.06-4.09 (1H, m), 6.41 (1H, s), 6.57 (1H, dd), 6.94 (1H, br s), 7.31 (1H, d), 7.37 (2H, d), 7.46 (2H, d), 7.57 (1H, t), 7.65 (1H, t), 7.82 (1H, d), 7.97 (2H, d), 8.06-8.10 (2H, m), 8.80 (1H, br s), 9.00 (1H, s), 9.14 (1H, s)

Example 40

2-(2-Methoxyethoxy)-1-(4-(3-(4-(4-(3-(3-tert-butyl-1-p-tolyl-1H-pyrazol-5-yl)ureido)naphthalen-1-yloxy)pyridin-2-yl)ureido)piperidin-1-yl)ethanone

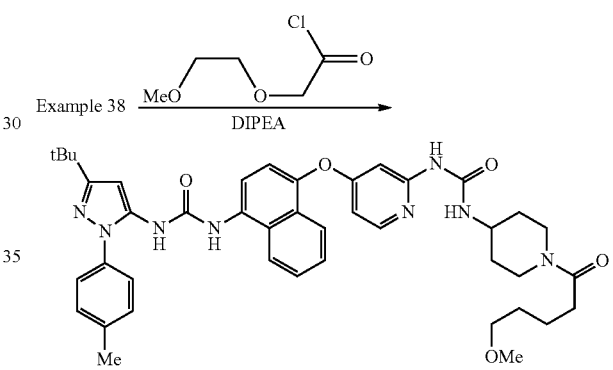

Example 40

To a solution of Example 38 (20 mg, 32 μmol) and DIPEA (11.0 μL, 63 μmol) in DCM (1.0 mL) at 0° C. under nitrogen was added a solution of 2-(2-methoxyethoxy)acetyl chloride (7.2 mg, 47 μmol) in DCM (0.5 mL) and the reaction mixture warmed to RT for 1 hr. An additional aliquot of 2-(2-methoxyethoxy)acetyl chloride (3.5 mg, 24 μmol) in DCM (0.3 mL) was added and after a further 1 hr saturated aq NaHCO$_3$ (2.0 mL) was added and the reaction mixture was filtered through a phase separation cartridge. The organic phase was evaporated in vacuo and the residue was purified by flash column chromatography (SiO$_2$, [5% MeOH in EtOAc] in isohexane, 50-100%, gradient elution) and then by SCX capture and release to afford the title compound, Example 40 as an off white solid (8.4 mg 32%): R$^t$ 5.18 min (Method 1 basic); m/z 749 (M+H)$^+$ (ES$^+$); $^1$H NMR (400 MHz, DMSO-d$_6$) δ ppm 1.15-1.41 (11H, m), 1.78-1.82 (2H, m), 2.40 (3H, s), 2.84 (1H, t), 3.10 (1H, t), 3.24 (3H, s), 3.45-3.46 (2H, m), 3.53-3.55 (2H, m), 3.65-3.72 (2H, m), 4.04-4.17 (3H, m), 6.41 (1H, s), 6.58 (1H, dd), 6.95 (1H, s), 7.31 (1H, d), 7.37 (2H, d), 7.46 (2H, d), 7.57 (1H, t), 7.65 (1H, t), 7.82 (1H, d), 7.96 (2H, d), 8.05-8.10 (2H, m), 8.79 (1H, s), 8.99 (1H, s), 9.13 (1H, s)

Example 41

N-Methylsulfonyl-4-(3-(4-(4-(3-(3-tert-butyl-1-p-tolyl-1H-pyrazol-5-yl)ureido)naphthalen-1-yloxy)pyridin-2-yl)ureido)piperidine

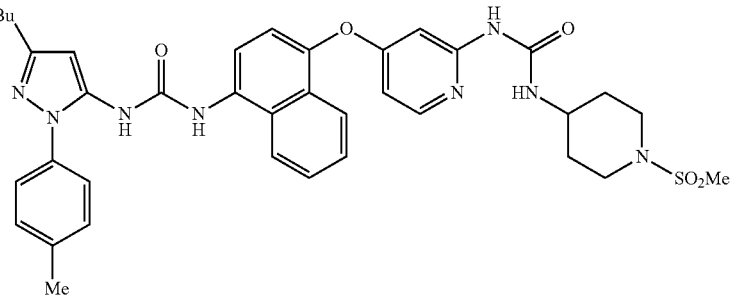

To a solution of Example 38 (40 mg, 63 µmol) and DIPEA (22.0 µL, 126 µmol) in DCM (1.0 mL) at 0° C. under nitrogen was added a solution of methanesulfonyl chloride (5.9 µL, 76 µmol) in DCM (0.5 mL). The reaction mixture was warmed to RT and after 1 hr an additional aliquot of methanesulfonyl chloride (2.0 µL, 28 µmol) in DCM (0.3 mL) was added. After 1 hr, the reaction mixture was washed with saturated aq NaHCO$_3$ (2.0 mL). The organic phase was evaporated and the residue was purified by flash column chromatography (SiO$_2$, 4 g, [5% MeOH in EtOAc] in isohexane, 50-100%, gradient elution) to afford the title compound, Example 41 as a light purple solid (28 mg, 60%): R$^t$ 5.20 min (Method 1 basic); m/z 711 (M+H)$^+$ (ES$^+$); $^1$H NMR (400 MHz, DMSO-d$_6$) δ ppm 1.29 (9H, s), 1.40-1.48 (2H, m), 1.87-1.91 (2H, m), 2.40 (3H, s), 2.84-2.92 (5H, m), 3.37-3.47 (2H, m), 3.60 (1H, br s), 6.41 (1H, s), 6.57 (1H, dd), 6.96 (1H, br s), 7.31 (1H, d), 7.37 (2H, d), 7.46 (2H, d), 7.57 (1H, t), 7.65 (1H, t), 7.82 (1H, d), 7.96 (1H, d), 8.00 (1H, br s), 8.07-8.10 (2H, m), 8.80 (1H, s), 9.01 (1H, s), 9.14 (1H, s).

Example 42

N-(4-(4-(3-(3-tert-Butyl-1-p-tolyl-1H-pyrazol-5-yl)ureido)naphthalen-1-yloxy)pyridin-2-yl)morpholine-4-carboxamide

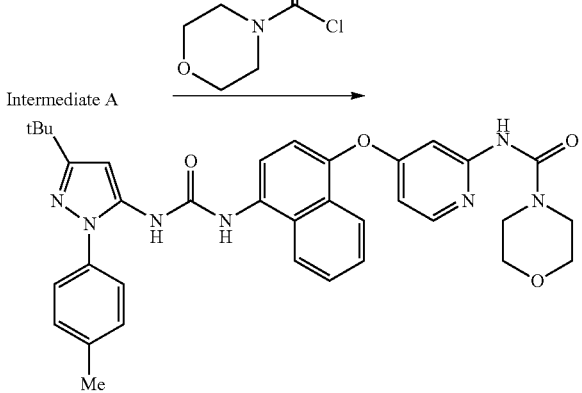

nitrogen at 0° C. was added morpholine-4-carbonyl chloride (14 µL, 0.12 mmol) dropwise The reaction mixture was maintained at 0° C. for 15 min, was warmed to 40° C. for 4 hr and then left at RT for 20 hr. The reaction mixture was reheated to 40° C. for 3 hr and was then quenched by the addition of 1% NH$_3$ in MeOH (2.0 mL). After 45 min the resulting mixture was evaporated in vacuo and the residue was purified by flash column chromatography (SiO$_2$, 12 g, [5% MeOH in EtOAc] in isohexane, 0-80%, gradient elution) to afford the title compound, Example 42 as a beige powder (16 mg, 25%): R$^t$ 2.18 min (Method 2); m/z 620 (M+H)$^+$ (ES$^+$); $^1$H NMR (400 MHz, DMSO-d$_6$) δ ppm 1.28 (9H, s), 2.40 (3H, s), 3.36 (4H, t), 3.53 (4H, t), 6.41 (1H, s), 6.61 (1H, dd), 7.31 (1H, d), 7.34-7.41 (3H, m), 7.46 (2H, d), 7.55-7.59 (1H, m), 7.63-7.68 (1H, m), 7.84 (1H, dd), 7.96 (1H, d), 8.08 (1H, d), 8.11 (1H, d), 8.80 (1H, s), 9.13 (1H, s), 9.25 (1H, s).

Example 43

N-(4-((4-(3-(3-(tert-Butyl)-1-(p-tolyl)-1H-pyrazol-5-yl)ureido)naphthalen-1-yl)oxy)pyridin-2-yl)-4-methylpiperazine-1-carboxamide

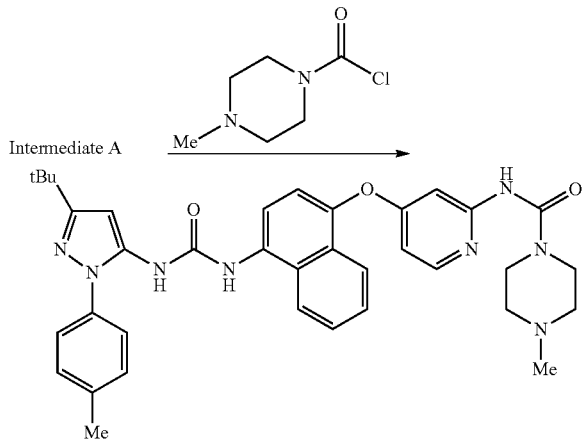

To a solution of Intermediate A (50 mg, 0.099 mmol) and DIPEA (52 µL, 0.30 mmol) in dry pyridine (1.5 mL) under To a solution of Intermediate A (70 mg, 0.138 mmol) and DIPEA (120 µL, 0.691 mmol) in dry pyridine (1.5 mL) was added 4-methylpiperazine-1-carbonyl chloride hydrochloride (138 mg, 0.691 mmol) and the mixture maintained at RT for 64 hr. The reaction was quenched by the addition of 1% NH₃ in MeOH (2.0 mL) and after 30 min the resulting mixture was evaporated in vacuo and the residue was taken up into EtOAc. The organic solution was washed with water and brine and was dried (MgSO₄) and evaporated in vacuo. The residue was purified by flash column chromatography (SiO₂, [7% NH₃ in MeOH] in DCM, 0-5%, gradient elution) to afford the title compound, Example 43 as a pale brown solid (28 mg, 31%): R$^t$ 5.15 min (Method 1 basic); m/z 633 (M+H)⁺ (ES⁺); ¹H NMR (400 MHz, DMSO-d₆) δ ppm 1.28 (9H, s), 2.15 (3H, s), 2.23 (4H, t), 2.40 (3H, s), 3.37 (4H, t), 6.41 (1H, s), 6.58 (1H, dd), 6.95 (1H, d), 7.31 (1H, d), 7.38 (2H, d), 7.46 (2H, d), 7.57 (1H, t), 7.65 (1H, t), 7.84 (1H, d), 7.95 (1H, d), 8.07-8.11 (2H, m), 8.79 (1H, s), 9.12 (1H, s), 9.19 (1H, s).

Example 44

3-(4-((4-(3-(3-(tert-Butyl)-1-(p-tolyl)-1H-pyrazol-5-yl)ureido)naphthalen-1-yl)oxy)pyridin-2-yl)-1,1-dimethylurea

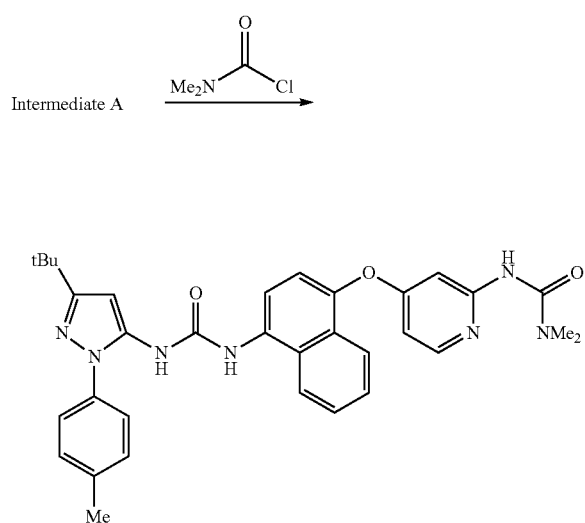

Example 44

To a solution of Intermediate A (50 mg, 0.099 mmol) and DIPEA (34 μL, 0.20 mmol) in dry pyridine (1.5 mL) was added dimethylcarbamoyl chloride (18 μL, 0.20 mmol) and the reaction mixture maintained at RT for 64 hr. The reaction was quenched by the addition of 1% NH₃ in MeOH (2.0 mL) and after 30 min the resulting mixture was evaporated in vacuo. The residue was purified by flash column chromatography (SiO₂, 12 g, MeOH in DCM, 0-5%, gradient elution; then SiO₂, 4 g, [5% MeOH in EtOAc] in isohexane, 50-90%, gradient elution) to afford the title compound, Example 44 as an off-white solid (5 mg, 8%): R$^t$ 5.15 min (Method 1 basic); m/z 578 (M+H)⁺ (ES⁺); ¹H NMR (400 MHz, DMSO-d₆) δ ppm 1.28 (9H, s), 2.40 (3H, s), 2.86 (6H, s), 6.41 (1H, s), 6.67 (1H, br s), 7.32 (2H, d), 7.37 (2H, d), 7.47 (2H, d), 7.58 (1H, t), 7.65 (1H, t), 7.84 (1H, d), 7.97 (1H, d), 8.09-8.13 (2H, m), 8.82 (1H, s), 9.00 (1H, br s), 9.15 (1H, s).

Example 45

N-(4-((4-(3-(3-(tert-Butyl)-1-(p-tolyl)-1H-pyrazol-5-yl)ureido)naphthalen-1-yl)oxy)pyridin-2-yl)piperidine-1-carboxamide

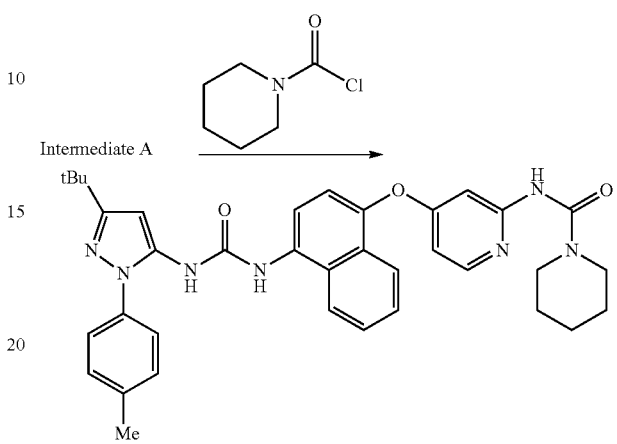

Example 45

To a solution of Intermediate A (130 mg, 0.257 mmol) and DIPEA (134 μL, 0.770 mmol) in dry pyridine (2 mL) was added piperidine-1-carbonyl chloride (64 μL, 0.51 mmol) and the mixture maintained at RT. for 64 hr. The reaction was quenched by the addition of 1% NH₃ in MeOH (2.0 mL) and after 1 hr the resulting mixture was evaporated in vacuo. The residue was purified by flash column chromatography (SiO₂, 12 g, MeOH in DCM, 0-5%, gradient elution then SiO₂, 12 g, EtOAc in isohexane, 40-100%, gradient elution then SiO₂, 12 g, MeOH in DCM, 0-3%, gradient elution) and finally by SCX capture and release to afford the title compound, Example 45 as a pink solid (30 mg, 18%): R$^t$ 5.40 min (Method 1 basic); m/z 618 (M+H)⁺ (ES⁺); ¹H NMR (400 MHz, DMSO-d₆) δ ppm 1.28 (9H, s), 1.39-1.42 (4H, m), 1.44-1.54 (2H, m), 2.40 (3H, s), 3.33-3.36 (4H, m), 6.41 (1H, s), 6.74 (1H, br s), 7.31 (1H, d), 7.35 (1H, br s), 7.37 (2H, d), 7.46 (2H, d), 7.57 (1H, t), 7.65 (1H, t), 7.85 (1H, d), 7.96 (1H, d), 8.07-8.11 (2H, m), 8.80 (1H, s), 9.13 (2H, s).

Intermediate J: Prop-1-en-2-yl-4-(4-(3-(3-tert-butyl-1-p-tolyl-1H-pyrazol-5-yl)ureido)naphthalen-1-yloxy)pyridin-2-ylcarbamate

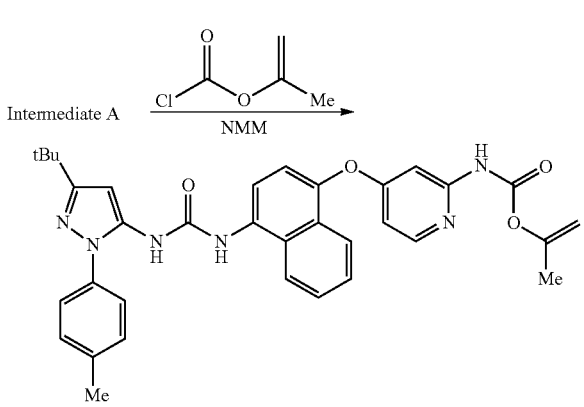

Intermediate J

To a solution of Intermediate A (50 mg, 0.099 mmol) and N-methyl morpholine (13 μL, 0.12 mmol) in THF (2.0 mL) at −78° C. was added dropwise, a solution of prop-1-en-2-yl carbonochloridate (13 μL, 0.12 mmol) in THF (2.0 mL). On completion of the addition the mixture was warmed to RT and after 72 hr the reaction was quenched by addition of 1% NH$_3$ in MeOH (10.0 mL). After 1 hr the resulting mixture was evaporated in vacuo. A portion (70%) of the residue was purified by flash column chromatography (SiO$_2$, 4 g, EtOAc in isohexane, 0-50%, gradient elution) to afford the title compound, Intermediate J as an off-white solid (21 mg, 50%) R$^t$ 2.74 min (Method 2); m/z 591 (M+H)$^+$ (ES$^+$); 589 (M−H)$^−$ (ES$^−$).

Example 46

N-Methyl-N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea

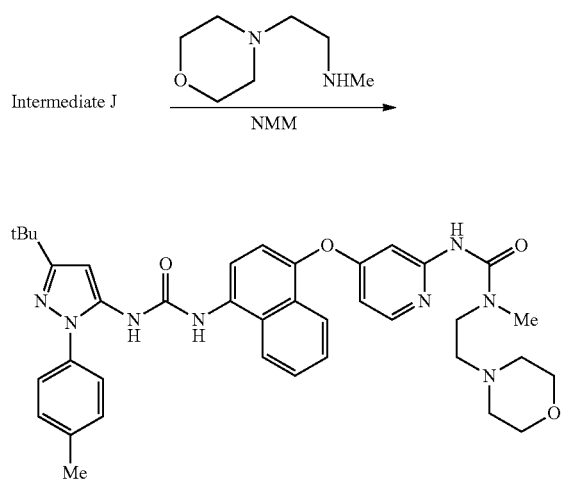

Example 46

To a solution of Intermediate J (50 mg, 85 μmol) and N-methyl morpholine (1.0 μL, 9 μmol) in THF (5.0 mL) was added N-methyl-2-morpholinoethanamine (12.2 mg, 85 μmol) and the reaction mixture heated to 55° C. for 16 hr. The resulting mixture was evaporated in vacuo and the residue was purified by flash column chromatography (SiO$_2$, 4 g, MeOH in DCM, 0-10%, gradient elution then SiO$_2$, 4 g silica, MeOH in DCM, 0-5%, gradient elution then SiO$_2$, 25 g, 2.5% MeOH in DCM, isocratic elution) to afford the title compound, Example 46 as a purple solid (15 mg, 25%): R$^t$ 1.90 min (Method 2); m/z 677 (M+H)$^+$ (ES$^+$); $^1$H NMR (400 MHz, DMSO-d$_6$) δ ppm 1.28 (9H, s), 2.39 (3H, s), 2.46 (6H, overlapping m, partially obscured by DMSO signal), 2.81 (3H, s), 3.33 (2H, m, partially obscured by H$_2$O peak) 3.67 (4H, m), 6.40 (1H, s), 6.57 (1H, dd), 7.29 (1H, d), 7.32 (1H, d), 7.37 (2H, d), 7.46 (2H, d), 7.56 (1H, m), 7.64 (1H, m), 7.83 (1H, d), 7.95 (1H, d), 8.06-8.10 (2H, overlapping m), 8.78 (1H, s), 9.10 (1H, s), 10.42 (1H, br s).

Example 47

N-(4-(Morpholin-4-yl)butyl)-N'-4-(4-(3-(3-tert-butyl-1-p-tolyl-1H-pyrazol-5-yl)ureido)naphthalen-1-yloxy)pyridin-2-ylurea

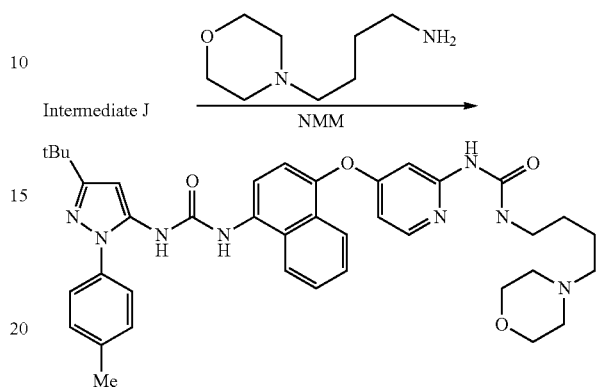

Example 47

To a solution of Intermediate J (50 mg, 85 μmol) and N-methyl morpholine (1.0 μL, 9 μmol) in THF (5 mL) was added 4-morpholinobutan-1-amine (13.4 mg, 0.085 mmol) and the reaction mixture heated to 55° C. for 16 hr. The resulting mixture was evaporated in vacuo and the residue was purified by flash column chromatography (SiO$_2$, 4 g, MeOH in DCM, 0-10%, gradient elution then SiO$_2$, 4 g, 2.5% MeOH in DCM, isocratic elution) to afford the title compound, Example 47 as a purple solid (15 mg, 25%): R$^t$ 1.94 min (Method 2); m/z 691 (M+H)$^+$ (ES$^+$); $^1$H NMR (400 MHz, DMSO-d$_6$) δ ppm 1.28 (9H, s), 1.38-1.44 (4H, overlapping m), 2.23 (2H, m), 2.29 (4H, overlapping m), 2.39 (3H, s), 3.08 (2H, m), 3.53 (4H, m), 6.40 (1H, s), 6.55 (1H, dd), 6.90 (1H, d), 7.30 (1H, d), 7.37 (2H, d), 7.46 (2H, d), 7.56 (1H, m), 7.64 (1H, m), 7.81 (1H, d), 7.95 (1H, d), 7.96 (1H, br s), 8.05 (1H, d), 8.07 (1H, d), 8.77 (1H, s), 9.01 (1H, s), 9.11 (1H, s).

Example 48

N-(2-(Morpholin-4-yl)ethyl)-N'-4-(4-(3-(3-tert-butyl-1-p-tolyl-1H-pyrazol-5-yl)ureido)naphthalen-1-yloxy)pyridin-2-ylurea

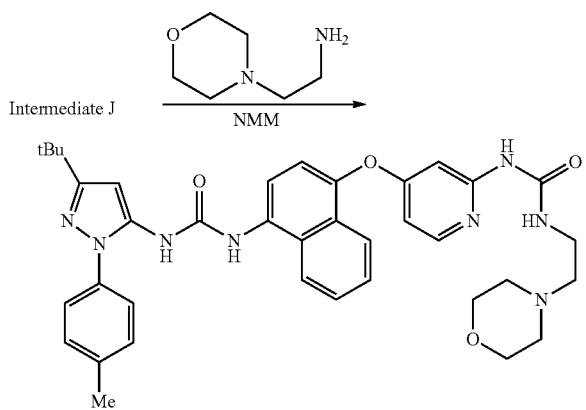

Example 48

To a solution of Intermediate J (50 mg, 85 μmol) and N-methyl morpholine (1.0 μL, 9 μmol) in THF (5.0 mL) was added 2-morpholinoethanamine (11.0 μL, 90 μmol) and the reaction mixture heated to 55° C. for 16 hr. The resulting mixture was evaporated in vacuo and the residue was purified by flash column chromatography (SiO$_2$, 4 g, MeOH in DCM, 2-5%, gradient elution) to afford the title compound, Example 48 as a purple solid (15 mg, 26%): R$^t$ 1.99 min (Method 2); m/z 663 (M+H)$^+$ (ES$^+$): R$^t$ 5.40 min; m/z 618 (M+H)$^+$ (ES$^+$); $^1$H NMR (400 MHz, DMSO-d$_6$) at 100° C. δ ppm 1.31 (9H, s), 2.39 (3H, s), 2.75 (~6H, br s, partially obscured by HOD signal), 3.37 (2H, br s), 3.69 (4H, br s), 6.34 (1H, s), 6.56 (1H, dd), 6.99 (1H, d), 7.23 (1H, d), 7.33 (2H, d), 7.46 (2H, d), 7.55 (1H, m), 7.61 (1H, m), 7.86 (1H, d), 7.87 (1H, d), 8.04 (1H, br s), 8.07 (1H, d), 8.11 (1H, d), 8.55 (1H, br s) 8.90 (1H, br s), 8.93 (1H, br s)

Example 49

N-(3-Methylisoxazol-5-yl)methyl-N'-4-(4-(3-(3-tert-butyl-1-p-tolyl-1H-pyrazol-5-yl)ureido)naphthalen-1-yloxy)pyridin-2-ylurea

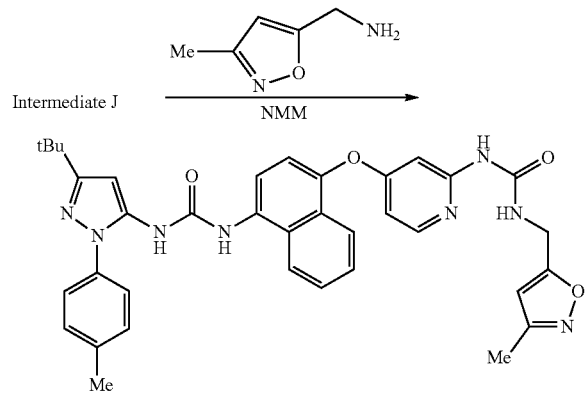

Example 49

To a solution of Intermediate J (50 mg, 85 μmol) and N-methyl morpholine (1.0 μL, 9 μmol) in THF (5.0 mL) was added (3-methylisoxazol-5-yl)methanamine (9.5 mg, 85 μmol) and the reaction mixture heated to 55° C. for 16 hr. The resulting mixture was evaporated in vacuo and the residue was purified by flash column chromatography (SiO$_2$, 4 g, MeOH in DCM, 2-5%, gradient elution) to afford the title compound, Example 49 as a purple solid (16 mg, 28%): R$^t$ 2.44 min (Method 2); m/z 645 (M+H)$^+$ (ES$^+$): $^1$H NMR (400 MHz, DMSO-d$_6$) δ ppm 1.27 (9H, s), 2.16 (3H, s), 2.39 (3H, s), 4.44 (2H, d), 6.13 (1H, s), 6.40 (1H, s), 6.59 (1H, dd), 6.88 (1H, d), 7.31 (1H, d), 7.36 (2H, d), 7.45 (2H, d), 7.56 (1H, m), 7.64 (1H, m), 7.81 (1H, d), 7.95 (1H, d), 8.06-8.10 (2H, overlapping m), 8.54 (1H, br s), 8.77 (1H, s), 9.12 (1H, s), 9.27 (1H, s).

Example 50

N-(1-Methyl)piperidin-4-yl-N'-4-(4-(3-(3-tert-butyl-1-p-tolyl-1H-pyrazol-5-yl)ureido)naphthalen-1-yloxy)pyridin-2-ylurea

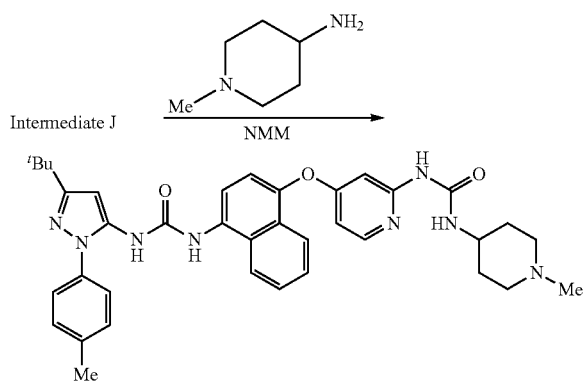

Example 50

To a solution of Intermediate J (50 mg, 85 μmol) and N-methyl morpholine (1.0 μL, 9 μmol) in THF (5 mL) was added 1-methylpiperidin-4-amine (9.7 mg, 85 μmol) and the reaction mixture heated to 55° C. for 16 hr. The resulting mixture was evaporated in vacuo and the residue was purified by flash column chromatography (SiO$_2$, 4 g, MeOH in DCM, 2-5%, gradient elution) to afford the title compound, Example 50 as a purple solid (19 mg, 34%): R$^t$ 1.96 min (Method 2); m/z 647 (M+H)$^+$ (ES$^+$): $^1$H NMR (400 MHz, DMSO-d$_6$) δ ppm 1.28 (9H, s), 1.36 (2H, m), 1.75 (2H, m), 2.00 (2H, m), 2.13 (3H, s), 2.39 (3H, s), 2.57 (2H, m), 3.43 (1H, s), 6.40 (1H, s), 6.56 (1H, dd), 6.94 (1H, d), 7.30 (1H, d), 7.37 (2H, d), 7.46 (2H, d), 7.56 (1H, m), 7.64 (1H, m), 7.81 (1H, d), 7.89 (1H, br s), 7.95 (1H, d), 8.06-8.10 (2H, overlapping m), 8.77 (1H, s), 8.96 (1H, s), 9.11 (1H, s).

Example 51

N-(4-(4-(3-(3-tert-Butyl-1-p-tolyl-1H-pyrazol-5-yl)ureido)naphthalen-1-yloxy)pyridin-2-yl)-4-hydroxypiperidine-1-carboxamide

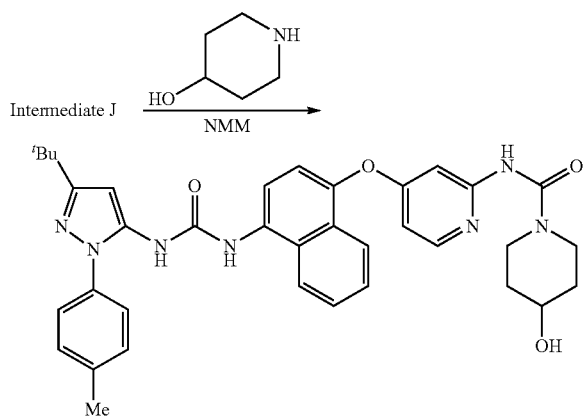

Example 51

To a solution of Intermediate J (50 mg, 85 μmol) and N-methyl morpholine (1.0 μL, 9 μmol) in THF (5.0 mL) was added piperidin-4-ol (8.6 mg, 85 μmol) and the reaction mixture heated to 55° C. for 16 hr. The resulting mixture was evaporated in vacuo and the residue was purified by flash column chromatography (SiO$_2$, 4 g, MeOH in DCM, 2-5%, gradient elution) to afford the title compound Example 51 as a purple solid (20 mg, 34%): R$^t$ 2.05 min (Method 2); m/z 634 (M+H)$^+$ (ES$^+$): $^1$H NMR (400 MHz, DMSO-d$_6$) δ ppm 1.27 (9H, s), 1.24 (2H, m), 1.65 (2H, m), 2.39 (3H, s), 2.99 (2H, m), 3.57 (1H, m), 3.74 (2H, m), 4.64 (1H, d), 6.40 (1H, s), 6.57 (1H, dd), 7.29 (1H, d), 7.32-7.37 (3H, overlapping m), 7.45 (2H, d), 7.56 (1H, m), 7.63 (1H, m), 7.84 (1H, d), 7.94 (1H, d), 8.06-8.10 (2H, overlapping m), 8.77 (1H, s), 9.10 (1H, s) 9.13 (1H, s).

Example 52

N-(3-(Imidazol-1-yl)propyl)-N'-4-(4-(3-(3-tert-butyl-1-p-tolyl-1H-pyrazol-5-yl)ureido)naphthalen-1-yloxy)pyridin-2-ylurea

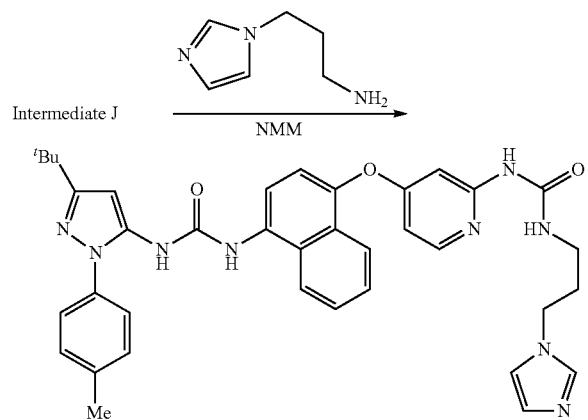

Example 52

To a solution of Intermediate J (50 mg, 85 μmol) and N-methyl morpholine (1.0 μL, 9 μmol) in THF (5.0 mL) was added 3-(1H-imidazol-1-yl)propan-1-amine (10.6 mg, 85 μmol) and the reaction mixture heated to 55° C. for 16 hr. The resulting mixture was evaporated in vacuo and the residue was purified by flash column chromatography (SiO$_2$, 4 g, MeOH in DCM, 2-5%, gradient elution then SiO$_2$, 12 g, 4% [1% NH$_3$ in MeOH] in DCM, isocratic elution) to afford the title compound, Example 52 as a purple solid (9 mg, 16%): R$^t$ 5.37 min (Method 1 basic); m/z 658 (M+H)$^+$ (ES$^+$): $^1$H NMR (400 MHz, DMSO-d$_6$) δ ppm 1.28 (9H, s), 1.85 (2H, m), 2.39 (3H, s), 3.06 (2H, m), 3.95 (2H, m), 6.40 (1H, s), 6.56 (1H, dd), 6.86 (1H, t), 6.89 (1H, d), 7.16 (1H, t), 7.31 (1H, d), 7.37 (2H, d), 7.46 (2H, d), 7.57 (1H, m), 7.60 (1H, t), 7.64 (1H, m), 7.81 (1H, d), 7.95 (1H, d), 8.06-8.10 (3H, overlapping m), 8.77 (1H, s), 9.07 (1H, s), 9.12 (1H, s).

Example 53

N-(2-(3-(4-(4-(3-(3-tert-Butyl-1-p-tolyl-1H-pyrazol-5-yl)ureido)naphthalen-1-yloxy)pyridin-2-yl)ureido)acetyl)pyrrolidine

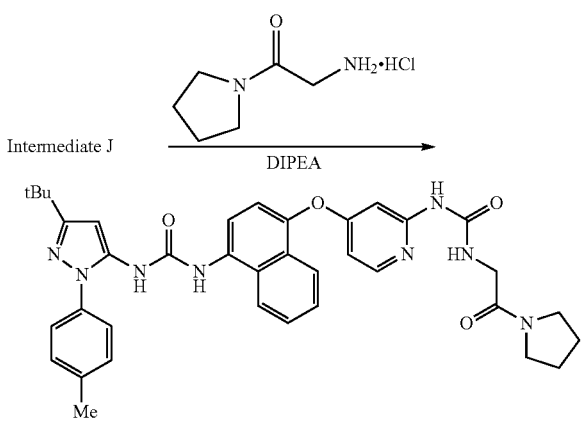

Example 53

To a solution of Intermediate J (50 mg, 85 μmol) and N-methyl morpholine (1.0 μL, 9 μmol) in THF (5.0 mL) was added 2-amino-1-(pyrrolidin-1-yl)ethanone hydrochloride (14.0 mg, 85 μmol) and DIPEA (14.0 μL, 85 μmol) and the reaction mixture was heated to 55° C. for 20 hr. The resulting mixture was evaporated in vacuo and the residue was purified by flash column chromatography (SiO$_2$, 12 g, 2% [1% NH$_3$ in MeOH] in DCM, isocratic elution) to afford the title compound, Example 53 as a purple solid (19 mg, 32%): R$^t$ 2.19 min (Method 2); m/z 661 (M+H)$^+$ (ES$^+$): $^1$H NMR (400 MHz, DMSO-d$_6$) δ ppm 1.28 (9H, s), 1.75 (2H, m), 1.86 (2H, m), 2.39 (3H, s), 3.29 (2H, m), 3.35 (2H, m), 3.88 (2H, d), 6.40 (1H, s), 6.58 (1H, dd), 6.96 (1H, br s), 7.32 (1H, d), 7.37 (2H, d), 7.46 (2H, d), 7.56 (1H, m), 7.64 (1H, m), 7.82 (1H, d), 7.95 (1H, d), 8.06-8.10 (2H, overlapping m), 8.14 (1H, br s), 8.77 (1H, s), 9.11 (1H, s), 9.29 (1H, s).

Other examples of the disclosure were derived via an alternative synthetic process in which 4-(4-nitronaphthalen-1-yloxy)pyridin-2-amine was converted into the phenyl carbamate and reacted with an amine to provide compounds represented by Intermediate K. Examples of the disclosure were obtained by reduction of an Intermediate K to the corresponding naphthylamine derivatives followed by reaction with Intermediate C or Intermediate D.

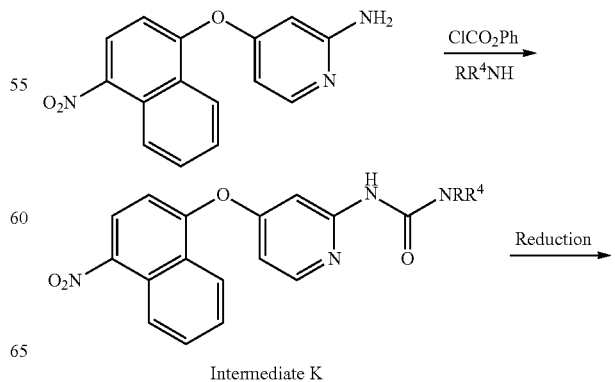

Intermediate K

-continued

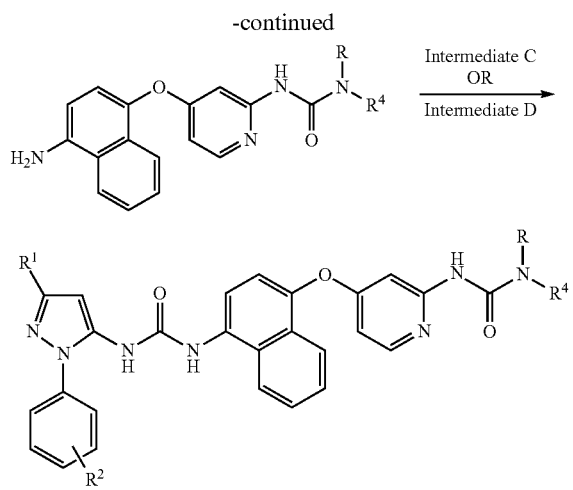

Example 54

(R)—N-(4-(4-(3-(3-tert-Butyl-1-p-tolyl-1H-pyrazol-5-yl)ureido)naphthalen-1-yloxy)pyridin-2-yl)-3-(dimethylamino)pyrrolidine-1-carboxamide

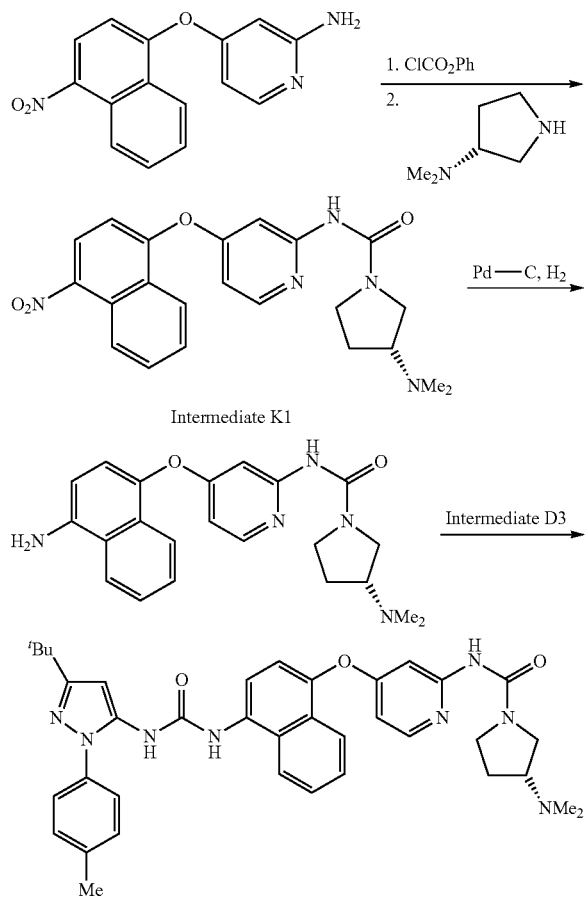

Example 54

To a solution of 4-(4-nitronaphthalen-1-yloxy)pyridin-2-amine (200 mg, 0.71 mmol) and Et$_3$N (0.20 mL, 1.42 mmol) in dry THF was added phenyl carbonochloridate (98 µL, 0.78 mmol) and the reaction mixture maintained at RT for 1 hr. An aliquot of (R)—N,N-dimethylpyrrolidin-3-amine (270 µL, 2.13 mmol) was added to this mixture and after 15 hr at RT a second aliquot of (R)—N,N-dimethylpyrrolidin-3-amine (100 µL, 0.79 mmol) was added and the mixture was maintained at RT for a further 1 hr. The resulting mixture was partitioned between aq. NH$_4$Cl (10 mL) and DCM (10 mL) and the aqueous layer was separated and extracted with DCM (3×10 mL) The combined organic extracts were dried (MgSO$_4$) and evaporated in vacuo. The residue was purified by flash column chromatography (SiO$_2$, 40 g, [5% MeOH in DCM] in DCM, 0-100%, gradient elution and then, 10% [2% NH$_3$ (7M in MeOH) in MeOH] in DCM, isocratic elution and finally, 30% MeOH in DCM, isocratic elution) to afford (R)-3-(dimethylamino)-N-(4-(4-nitronaphthalen-1-yloxy)pyridin-2-yl)pyrrolidine-1-carboxamide, Intermediate K1, as a yellow/brown solid (250 mg, 81%); R$^t$ 1.54 min (Method 2); m/z 422 (M+H)$^+$ (ES$^+$).

A solution of Intermediate K1 (250 mg, 0.593 mmol) in MeOH (40 mL) containing AcOH (4 drops) was subjected to hydrogenation by passage through a Thales H-cube (1.0 mL min$^{-1}$, 25° C., 70 mm 10% Pt/C Cat-Cart, full hydrogen mode) and was then evaporated in vacuo. The crude product was partitioned between DCM (20 mL) and aqueous NaHCO$_3$ solution (10 mL) and the organic layer was washed with brine (10 mL), dried (MgSO$_4$) and evaporated in vacuo to afford (R)—N-(4-(4-aminonaphthalen-1-yloxy)pyridin-2-yl)-3-(dimethylamino)pyrrolidine-1-carboxamide, as a green amorphous solid (200 mg, 78%, 90% pure); R$^t$ 1.13 min (Method 2); m/z 392 (M+H)$^+$ (ES$^+$), which was used directly in the next step.

To a solution of CDI (100 mg, 0.370 mmol) in dry DCM (1.0 mL) was added 3-tert-butyl-1-p-tolyl-1H-pyrazol-5-amine (85 mg, 0.370 mmol), portionwise, over 20 min and the resulting solution maintained at RT for 2.5 hr. A portion of this solution (0.70 mL) was added to a solution of (R)—N-(4-(4-aminonaphthalen-1-yloxy)pyridin-2-yl)-3-(dimethylamino)pyrrolidine-1-carboxamide (100 mg, 0.255 mmol) in DCM (1.0 mL) and the mixture was maintained at RT for 18 hr. The reaction was quenched by the addition of MeOH (3.0 mL) and the mixture was evaporated in vacuo. The residue was purified by flash column chromatography (SiO$_2$, 4 g, [5% NH$_3$ (7M in MeOH) in DCM] in DCM, 0-100%, gradient elution) to afford the title compound, Example 54, as a brown glass (52 mg, 30%); R$^t$ 4.92 min (Method 1 basic); m/z 647 (M+H)$^+$ (ES$^+$); $^1$H NMR (400 MHz, DMSO-d$_6$) δ: 1.28 (9H, s), 1.61 (1H, m), 1.98 (1H, m), 2.12 (6H, s), 2.39 (3H, s), 2.58 (1H, m), 3.03 (1H, m), 3.25 (1H, m), 3.49 (1H, m), 3.58 (1H, m), 6.41 (1H, s), 6.60 (1H, dd), 7.30 (1H, d), 7.37 (2H, d), 7.44-7.47 (3H, overlapping m), 7.56 (1H, m), 7.64 (1H, m), 7.83 (1H, d), 7.95 (1H, d), 8.08 (1H, d), 8.10 (1H, d), 8.70 (1H, s), 8.79 (1H, s), 9.12 (1H, s)

Example 55

N-(4-(4-(3-(3-tert-Butyl-1-p-tolyl-1H-pyrazol-5-yl)ureido)naphthalen-1-yloxy)pyridin-2-yl)pyrrolidine-1-carboxamide

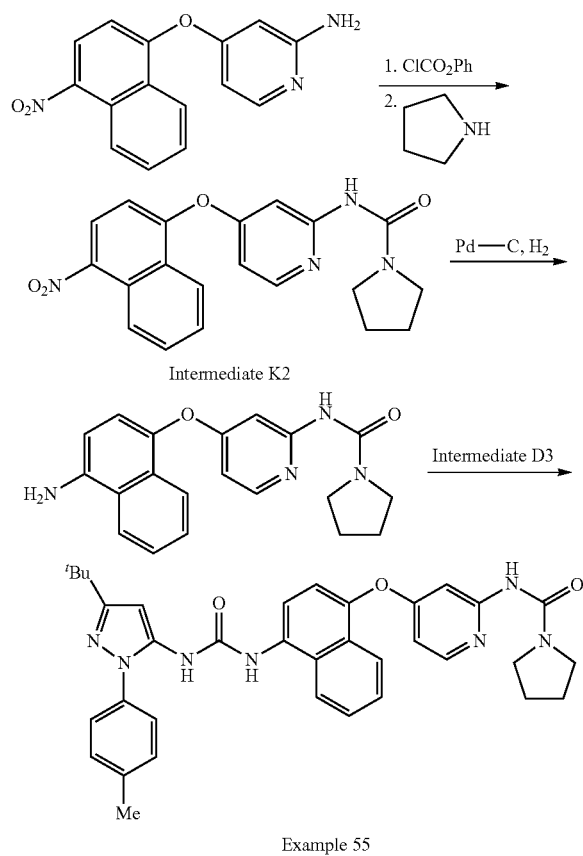

Example 55

To a solution of 4-(4-nitronaphthalen-1-yloxy)pyridin-2-amine (100 mg, 0.356 mmol) and Et$_3$N (100 μL, 0.71 mmol) in dry THF was added phenyl carbonochloridate (49 μL, 0.39 mmol) and the mixture maintained at RT for 2 hr. Pyrrolidine (88 μL, 1.068 mmol) was added and after 16 h at RT the resulting mixture was partitioned between aq NH$_4$Cl (10 mL) and DCM (10 mL). The aq layer was separated and extracted with DCM (3×10 mL) and the combined organic extracts were dried (MgSO$_4$) and evaporated in vacuo. The residue was purified by flash column chromatography (SiO$_2$, 40 g, EtOAc in isohexane, 0-100%, gradient elution) to afford N-(4-(4-nitronaphthalen-1-yloxy)pyridin-2-yl)pyrrolidine-1-carboxamide, Intermediate K2, as a yellow solid (110 mg, 79%); R$^t$ 1.84 min (Method 2); m/z 379 (M+H)$^+$ (ES$^+$).

A solution of Intermediate K2 (110 mg, 0.29 mmol) in MeOH (20 mL) containing AcOH (4 drops) was subjected to hydrogenation by passage through a Thales H-cube (1.0 mL min$^{-1}$, 25° C., 70 mm 10% Pt/C Cat-Cart, full hydrogen mode) and was then evaporated in vacuo. The crude product was partitioned between DCM (20 mL) and aqueous NaHCO$_3$ (10 mL) and the organic layer was washed with brine (10 mL) and evaporated in vacuo to afford N-(4-(4-aminonaphthalen-1-yloxy)pyridin-2-yl)pyrrolidine-1-carboxamide as a brown solid (680 mg, 66%); R$^t$ 1.43 min (Method 2); m/z 349 (M+H)$^+$ (ES$^+$), which was used directly in the next step. To a solution of CDI (100 mg, 0.197 mmol) in dry DCM (1.0 mL) was added 3-tert-butyl-1-p-tolyl-1H-pyrazol-5-amine (85 mg, 0.370 mmol), portionwise, over 20 min and the resulting solution maintained at RT for 16 hr. A portion of this solution (0.6 mL) was added to a solution of N-(4-(4-aminonaphthalen-1-yloxy)pyridin-2-yl)pyrrolidine-1-carboxamide (680 g, 0.255 mmol) in DCM (1.0 mL) and the mixture maintained at RT for 18 hr. The reaction was quenched by the addition of MeOH (2.0 mL) and the resulting mixture was evaporated in vacuo. The residue was purified by flash column chromatography (SiO$_2$, 4 g, [5% MeOH in DCM] in DCM, 0-100%, gradient elution) to afford the title compound, Example 55, as a yellow brown solid (29 mg, 24%); R$^t$ 5.00 min (Method 1 basic); m/z 604 (M+H)$^+$ (ES$^+$); $^1$H NMR (400 MHz, DMSO-d$_6$) δ: 1.28 (9H, s), 1.78 (4H, m), 2.39 (3H, s), 3.30 (4H, m, partially obscured by HOD peak), 6.40 (1H, s), 6.60 (1H, dd), 7.30 (1H, d), 7.37 (2H, d), 7.45-7.47 (3H, overlapping m), 7.56 (1H, m), 7.64 (1H, m), 7.84 (1H, d), 7.95 (1H, d), 8.07 (1H, d), 8.09 (1H, d), 8.63 (1H, s), 8.77 (1H, s), 9.10 (1H, s)

Still other examples of the disclosure were prepared by the conversion of an Intermediate A into a carboxylic acid represented by Intermediate L followed by the reaction of Intermediate L with amines under peptide coupling conditions.

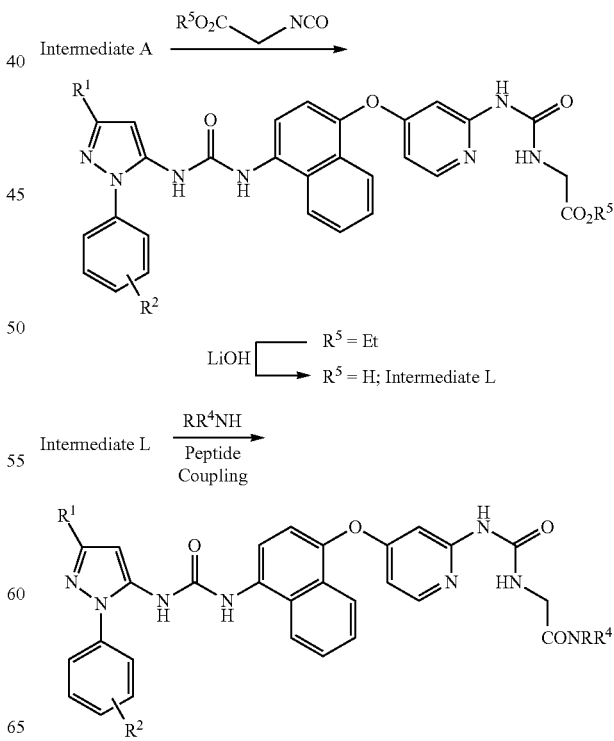

Intermediate L1: 2-(3-(4-(4-(3-(3-tert-Butyl-1-p-tolyl-1H-pyrazol-5-yl)ureido)naphthalen-1-yloxy)pyridin-2-yl)ureido)acetic acid

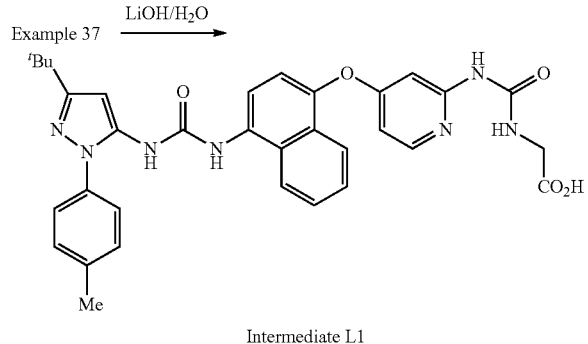

Intermediate L1

To a solution of Example 37 (160 mg, 0.252 mmol) in THF (4.0 mL) and water (1.0 mL) was added lithium hydroxide (9.0 mg, 0.38 mmol) and the reaction mixture maintained at RT for 1 hr. Water (5.0 mL) was added and the THF was removed by evaporation in vacuo. The resulting aqueous solution was acidified to pH3 with hydrochloric acid HCl (1 M) and the precipitate so formed was isolated by filtration to afford the title compound, Intermediate L1 as a white solid (139 mg, 90%): R$^t$ 3.72 min (Method 1 basic); m/z 608 (M+H)$^+$ (ES$^+$); $^1$H NMR (400 MHz, DMSO-d$_6$) δ ppm 1.29 (9H, s), 2.39 (3H, s), 3.82 (6H, s), 6.40 (1H, s), 6.79 (2H, br s), 7.35-7.38 (3H, m), 7.47 (2H, d), 7.59 (1H, t), 7.66 (1H, t), 7.81 (1H, d), 7.99 (2H, d), 8.14 (1H, d), 8.19 (1H, d), 8.99 (1H, s), 9.32 (1H, s)

Example 56

2-(3-(4-(4-(3-(3-tert-Butyl-1-p-tolyl-1H-pyrazol-5-yl)ureido)naphthalen-1-yloxy)pyridin-2-yl)ureido)-N-methylacetamide

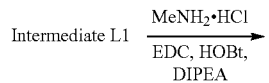

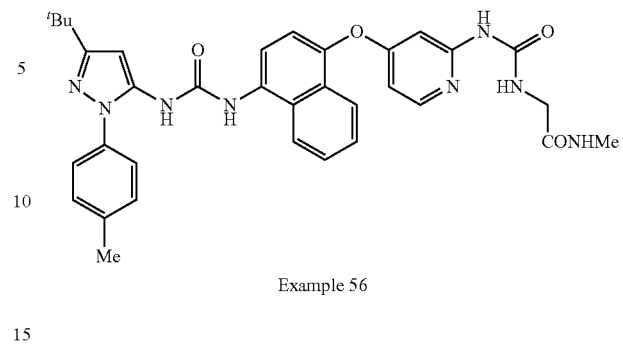

Example 56

To a solution of Intermediate L1 (30 mg, 0.049 mmol) in DMF (1.5 mL) was added DIPEA (86 µL, 0.49 mmol), EDC (14.2 mg, 0.074 mmol), HOBt (10.01 mg, 0.074 mmol) and methylamine hydrochloride (33.3 mg, 0.494 mmol) and the reaction mixture maintained at RT for 64 hr. The resulting mixture was diluted with methanol (1.0 mL) and acetic acid (0.4 mL) and was purified by SCX capture and release. The crude product so obtained was purified by flash column chromatography (SiO$_2$, 4 g silica, MeOH in DCM, 0-5%, gradient elution) to afford the title compound, Example 56 as an off-white solid (9.3 mg, 29%): R$^t$ 4.97 min (Method 1 basic); m/z 621 (M+H)$^+$ (ES$^+$); $^1$H NMR (400 MHz, DMSO-d$_6$) δ ppm 1.28 (9H, s), 2.40 (3H, s), 2.57 (3H, d), 3.70 (3H, d), 6.41 (1H, s), 6.58-6.60 (1H, m), 6.92 (1H, br s), 7.32 (1H, d), 7.38 (2H, m), 7.46 (2H, d), 7.57 (1H, t), 7.65 (1H, t), 7.81-7.84 (2H, m), 7.96 (1H, d), 8.07-8.10 (2H, m), 8.20 (1H, br s), 8.79 (1H, s), 9.14 (1H, s), 9.26 (1H, br s)

Example 57

2-(3-(4-(4-(3-(3-tert-Butyl-1-p-tolyl-1H-pyrazol-5-yl)ureido)naphthalen-1-yloxy)pyridin-2-yl)ureido)-N-(2-morpholinoethyl)acetamide

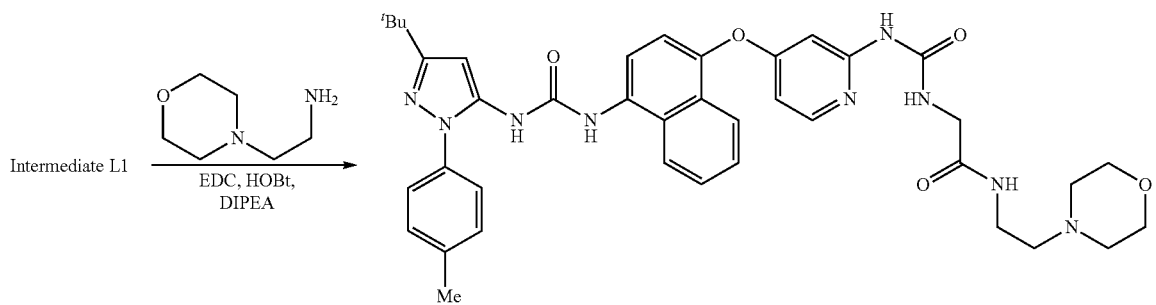

Example 57

To a solution of Intermediate 1: 1 (50 mg, 0.082 mmol) in DMF (1.5 mL) was added DIPEA (43.0 μL, 0.247 mmol), EDC (23.7 mg, 0.123 mmol), HOBt (16.7 mg, 0.123 mmol) and 2-morpholinoethanamine (32.4 μL, 0.247 mmol) and after 64 hr at RT a catalytic quantity of DMAP (10 mg). After a further 24 hr the reaction mixture was diluted with methanol (1.0 mL), then acidified with acetic acid and was purified by SCX capture and release. The crude product so obtained was purified by flash column chromatography (SiO$_2$, MeOH in DCM, 0-10%, gradient elution) and then by trituration with diethyl ether to afford the title compound, Example 57 as a white solid (16 mg, 26%); R$^t$ 5.03 min (Method 1 basic); m/z 721 (M+H)$^+$ (ES$^+$); $^1$H NMR (400 MHz, DMSO-d$_6$) δ ppm 1.28 (9H, s), 2.34 (4H br s), 2.40 (3H, s), 3.18 (2H, br s), 3.54 (4H, br s), 3.73 (2H, br s), 6.41 (1H, s), 6.58 (1H, dd), 6.91 (1H, br s), 7.31 (1H, d), 7.37 (2H, d), 7.46 (2H, d), 7.57 (1H, t), 7.65 (1H, t), 7.80-7.86 (2H, m), 7.96 (1H, d), 8.07-8.11 (2H, m), 8.27 (1H, br s), 8.82 (1H, s), 9.16 (1H, s), 9.26 (1H, br s).

Example 58

2-(3-(4-(4-(3-(3-tert-Butyl-1-p-tolyl-1H-pyrazol-5-yl)ureido)naphthalen-1-yloxy)pyridin-2-yl)ureido) acetyl morpholine

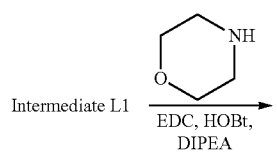

Intermediate L1 → EDC, HOBt, DIPEA

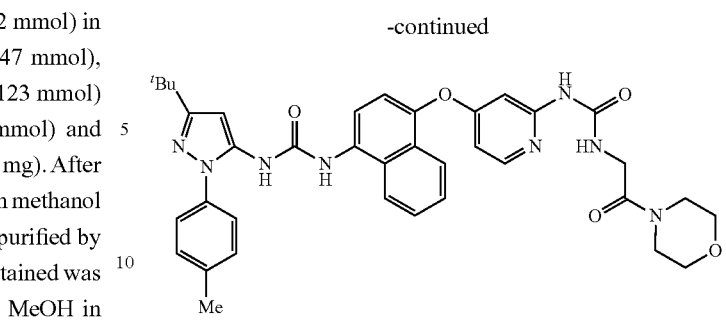

Example 58

To a solution of Intermediate 1: 1 (60 mg, 0.099 mmol) in DMF (1.5 mL) was added DIPEA (52 μL, 0.296 mmol), EDC (28.4 mg, 0.148 mmol), HOBt (20.0 mg, 0.148 mmol) and morpholine (26 μL, 0.296 mmol) and the reaction mixture maintained at RT for 16 hr. The resulting mixture was diluted with methanol (1.0 mL), then acidified with acetic acid and was subjected to SCX capture and release. The crude product so obtained was purified by flash column chromatography (SiO$_2$, MeOH in DCM, 0-5%, gradient elution) and then by recrystallization from methanol (1.5 mL) to afford the title compound, Example 58 as a white solid (25 mg, 36%): R$^t$ 5.02 min (Method 1 basic); m/z 677 (M+H)$^+$ (ES$^+$); $^1$H NMR (400 MHz, DMSO-d$_6$) δ ppm 1.28 (9H, s), 2.40 (3H, s), 3.36-3.38 (2H, m), 3.41-3.43 (2H, m), 3.53-3.57 (4H, m), 3.99 (2H, d), 6.41 (1H, s), 6.58 (1H, dd), 6.94 (1H, br s), 7.32 (1H, d), 7.37 (2H, d), 7.46 (2H, d), 7.57 (1H, t), 7.64 (1H, t), 7.82 (1H, d), 7.96 (1H, d), 8.06-8.08 (2H, m), 8.18 (1H, br s), 8.79 (1H, br s), 9.13 (1H, s), 9.32 (1H, s).

Example 59

2-(3-(4-(4-(3-(3-tert-Butyl-1-p-tolyl-1H-pyrazol-5-yl)ureido)naphthalen-1-yloxy)pyridin-2-yl)ureido)-N-(2-(pyridin-4-yl)ethyl)acetamide

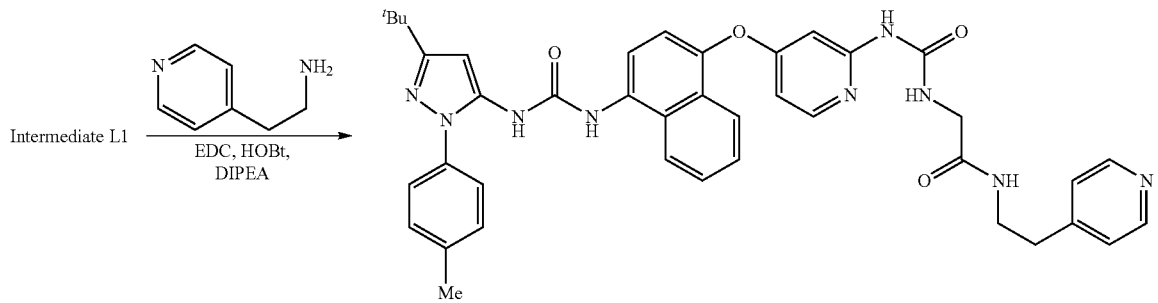

Example 59

To a solution of Intermediate L1 (60 mg, 0.099 mmol) in DMF (1.5 mL) was added DIPEA (52 μL, 0.296 mmol), EDC (28.4 mg, 0.148 mmol), HOBt (20.0 mg, 0.148 mmol) and 2-(pyridin-4-yl)ethanamine (36.2 mg, 0.296 mmol) and the reaction mixture maintained at RT for 16 hr. The resulting mixture was acidified with acetic acid (0.2 mL) and subjected to SCX capture and release. The crude product so obtained was purified twice by flash column chromatography (SiO$_2$, 12 g, [7M NH$_3$ in MeOH] in DCM, 0-5%, gradient elution then; SiO$_2$, {5% [7M NH$_3$ in MeOH] in ethyl acetate} in hexane, 50-100%, gradient elution) to afford the title compound, Example 59 as a pale yellow solid (15 mg, 21%): R$^t$ 1.94 min (Method 2); m/z 712 (M+H)$^+$ (ES$^+$); $^1$H NMR (400 MHz, DMSO-d$_6$) δ ppm 1.28 (9H, s), 2.39 (3H, s), 2.71 (2H, t), 3.28-3.32 (2H, m), 3.69 (2H, d), 6.41 (1H, s), 6.57 (1H, dd), 6.92 (1H, br s), 7.21 (2H, d), 7.31 (1H, d), 7.37 (2H, d), 7.46 (2H, d), 7.57 (1H, t), 7.64 (1H, t), 7.82 (1H, d), 7.95 (1H, d), 8.01 (1H, t), 8.07-8.09 (2H, m), 8.22 (1H, br s), 8.43 (2H, d), 8.78 (1H, s), 9.12 (1H, s), 9.24 (1H, s)

Example 60

N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide

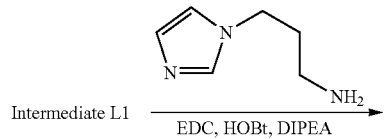

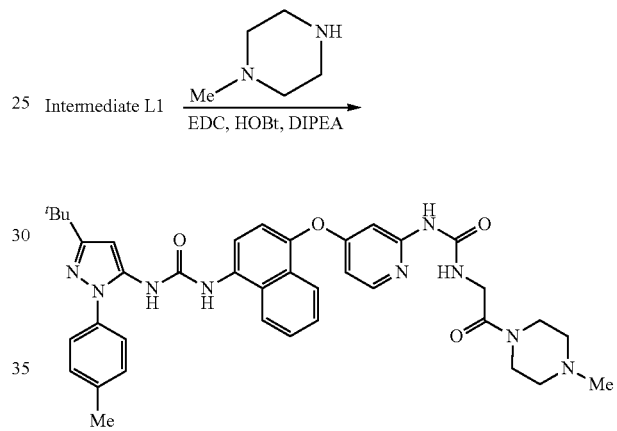

Example 60

To a solution of Intermediate L (50 mg, 0.082 mmol) in DMF (1.5 mL) was added DIPEA (43 μL, 0.247 mmol), EDC (31.5 mg, 0.167 mmol), HOBt (22.2 mg, 0.165 mmol) and 3-(1H-imidazol-1-yl)propan-1-amine (30.9 mg, 0.247 mmol) and the reaction mixture maintained at RT for 16 hr. The resulting mixture was diluted with water (10 mL) and extracted with ethyl acetate (2×10 mL) and the combined organic extracts were washed with brine (2×10 mL), dried (MgSO$_4$), and evaporated in vacuo. The residue was purified by flash column chromatography (SiO$_2$, 4 g, {5% [7M NH$_3$ in MeOH] in ethyl acetate} in hexane, 50-100%, gradient elution) to afford the title compound, Example 60 as a white solid (13 mg, 22%): R$^t$ 1.90 min (Method 2); m/z 715 (M+H)$^+$ (ES$^+$); $^1$H NMR (400 MHz, DMSO-d$_6$) δ ppm 1.28 (9H, s), 1.75-1.85 (2H, m), 2.40 (3H, s), 2.99-3.04 (2H, m), 3.73 (2H, d), 3.94 (2H, t), 6.41 (1H, s), 6.57 (1H, dd), 6.87 (1H, br s), 6.93 (1H, br s), 7.15 (1H, s), 7.31 (1H, d), 7.37 (2H, d), 7.46 (2H, d), 7.55-7.59 (2H, m), 7.65 (1H, t), 7.82 (1H, d), 7.94-7.98 (2H, m), 8.07-8.09 (2H, m), 8.25 (1H, br s), 8.79 (1H, s), 9.13 (1H, s), 9.24 (1H, s).

Example 61

1-(2-(3-(4-(4-(3-(3-tert-Butyl-1-p-tolyl-1H-pyrazol-5-yl)ureido)naphthalen-1-yloxy)pyridin-2-yl)ureido)acetyl)-4-methylpiperazine Example 61

To a solution of Intermediate L1 (50 mg, 0.082 mmol) in DMF (1.5 mL) was added DIPEA (43 μL, 0.247 mmol), EDC (31.5 mg, 0.167 mmol), HOBt (22.2 mg, 0.165 mmol) and 1-methylpiperazine (24.72 mg, 0.247 mmol) and the reaction mixture maintained at RT for 16 hr. The resulting mixture was diluted with water (5 mL) and extracted with ethyl acetate (2×10 mL) and the combined organic extracts were washed with brine (2×10 mL), dried (MgSO$_4$), and evaporated in vacuo and the residue was purified by flash column chromatography (SiO$_2$, 12 g, [7M NH$_3$ in MeOH] in DCM, 0-5%, gradient elution) and SCX capture and release. The product so obtained was dissolved in DCM (0.3 mL) and isohexane (2.0 mL) was added. The white precipitate was isolated by filtration and purified by flash column chromatography (SiO$_2$, 12 g, [7M NH$_3$ in MeOH] in DCM, 0-5%, gradient elution) to afford the title compound, Example 61 as a white solid (9 mg, 15%): R$^t$ 5.12 min (Method 1 basic); m/z 690 (M+H)$^+$ (ES$^+$); $^1$H NMR (400 MHz, DMSO-d$_6$) δ ppm 1.28 (9H, s), 2.17-2.50 (10H, m), 3.24-3.51 (4H, m), 3.97 (2H, d), 6.40 (1H, s), 6.58 (1H, dd), 6.94 (1H, br s), 7.31 (1H, d), 7.37 (2H, d), 7.46 (2H, d), 7.57 (1H, t), 7.64 (1H, t), 7.82 (1H, d), 7.95 (1H, d), 8.06-8.10 (2H, m), 8.16 (1H, br s), 8.80 (1H, s), 9.13 (1H, s), 9.30 (1H, s).

Example 62

N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide

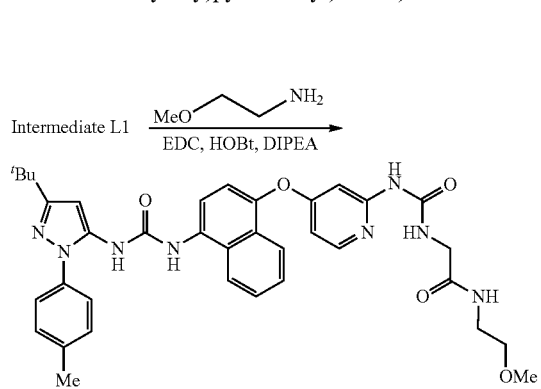

Example 62

To a solution of Intermediate L1 (50 mg, 0.082 mmol) in DMF (1.5 mL) was added DIPEA (43 μL, 0.247 mmol), EDC (31.5 mg, 0.167 mmol), HOBt (22.2 mg, 0.165 mmol) and 2-methoxyethanamine (21.5 μL, 0.247 mmol) and the reaction mixture maintained at RT for 16 hr. The resulting mixture was diluted with water (10 mL) and extracted with ethyl acetate (2×10 mL) and the combined organic extracts were washed with brine (2×10 mL), dried (MgSO$_4$), and evaporated in vacuo. The residue was purified by flash column chromatography (SiO$_2$, [5% MeOH in ethyl acetate] in isohexane, 50-100%, gradient elution) twice to afford the title compound, Example 62 as a white solid (11 mg, 20%): R$^t$ 5.07 min (Method 1 basic); m/z 665 (M+H)$^+$ (ES$^+$); $^1$H NMR (400 MHz, DMSO-d$_6$) δ ppm 1.28 (9H, s), 2.40 (3H, s), 3.19-3.23 (5H, m), 3.30 (2H, t), 3.73 (2H, d), 6.41 (1H, s), 6.57 (1H, dd), 6.93 (1H, br s), 7.31 (1H, d), 7.37 (2H, d), 7.46 (2H, d), 7.57 (1H, t), 7.64 (1H, t), 7.82 (1H, d), 7.94-7.99 (2H, m), 8.07-8.09 (2H, m), 8.19 (1H, br s), 8.77 (1H, s), 9.12 (1H, s), 9.23 (1H, s).

Additional examples of the disclosure were generated from Intermediate M (for naphthylamine derivatives) and from Intermediate N (for anilino derivatives) by reaction with Intermediate C or Intermediate D.

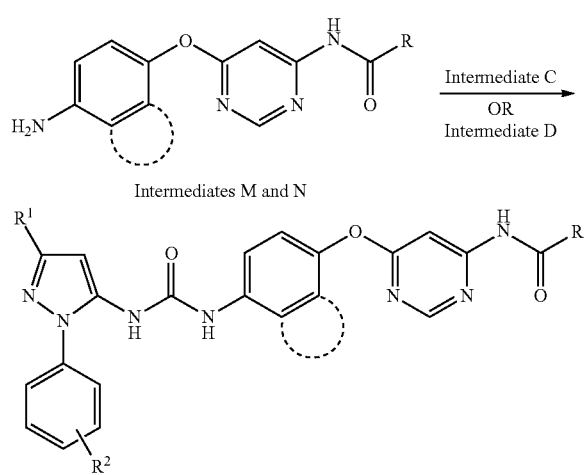

Intermediates M and N

Intermediate M1: N-(6-(4-Aminonaphthalen-1-yloxy)pyrimidin-4-yl)-2-methoxy acetamide

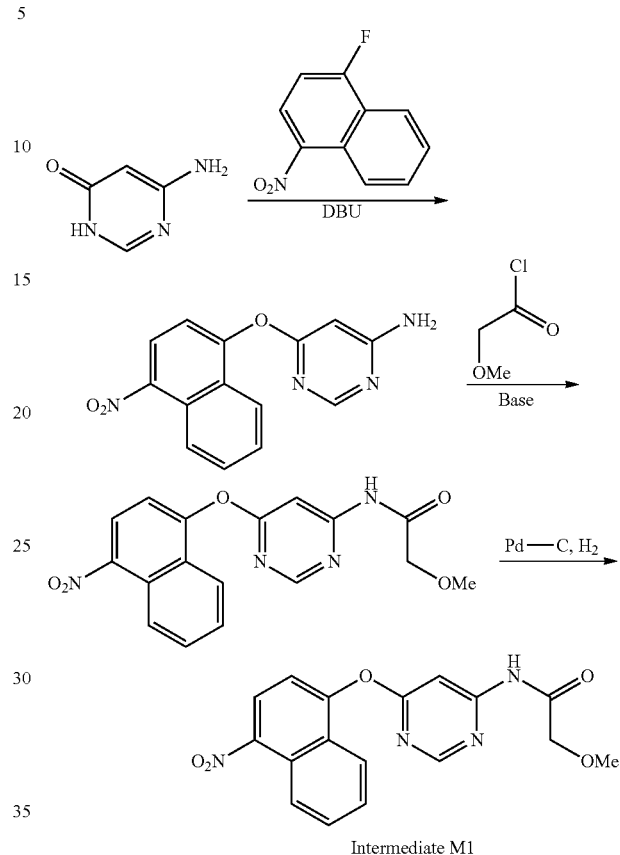

Intermediate M1

6-(4-Nitronaphthalen-1-yloxy)pyrimidin-4-amine

To a solution of 6-aminopyrimidin-4(3H)-one (866 mg, 7.79 mmol) in DMSO (10.0 mL) at RT was added DBU (1.29 mL, 8.57 mmol) and after 30 min a solution of 1-fluoro-4-nitronaphthalene (1.57 g, 8.18 mmol) in DMSO (3.0 mL) was added over 2 min. The resulting mixture was maintained at RT for 2 hr and was diluted with MeOH (20 mL) and TFA (2.0 mL) was added. The solution was subjected to SCX capture and release and the crude product so obtained was purified by flash column chromatography (SiO$_2$, 80 g, EtOAc in isohexane, 50-100%, gradient elution) to afford the title compound as a yellow solid (370 mg, 16.48%); R$^t$ 3.82 min (Method 1 basic); m/z 283 (M+H)$^+$ (ES$^+$)

2-Methoxy-N-(6-(4-nitronaphthalen-1-yloxy)pyrimidin-4-yl)acetamide

To a suspension of 6-(4-nitronaphthalen-1-yloxy)pyrimidin-4-amine (350 mg, 1.24 mmol) in DCM (10.0 mL) and DIPEA (433 μL, 2.48 mmol) at 0° C. was added 2-methoxyacetyl chloride (170 μL, 1.860 mmol). The mixture was warmed to RT and after 3 hr the reaction was quenched by the addition of a solution of NH$_3$ in MeOH (7M, 20 mL) and after a further 10 min was evaporated in vacuo. The residue was partitioned between DCM (30 mL) and saturated aq NaHCO$_3$ solution (30 mL) and the organic layer was separated and washed with brine (30 mL) and then dried (Na$_2$SO$_4$) and evaporated in vacuo. The residue was purified by flash column chromatography (SiO$_2$, 40 g, MeOH in DCM, 0-100%, gradient elution) to furnish the title compound as a yellow solid (400 mg, 86%); R$^t$ 4.60 min (Method 1 basic); m/z 355 (M+H)$^+$ (ES$^+$).

Intermediate M1: N-(6-(4-Aminonaphthalen-1-yloxy)pyrimidin-4-yl)-2-methoxy acetamid A solution of 2-methoxy-N-(6-(4-nitronaphthalen-1-yloxy)pyrimidin-4-yl)acetamide (400 mg, 1.13 mmol) in a mixture of MeOH and DCM and AcOH (2:2:1 v/v/v, 15 mL) was subjected to hydrogenation by passage through a Thales H-cube (1.0 mL min$^{-1}$, RT, 55 mm CatCart, 10% Pt/C, full hydrogen mode) and was then evaporated in vacuo to afford the title compound, Intermediate M1, as a brown oil (400 mg, 90% purity, 98%); R$^t$ 3.57 min (Method 1 basic); m/z 325 (M+H)$^+$ (ES$^+$).

Intermediate N1: N-(6-(4-Aminophenoxy)pyrimidin-4-yl)-2-methoxyacetamide

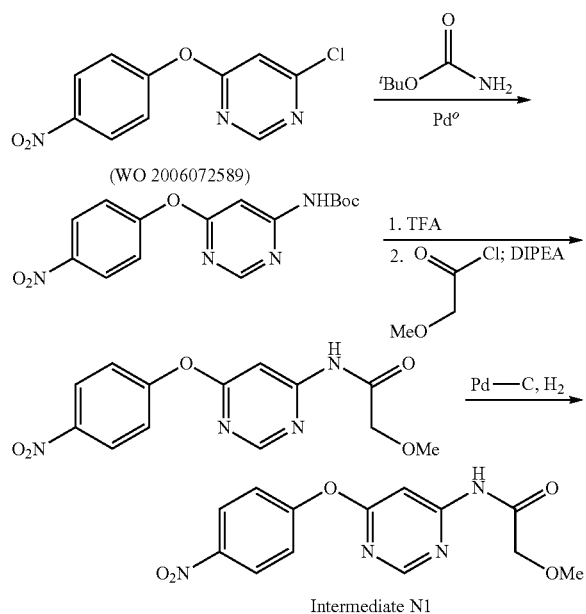

Intermediate N1 tert-Butyl 6-(4-nitrophenoxy)pyrimidin-4-ylcarbamate

A degassed mixture of 4-chloro-6-(4-nitrophenoxy)pyrimidine (WO 2006072589) (1.50 g, 5.96 mmol), tert-butyl carbamate (2.10 g, 17.9 mmol), cesium carbonate (2.91 g, 8.94 mmol), Pd$_2$dba$_3$ (0.218 g, 0.238 mmol) and Xantphos (0.276 g, 0.477 mmol) in DMF was heated at reflux for 1 hr and then maintained at RT for 16 hr. The resulting mixture was partitioned between water (100 mL) and EtOAc (100 mL) and the organic layer was separated and washed with water (2×50 mL) and brine (50 mL) and then dried (MgSO$_4$) and evaporated in vacuo. The residue was purified by flash column chromatography (SiO$_2$, EtOAc in DCM, 0-100%, gradient elution) to afford the title compound as a beige solid (1.22 g, 85% purity, 52%); R$^t$ 4.90 min (Method 1 basic); m/z 331 (M−H)$^−$ (ES$^−$).

4-Amino-6-(4-nitrophenoxy)pyrimidine

To a suspension of tert-butyl 6-(4-nitrophenoxy)pyrimidin-4-ylcarbamate (1.22 g, 85% purity, 3.12 mmol) in DCM (12.0 mL) was added TFA (1.4 mL, 18.4 mmol) and the reaction mixture stirred at RT for 1 hr. An additional aliquot of TFA (0.70 mL) was added and the mixture was kept at RT for 15 hr and was then evaporated in vacuo. The residue was partitioned between EtOAc (50 mL) and saturated aq NaHCO$_3$ solution (50 mL) and the organic layer was separated and washed with brine (25 mL) and then dried (MgSO$_4$). Evaporation of the volatiles in vacuo the title compound as a yellow solid (0.66 g, 89%); R$^t$ 1.38 min (Method 2); m/z 233 (M−H)$^+$ (ES$^+$).

2-Methoxy-N-(6-(4-nitrophenoxy)pyrimidin-4-yl)acetamide

To a solution of 4-amino-6-(4-nitrophenoxy)pyrimidine (560 mg, 2.41 mmol) and DIPEA (630 μL, 3.62 mmol) in DCM (15 mL) under nitrogen at 0° C. was added 2-methoxyacetyl chloride (330 μL, 3.62 mmol) dropwise over 5 min. The mixture was warmed to RT for 1 hr and the reaction was quenched by addition of a 1% solution of NH$_3$ in MeOH (10 mL) and then evaporated in vacuo. The residue was partitioned between DCM (50 mL) and water (25 mL) and the organic layer was separated and washed with brine (25 mL) and was then dried (MgSO$_4$). Evaporation of the volatiles in vacuo gave the title compound as a beige solid (730 mg, 97%): R$^t$ 1.87 min (Method 2); m/z 305 (M−H)$^+$ (ES$^+$).

Intermediate N1: N-(6-(4-Aminophenoxy)pyrimidin-4-yl)-2-methoxyacetamide

A solution of 2-methoxy-N-(6-(4-nitrophenoxy)pyrimidin-4-yl)acetamide (730 mg, 2.53 mmol) in a mixture of MeOH and DCM (1:1 v/v, 80 mL) containing AcOH (5 drops) was subjected to hydrogenation by passage through a Thales H-cube (1.0 mL min$^{-1}$, RT, 10% Pt/C, full hydrogen mode) and was then evaporated in vacuo. The residue was partitioned between DCM (100 mL) and saturated aq NaHCO$_3$ solution (25 mL). The organic layer was separated and washed with brine (25 mL) and then dried (MgSO$_4$). Evaporation of the volatiles in vacuo gave the title compound, Intermediate N1, (560 mg, 66%, estimated 82% purity); R$^t$ 0.93 min (Method 2); m/z 275 (M+H)$^+$ (ES$^+$). This material was used directly in the next step without further purification.

Example 63

N-(6-(4-(3-(3-tert-Butyl-1-p-tolyl-1H-pyrazol-5-yl)ureido) naphthalen-1-yloxy)pyrimidin-4-yl)-2-methoxyacetamide

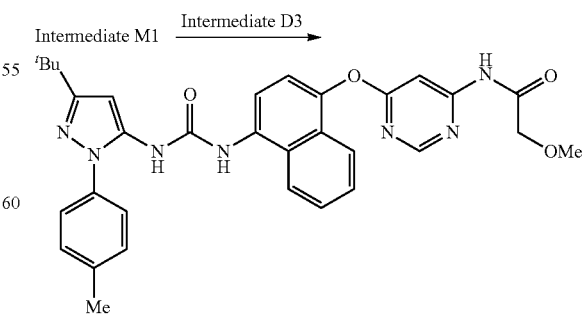

Example 63

To a solution of 3-tert-butyl-1-p-tolyl-1H-pyrazol-5-amine (509 mg, 2.220 mmol) in DCM (10.0 mL) was added CDI (360 mg, 2.22 mmol) and the reaction mixture maintained at RT for 3 hr to provide a solution containing Intermediate D3 [Batch 1]. In an analogous manner an additional quantity of the activated amino pyrazole was also prepared from 3-tert-butyl-1-p-tolyl-1H-pyrazol-5-amine (7.57 g, 33.0 mmol) in DCM (50 mL) by reaction with CDI (5.36 g, 33 mmol) at RT for 3 hr to provide a second solution containing Intermediate D3 [Batch 2].

A solution of Intermediate M1 (360 mg, 1.00 mmol) in DCM (6.0 mL) was added to the solution prepared above, containing Intermediate D3 [Batch 1] and the mixture was maintained at RT for 1 hr. A second aliquot of the CDI adduct (3.0 mL, Batch 2) was added and the reaction mixture was kept at RT for 16 hr and was evaporated in vacuo onto silica and the residue purified by flash column chromatography ($SiO_2$, 12 g, EtOAc in isohexane, 0-100%, gradient elution). The crude material so obtained was taken up into DCM (3.0 mL) and was precipitated by the addition of $Et_2O$ (5.0 mL) and isohexanes (8.0 mL). The precipitate was taken up into boiling EtOAc (3.0 mL), cooled to 0° C. and isohexane (3.0 mL) was added to give two batches of a precipitate [Batch P1 and Batch P2].

Batch P1 of the precipitate was dissolved in MeCN (2.0 mL), water (2.0 mL) was added and the mixture was heated to boiling and then cooled to 0° C. and finally kept at RT for 16 hr. The precipitate which formed was collected by filtration and combined with Batch P2 to afford the title compound, Example 63, as a pale pink solid (120 mg, 18%); $R^t$ 5.03 min (Method 1 basic); m/z 580 (M+H)$^+$ (ES$^+$); $^1$H NMR (400 MHz, DMSO-$d_6$) δ: 1.28 (9H, s), 2.40 (3H, s), 3.33 (3H, s), 4.10 (2H, s), 6.41 (1H, s), 7.34-7.39 (3H, overlapping m), 7.46 (2H, m), 7.55 (1H, m), 7.63 (1H, m), 7.66 (1H, d), 7.77 (1H, d), 7.92 (1H, d), 8.06 (1H, d), 8.45 (1H, d), 8.78 (1H, s), 9.12 (1H, s) and 10.71 (1H, s)

Example 64

N-(6-(4-(3-(3-tert-Butyl-1-p-tolyl-1H-pyrazol-5-yl)ureido)phenoxy)pyrimidin-4-yl)-2-methoxyacetamide

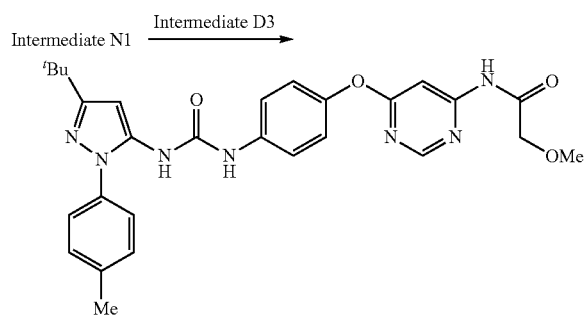

Example 64

To a suspension of CDI (296 mg, 1.82 mmol) in DCM (5.0 mL) was added 3-tert-butyl-1-p-tolyl-1H-pyrazol-5-amine (418 mg, 1.82 mmol) in three portions and the reaction mixture was maintained at RT for 4 hr. To an aliquot of this solution (2.7 mL), containing Intermediate D3, was added to a solution of Intermediate N1 prepared above (100 mg, 82% purity, 0.30 mmol) in DCM (1.5 mL) and the mixture maintained at RT for 16 hr. The reaction was quenched by addition of MeOH (2.0 mL), under vigorous stirring, and the mixture was then evaporated in vacuo. The residue was purified by flash column chromatography ($SiO_2$, 12 g, EtOAc in isohexane, 25-75%, gradient elution) to afford the title compound, Example 64, as a pale brown solid (50 mg, 25%); $R^t$ 2.43 min (Method 2); m/z 530 (M+H)$^+$ (ES$^+$); $^1$H NMR (400 MHz, DMSO-$d_6$) δ: 1.27 (9H, s), 2.38 (3H, s), 3.33 (3H, s), 4.08 (2H, s), 6.36 (1H, s), 7.11 (2H, d), 7.34 (2H, d), 7.39 (2H, d), 7.46 (2H, d), 7.50 (1H, s), 8.36 (1H, br s), 8.50 (1H, s), 9.11 (1H, s), 10.64 (1H, br s).

Additional examples of the disclosure resulted from the N-acylation of a compound represented by Intermediate P.

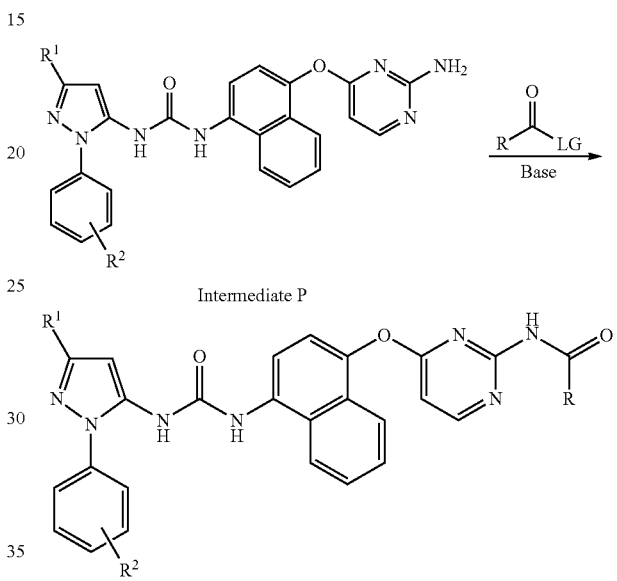

Intermediate P1: 1-(4-(2-Aminopyrimidin-4-yloxy)naphthalen-1-yl)-3-(3-tert-butyl-1-p-tolyl-1H-pyrazol-5-yl)urea [Route1]

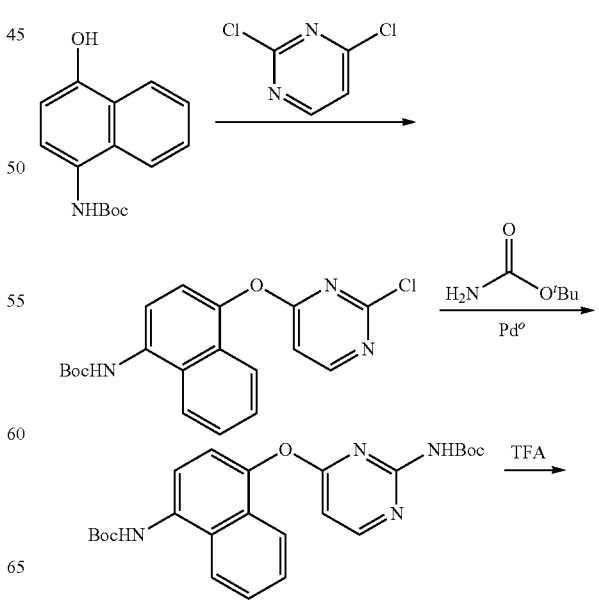

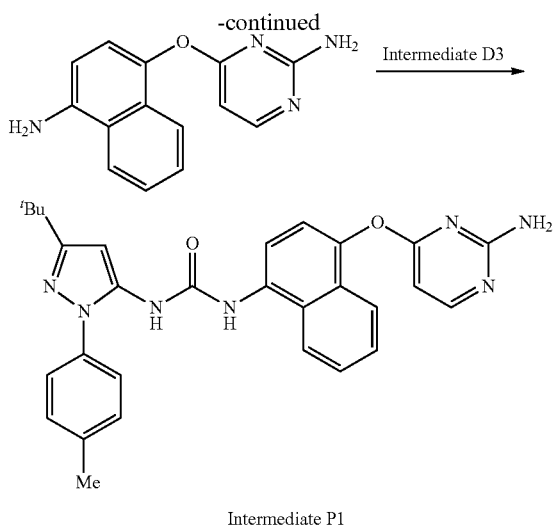

Intermediate P1 tert-Butyl 4-(2-chloropyrimidin-4-yloxy)naphthalen-1-ylcarbamate

To a degassed solution of tert-butyl 4-hydroxynaphthalen-1-ylcarbamate (13.3 g, 51.3 mmol) and DBU (12.6 mL, 51.3 mmol) in MeCN (80 mL) under nitrogen was added 2,4-dichloropyrimidine (7.65 g, 51.3 mmol) in acetonitrile (19 mL) and the reaction mixture was heated to reflux for 4 hr. The solvent was evaporated in vacuo and the residue was taken up into DCM (100 mL) and was washed with water (2×100 mL) and brine (100 mL), then dried (MgSO$_4$) and evaporated in vacuo. The residue was purified by flash column chromatography (SiO$_2$, 330 g, EtOAc in isohexane, 0-50%, gradient elution) to afford the title compound as a pale pink solid (6.80 g, 34%); R$^t$ 2.50 min (Method 2); m/z 372/374 (M+H)$^+$, (ES$^+$)$^+$.

tert-Butyl 4-(4-(tert-butoxycarbonylamino)naphthalen-1-yloxy)pyrimidin-2-ylcarbamate To a degassed suspension of tert-butyl carbamate (1.89 g, 16.1 mmol), tert-butyl 4-(2-chloropyrimidin-4-yloxy)naphthalen-1-ylcarbamate (2.00 g, 5.38 mmol), Cs$_2$CO$_3$ (4.38 g, 13.45 mmol) and Xanthphos (0.249 g, 0.430 mmol) in THF (50 mL) was added Pd$_2$dba$_3$ (197 mg, 0.215 mmol) and the reaction mixture was heated at 75° C. for 16 hr. The reaction mixture was cooled to RT and was partitioned between EtOAc (40 mL) and water (40 mL). The aq layer was separated and extracted with EtOAc (40 mL) and the combined organic extracts were dried (MgSO$_4$) and evaporated in vacuo. The residue was purified by flash column chromatography (SiO$_2$, EtOAc in isohexane, 15-60%, gradient elution to afford the title compound as an off-white solid (1.365 g 53%.); R$^t$ 2.53 min (Method 2); m/z 453 (M+H)$^+$, (ES$^+$)$^+$

4-(4-Aminonaphthalen-1-yloxy)pyrimidin-2-amine

To a solution of tert-butyl 4-(4-(tert-butoxycarbonylamino)naphthalen-1-yloxy)pyrimidin-2-ylcarbamate (1.35 g, 2.98 mmol) in DCM (15 mL) was added TFA (5.0 mL) and the reaction mixture was set aside at RT for 3 hr. The mixture was evaporated in vacuo and the residue was taken up into EtOAc (25 mL) and washed with saturated NaHCO$_3$ solution (25 mL) and brine (25 mL) and then dried (MgSO$_4$) Evaporation in vacuo afforded the title compound as a beige solid (735 mg, 96%); R$^t$ 0.98 min (Method 2); m/z 253 (M+H)$^+$, (ES$^+$)$^+$.

Intermediate P1: 1-(4-(2-Aminopyrimidin-4-yloxy)naphthalen-1-yl)-3-(3-tert-butyl-1-p-tolyl-1 H-pyrazol-5-yl)urea To a suspension of CDI (17.24 g, 106 mmol) in DCM (150 mL) was added 3-tert-butyl-1-p-tolyl-1H-pyrazol-5-amine (24.38 g, 106 mmol) in 1 g portions over 40 min and the reaction stirred at RT for 2 hr. An aliquot of this solution (5.0 mL,) was added dropwise to a suspension of 4-(4-aminonaphthalen-1-yloxy)pyrimidin-2-amine (720 mg, 2.85 mmol) in DCM (15 mL) and the mixture maintained at RT for 2 hr. The reaction mixture was diluted with DCM (20 mL) and was washed with water (30 mL) and brine (30 mL) and then dried (MgSO$_4$) and evaporated in vacuo. The residue was purified by flash column chromatography (SiO$_2$, EtOAc in isohexane, 20-60%, gradient elution) to afford the title compound, Intermediate P1, as a beige solid (1.21 g, 83%); R$^t$ 2.12 min (Method 2); m/z 508 (M+H)$^+$, (ES$^+$)$^+$.

Intermediate P1: 1-(4-(2-Aminopyrimidin-4-yloxy)naphthalen-1-yl)-3-(3-tert-butyl-1-p-tolyl-1 H-pyrazol-5-yl)urea [Route2]

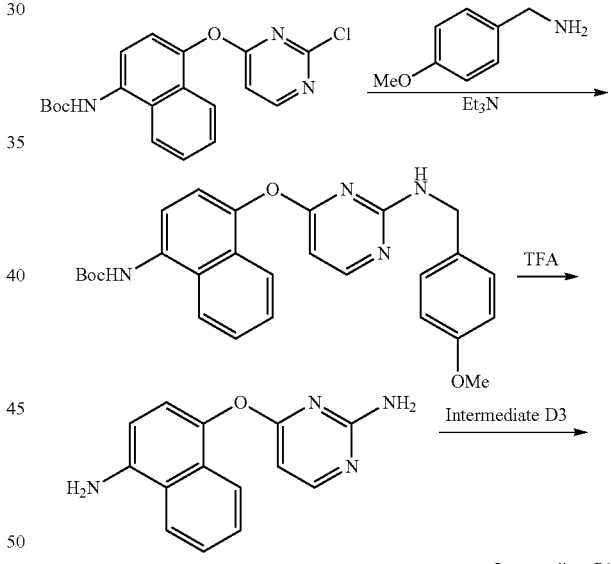

4-(4-Aminonaphthalen-1-yloxy)pyrimidin-2-amine [Route2]

To a solution of tert-butyl 4-(2-chloropyrimidin-4-yloxy)naphthalen-1-ylcarbamate (1.00 g, 2.69 mmol) and triethylamine (0.374 mL, 2.69 mmol) in DMSO (10 mL) was added (4-methoxyphenyl)methanamine (350 μl, 2.69 mmol) and the reaction mixture was heated in a sealed tube at 95° C. for 16 hr. The resulting mixture was partitioned between water and EtOAc and the organic layer was separated and washed with brine and then dried (MgSO$_4$) and evaporated in vacuo. The residue was purified by flash column chromatography (SiO$_2$, ethyl acetate in isohexane, 0-50%, gradient elution) to afford

[as judged by LCMS] a 1:1 mixture of the desired compound: tert-butyl 4-(2-(4-methoxybenzylamino)pyrimidin-4-yloxy) naphthalen-1-ylcarbamate together with 2-chloro-N-(4-methoxybenzyl)pyrimidin-4-amine. This material was used directly in the next step without further purification.

A solution of impure tert-butyl 4-(2-(4-methoxybenzylamino)pyrimidin-4-yloxy)naphthalen-1-ylcarbamate described above (0.77 g, ~50% purity, 0.8 mmol) in TFA (10 mL) was heated at reflux for 8 hr and then kept at RT for 16 hr. The reaction mixture was evaporated in vacuo and the residue was taken up into EtOAc and was washed with saturated aq NaHCO$_3$ solution and with brine and then dried (MgSO$_4$) and evaporated in vacuo. The residue was purified by flash column chromatography (SiO$_2$, ethyl acetate in isohexane, 50-100%, gradient elution) to afford the title compound (111 mg, 54%) as a brown solid; m/z 253 (M+H)$^+$, (ES$^+$)$^+$ Example 65

N-(4-(4-(3-(3-tert-Butyl-1-p-tolyl-1H-pyrazol-5-yl) ureido)naphthalen-1-yloxy)pyrimidin-2-yl)-2-methoxyacetamide

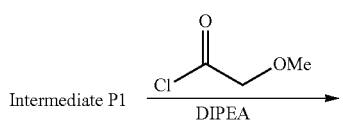

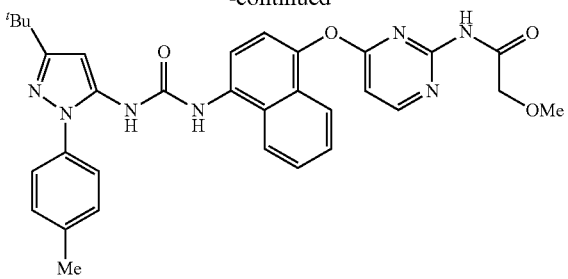

Example 65

To solution of Intermediate P1 (65 mg, 0.128 mmol) in DCM (2.0 ml) at 0° C. was added DIPEA (114 µL, 0.640 mmol) and 2-methoxyacetyl chloride (35 µL, 0.38 mmol) and the reaction mixture was warmed to RT for 16 hr. The reaction was quenched by addition of a solution of 1% NH$_3$ in methanol (2.0 mL) and after 30 min the volatiles were by evaporated in vacuo. The residue was partitioned between DCM (5.0 mL), and saturated aq NaHCO$_3$ solution (5.0 mL) and the organic phase was separated and evaporated in vacuo. The residue was purified by flash column chromatography (SiO$_2$, EtOAc in isohexane, 20-100%, gradient elution) and then by trituration with MeOH (2.0 mL) to afford the title compound, Example 65, as a white solid (13 mg, 17%); R$^t$ 2.37 min (Method 2); m/z 580.1 (M+H)$^+$, (ES$^+$)$^+$. $^1$H NMR (400 MHz, DMSO-d$_6$) δ: 1.28 (9H, s), 2.40 (3H, s), 3.04 (3H, s), 3.70 (2H, s), 6.41 (1H, s), 6.84 (1H, d), 7.38-7.45 (5H, overlapping m), 7.57 (1H, t), 7.64 (1H, t), 7.78 (1H, d), 7.96 (1H, d), 8.08 (1H, d), 8.53 (1H, d), 8.76 (1H, s), 9.13 (1H, s), 10.30 (1H, s).

Further examples of the disclosure were obtained by the reaction of Intermediate P with isocyanates and by conversion of Intermediate P into Intermediate Q followed by reaction with an amine.

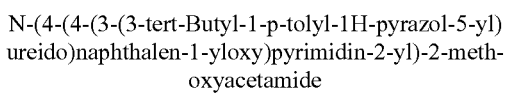

Intermediate P

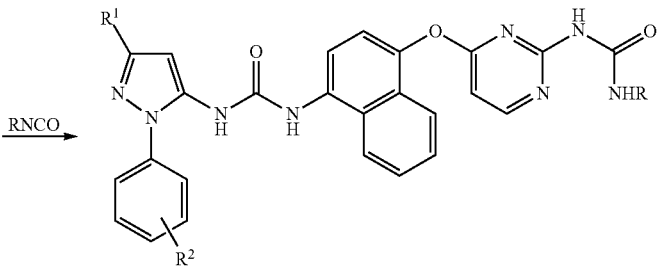

2-Aminopyrimidine Ureas

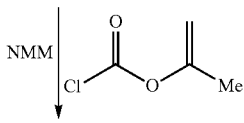

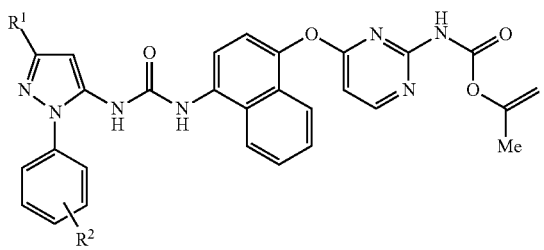

Intermediate Q

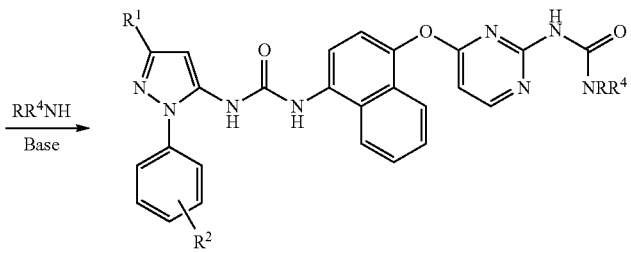

2-Aminopyrimidine Ureas

Example 66

3-(4-(4-(3-(3-tert-Butyl-1-p-tolyl-1H-pyrazol-5-yl)ureido)naphthalen-1-yloxy)pyrimidin-2-yl)urea

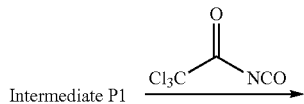

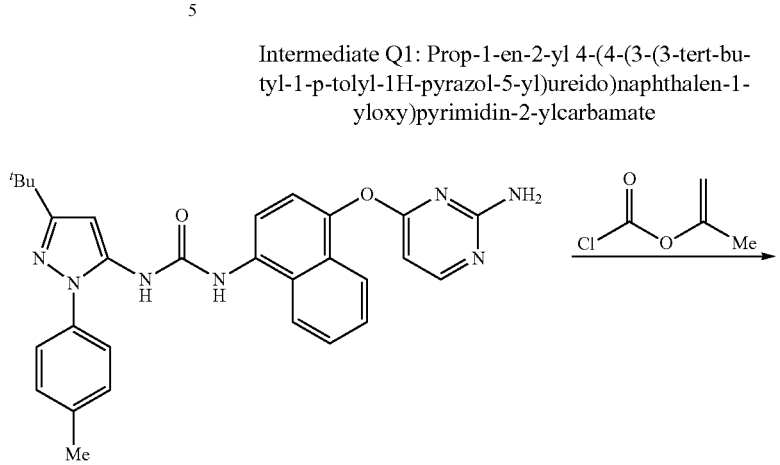

Intermediate P1

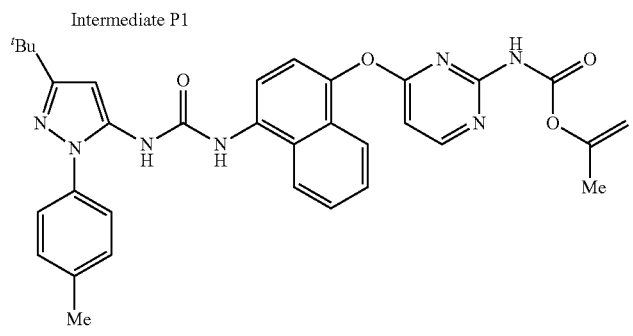

Intermediate Q1

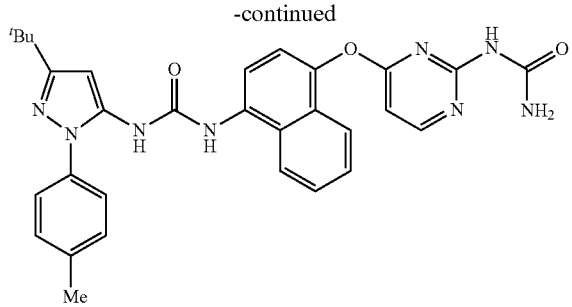

Example 66

To a solution of Intermediate P1 (65 mg, 0.128 mmol) in pyridine (2.0 mL) was added trichloroacetyl isocyanate (24.1 mg, 0.128 mmol) and the reaction mixture kept at RT for 16 hr. The reaction was quenched by addition of a solution of 1% $NH_3$ in MeOH and after 30 min. the mixture was evaporated in vacuo. The residue was purified by flash column chromatography ($SiO_2$, [5% MeOH in EtOAc] in isohexane, 20-70%, gradient elution) to afford the title compound, Example 66, as a white solid (24 mg, 32%); $R^t$ 2.30 min (Method 2); m/z 551.0 (M+H)$^+$ (ES$^+$); $^1$H NMR (400 MHz, DMSO-d$_6$) δ: 1.29 (9H, s), 2.40 (3H, s), 6.41 (1H, s), 6.63 (1H, d), 6.76 (1H, br s), 7.39-7.45 (5H, overlapping m), 7.58 (1H, t), 7.64 (1H, t), 7.79 (1H, d), 7.82 (1H, br s), 7.96 (1H, d), 8.08 (1H, d), 8.44 (1H, d), 8.79 (1H, s), 9.11 (1H, s), 9.45 (1H, s).

Intermediate Q1: Prop-1-en-2-yl 4-(4-(3-(3-tert-butyl-1-p-tolyl-1H-pyrazol-5-yl)ureido)naphthalen-1-yloxy)pyrimidin-2-ylcarbamate To a solution of Intermediate P (1.14 g, 2.246 mmol) and NMM (370 µl, 3.37 mmol) in THF (20 mL) at 0° C. was added prop-1-en-2-yl carbonochloridate (365 µl, 3.37 mmol), dropwise. And the reaction mixture stirred at 0° C. for 1.5 hr. The resulting mixture was diluted with EtOAc (20 mL) and was washed with saturated NaHCO$_3$ solution (20 mL) and brine (20 mL) and then dried (MgSO$_4$) and evaporated in vacuo to provide Intermediate Q, as a beige solid (1.08 g, 81%); $R^t$ 2.58 min (Method 2); m/z 592 (M+H)$^+$, (ES)$^+$.

Example 67

1-Methyl-3-(4-(4-(3-(3-tert-butyl-1-p-tolyl-1H-pyrazol-5-yl)ureido)naphthalen-1-yloxy)pyrimidin-2-yl)urea

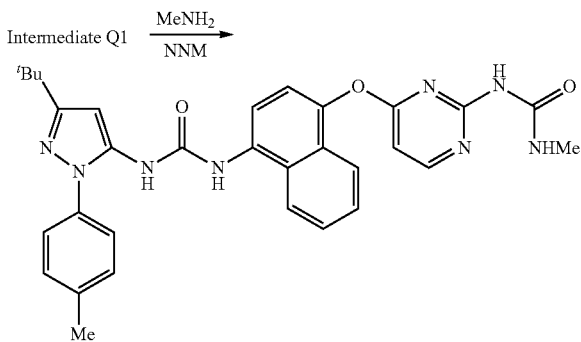

Example 67

To a suspension of Intermediate Q1 (70 mg, 0.118 mmol) and 4-methylmorpholine (1.3 µL, 12 µmol) in THF (5.0 mL) was added methanamine (2M in THF, 89 µL, 0.177 mmol) and the reaction mixture was heated in a sealed tube at 55° C. for 16 hr. The reaction mixture was cooled to RT and partitioned between EtOAc (10 mL) and water (10 mL). The organic layer was washed with brine (10 mL) and dried (MgSO$_4$) and was evaporated in vacuo. The residue was purified by flash column chromatography (SiO$_2$, MeOH in DCM, 0-5%, gradient elution) and then by recrystallization from methanol to afford the title compound, Example 67, RV1581 as a white solid (21 mg, 31%); R$^t$ 5.07 min (Method 1 basic); m/z 565 (M+H)$^+$, (ES$^+$); $^1$H NMR (400 MHz, DMSO-d$_6$) δ: 1.29 (9H, s), 2.23 (3H, d), 2.39 (3H, s), 6.41 (1H, s), 6.77 (1H, d), 7.37 (2H, d), 7.42-7.47 (3H, overlapping m), 7.59 (1H, t), 7.66 (1H, t), 7.78 (1H, d), 7.84 (1H, br s), 7.97 (1H, d), 8.09 (1H, d), 8.47 (1H, d), 8.74 (1H, s), 9.16 (1H, s), 9.64 (1H, s).

Example 68

1,1-Dimethyl-3-(4-(4-(3-(3-tert-butyl-1-p-tolyl-1H-pyrazol-5-yl)ureido)naphthalen-1-yloxy)pyrimidin-2-yl)urea

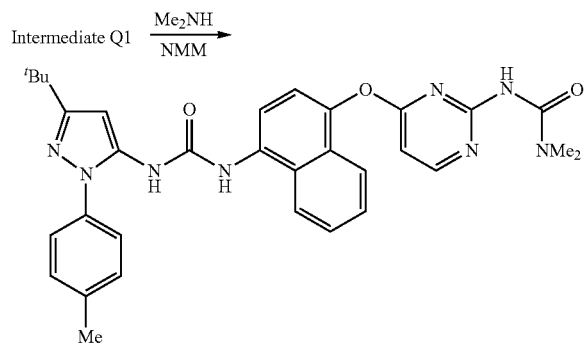

Example 68

To a suspension of Intermediate Q1 (70 mg, 118 µmol) and 4-methylmorpholine (1.3 µL, 12 µmol) in THF (10 mL) was added dimethylamine (2M in THF, 89 µL, 177 µmol) and the reaction mixture was heated in a sealed tube at 55° C. for 64 hr. The reaction mixture was cooled to RT and partitioned between EtOAc (10 mL) and water (10 mL). The organic layer was washed with brine (10 mL) and dried (MgSO$_4$) and was evaporated in vacuo. The residue was purified by flash column chromatography (SiO$_2$, MeOH in DCM, 0-5%, gradient elution, then SiO$_2$, [5% MeOH in EtOAc] in isohexane, 20-70%, gradient elution) and then by preparative HPLC (Reverse Phase C$_{18}$, water/MeCN gradient) to afford the title compound, Example 68, as a white solid (16 mg, 22%); R$^t$ 4.64 min (Method 1 basic); m/z 579 (M+H)$^+$, (ES$^+$); $^1$H NMR (400 MHz, DMSO-d$_6$) δ: 1.28 (9H, s), 2.39 (3H, s), 2.71 (6H, s), 6.39 (1H, s), 6.53 (1H, d), 7.36-7.39 (3H, overlapping m), 7.46 (2H, d), 7.57 (1H, t), 7.63 (1H, t), 7.80 (1H, d), 7.89 (1H, d), 8.06 (1H, d), 8.37 (1H, d), 8.83 (1H, s), 9.14 (1H, s), 9.18 (1H, s).

Example 69

1-Cyclopropyl-3-(4-(4-(3-(3-tert-butyl-1-p-tolyl-1H-pyrazol-5-yl)ureido)naphthalen-1-yloxy)pyrimidin-2-yl)urea

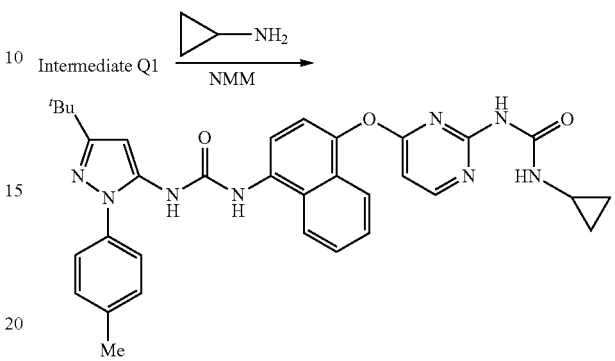

Example 69

To a suspension of Intermediate Q1 (70 mg, 118 µmol) and 4-methylmorpholine (1.3 µL, 12 µmol) in THF (10 mL) was added cyclopropylamine (12.3 µL, 177 µmol) and the reaction mixture was heated at 50° C. for 96 hr. The reaction mixture was cooled to RT and partitioned between EtOAc (10 mL) and water (10 mL). The organic layer was separated and was washed with brine (10 mL), dried (MgSO$_4$) and evaporated in vacuo. The residue was purified by flash column chromatography (SiO$_2$, MeOH in DCM, 0-5%, gradient elution) to afford the title compound, Example 69, as a white solid (29 mg, 41%); R$^t$ 2.53 min (Method 2); m/z 591 (M+H)$^+$, (ES$^+$); $^1$H NMR (400 MHz, DMSO-d$_6$) δ: −0.25 (2H, m), 0.26 (2H, m), 1.29 (9H, s), 2.22 (1H, m), 2.39 (3H, s), 6.42 (1H, s), 6.78 (1H, d), 7.38-7.46 (5H, overlapping m), 7.58 (1H, t), 7.66 (1H, t), 7.76 (1H, d), 8.00 (1H, br s), 8.03 (1H, d), 8.12 (1H, d), 8.47 (1H, d), 8.78 (1H, s), 9.17 (1H, s), 9.66 (1H, s).

Example 70

(4-(4-(3-(3-tert-Butyl-1-p-tolyl-1H-pyrazol-5-yl)ureido)naphthalen-1-yloxy)pyrimidin-2-yl)morpholine-4-carboxamide

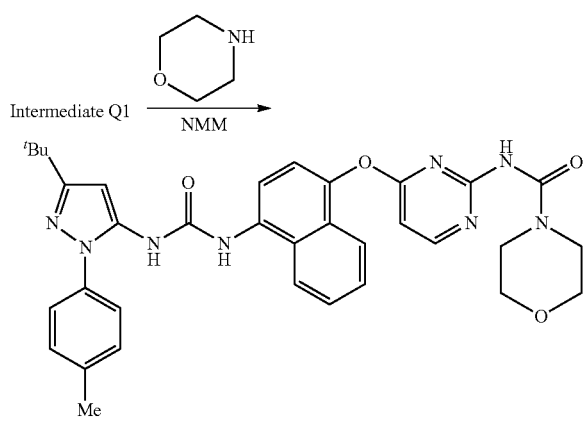

Example 70

To a suspension of Intermediate Q1 (70 mg, 118 μmol) and 4-methylmorpholine (1.3 μL, 12 μmol) in THF (10 mL) was added morpholine (15.6 μL, 177 μmol) and the reaction mixture was heated at 55° C. for 16 hr. The reaction mixture was cooled to RT and partitioned between EtOAc (10 mL) and water (10 mL). The organic layer was separated and washed with brine (10 mL) and then dried ($MgSO_4$) and evaporated in vacuo. The residue was purified by flash column chromatography ($SiO_2$, MeOH in DCM, 0-5%, gradient elution) and trituration with ether to afford the title compound, Example 70, as a white solid (20 mg, 27%); $R^t$ 2.26 min (Method 2); m/z 621 (M+H)$^+$, (ES$^+$); $^1$H NMR (400 MHz, DMSO-$d_6$) δ: 1.28 (9H, s), 2.40 (3H, s), 3.25 (4H, m), 3.46 (4H, m), 6.40 (1H, s), 6.56 (1H, d), 7.38-7.40 (3H, overlapping m), 7.46 (2H, d), 7.57 (1H, t), 7.63 (1H, t), 7.81 (1H, d), 7.90 (1H, d), 8.06 (1H, d), 8.40 (1H, d), 8.75 (1H, s), 9.10 (1H, s), 9.38 (1H, s).

Still further examples of the disclosure were obtained by the reaction of compounds represented by Intermediate R with Intermediate C or Intermediate D.

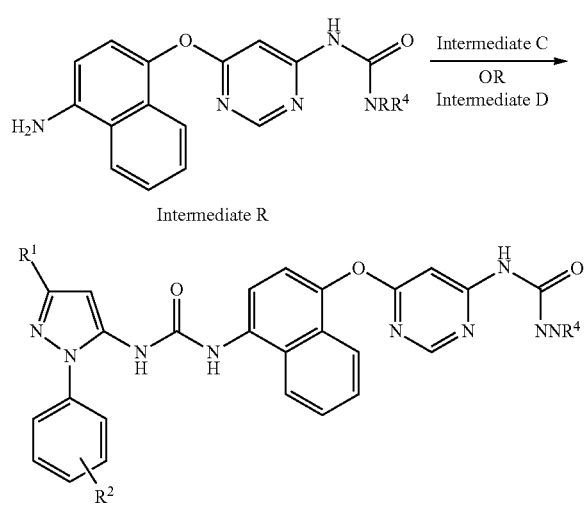

Intermediate R1: 1-(6-(4-Aminonaphthalen-1-yloxy)pyrimidin-4-yl)urea

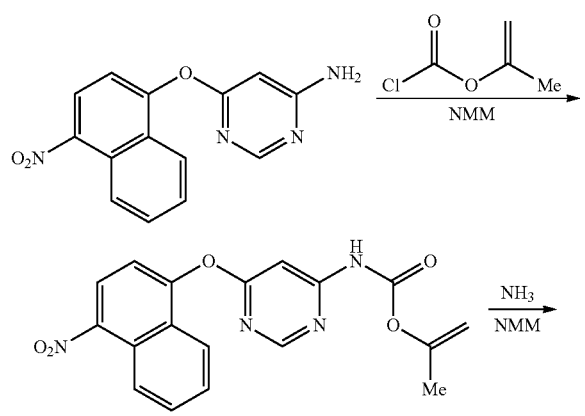

Prop-1-en-2-yl 6-(4-nitronaphthalen-1-yloxy)pyrimidin-4-ylcarbamate

To a solution of 6-(4-nitronaphthalen-1-yloxy)pyrimidin-4-amine (89 mg, 0.315 mmol) and NMM (45 μl, 0.410 mmol) in THF (2.0 mL) at 0° C. was added, dropwise, a solution of prop-1-en-2-yl carbonochloridate (45 μl, 0.410 mmol) in THF (1.0 mL) and the reaction mixture warmed to RT for 15 hr and then partitioned between EtOAc (20 mL) and water (5.0 mL). The aq layer was separated and extracted with EtOAc and the combined organic layers were dried ($MgSO_4$) and then evaporated in vacuo to afford the title compound as a yellow oil (109 mg, 87%); $R^t$ 2.54 min (Method 2); m/z 367 (M+H)$^+$ (ES$^+$). This material was used directly in the next step (below) without further purification.

1-(6-(4-Nitronaphthalen-1-yloxy)pyrimidin-4-yl)urea

To a solution of prop-1-en-2-yl 6-(4-nitronaphthalen-1-yloxy)pyrimidin-4-ylcarbamate (109 mg, 0.298 mmol) and 4-methylmorpholine (3.3 μL, 0.030 mmol) in dry THF (27 mL) was added a solution of $NH_3$ in MeOH (0.6 mL, 1M, 0.6 mmol) and the reaction mixture heated to 55° C. Further aliquots of the methanolic $NH_3$ solution were added after 1 hr (0.6 ml, 0.6 mmol) and after 5 hr (1.0 mL, 1 mmol) and after a further 16 hr the reaction mixture was evaporated in vacuo. The residue was taken up into THF (3.0 mL) and NMM (3.3 μL, 0.030 mmol) and $NH_3$ in MeOH (0.6 mL, 1M, 0.6 mmol) were added and the reaction mixture was heated to 55° C. Further aliquots of the methanolic $NH_3$ solution (1M, 1.0 mL, 1.0 mmol) were added after 2 hr and after 3 hr. After 3.5 hr additional aliquots of NMM (3.3 μL, 0.030 mmol) and methanolic $NH_3$ (1M, 1.0 mL, 1.0 mmol) were added and the reaction mixture was maintained at 55° C. for 15 hr. The reaction mixture was evaporated in vacuo and the residue was purified by flash column chromatography ($SiO_2$, 4 g, EtOAc in isohexane, 0-100%, gradient elution) to afford the title compound as a yellow solid (60 mg, 61%); $R^t$ 1.87 min (Method 2); m/z 326 (M+H)$^+$ (ES$^+$).

Intermediate R$^1$: 1-(6-(4-aminonaphthalen-1-yloxy)pyrimidin-4-yl)urea

A solution of 1-(6-(4-nitronaphthalen-1-yloxy)pyrimidin-4-yl)urea (60 mg, 0.184 mmol) in a mixture of MeOH, DCM and THF (1:1:1 v/v/v, 30 mL) containing AcOH (2 drops) was subjected to hydrogenation by passage through a Thales H-cube (1.0 mL min$^{-1}$, RT, 70 mm CatCart, 10% Pt/C, full hydrogen mode). The resulting solution was evaporated in vacuo to afford the title compound, Intermediate R1, as a brown glassy solid (58 mg, 76% purity, 81%); $R^t$ 1.23 min (Method 1 basic); m/z 296 (M+H)$^+$ (ES$^+$). This material was used directly in the next step (below) without further purification.

Example 71

3-(6-(4-(3-(3-tert-Butyl-1-p-tolyl-1H-pyrazol-5-yl)ureido)naphthalen-1-yloxy)pyrimidin-4-yl)urea

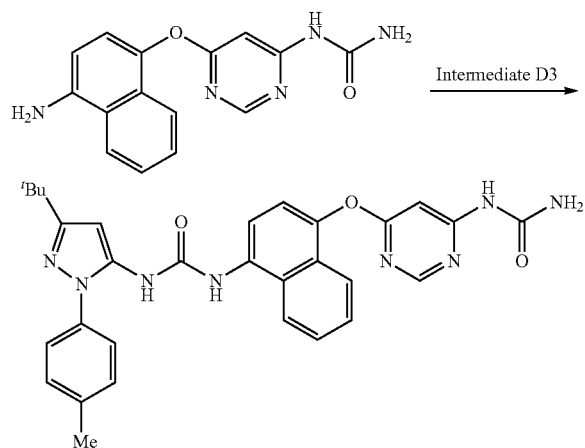

Example 71

To a suspension of CDI (17.24 g, 106 mmol) in DCM (150 mL) was added 3-tert-butyl-1-p-tolyl-1H-pyrazol-5-amine (24.38 g, 106 mmol) in 1 g portions over 40 min and the reaction mixture stirred at RT for 2 hr. An aliquot of this solution (0.36 mL), containing Intermediate D3, was added to a solution of Intermediate R1 (58 mg, 0.179 mmol) in DCM (500 mpL) and the mixture kept at RT for 1.5 hr. The reaction was quenched by the addition of MeOH (5.0 mL) and after 30 min the mixture was evaporated in vacuo and the residue was purified by flash column chromatography (SiO$_2$, 4 g, [5% MeOH in EtOAc] in isohexane, 0-100%, gradient elution) The crude product so obtained was taken up into a mixture of DCM and EtOAc (1:1, v/v, 20 mL) and was washed with water (5.0 mL) and brine (5 mL) and then dried (MgSO$_4$) and evaporated in vacuo. The residue so obtained was dissolved in EtOAc (10 mL) was washed with water (5.0 mL) and brine (5.0 mL), and the dried (MgSO$_4$) and evaporated in vacuo to afford the title compound, Example 71, as a brown solid (34 mg, 34%); $R^t$ 2.23 min (Method 2); m/z 551 (M+H)$^+$ (ES$^+$); $^1$H NMR (400 MHz, DMSO-d$_6$) δ: 1.28 (9H, s), 2.39 (3H, s), 6.41 (1H, s), 6.80 (2H, br peak), 7.22 (1H, s), 7.32 (1H, d), 7.37 (2H, d), 7.46 (2H, d), 7.56 (1H, m), 7.62 (1H, m), 7.77 (1H, d), 7.90 (1H, d), 8.06 (1H, d), 8.31 (1H, s), 8.77 (1H, s), 9.10 (1H, s), 9.52 (1H, s).

Biological Testing

All compounds exemplified here showed an IC$_{50}$<5 μM versus p38α in an enzyme activity assay. The broader profiles of action of selected compound examples are presented in the Tables below.

TABLE 1

| | Enzyme | | THP-1 (LPS) | DU937 (LPS) | DU937 (LPS) | BEAS2B (polyIC) | DU937 (cell viability) | |
| | p38α | p38γ | TNFα | TNFα | IL-8 | ICAM1 | MTT assay | |
| Example No | IC$_{50}$$^a$ (nM) | IC$_{50}$$^a$ (nM) | IC$_{50}$$^a$ (Nm) | REC$_{50}$$^a$ (nM) | IC$_{50}$$^a$ (nM) | IC$_{50}$$^a$ (nM) | 4 h$^c$ % | 4 h$^c$ % |
|---|---|---|---|---|---|---|---|---|
| 63 | ++ | + | ++ | ++ | ++ | + | −$^$ | +$^$ |
| 65 | + | + | ++ | ++ | + | + | − | − |
| 66 | + | + | ++ | ++ | ++ | + | − | − |
| 67 | + | + | ++ | ++ | ++ | + | − | − |
| 68 | ++ | + | + | ++ | ++ | ++ | − | − |
| 69 | ++ | + | + | ++ | ++ | NT | − | − |

$^a$++: EC$_{50}$/IC$_{50}$ < 10 nM, +: EC$_{50}$/IC$_{50}$ < 5000 nM, −: EC$_{50}$/IC$_{50}$ >= 5000 nM
$^b$++: EC$_{50}$/IC$_{50}$ < 100 nM, +: EC$_{50}$/IC$_{50}$ < 5000 nM, −: EC$_{50}$/IC$_{50}$ >= 5000 nM
$^c$+: >30%, −: <=30%, at 1 μg/ml; "$" indicates test conducted at 10 μg/ml
NT: not tested

TABLE 2

| | Enzyme | | THP-1 (LPS) | DU937 (LPS) | DU937 (LPS) | BEAS2B (polyIC) | DU937 (cell viability) | |
| | p38α | p38γ | TNFα | TNFα | IL-8 | ICAM1 | MTT assay | |
| Example No | IC$_{50}$$^a$ (nM) | IC$_{50}$$^b$ (nM) | IC$_{50}$$^a$ (nM) | REC$_{50}$$^a$ (nM) | IC$_{50}$$^a$ (nM) | IC$_{50}$$^a$ (nM) | 4 h$^c$ % | 24 h$^c$ % |
|---|---|---|---|---|---|---|---|---|
| 1 | ++ | ++ | ++ | ++ | + | + | −$^$ | +$^$ |
| 2 | ++ | ++ | ++ | + | ++ | ++ | −$^$ | +$^$ |
| 3 | ++ | ++ | ++ | + | ++ | + | −$^$ | +$^$ |
| 4 | ++ | + | ++ | ++ | ++ | ++ | −$^$ | +$^$ |
| 5 | + | + | ++ | ++ | ++ | ++ | +$^$ | +$^$ |
| 6 | ++ | − | ++ | ++ | + | + | − | − |
| 7 | ++ | − | ++ | ++ | ++ | + | − | − |
| 8 | + | + | + | ++ | ++ | ++ | − | + |

TABLE 2-continued

| Example No | Enzyme | | THP-1 (LPS) | DU937 (LPS) | DU937 (LPS) | BEAS2B (polyIC) | DU937 (cell viability) | |
|---|---|---|---|---|---|---|---|---|
| | p38α | p38γ | TNFα | TNFα | IL-8 | ICAM1 | MTT assay | |
| | $IC_{50}{}^a$ (nM) | $IC_{50}{}^b$ (nM) | $IC_{50}{}^a$ (nM) | $REC_{50}{}^a$ (nM) | $IC_{50}{}^a$ (nM) | $IC_{50}{}^a$ (nM) | 4 h$^c$ % | 24 h$^c$ % |
| 9 | ++ | + | ++ | ++ | ++ | + | − | − |
| 10 | ++ | ++ | ++ | ++ | ++ | ++ | − | + |
| 11 | ++ | ++ | ++ | ++ | ++ | + | −$^$ | +$^$ |
| 12 | ++ | + | ++ | ++ | ++ | + | −$^$ | +$^$ |
| 13 | ++ | ++ | ++ | ++ | ++ | ++ | −$^$ | +$^$ |
| 14 | ++ | ++ | + | + | + | + | − | − |
| 15 | ++ | ++ | ++ | ++ | ++ | ++ | − | + |
| 16 | ++ | ++ | ++ | ++ | ++ | ++ | − | + |
| 17 | ++ | ++ | ++ | ++ | ++ | ++ | − | + |
| 19 | ++ | ++ | ++ | ++ | ++ | ++ | − | + |
| 20 | ++ | ++ | ++ | ++ | + | + | − | − |
| 22 | + | ++ | ++ | ++ | ++ | + | − | + |
| 23 | + | ++ | ++ | ++ | ++ | + | − | − |
| 24 | + | ++ | ++ | ++ | ++ | NT | − | + |
| 26 | + | + | ++ | ++ | ++ | ++ | − | + |

$^a$++: $EC_{50}/IC_{50} < 10$ nM, +: $EC_{50}/IC_{50} < 5000$ nM, −: $EC_{50}/IC_{50} >= 5000$ nM
$^b$++: $EC_{50}/IC_{50} < 100$ nM, +: $EC_{50}/IC_{50} < 5000$ nM, −: $EC_{50}/IC_{50} >= 5000$ nM
$^c$+: >30%, −: <=30%, at 1 μg/ml; "$" indicates test conducted at 10 μg/ml
NT: not tested

TABLE 3

| Example No | Enzyme | | THP-1 (LPS) | DU937 (LPS) | DU937 (LPS) | BEAS2B (polyIC) | DU937 (cell viability) | |
|---|---|---|---|---|---|---|---|---|
| | p38α | p38γ | TNFα | TNFα | IL-8 | ICAM1 | MTT assay | |
| | $IC_{50}{}^a$ (nM) | $IC_{50}{}^b$ (nM) | $IC_{50}{}^a$ (nM) | $REC_{50}{}^a$ (nM) | $IC_{50}{}^a$ (nM) | $IC_{50}{}^a$ (nM) | 4 h$^c$ % | 4 h$^c$ % |
| 28 | + | + | ++ | + | + | + | −$^$ | −$^$ |
| 29 | ++ | + | ++ | ++ | + | ++ | − | − |
| 33 | + | − | ++ | ++ | NT | + | − | − |
| 34 | + | − | ++ | + | + | + | −$^$ | +$^$ |
| 36 | + | + | ++ | ++ | + | ++ | − | − |
| 39 | ++ | + | ++ | ++ | ++ | + | − | + |
| 40 | ++ | ++ | ++ | ++ | ++ | ++ | − | + |
| 41 | ++ | − | ++ | + | + | NT | − | + |
| 42 | + | ++ | ++ | ++ | + | ++ | − | − |
| 43 | ++ | ++ | ++ | ++ | ++ | ++ | − | − |
| 44 | + | ++ | ++ | ++ | ++ | ++ | − | − |
| 45 | ++ | ++ | ++ | ++ | ++ | ++ | − | − |
| 46 | ++ | + | + | ++ | ++ | + | − | − |
| 47 | ++ | ++ | ++ | ++ | ++ | ++ | − | − |
| 49 | ++ | + | ++ | ++ | + | + | − | − |
| 50 | ++ | ++ | ++ | ++ | ++ | ++ | − | + |
| 51 | ++ | + | ++ | ++ | ++ | ++ | − | + |
| 52 | + | + | ++ | ++ | ++ | ++ | − | − |
| 53 | ++ | + | ++ | ++ | + | ++ | − | − |
| 54 | ++ | ++ | ++ | ++ | ++ | ++ | − | − |
| 55 | ++ | + | ++ | ++ | ++ | ++ | − | − |
| 57 | ++ | ++ | ++ | + | + | + | − | − |
| 58 | ++ | + | ++ | NT | ++ | ++ | − | − |
| 61 | ++ | ++ | ++ | ++ | ++ | ++ | − | − |
| 62 | ++ | ++ | ++ | ++ | ++ | ++ | − | − |

$^a$++: $EC_{50}/IC_{50} < 10$ nM, +: $EC_{50}/IC_{50} < 5000$ nM, −: $EC_{50}/IC_{50} >= 5000$ nM
$^b$++: $EC_{50}/IC_{50} < 100$ nM, +: $EC_{50}/IC_{50} < 5000$ nM, −: $EC_{50}/IC_{50} >= 5000$ nM
$^c$+: >30%, −: <=30%, at 1 μg/ml; "$" indicates test conducted at 10 μg/ml
NT: not tested Experimental Methods Enzyme Inhibition Assay The enzyme inhibitory activity of compound was determined by fluorescence resonance energy transfer (FRET) using synthetic peptides labelled with both donor and acceptor fluorophores (Z-LYTE, Invitrogen). Briefly, recombinant, phosphorylated p38 MAPK gamma (MAPK12:Millipore) was diluted in HEPES buffer, mixed with compound at desired final concentrations and incubated for two hours at room temperature. The FRET peptide (2 μM) and ATP (100 μM) were next added to the enzyme/compound mixture and incubated for one hour. Development reagent (protease) was added for one hour prior to detection in a fluorescence microplate reader (Varioskan® Flash, ThermoFisher Scientific). The site-specific protease only cleaves non-phosphorylated peptide and eliminates the FRET signal. Phosphorylation levels of each reaction were calculated using the ratio of coumarin emission (donor) over fluorescein emission (acceptor) with high ratios indicating high phosphorylation and low ratios, low phosphorylation levels. The percentage inhibition of each reaction was calculated relative to non-inhibited control, and the 50% inhibitory concentration ($IC_{50}$ value) then calculated from the concentration-response curve.

For p38 MAPK alpha (MAPK14: Invitrogen), enzyme activity was evaluated indirectly by determining activation/phosphorylation of the down-stream molecule, MAPKAP-K2. The p38 MAPK alpha protein was mixed with its inactive target MAPKAP-K2 (Invitrogen) and compound for two hours at room temperature. The FRET peptide (2 μM), which is a phosphorylation target for MAPKAP-K2, and ATP (10 μM) were then added to the enzymes/compound mixture and incubated for one hour. Development reagent was then added and the mixture incubated for one hour before detection by fluorescence completed the assay protocol.

LPS-Induced TNF Alpha/IL-8 Release in U937 Cells: Potency

U937 cells, human monocytic cell line, were differentiated to macrophage-type cells by incubation with phorbol myristate acetate (PMA; 100 ng/ml) for 48 to 72 hours. Cells were pre-incubated with final concentrations of compound for 2 hrs. Cells were then stimulated with 0.1 μg/ml of LPS (from E. Coli: O111:B4, Sigma) for 4 hrs, and the supernatant collected for determination of TNFα and IL-8 concentration by sandwich ELISA (Duo-set, R&D systems). The inhibition of TNF (production was calculated as a percentage of that achieved by 10 g/ml of BIRB796 at each concentration of test compound by comparison with vehicle control. The relative 50% effective concentration (R-EC50) was determined from the resultant concentration-response curve. The inhibition of IL-8 production was calculated at each concentration of test compound by comparison with vehicle control. The 50% inhibitory concentration ($IC_{50}$) was determined from the resultant concentration-response curve.

LPS-Induced TNF Alpha Release in THP-1 Cells: Potency

THP-1 cells, a human monocytic cell line, were stimulated with 1 μg/mL of LPS (from E. Coli; O111:B4, Sigma) for 4 hr and the supernatant collected for determination of TNFα concentration by sandwich ELISA (Duo-set, R&D systems). The inhibition of TNFα production was calculated at each concentration by comparison with vehicle control. The 50% inhibitory concentration ($IC_{50}$) was determined from the resultant concentration-response curve.

Poly I:C-Induced ICAM-1 Induction in BEAS2B Cells: Potency

Poly I:C (1 ug/ml) (Invivogen Ltd., San Diego, Calif.) was transfected into BEAS2B cells (human bronchial epithelial cells, ATCC) with Oligofectamine (Invitrogen, Carlsbad, Calif.). Cells were pre-incubated with final concentrations of compound for 2 hrs. The level of ICAM1 expression on the cell surface was determined by cell-based ELISA. Briefly, at 18 hrs after poly I:C transfection, cells were fixed with 4% formaldehyde in PBS. After quenching endogenous peroxidase by adding 0.1% sodium azide and 1% hydrogen peroxide, cells were washed with wash-buffer (0.1% Tween in PBS: PBS-Tween). After blocking the wells with 5% milk in PBS-Tween for 1 hr, the cells were incubated with anti-human ICAM-1 antibody (Cell Signaling Technology, Danvers, Mass.) in 1% BSA PBS overnight at 4° C. Cells were washed with PBS-Tween and incubated with the secondary antibody (HRP-conjugated anti-rabbit IgG, Dako Ltd., Glostrup, Denmark). The ICAM-1 signal was detected by adding substrate and reading at 450 nm with a reference wavelength of 655 nm using a spectrophotometer. The cells were then washed with PBS-Tween and total cell numbers in each well were determined by reading absorbance at 595 nm after Crystal Violet staining and elution by 1% SDS solution. The measured OD 450-655 readings were corrected for cell number by dividing with the OD595 reading in each well.

MTT Assay

Differentiated U937 cells were pre-incubated with compound for 4 hrs in 5% FCS or 10% FCS for 24 hrs. The supernatant was replaced with 200 ul of new media and 10 ul of MTT stock solution (5 mg/ml) added to each well. After 1 hr incubation, the media were removed, 200 ul of DMSO added to each well and the plates were shaken lightly for 1 h prior to reading the absorbance at 550 nm.

The percentage loss of cell viability was calculated for each well relative to vehicle (0.5% DMSO)-treatment. Consequently an apparent increase in cell viability for drug treatment relative to vehicle is tabulated as a negative percentage.

LPS-Induced Neutrophils Accumulation in Mice

Non-fasted mice were dosed by the intra tracheal route with either vehicle, or the test substance at the indicated times (within the range 2-12 hr) before starting LPS treatment. At T=0, mice were placed into an exposure chamber and exposed to LPS. Eight hours after LPS challenge, animals were under anesthetized, the trachea cannulated and BALF extracted by infusing and withdrawing 1 ml of PBS into the lungs via a tracheal catheter. Total and differential white cell counts in the BALF samples were measured using a Neubaur haemocytometer. Cytospin smears of the BALF samples were prepared by centrifugation at 200 rpm for 5 min at room temperature and stained using a DiffQuik stain system (Dade Behring). Cells were counted using oil immersion microscopy.

TABLE

Effects of treatment with Example 8

| Treatment | Neutrophil numbers in BAL ($\times 10^5$/mL) 2 hr pre-dose | Neutrophil numbers in BAL ($\times 10^5$/mL) 12 hr pre-dose |
|---|---|---|
| Vehicle | 20.2 ± 3.7 | — |
| 0.02 mg/ml Example 8 | 15.1 ± 2.1 | 20.1 ± 2.9 |
| 0.1 mg/ml Example 8 | 10.4 ± 1.6 | 16.7 ± 2.4 |
| 0.2 mg/ml Example 8 | 4.6 ± 1.2 | 14.3 ± 2.0 |

Results are presented as the mean ± SEM, n = 8

TABLE

Effects of treatment with Example 8 or Example 42

| Treatment | Neutrophil numbers in BAL ($\times 10^5$/mL) 8 hr pre-dose |
|---|---|
| Vehicle | 16.38 ± 2.53 |
| Example 8 0.2 mg/ml | 9.65 ± 1.50 |
| Example 42 0.2 mg/ml | 8.60 ± 1.59 |

Results are presented as the mean ± SEM, n = 8

Allergen-Induced Eosinophil Accumulation in Guinea Pigs

Dunkin Hartley guinea pigs were immunized with ovalbumin. Six doses of vehicle or Example 8 (1.5 mg/ml) were administered by aerosol every 12 hours with the final dose being administered 2 hr before initiating of the allergen challenge (grade V, OVA; 10 μg/mL solution aerosolised using a De Vibliss ultrasonic nebuliser 2000, over a 30 min period). Two groups of animals received 6 doses of Example 8 whilst a further two groups received 6 doses of vehicle. 8 or 24 hours after OVA challenge (see group details above), the trachea was cannulated and BALF extracted. The procedure for this involved aspirating 5 ml of PBS into the lungs via a tracheal catheter. Total and differential white cell counts in the BAL fluid samples were measured using a Neubaur haemocytometer. Cytospin smears of the BAL fluid samples were prepared by centrifugation at 200 rpm for 5 min at room temperature and stained using a DiffQuik stain system (Dade Behring). Cells were counted blind using oil immersion microscopy.

Treatment of guinea pigs with Example 8 was found to inhibit eosinophil accumulation into the BALF when investigated at 8 and 24 hr post ovalbumin challenge (see table below)

Inhibition of Eosinophils in BALF Following Allergen Challenge

| Treatment | Neutrophil numbers in BAL (×105/mL) 2 hr pre-dose | Neutrophil numbers in BAL (×105/mL) 12 hr pre-dose |
| --- | --- | --- |
| Example 8 | 12.4 ± 1.7 | 21.6 ± 3.9 |

Results are presented as the mean ± SEM, n = 6

Cigarette Smoke Model

A/J mice (males, 5 weeks old) were exposed to cigarette smoke (4% cigarette smoke, diluted with compressed air) for 30 min/day for 11 days using a Tobacco Smoke Inhalation Experiment System for small animals (Model SIS-CS; Sibata Scientific Technology, Tokyo, Japan). Test substances were given intra-nasally (35 µL of solution in 50% DMSO/PBS) and therapeutically twice daily for 3 days after the final cigarette smoke exposure. Twelve hours after the last dosing, animals were anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

The results of treatment with Example 8 are shown in FIGS. 1 (neutrophils) and 2 (activated alveolar macrophages). Those for treatment with Example 42 are shown in FIGS. 3 (neutrophils) and 4 (activated alveolar macrophages). Data for cell numbers are shown as the mean±SEM. The cigarette smoke model used for this study is reported as a corticosteroid refractory system, (Medicherla S. et al., (2008); *J. Pharmacol. Exp. Ther.* 324(3):921-9) and it was confirmed that fluticasone propionate did not inhibit either neutrophil or macrophage accumulation into airways at 50 µg/mL (35 µl, bid, m), the same dose that produced >80% inhibition of LPS-induced neutrophil accumulation.

Ovalbumin Challenge/Parainfluenza Infection Model

Male Dunkin-Hartley guinea-pigs (300-350 g, n=6/group) were sensitised with 100 µg ovalubumin (OVA)+100 mg $Al_2(OH)_3$ in 1 ml normal saline (i.p.) on days 2 and 6. Parainfluenza virus (PIV-3; $10^6$ infectious units) or media without virus was nasally instilled on days 11 and 12. Animals were treated with either nebulised (i) fluticasone propionate at a dose of 1.5 mg per day (initial studies established that this dose of fluticasone propionate inhibited ovalbumin-mediated lung function changes in sensitized animals treated with PIV3 medium) or (ii) Example 8 (0.15 mg per day) or (iii) a combination of fluticasone and Example 8 at the doses indicated above or (iv) the vehicle (DMSO:ethanol:saline, 30:30:40%) from days 10-15. All animals were challenged for 1 h with nebulised OVA (10 µg/ml) on day 15 and repeated measurements of specific airways conductance ($sG_{aw}$) were made over a 24 h period using whole body plethysmography. Measurements of $sG_{aw}$ after OVA challenge are plotted as % change from baseline. FIG. 5. shows the effect of Example 8 as monotherapy, while FIG. 6 shows its effects when administered in combination with fluticasone propionate.

Summary

The biological studies in vitro show that the compounds of the disclosure are potent inhibitor of p38 MAP kinase subtypes alpha and gamma and the compounds tested in vitro showed good efficacy in models of anti-inflammatory activity (including LPS-induced TNFalpha release from differentiated U937 cells and THP-1 cells). From the MTT results it may be concluded that the compounds tested do not exhibit overt cellular toxicity at the concentrations used.

The biological studies in vivo show that the compounds tested are effective in inhibiting LPS-induced neutrophil accumulation in an animal model, with a long duration of effect as shown by the significant inhibition even at 8 hours of pre-dosing.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims.

The invention claimed is:

1. A compound of formula (I)

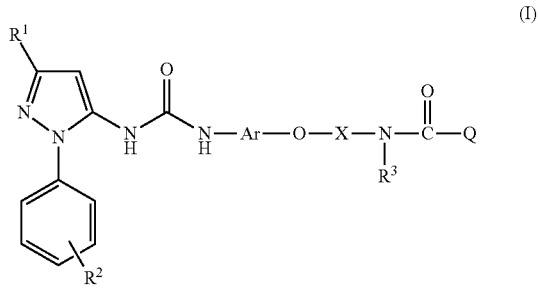

wherein $R^1$ is $C_{1-6}$ alkyl optionally substituted by a hydroxyl group;
$R^2$ is H or $C_{1-6}$ alkyl optionally substituted by a hydroxyl group;
$R^3$ is H, $C_{1-6}$ alkyl or $C_{0-3}$ alkyl$C_{3-6}$ cycloalkyl;
Ar is a naphthyl or a phenyl ring either of which may be optionally substituted by one or more (for example 1 or 2) groups independently selected from $C_{1-6}$ alkyl, $C_{1-6}$ alkoxy, amino, $C_{1-4}$ mono or di-alkyl amino;

X is 5 or 6 membered heteroaryl group containing at least one nitrogen atom and optionally including 1 or 2 further heteroatoms selected from O, S and N;

Q is selected from:

a) a saturated or unsaturated, branched or unbranched $C_{1-10}$ alkyl chain, wherein at least one carbon (for example 1, 2 or 3 carbons, suitably 1 or 2, in particular 1 carbon) is replaced by a heteroatom selected from O, N, $S(O)_p$, wherein said chain is optionally, substituted by one or more groups (for example 1, 2 or 3 groups) independently selected from oxo, halogen, an aryl group, a heteroaryl group, a heterocyclyl group or a $C_{3-8}$ cycloalkyl group, each aryl, heteroaryl, heterocyclyl or $C_{3-8}$ cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O)$C_{1-6}$ alkyl or $C_{0-6}$ alkylC(O)$C_{1-6}$ heteroalkyl, with the proviso that the atom linked directly to the carbonyl in —NR$^3$C(O)— is not an oxygen or a sulfur atom; and b) a $C_{0-8}$ alkyl-heterocycle said heterocyclyl group comprising at least one heteroatom (for example 1, 2 or 3, suitably 1 or 2, in particular 1 heteroatom) selected from O, N, and S, and is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and di-alkyl amino, $C_{1-4}$ mono or di-acyl amino, $S(O)_q C_{1-6}$ alkyl, $C_{0-6}$ alkylC(O)$C_{1-6}$ alkyl or $C_{0-6}$ alkylC(O)$C_{1-6}$ heteroalkyl; and p is 0, 1 or 2;
q is 0, 1 or 2 a pharmaceutically acceptable salt or solvate thereof, including all stereoisomers, tautomers, and deuterated compounds thereof.

2. A compound of formula (I) according to claim 1, wherein Ar is napthyl.

3. A compound of formula (I) according to claim 1, wherein $R^1$ is tert-butyl.

4. A compound of formula (I) according to claim 1, wherein $R^2$ is methyl.

5. A compound of formula (I) according to claim 1, wherein $R^2$ is in the para position.

6. A compound of formula (I) according to claim 1, wherein $R^3$ is H.

7. A compound of formula (I) according to claim 1, wherein NR$^3$C(O)Q is selected from: —NR$^3$C(O)CH$_2$OC$_{1-6}$ alkyl, —NR$^3$C(O)CH$_2$O(CH$_2$)$_2$OCH$_3$, —NR$^3$C(O)CH(CH$_3$)OCH$_3$, —NR$^3$C(O)CH$_2$NHCH$_3$, —NR$^3$C(O)CH$_2$NHCH$_2$CH$_2$OCH$_3$, —NR$^3$C(O)CH$_2$SCH$_3$, —NR$^3$C(O)NH$_2$, —NR$^3$C(O)CH$_2$S(O)$_2$CH$_3$, —NR$^3$C(O)NHC$_{1-7}$ alkyl, —NR$^3$C(O)N(C$_{1-4}$ alkyl)C$_{1-5}$ alkyl, and —NR$^3$C(O)CHN[(CH$_2$)$_2$OCH$_3$]$_2$.

8. A compound of formula (I) according to claim 7, wherein NR$^3$C(O)Q is selected from: —NHC(O)CH$_2$OCH$_3$; —NHC(O)CH$_2$O(CH$_2$)$_2$OCH$_3$; —NHC(O)CH(CH$_3$)OCH$_3$; —NHC(O)CH$_2$NHCH$_3$; —NHC(O)CH$_2$NH(CH$_2$)$_2$OCH$_3$; —NHC(O)CH$_2$SCH$_3$; —NHC(O)NH$_2$; —NHC(O)CH$_2$S(O)$_2$CH$_3$; —NHC(O)NHCH$_3$; —NHC(O)N(CH$_3$)$_2$; and —NHC(O)CHN[(CH$_2$)$_2$OCH$_3$]$_2$.

9. A compound of formula (I) according to claim 1, wherein the compound is of formula (IA):

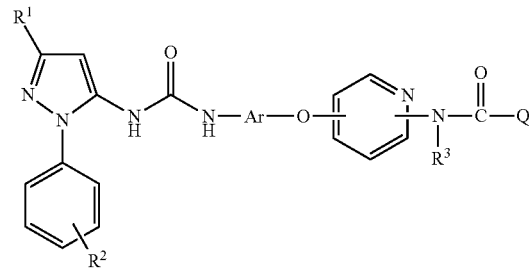

(IA)

or a pharmaceutically acceptable salt or solvate thereof, including all stereoisomers, tautomers, and deuterated compounds thereof.

10. A compound of formula (I) according to claim 9, wherein the compound is of formula (IB):

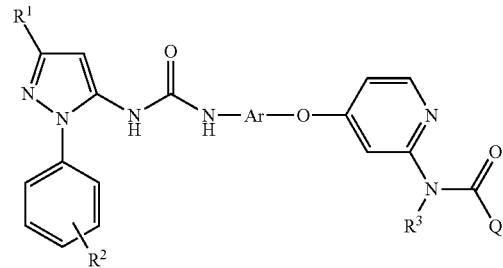

(IB)

or a pharmaceutically acceptable salt or solvate thereof, including all stereoisomers, tautomers, and deuterated compounds thereof.

11. A compound of formula (I) according claim 1, wherein the compound is of formula (IC):

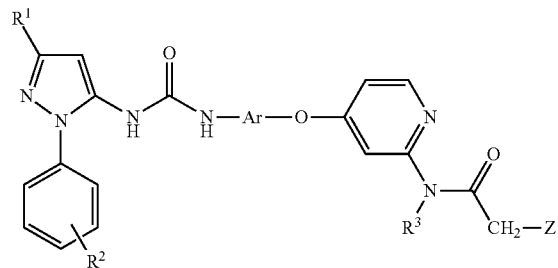

(IC)

wherein $R^1$, $R^2$, Ar and $R^3$ are as defined in claim 1 and

Z represents a saturated or unsaturated, branched or unbranched $C_{1-9}$ alkyl chain, wherein at least one carbon (for example 1, 2 or 3 carbons, suitably 1 or 2, in particular 1) is replaced by a heteroatom selected from O, N, $S(O)_p$, or a $C_{0-7}$ alkylC$_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from halogen, $C_{1-6}$ alkyl, $C_{1-6}$ alkoxy, $C_{1-6}$ haloalkyl, amino, $C_{1-4}$ mono and di-alkyl amino or a pharmaceutically acceptable salt or solvate thereof, including all stereoisomers, tautomers, and deuterated compounds thereof.

12. A compound of formula (I) according to claim 1, wherein the compound is of formula (ID):

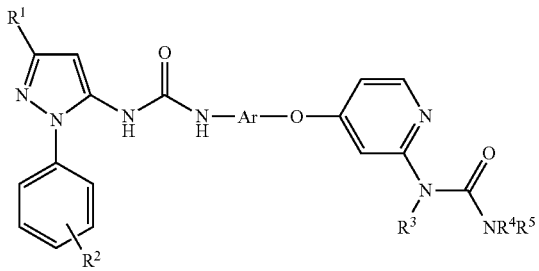

wherein $R^1$, $R^2$, Ar and $R^3$ are as defined in claim 1 and $R^4$ and $R^5$ independently represent hydrogen, $C_{1-6}$ alkyl, or $R^4$ and $R^5$ together with the nitrogen to which they are attached represents a 5 or 6 membered heterocycle optionally comprising a further heteroatom selected from O, N and S, wherein said heterocycle is optionally substituted by one or two or three groups independently selected from halogen, $C_{1-6}$ alkyl, $C_{1-6}$ alkoxy, $C_{1-6}$ haloalkyl, amino, $C_{1-4}$ mono and di-alkyl amino, or a pharmaceutically acceptable salt or solvate thereof, including all stereoisomers, tautomers, and deuterated compounds thereof.

13. A compound of formula (I) according to claim 1, wherein the compound is of formula (IE)

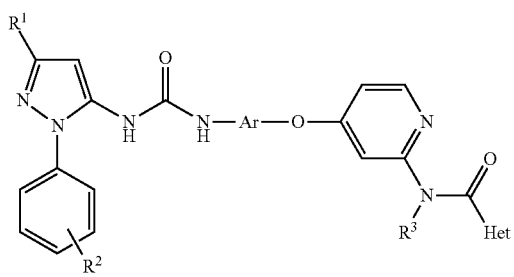

wherein $R^1$, $R^2$, Ar and $R^3$ are as defined in claim 1 and Het represents a $C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from halogen, $C_{1-6}$ alkyl, $C_{1-6}$ alkoxy, $C_{1-6}$ haloalkyl, amino, $C_{1-4}$ mono and di-alkyl amino.

14. A compound of formula (I) according to claim 1, wherein the compound is selected from:

N-(4-(4-(3-(3-tert-Butyl-1-p-tolyl-1H-pyrazol-5-yl)ureido)naphthalen-1-yloxy)pyridin-2-yl)-2-(2-methoxyethoxy)acetamide;

N-(4-(4-(3-(3-tert-Butyl-1-p-tolyl-1H-pyrazol-5-yl)ureido)naphthalen-1-yloxy)pyridin-2-yl)tetrahydro-2H-pyran-4-carboxamide;

N-(4-(4-(3-(3-tert-Butyl-1-p-tolyl-1H-pyrazol-5-yl)ureido)naphthalen-1-yloxy)pyridin-2-yl)-2-(methylthio)acetamide;

N-(4-(4-(3-(3-tert-Butyl-1-p-tolyl-1H-pyrazol-5-yl)ureido)naphthalen-1-yloxy)pyridin-2-yl)-3-methoxypropanamide;

N-(4-(4-(3-(3-tert-Butyl-1-p-tolyl-1H-pyrazol-5-yl)ureido)naphthalen-1-yloxy)pyridin-2-yl)-2-hydroxyacetamide;

N-(4-(4-(3-(3-Isopropyl-1-p-tolyl-1H-pyrazol-5-yl)ureido)naphthalen-1-yloxy)pyridin-2-yl)-2-methoxyacetamide;

N-(4-(4-(3-(3-Ethyl-1-p-tolyl-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-methoxyacetamide;

N-(4-(4-(3-(3-(1-Hydroxy-2-methylpropan-2-yl)-1-p-tolyl-1H-pyrazol-5-yl)ureido)naphthalen-1-yloxy)pyridin-2-yl)-2-methoxyacetamide;

N-(4-(4-(3-(3-tert-butyl-1-(2,3,5,6-tetradeutero-4-(trideuteromethyl)phenyl)-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-morpholinoacetamide;

N-(4-(4-(3-(3-tert-Butyl-1-p-tolyl-1H-pyrazol-5-yl)ureido)naphthalen-1-yloxy)pyridin-2-yl)-(dimethylamino)acetamide;

N-(4-(4-(3-(3-tert-Butyl-1-p-tolyl-1H-pyrazol-5-yl)ureido)naphthalen-1-yloxy)pyridin-2-yl)-2-(2-methoxyethylamino)acetamide;

N-(4-(4-(3-(3-tert-Butyl-1-p-tolyl-1H-pyrazol-5-yl)ureido)naphthalen-1-yloxy)pyridin-2-yl)-2-ureidoacetamide;

N-(4-(4-(3-(3-tert-Butyl-1-p-tolyl-1H-pyrazol-5-yl)ureido)naphthalen-1-yloxy)pyridin-2-yl)-2-(2-methoxyacetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)tetrahydro-2H-pyran-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)isonicotinamide;

N-(4-(4-(3-(3-tert-Butyl-1-p-tolyl-1H-pyrazol-5-yl)ureido)naphthalen-1-yloxy)pyridin-2-yl)-2-(2-(methylsulfonyl)acetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-3-morpholinopropanamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)morpholine-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-2,6-difluoro-3-(2-(2-methoxyethoxy)ethoxy)benzamide;

N-(4-(4-(3-(3-tert-Butyl-1-p-tolyl-1H-pyrazol-5-yl)ureido)phenoxy)pyridin-2-yl)-2-methoxyacetamide;

N-(4-(4-(3-(3-tert-Butyl-1-p-tolyl-1H-pyrazol-5-yl)ureido)-2-methylphenoxy)pyridin-2-yl)-2-methoxyacetamide;

N-(4-(4-(3-(3-tert-Butyl-1-p-tolyl-1H-pyrazol-5-yl)ureido)-3-methylphenoxy)pyridin-2-yl)-2-methoxyacetamide;

N-(4-(4-(3-(3-tert-Butyl-1-p-tolyl-1H-pyrazol-5-yl)ureido)-2-methoxy phenoxy)pyridin-2-yl)-2-methoxyacetamide;

N-(4-(4-(3-(3-tert-Butyl-1-p-tolyl-1H-pyrazol-5-yl)ureido)-2,3-dimethylphenoxy)pyridin-2-yl)-2-methoxyacetamide;

N-(4-(4-(3-(3-tert-Butyl-1-p-tolyl-1H-pyrazol-5-yl)ureido)-3-methoxy phenoxy)pyridin-2-yl)-2-methoxyacetamide;

N-Ethyl-N'-4-(4-(3-(3-tert-butyl-1-p-tolyl-1H-pyrazol-5-yl)ureido)naphthalen-1-yloxy)pyridin-2-ylurea;

4-(4-(3-(3-tert-Butyl-1-p-tolyl-1H-pyrazol-5-yl)ureido) naphthalen-1-yloxy)pyridin-2-ylurea;

N-Propan-2-yl-N'-4-(4-(3-(3-tert-butyl-1-p-tolyl-1H-pyrazol-5-yl)ureido)naphthalen-1-yloxy)pyridin-2-ylurea;

1-(3-(tert-Butyl)-1-(p-tolyl)-1H-pyrazol-5-yl)-3-(4-((2-(3-phenylureido)pyridin-4-yl)oxy)naphthalen-1-yl) urea;

1-(4-((2-(3-Benzylureido)pyridin-4-yl)oxy)naphthalen-1-yl)-3-(3-(tert-butyl)-1-(p-tolyl)-1H-pyrazol-5-yl)urea;

1-(4-((2-(3-Cyclopropylureido)pyridin-4-yl)oxy)naphthalen-1-yl)-3-(3-(tert-butyl)-1-(p-tolyl)-1H-pyrazol-5-yl)urea;

1-(3-(tert-Butyl)-1-(p-tolyl)-1H-pyrazol-5-yl)-3-(4-((2-(3-(2-methoxyethyl)ureido)pyridin-4-yl)oxy)naphthalen-1-yl)urea;

1-(3-(tert-Butyl)-1-(p-tolyl)-1H-pyrazol-5-yl)-3-(4-((2-(3-cyclopentyl)ureido)pyridin-4-yl)oxy)naphthalen-1-yl)urea;

1-(3-(tert-Butyl)-1-(p-tolyl)-1H-pyrazol-5-yl)-3-(4-((2-(3-methyl)ureido)pyridin-4-yl)oxy)naphthalen-1-yl) urea;

Ethyl 2-(3-(4-((4-(3-(3-(tert-butyl)-1-(p-tolyl)-1H-pyrazol-5-yl)ureido)naphthalen-1-yl)oxy)pyridin-2-yl)ureido)acetate;

4-(3-(4-(4-(3-(3-tert-Butyl-1-p-tolyl-1H-pyrazol-5-yl) ureido)naphthalen-1-yloxy)pyridin-2-yl)ureido)piperidine;

N-Acetyl 4-(3-(4-(4-(3-(3-tert-butyl-1-p-tolyl-1H-pyrazol-5-yl)ureido)naphthalen-1-yloxy)pyridin-2-yl)ureido)piperidine;

2-(2-Methoxyethoxy)-1-(4-(3-(4-(4-(3-(3-tert-butyl-1-p-tolyl-1H-pyrazol-5-yl)ureido)naphthalen-1-yloxy)pyridin-2-yl)ureido)piperidin-1-yl)ethanone;

N-Methylsulfonyl-4-(3-(4-(4-(3-(3-tert-butyl-1-p-tolyl-1H-pyrazol-5-yl)ureido)naphthalen-1-yloxy)pyridin-2-yl)ureido)piperidine;

N-(4-(4-(3-(3-tert-Butyl-1-p-tolyl-1H-pyrazol-5-yl)ureido)naphthalen-1-yloxy)pyridin-2-yl)morpholine-4-carboxamide;

N-(4-((4-(3-(3-(tert-butyl)-1-(p-tolyl)-1H-pyrazol-5-yl) ureido)naphthalen-1-yl)oxy)pyridin-2-yl)-4-methylpiperazine-1-carboxamide;

3-(4-((4-(3-(3-(tert-butyl)-1-(p-tolyl)-1H-pyrazol-5-yl) ureido)naphthalen-1-yl)oxy)pyridin-2-yl)-1,1-dimethylurea;

N-(4-((4-(3-(3-(tert-Butyl)-1-(p-tolyl)-1H-pyrazol-5-yl) ureido)naphthalen-1-yl)oxy)pyridin-2-yl)piperidine-1-carboxamide;

N-Methyl-N-(2-(morpholin-4-ylethyl)-N'-4-(4-(3-(3-tert-butyl-1-p-tolyl-1H-pyrazol-5-yl)ureido)naphthalen-1-yloxy)pyridin-2-ylurea;

N-(4-(morpholin-4-yl)butyl)-N'-4-(4-(3-(3-tert-butyl-1-p-tolyl-1H-pyrazol-5-yl)ureido)naphthalen-1-yloxy)pyridin-2-ylurea;

N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;

N-(3-methylisoxazol-5-yl)methyl-N'-4-(4-(3-(3-tert-butyl-1-p-tolyl-1H-pyrazol-5-yl)ureido)naphthalen-1-yloxy)pyridin-2-ylurea;

N-(1-methyl)piperidin-4-yl-N'-4-(4-(3-(3-tert-butyl-1-p-tolyl-1H-pyrazol-5-yl)ureido)naphthalen-1-yloxy)pyridin-2-ylurea;

N-(4-(4-(3-(3-tert-Butyl-1-p-tolyl-1H-pyrazol-5-yl)ureido)naphthalen-1-yloxy)pyridin-2-yl)-4-hydroxypiperidine-1-carboxamide;

N-(3-(imidazol-1-yl)propyl)-N'-4-(4-(3-(3-tert-butyl-1-p-tolyl-1H-pyrazol-5-yl)ureido)naphthalen-1-yloxy)pyridin-2-ylurea;

N-(2-(3-(4-(4-(3-(3-tert-Butyl-1-p-tolyl-1H-pyrazol-5-yl) ureido)naphthalen-1-yloxy)pyridin-2-yl)ureido)acetyl) pyrrolidine;

(R)—N-(4-(4-(3-(3-tert-Butyl-1-p-tolyl-1H-pyrazol-5-yl) ureido)naphthalen-1-yloxy)pyridin-2-yl)-3-(dimethylamino)pyrrolidine-1-carboxamide;

N-(4-(4-(3-(3-tert-Butyl-1-p-tolyl-1H-pyrazol-5-yl)ureido)naphthalen-1-yloxy)pyridin-2-yl)pyrrolidine-1-carboxamide;

2-(3-(4-(4-(3-(3-tert-Butyl-1-p-tolyl-1H-pyrazol-5-yl) ureido)naphthalen-1-yloxy)pyridin-2-yl)ureido)-N-methylacetamide;

2-(3-(4-(4-(3-(3-tert-Butyl-1-p-tolyl-1H-pyrazol-5-yl) ureido)naphthalen-1-yloxy)pyridin-2-yl)ureido)-N-(2-morpholinoethyl)acetamide;

2-(3-(4-(4-(3-(3-tert-Butyl-1-p-tolyl-1H-pyrazol-5-yl) ureido)naphthalen-1-yloxy)pyridin-2-yl)ureido)acetyl morpholine;

2-(3-(4-(4-(3-(3-tert-Butyl-1-p-tolyl-1H-pyrazol-5-yl) ureido)naphthalen-1-yloxy)pyridin-2-yl)ureido)-N-(2-(pyridin-4-yl)ethyl)acetamide;

N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide;

1-(2-(3-(4-(4-(3-(3-tert-Butyl-1-p-tolyl-1H-pyrazol-5-yl) ureido)naphthalen-1-yloxy)pyridin-2-yl)ureido) acetyl)-4-methylpiperazine;

N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide;

N-(6-(4-(3-(3-tert-Butyl-1-p-tolyl-1H-pyrazol-5-yl)ureido) naphthalen-1-yloxy)pyrimidin-4-yl)-2-methoxyacetamide;

N-(6-(4-(3-(3-tert-Butyl-1-p-tolyl-1H-pyrazol-5-yl)ureido)phenoxy)pyrimidin-4-yl)-2-methoxyacetamide;

N-(4-(4-(3-(3-tert-Butyl-1-p-tolyl-1H-pyrazol-5-yl)ureido)naphthalen-1-yloxy)pyrimidin-2-yl)-2-methoxyacetamide;

3-(4-(4-(3-(3-tert-Butyl-1-p-tolyl-1H-pyrazol-5-yl)ureido)naphthalen-1-yloxy)pyrimidin-2-yl)urea;

1-Methyl-3-(4-(4-(3-(3-tert-butyl-1-p-tolyl-1H-pyrazol-5-yl)ureido)naphthalen-1-yloxy)pyrimidin-2-yl)urea;

1,1-Dimethyl-3-(4-(4-(3-(3-tert-butyl-1-p-tolyl-1H-pyrazol-5-yl)ureido)naphthalen-1-yloxy)pyrimidin-2-yl) urea;

1-Cyclopropyl-3-(4-(4-(3-(3-tert-butyl-1-p-tolyl-1H-pyrazol-5-yl)ureido)naphthalen-1-yloxy)pyrimidin-2-yl)urea;

(4-(4-(3-(3-tert-butyl-1-p-tolyl-1H-pyrazol-5-yl)ureido) naphthalen-1-yloxy)pyrimidin-2-yl)morpholine-4-carboxamide;

3-(6-(4-(3-(3-tert-Butyl-1-p-tolyl-1H-pyrazol-5-yl)ureido)naphthalen-1-yloxy)pyrimidin-4-yl)urea; or 2-(3-(4-(4-(3-(3-tert-Butyl-1-p-tolyl-1H-pyrazol-5-yl)ureido)naphthalen-1-yloxy)pyridin-2-yl)ureido)acetic acid, and a pharmaceutically acceptable salt or solvate thereof, including all stereoisomers, tautomers, and deuterated compounds thereof.

15. A pharmaceutical composition comprising a compound according to claim 1, in combination with one or more pharmaceutically acceptable diluents or carriers.

16. A method of treatment of a condition selected from the group consisting of COPD, asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, and cachexia, which comprises administering to a subject an effective amount of a compound of formula (I) according to claim 1.

17. A method of treatment of a condition selected from the group consisting of COPD, asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, and cachexia, which comprises administering to a subject an effective amount of a pharmaceutical composition according to claim 15.

\* \* \* \* \*